(12) United States Patent
Alexander et al.

(10) Patent No.: US 8,679,457 B2
(45) Date of Patent: Mar. 25, 2014

(54) METABOLITE BIOMARKERS TO DISTINGUISH CROHN'S DISEASE FROM ULCERATIVE COLITIS AND METHODS USING THE SAME

(75) Inventors: Danny Alexander, Cary, NC (US); Jeffrey Shuster, Chapel Hill, NC (US); Joshua Korzenik, Dover, MA (US); Garrett Zella, Newton, MA (US)

(73) Assignees: Metabolon, Inc., Durham, NC (US); The Massachusetts General Hospital, Boston, MA (US)

( * ) Notice: Subject to any disclaimer, the term of this patent is extended or adjusted under 35 U.S.C. 154(b) by 0 days.

(21) Appl. No.: 13/082,843

(22) Filed: Apr. 8, 2011

(65) Prior Publication Data

US 2012/0003158 A1    Jan. 5, 2012

Related U.S. Application Data

(63) Continuation-in-part of application No. PCT/US2009/060426, filed on Oct. 13, 2009.

(60) Provisional application No. 61/104,934, filed on Oct. 13, 2008.

(51) Int. Cl.
    *A61K 49/00* (2006.01)

(52) U.S. Cl.
    USPC ........................................ 424/9.1; 435/7.92

(58) Field of Classification Search
    None
    See application file for complete search history.

(56) References Cited

U.S. PATENT DOCUMENTS 6,562,629 B1    5/2003  Lin et al.
7,833,720 B2 *  11/2010 Harris et al. ................ 435/6.17
8,227,589 B2 *  7/2012  Harris et al. ................ 536/24.3
2001/0026922 A1 10/2001 Holland
2006/0035845 A1 2/2006  Mercep et al.

FOREIGN PATENT DOCUMENTS

WO    WO 89/05452    6/1989

OTHER PUBLICATIONS

Zella G. et al. The Serum Metabolome in IBD. Gastroenterology 136(5)Suppl 1, pp. A349 May 2009.*
International Search Report, issued in PCT/US2009/060426, dated Dec. 14, 2009.
International Preliminary Report on Patentability, issued in PCT/US2009/060426, dated Apr. 28, 2011.
Mingrone et al., "The Steroid Resistance of Crohn's Disease," Journal of Investigative Medicine, vol. 47, No. 6, (Jul. 1999), pp. 319-325, Search Report.

* cited by examiner

*Primary Examiner* — Ralph Gitomer
(74) *Attorney, Agent, or Firm* — Brinks Gilson & Lione

(57) ABSTRACT

The present invention provides various biomarkers of inflammatory bowel disease, including biomarkers for Crohn's disease and biomarkers for Ulcerative colitis. The present invention also provides various methods of using the biomarkers, including methods for diagnosis of inflammatory bowel disease, methods for distinguishing between inflammatory bowel diseases, methods of determining predisposition to inflammatory bowel disease, methods of monitoring progression/regression of inflammatory bowel disease, methods of assessing efficacy of compositions for treating inflammatory bowel disease, methods of screening compositions for activity in modulating biomarkers of inflammatory bowel disease, methods of treating inflammatory bowel disease, as well as other methods based on biomarkers of inflammatory bowel disease.

4 Claims, 1 Drawing Sheet

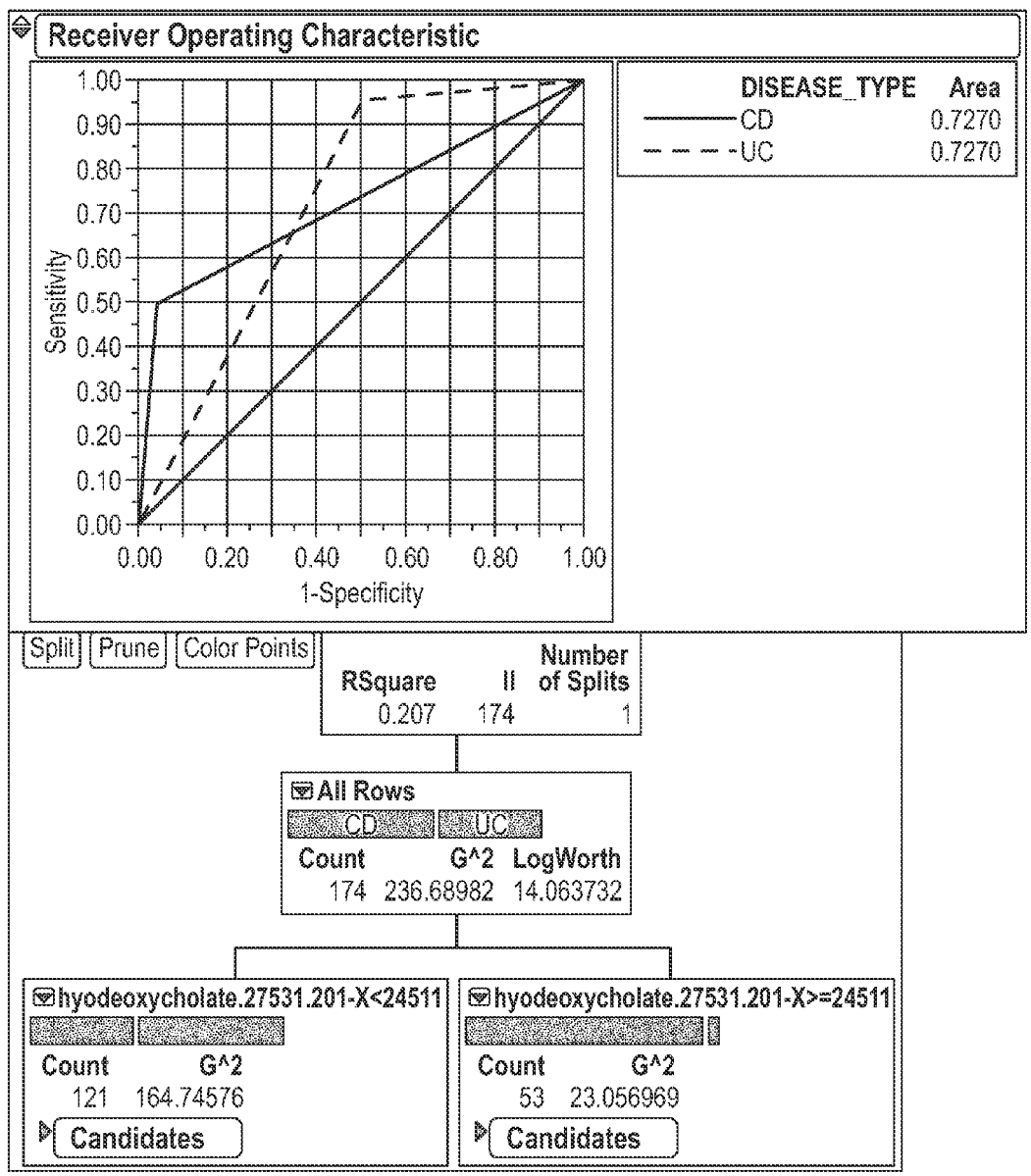

METABOLITE BIOMARKERS TO DISTINGUISH CROHN'S DISEASE FROM ULCERATIVE COLITIS AND METHODS USING THE SAME

CROSS-REFERENCE TO RELATED APPLICATIONS

This application in a Continuation-in-Part of International Application No. PCT/US2009/060426, filed Oct. 13, 2009, which claims the benefit of U.S. Provisional Application No. 61/104,934, filed Oct. 13, 2008, the entirety of which is hereby incorporated by reference.

FIELD

The invention generally relates to biomarkers for inflammatory bowel disease and methods based on the same biomarkers.

BACKGROUND

According to recent estimates, over one million Americans suffer from ulcerative colitis or Crohn's disease, the most common forms of inflammatory bowel disease (IBD). These diseases are so similar that they are often mistaken for one another. Both inflame the lining of the digestive tract and cause severe bouts of watery diarrhea and abdominal pain. However, Crohn's disease can occur anywhere in the digestive tract, often spreading deep into the layers of affected tissues. In contrast, ulcerative colitis usually affects only the innermost lining (mucosa) of the large intestine (colon) and rectum.

IBD is especially common in older children and adolescents. Young patients are at particular risk for growth retardation, or for delay of sexual maturation. Moreover, given the length of time that these patients need treatment, they are susceptible to long-term complications from their medications.

IBD patients may experience a series of complications that affect the body beyond the intestinal tract. For example, patients with ulcerative colitis can develop severe arthritis, liver disease, kidney stones, gallstones and mouth ulcers that prohibit swallowing or eating.

The present invention provides biochemical markers that aid in determination of predisposition to and the diagnosis of inflammatory bowel disease, determining treatment efficacy and provide for therapeutic agent discovery and development. The markers may distinguish classes of inflammatory bowel disease (e.g. Crohn's Disease, Ulcerative Colitis, pouchitis), subtypes of Crohn's Disease (e.g., ileitis, ileocolitis, gastroduodenal CD, jejunoileitis, granulomatous) and distinguish inflammatory bowel disease from other gastrointestinal disorders or disorders presenting with similar clinical symptoms.

SUMMARY

Methods relating to metabolites for inflammatory bowel disease are provided. In one aspect, a method of diagnosing whether a subject has inflammatory bowel disease is provided, where the method comprises, analyzing a biological sample from a subject to determine the level(s) of one or more biomarkers for inflammatory bowel disease in the sample, where the one or more biomarkers are selected from Tables 1A, 1B, 1C, 2, 3, 4B, 4D and/or 5B and comparing the level(s) of the one or more biomarkers in the sample to inflammatory bowel disease-positive and/or inflammatory bowel disease-negative reference levels of the one or more biomarkers in order to diagnose whether the subject has inflammatory bowel disease.

In another aspect, a method is provided for distinguishing Crohn's disease from Ulcerative colitis in a subject, comprising: analyzing a biological sample from a subject to determine the level(s) of one or more biomarkers for inflammatory bowel disease in the sample, where the one or more biomarkers are selected from Tables 1A, 1B, 1C and 4D and comparing the level(s) of the one or more biomarkers in the sample to Crohn's disease-positive reference levels that distinguish over Ulcerative colitis and/or to Ulcerative Colitis-positive reference levels that distinguish over Crohn's disease in order to determine whether the subject has Crohn's disease or Ulcerative colitis.

In still another aspect, a method for distinguishing inactive Crohn's disease from active Crohn's disease in a subject is provided, the method comprising: analyzing a biological sample from a subject to determine the level(s) of one or more biomarkers for inflammatory bowel disease in the sample, where the one or more biomarkers are selected from Tables 2 and 4D, and comparing the level(s) of the one or more biomarkers in the sample to active-Crohn's disease reference levels that distinguish over inactive-Crohn's disease and/or inactive-Crohn's disease reference levels that distinguish over active-Crohn's disease in order to determine whether the subject has active or inactive Crohn's disease.

Also provided is a method of distinguishing inactive Ulcerative colitis from active Ulcerative colitis in a subject, comprising: analyzing a biological sample from a subject to determine the level(s) of one or more biomarkers for inflammatory bowel disease in the sample, where the one or more biomarkers are selected from Tables 3 and 5B, and comparing the level(s) of the one or more biomarkers in the sample to active-Ulcerative colitis reference levels that distinguish over inactive-Ulcerative colitis and/or inactive-Ulcerative colitis reference levels that distinguish over active-Ulcerative colitis in order to determine whether the subject has active or inactive Ulcerative colitis.

In another aspect, a method of determining whether a subject is predisposed to developing inflammatory bowel disease is provided, the method comprising: analyzing a biological sample from a subject to determine the level(s) of one or more biomarkers for inflammatory bowel disease in the sample, where the one or more biomarkers are selected from Tables 1A, 1B, 1C, 2, 3, 4B, 4D and/or 5B; and comparing the level(s) of the one or more biomarkers in the sample to inflammatory bowel disease-positive and/or inflammatory bowel disease-negative reference levels of the one or more biomarkers in order to determine whether the subject is predisposed to developing inflammatory bowel disease.

Also provided is a method of monitoring progression/regression of inflammatory bowel disease in a subject comprising: analyzing a first biological sample from a subject to determine the level(s) of one or more biomarkers for inflammatory bowel disease in the sample, where the one or more biomarkers are selected from Tables 1A, 1B, 1C, 2, 3, 4B, 4D and/or 5B and the first sample is obtained from the subject at a first time point; analyzing a second biological sample from a subject to determine the level(s) of the one or more biomarkers, where the second sample is obtained from the subject at a second time point; and comparing the level(s) of one or more biomarkers in the first sample to the level(s) of the one or more biomarkers in the second sample in order to monitor the progression/regression of inflammatory bowel disease in the subject.

In another aspect, a method of assessing the efficacy of a composition for treating inflammatory bowel disease is provided, comprising: analyzing, from a subject having inflammatory bowel disease and currently or previously being treated with a composition, a biological sample to determine the level(s) of one or more biomarkers for inflammatory bowel disease selected from Tables 1A, 1B, 1C, 2, 3, 4B, 4D and/or 5B; and comparing the level(s) of the one or more biomarkers in the sample to (a) levels of the one or more biomarkers in a previously-taken biological sample from the subject, where the previously-taken biological sample was obtained from the subject before being treated with the composition, (b) inflammatory bowel disease-positive reference levels of the one or more biomarkers, and/or (c) inflammatory bowel disease-negative reference levels of the one or more biomarkers.

Further provided is a method for assessing the efficacy of a composition in treating inflammatory bowel disease, comprising: analyzing a first biological sample from a subject to determine the level(s) of one or more biomarkers for inflammatory bowel disease selected from Tables 1A, 1B, 1C, 2, 3, 4B, 4D and/or 5B, the first sample obtained from the subject at a first time point; administering the composition to the subject; analyzing a second biological sample from the subject to determine the level(s) of the one or more biomarkers, the second sample obtained from the subject at a second time point after administration of the composition; comparing the level(s) of one or more biomarkers in the first sample to the level(s) of the one or more biomarkers in the second sample in order to assess the efficacy of the composition for treating inflammatory bowel disease.

In another aspect, a method of assessing the relative efficacy of two or more compositions for treating inflammatory bowel disease is provided, comprising: analyzing, from a first subject having inflammatory bowel disease and currently or previously being treated with a first composition, a first biological sample to determine the level(s) of one or more biomarkers selected from Tables 1A, 1B, 1C, 2, 3, 4B, 4D and/or 5B; analyzing, from a second subject having inflammatory bowel disease and currently or previously being treated with a second composition, a second biological sample to determine the level(s) of the one or more biomarkers; and comparing the level(s) of one or more biomarkers in the first sample to the level(s) of the one or more biomarkers in the second sample in order to assess the relative efficacy of the first and second compositions for treating inflammatory bowel disease.

In yet another aspect, a method for screening a composition for activity in modulating one or more biomarkers of inflammatory bowel disease is provided, comprising: contacting one or more cells with a composition; analyzing at least a portion of the one or more cells or a biological sample associated with the cells to determine the level(s) of one or more biomarkers of inflammatory bowel disease selected from Tables 1A, 1B, 1C, 2, 3, 4B, 4D and/or 5B; and comparing the level(s) of the one or more biomarkers with predetermined standard levels for the biomarkers to determine whether the composition modulated the level(s) of the one or more biomarkers.

In another aspect, a method is provided for identifying a potential drug target for inflammatory bowel disease comprising: identifying one or more biochemical pathways associated with one or more biomarkers for inflammatory bowel disease selected from Tables 1A, 1B, 1C, 2, 3, 4B, 4D and/or 5B; and identifying a protein affecting at least one of the one or more identified biochemical pathways, the protein being a potential drug target for inflammatory bowel disease.

DESCRIPTION OF THE FIGURES

FIG. 1 provides one embodiment of hyodeoxycholate levels that may indicate the presence of a Crohn's Disease (CD) subtype in the Crohn's disease population. In this embodiment, high levels of hyodeoxycholate indicate a high chance of Crohn's Disease, but the presence of many false negatives at the low end indicates a sub-population within CD.

DETAILED DESCRIPTION

The present invention relates to biomarkers of inflammatory bowel disease, methods for diagnosis of inflammatory bowel disease, methods of determining predisposition to inflammatory bowel disease, methods of monitoring progression/regression of inflammatory bowel disease, methods of assessing efficacy of compositions for treating inflammatory bowel disease, methods of screening compositions for activity in modulating biomarkers of inflammatory bowel disease, methods of treating inflammatory bowel disease, as well as other methods based on biomarkers of inflammatory bowel disease. Prior to describing this invention in further detail, however, the following terms will first be defined.

DEFINITIONS

"Biomarker" means a compound, preferably a metabolite, that is differentially present (i.e., increased or decreased) in a biological sample from a subject or a group of subjects having a first phenotype (e.g., having a disease) as compared to a biological sample from a subject or group of subjects having a second phenotype (e.g., not having the disease). A biomarker may be differentially present at any level, but is generally present at a level that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent). A biomarker is preferably differentially present at a level that is statistically significant (i.e., a p-value less than 0.05 and/or a q-value of less than 0.10 as determined using either Welch's T-test or Wilcoxon's rank-sum Test).

The "level" of one or more biomarkers means the absolute or relative amount or concentration of the biomarker in the sample.

"Sample" or "biological sample" means biological material isolated from a subject. The biological sample may contain any biological material suitable for detecting the desired biomarkers, and may comprise cellular and/or non-cellular material from the subject. The sample can be isolated from any suitable biological tissue or fluid such as, for example, stool, blood, blood plasma, blood serum, urine, or cerebral spinal fluid (CSF).

"Subject" means any animal, but is preferably a mammal, such as, for example, a human, monkey, mouse, or rabbit.

A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype. For example, an "inflammatory bowel disease-positive reference level" of a biomarker means a level of a biomarker that is indicative of a positive diagnosis of inflammatory bowel disease in a subject, and an "inflammatory bowel disease-negative reference level" of a biomarker means a level of a biomarker that is indicative of a negative diagnosis of inflammatory bowel disease in a subject. A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate positive and negative reference levels of biomarkers for a particular disease state, phenotype, or lack thereof may be determined by measuring levels of desired biomarkers in one or more appropriate subjects, and such reference levels may be tailored to specific populations of subjects (e.g., a reference level may be age-matched so that comparisons may be made between biomarker levels in samples from subjects of a certain age and reference levels for a particular disease state, phenotype, or lack thereof in a certain age group). Such reference levels may also be tailored to specific techniques that are used to measure levels of biomarkers in biological samples (e.g., LC-MS, GC-MS, etc.), where the levels of biomarkers may differ based on the specific technique that is used.

"Non-biomarker compound" means a compound that is not differentially present in a biological sample from a subject or a group of subjects having a first phenotype (e.g., having a first disease) as compared to a biological sample from a subject or group of subjects having a second phenotype (e.g., not having the first disease). Such non-biomarker compounds may, however, be biomarkers in a biological sample from a subject or a group of subjects having a third phenotype (e.g., having a second disease) as compared to the first phenotype (e.g., having the first disease) or the second phenotype (e.g., not having the first disease).

"Metabolite", or "small molecule", means organic and inorganic molecules which are present in a cell. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000). The small molecules of the cell are generally found free in solution in the cytoplasm or in other organelles, such as the mitochondria, where they form a pool of intermediates which can be metabolized further or used to generate large molecules, called macromolecules. The term "small molecules" includes signaling molecules and intermediates in the chemical reactions that transform energy derived from food into usable forms. Examples of small molecules include sugars, fatty acids, amino acids, nucleotides, intermediates formed during cellular processes, and other small molecules found within the cell.

"Metabolic profile", or "small molecule profile", means a complete or partial inventory of small molecules within a targeted cell, tissue, organ, organism, or fraction thereof (e.g., cellular compartment). The inventory may include the quantity and/or type of small molecules present. The "small molecule profile" may be determined using a single technique or multiple different techniques.

"Metabolome" means all of the small molecules present in a given organism.

"Inflammatory bowel disease" or "IBD" refers to diseases which cause inflammation in the digestive tract, including Crohn's disease and ulcerative colitis. The causes of IBD are unknown and symptoms include abdominal cramps, bloody diarrhea, fever and weight loss.

"Irritable bowel syndrome" or "IBS" refers to a functional disorder that differs from IBD and does not cause inflammation, ulcers, or damage to the bowel. IBS has also been referred to as spastic colon or spastic bowel.

"Crohn's disease" or "CD" refers to a chronic inflammatory disorder of the gastrointestinal (GI) tract. It may occur in any portion of the GI tract but is most often found to affect the small intestine and/or colon. Unlike ulcerative colitis, CD can affect the entire thickness of the bowel wall.

"Ulcerative colitis" or "UC" refers to a chronic disease marked by inflammation and ulceration of the mucosa (innermost lining) of the colon or large intestine. UC differs from CD in that UC involves only the colon, the inflammation involves the entire rectum extending up the colon in a continuous manner without areas of normal intestine interspersed with diseased areas, and UC affects only the innermost lining of the colon.

I. Biomarkers

The inflammatory bowel disease biomarkers described herein were discovered using metabolomic profiling techniques. Such metabolomic profiling techniques are described in more detail in the Examples set forth below as well as in U.S. Pat. No. 7,005,255 and U.S. Pat. No. 7,329,489, the entire contents of which are hereby incorporated herein by reference.

Generally, metabolic profiles were determined for biological samples from human subjects diagnosed with inflammatory bowel disease as well as from one or more other groups of human subjects (e.g., healthy control subjects not diagnosed with inflammatory bowel disease). The metabolic profile for inflammatory bowel disease was compared to the metabolic profile for biological samples from the one or more other groups of subjects. The comparisons may be conducted using models or algorithms, such as those described herein. Those molecules differentially present, including those molecules differentially present at a level that is statistically significant, in the metabolic profile of samples from subjects with inflammatory bowel disease as compared to another group (e.g., healthy control subjects not diagnosed with inflammatory bowel disease) were identified as biomarkers to distinguish those groups.

The biomarkers are discussed in more detail herein. The biomarkers that were discovered correspond with the following group(s):

Biomarkers for distinguishing Crohn's disease vs. Ulcerative colitis (see Tables 1A, 1B, 1C, 4B).

Biomarkers for distinguishing active Crohn's disease vs. inactive Crohn's disease (see Tables 2, 4D).

Biomarkers for distinguishing active ulcerative colitis vs. inactive ulcerative colitis (see Tables 3, 5B).

Although the identities of some of the biomarkers compounds are not known at this time, such identities are not necessary for the identification of the biomarkers in biological samples from subjects, as the "unnamed" compounds have been sufficiently characterized by analytical techniques to allow such identification. The analytical characterization of all such "unnamed" compounds is listed in the Examples, for example, in Table 7. Such "unnamed" biomarkers are designated herein using the nomenclature "Metabolite" followed by a specific metabolite number. In addition, where the identity of an unnamed biomarker has been determined, the identity of the biomarkers is presented in Table 7.

II. Diagnosis of Inflammatory Bowel Disease

The identification of biomarkers for inflammatory bowel disease allows for the diagnosis of (or for aiding in the diagnosis of) inflammatory bowel disease in subjects presenting one or more symptoms of inflammatory bowel disease. A method of diagnosing (or aiding in diagnosing) whether a subject has inflammatory bowel disease comprises (1) analyzing a biological sample from a subject to determine the level(s) of one or more biomarkers of inflammatory bowel disease in the sample and (2) comparing the level(s) of the one or more biomarkers in the sample to inflammatory bowel disease-positive and/or inflammatory bowel disease-negative reference levels of the one or more biomarkers in order to diagnose (or aid in the diagnosis of) whether the subject has inflammatory bowel disease. The one or more biomarkers that are used are selected from Tables 1A, 1B, 1C, 2, 3, 4B, 4D and/or 5B and combinations thereof. When such a method is used to aid in the diagnosis of inflammatory bowel disease, the results of the method may be used along with other methods (or the results thereof) useful in the clinical determination of whether a subject has inflammatory bowel disease.

Any suitable method may be used to analyze the biological sample in order to determine the level(s) of the one or more biomarkers in the sample. Suitable methods include chromatography (e.g., HPLC, gas chromatography, liquid chromatography), mass spectrometry (e.g., MS, MS-MS), enzyme-linked immunosorbent assay (ELISA), antibody linkage, other immunochemical techniques, and combinations thereof. Further, the level(s) of the one or more biomarkers may be measured indirectly, for example, by using an assay that measures the level of a compound (or compounds) that correlates with the level of the biomarker(s) that are desired to be measured.

The levels of one or more of the biomarkers of Tables 1A, 1B, 1C, 2, 3, 4B, 4D and/or 5B may be determined in the methods of diagnosing and methods of aiding in diagnosing whether a subject has inflammatory bowel disease. For example, the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, etc., including a combination of all of the biomarkers in Tables 1A, 1B, 1C, 2, 3, 4B, 4D and/or 5B or any fraction thereof, may be determined and used in such methods. Determining levels of combinations of the biomarkers may allow greater sensitivity and specificity in diagnosing inflammatory bowel disease and aiding in the diagnosis of inflammatory bowel disease, and may allow better differentiation of inflammatory bowel disease from other gastrointestinal disorders (e.g., spastic colon, spastic bowel, infections (e.g., bacterial, viral), etc.) that may have similar or overlapping biomarkers to inflammatory bowel disease (as compared to a subject not having inflammatory bowel disease). For example, ratios of the levels of certain biomarkers (and non-biomarker compounds) in biological samples may allow greater sensitivity and specificity in diagnosing inflammatory bowel disease and aiding in the diagnosis of inflammatory bowel disease, and may allow better differentiation of inflammatory bowel disease from other inflammatory bowel disorders that may have similar or overlapping biomarkers to inflammatory bowel disease (as compared to a subject not having a inflammatory bowel disorder).

One or more biomarkers that are specific for diagnosing inflammatory bowel disease (or aiding in diagnosing inflammatory bowel disease) in a certain type of sample (e.g., urine sample, stool sample or blood sample) may also be used. For example, when the biological sample is blood, one or more biomarkers listed in Tables 1A, 1B, 1C, 2, 3, 4B, 4D and/or 5B may be used to diagnose (or aid in diagnosing) whether a subject has inflammatory bowel disease.

After the level(s) of the one or more biomarkers in the sample are determined, the level(s) are compared to inflammatory bowel disease-positive and/or inflammatory bowel disease-negative reference levels to aid in diagnosing or to diagnose whether the subject has inflammatory bowel disease. Levels of the one or more biomarkers in a sample matching the inflammatory bowel disease-positive reference levels (e.g., levels that are the same as the reference levels, substantially the same as the reference levels, above and/or below the minimum and/or maximum of the reference levels, and/or within the range of the reference levels) are indicative of a diagnosis of inflammatory bowel disease in the subject. Levels of the one or more biomarkers in a sample matching the inflammatory bowel disease-negative reference levels (e.g., levels that are the same as the reference levels, substantially the same as the reference levels, above and/or below the minimum and/or maximum of the reference levels, and/or within the range of the reference levels) are indicative of a diagnosis of no inflammatory bowel disease in the subject. In addition, levels of the one or more biomarkers that are differentially present (especially at a level that is statistically significant) in the sample as compared to inflammatory bowel disease-negative reference levels are indicative of a diagnosis of inflammatory bowel disease in the subject. Levels of the one or more biomarkers that are differentially present (especially at a level that is statistically significant) in the sample as compared to inflammatory bowel disease-positive reference levels are indicative of a diagnosis of no inflammatory bowel disease in the subject.

The level(s) of the one or more biomarkers may be compared to inflammatory bowel disease-positive and/or inflammatory bowel disease-negative reference levels using various techniques, including a simple comparison (e.g., a manual comparison) of the level(s) of the one or more biomarkers in the biological sample to inflammatory bowel disease-positive and/or inflammatory bowel disease-negative reference levels. The level(s) of the one or more biomarkers in the biological sample may also be compared to inflammatory bowel disease-positive and/or inflammatory bowel disease-negative reference levels using one or more statistical analyses (e.g., t-test, Welch's T-test, Wilcoxon's rank sum test, random forest).

In addition, the biological samples may be analyzed to determine the level(s) of one or more non-biomarker compounds. The level(s) of such non-biomarker compounds may also allow differentiation of inflammatory bowel disease from other inflammatory bowel disorders that may have similar or overlapping biomarkers to inflammatory bowel disease (as compared to a subject not having a inflammatory bowel disorder). For example, a known non-biomarker compound present in biological samples of subjects having inflammatory bowel disease and subjects not having inflammatory bowel disease could be monitored to verify a diagnosis of inflammatory bowel disease as compared to a diagnosis of another inflammatory bowel disorder when biological samples from subjects having the inflammatory bowel disorder do not have the non-biomarker compound.

III. Methods of Determining Predisposition to Inflammatory Bowel Disease

The identification of biomarkers for inflammatory bowel disease also allows for the determination of whether a subject having no symptoms of inflammatory bowel disease is predisposed to developing inflammatory bowel disease. A method of determining whether a subject having no symptoms of inflammatory bowel disease is predisposed to developing inflammatory bowel disease comprises (1) analyzing a biological sample from a subject to determine the level(s) of one or more biomarkers listed in Tables 1A, 1B, 1C, 2, 3, 4B, 4D and/or 5B in the sample and (2) comparing the level(s) of the one or more biomarkers in the sample to inflammatory bowel disease-positive and/or inflammatory bowel disease-negative reference levels of the one or more biomarkers in order to determine whether the subject is predisposed to developing inflammatory bowel disease. The results of the method may be used along with other methods (or the results thereof) useful in the clinical determination of whether a subject is predisposed to developing inflammatory bowel disease.

As described above in connection with methods of diagnosing (or aiding in the diagnosis of) inflammatory bowel disease, any suitable method may be used to analyze the biological sample in order to determine the level(s) of the one or more biomarkers in the sample.

As with the methods of diagnosing (or aiding in the diagnosis of) inflammatory bowel disease described above, the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, etc., including a combination of all of the biomarkers in Tables 1A, 1B, 1C, 2, 3, 4B, 4D and/or 5B or any fraction thereof, may be determined and used in methods of determining whether a subject having no symptoms of inflammatory bowel disease is predisposed to developing inflammatory bowel disease.

After the level(s) of the one or more biomarkers in the sample are determined, the level(s) are compared to inflammatory bowel disease-positive and/or inflammatory bowel disease-negative reference levels in order to predict whether the subject is predisposed to developing inflammatory bowel disease. Levels of the one or more biomarkers in a sample matching the inflammatory bowel disease-positive reference levels (e.g., levels that are the same as the reference levels, substantially the same as the reference levels, above and/or below the minimum and/or maximum of the reference levels, and/or within the range of the reference levels) are indicative of the subject being predisposed to developing inflammatory bowel disease. Levels of the one or more biomarkers in a sample matching the inflammatory bowel disease-negative reference levels (e.g., levels that are the same as the reference levels, substantially the same as the reference levels, above and/or below the minimum and/or maximum of the reference levels, and/or within the range of the reference levels) are indicative of the subject not being predisposed to developing inflammatory bowel disease. In addition, levels of the one or more biomarkers that are differentially present (especially at a level that is statistically significant) in the sample as compared to inflammatory bowel disease-negative reference levels are indicative of the subject being predisposed to developing inflammatory bowel disease. Levels of the one or more biomarkers that are differentially present (especially at a level that is statistically significant) in the sample as compared to inflammatory bowel disease-positive reference levels are indicative of the subject not being predisposed to developing inflammatory bowel disease.

Furthermore, it may also be possible to determine reference levels specific to assessing whether or not a subject that does not have inflammatory bowel disease is predisposed to developing inflammatory bowel disease. For example, it may be possible to determine reference levels of the biomarkers for assessing different degrees of risk (e.g., low, medium, high) in a subject for developing inflammatory bowel disease. Such reference levels could be used for comparison to the levels of the one or more biomarkers in a biological sample from a subject.

As with the methods described above, the level(s) of the one or more biomarkers may be compared to inflammatory bowel disease-positive and/or inflammatory bowel disease-negative reference levels using various techniques, including a simple comparison, one or more statistical analyses, and combinations thereof.

As with the methods of diagnosing (or aiding in diagnosing) whether a subject has inflammatory bowel disease, the methods of determining whether a subject having no symptoms of inflammatory bowel disease is predisposed to developing inflammatory bowel disease may further comprise analyzing the biological sample to determine the level(s) of one or more non-biomarker compounds.

IV. Methods of Monitoring Progression/Regression of Inflammatory Bowel Disease

The identification of biomarkers for inflammatory bowel disease also allows for monitoring progression/regression of inflammatory bowel disease in a subject. A method of monitoring the progression/regression of inflammatory bowel disease in a subject comprises (1) analyzing a first biological sample from a subject to determine the level(s) of one or more biomarkers for inflammatory bowel disease selected from Tables 1A, 1B, 1C, 2, 3, 4B, 4D and/or 5B, the first sample obtained from the subject at a first time point, (2) analyzing a second biological sample from a subject to determine the level(s) of the one or more biomarkers, the second sample obtained from the subject at a second time point, and (3) comparing the level(s) of one or more biomarkers in the first sample to the level(s) of the one or more biomarkers in the second sample in order to monitor the progression/regression of inflammatory bowel disease in the subject. The results of the method are indicative of the course of inflammatory bowel disease (i.e., progression or regression, if any change) in the subject.

The change (if any) in the level(s) of the one or more biomarkers over time may be indicative of progression or regression of inflammatory bowel disease in the subject. In order to characterize the course of inflammatory bowel disease in the subject, the level(s) of the one or more biomarkers in the first sample, the level(s) of the one or more biomarkers in the second sample, and/or the results of the comparison of the levels of the biomarkers in the first and second samples may be compared to inflammatory bowel disease-positive and/or inflammatory bowel disease-negative reference levels of the one or more biomarkers. If the comparisons indicate that the level(s) of the one or more biomarkers are increasing or decreasing over time (e.g., in the second sample as compared to the first sample) to become more similar to the inflammatory bowel disease-positive reference levels (or less similar to the inflammatory bowel disease-negative reference levels), then the results are indicative of inflammatory bowel disease progression. If the comparisons indicate that the level(s) of the one or more biomarkers are increasing or decreasing over time to become more similar to the inflammatory bowel disease-negative reference levels (or less similar to the inflammatory bowel disease-positive reference levels), then the results are indicative of inflammatory bowel disease regression.

As with the other methods described herein, the comparisons made in the methods of monitoring progression/regression of inflammatory bowel disease in a subject may be carried out using various techniques, including simple comparisons, one or more statistical analyses, and combinations thereof.

The results of the method may be used along with other methods (or the results thereof) useful in the clinical monitoring of progression/regression of inflammatory bowel disease in a subject.

As described above in connection with methods of diagnosing (or aiding in the diagnosis of) inflammatory bowel disease, any suitable method may be used to analyze the biological samples in order to determine the level(s) of the one or more biomarkers in the samples. In addition, the level(s) one or more biomarkers, including a combination of all of the biomarkers in Tables 1A, 1B, 1C, 2, 3, 4B, 4D and/or 5B or any fraction thereof, may be determined and used in methods of monitoring progression/regression of inflammatory bowel disease in a subject.

Such methods could be conducted to monitor the course of inflammatory bowel disease in subjects having inflammatory bowel disease or could be used in subjects not having inflammatory bowel disease (e.g., subjects suspected of being predisposed to developing inflammatory bowel disease) in order to monitor levels of predisposition to inflammatory bowel disease.

V. Methods of Assessing Efficacy of Compositions for Treating Inflammatory Bowel Disease The identification of biomarkers for inflammatory bowel disease also allows for assessment of the efficacy of a composition for treating inflammatory bowel disease as well as the assessment of the relative efficacy of two or more compositions for treating inflammatory bowel disease. Such assessments may be used, for example, in efficacy studies as well as in lead selection of compositions for treating inflammatory bowel disease.

A method of assessing the efficacy of a composition for treating inflammatory bowel disease comprises (1) analyzing, from a subject having inflammatory bowel disease and currently or previously being treated with a composition, a biological sample to determine the level(s) of one or more biomarkers selected from Tables 1A, 1B, 1C, 2, 3, 4B, 4D and/or 5B, and (2) comparing the level(s) of the one or more biomarkers in the sample to (a) level(s) of the one or more biomarkers in a previously-taken biological sample from the subject, wherein the previously-taken biological sample was obtained from the subject before being treated with the composition, (b) inflammatory bowel disease-positive reference levels of the one or more biomarkers, and/or (c) inflammatory bowel disease-negative reference levels of the one or more biomarkers. The results of the comparison are indicative of the efficacy of the composition for treating inflammatory bowel disease.

Thus, in order to characterize the efficacy of the composition for treating inflammatory bowel disease, the level(s) of the one or more biomarkers in the biological sample are compared to (1) inflammatory bowel disease-positive reference levels, (2) inflammatory bowel disease-negative reference levels, and/or (3) previous levels of the one or more biomarkers in the subject before treatment with the composition.

When comparing the level(s) of the one or more biomarkers in the biological sample (from a subject having inflammatory bowel disease and currently or previously being treated with a composition) to inflammatory bowel disease-positive reference levels and/or inflammatory bowel disease-negative reference levels, level(s) in the sample matching the inflammatory bowel disease-negative reference levels (e.g., levels that are the same as the reference levels, substantially the same as the reference levels, above and/or below the minimum and/or maximum of the reference levels, and/or within the range of the reference levels) are indicative of the composition having efficacy for treating inflammatory bowel disease. Levels of the one or more biomarkers in the sample matching the inflammatory bowel disease-positive reference levels (e.g., levels that are the same as the reference levels, substantially the same as the reference levels, above and/or below the minimum and/or maximum of the reference levels, and/or within the range of the reference levels) are indicative of the composition not having efficacy for treating inflammatory bowel disease. The comparisons may also indicate degrees of efficacy for treating inflammatory bowel disease based on the level(s) of the one or more biomarkers.

When the level(s) of the one or more biomarkers in the biological sample (from a subject having inflammatory bowel disease and currently or previously being treated with a composition) are compared to level(s) of the one or more biomarkers in a previously-taken biological sample from the subject before treatment with the composition, any changes in the level(s) of the one or more biomarkers are indicative of the efficacy of the composition for treating inflammatory bowel disease. That is, if the comparisons indicate that the level(s) of the one or more biomarkers have increased or decreased after treatment with the composition to become more similar to the inflammatory bowel disease-negative reference levels (or less similar to the inflammatory bowel disease-positive reference levels), then the results are indicative of the composition having efficacy for treating inflammatory bowel disease. If the comparisons indicate that the level(s) of the one or more biomarkers have not increased or decreased after treatment with the composition to become more similar to the inflammatory bowel disease-negative reference levels (or less similar to the inflammatory bowel disease-positive reference levels), then the results are indicative of the composition not having efficacy for treating inflammatory bowel disease. The comparisons may also indicate degrees of efficacy for treating inflammatory bowel disease based on the amount of changes observed in the level(s) of the one or more biomarkers after treatment. In order to help characterize such a comparison, the changes in the level(s) of the one or more biomarkers, the level(s) of the one or more biomarkers before treatment, and/or the level(s) of the one or more biomarkers in the subject currently or previously being treated with the composition may be compared to inflammatory bowel disease-positive and/or inflammatory bowel disease-negative reference levels of the one or more biomarkers.

Another method for assessing the efficacy of a composition in treating inflammatory bowel disease comprises (1) analyzing a first biological sample from a subject to determine the level(s) of one or more biomarkers selected from Tables 1, 2, and/or 3, the first sample obtained from the subject at a first time point, (2) administering the composition to the subject, (3) analyzing a second biological sample from a subject to determine the level(s) of the one or more biomarkers, the second sample obtained from the subject at a second time point after administration of the composition, and (4) comparing the level(s) of one or more biomarkers in the first sample to the level(s) of the one or more biomarkers in the second sample in order to assess the efficacy of the composition for treating inflammatory bowel disease. As indicated above, if the comparison of the samples indicates that the level(s) of the one or more biomarkers have increased or decreased after administration of the composition to become more similar to the inflammatory bowel disease-negative reference levels (or less similar to the inflammatory bowel disease-positive reference levels), then the results are indicative of the composition having efficacy for treating inflammatory bowel disease. If the comparison indicates that the level(s) of the one or more biomarkers have not increased or decreased after administration of the composition to become more similar to the inflammatory bowel disease-negative reference levels (or less similar to the inflammatory bowel disease-positive reference levels), then the results are indicative of the composition not having efficacy for treating inflammatory bowel disease. The comparison may also indicate a degree of efficacy for treating inflammatory bowel disease based on the amount of changes observed in the level(s) of the one or more biomarkers after administration of the composition. In order to help characterize such a comparison, the changes in the level(s) of the one or more biomarkers, the level(s) of the one or more biomarkers before administration of the composition, and/or the level(s) of the one or more biomarkers after administration of the composition may be compared to inflammatory bowel disease-positive and/or inflammatory bowel disease-negative reference levels of the one or more biomarkers of the two compositions.

A method of assessing the relative efficacy of two or more compositions for treating inflammatory bowel disease comprises (1) analyzing, from a first subject having inflammatory bowel disease and currently or previously being treated with a first composition, a first biological sample to determine the level(s) of one or more biomarkers selected from Tables 1A, 1B, 1C, 2, 3, 4B, 4D and/or 5B (2) analyzing, from a second subject having inflammatory bowel disease and currently or previously being treated with a second composition, a second biological sample to determine the level(s) of the one or more biomarkers, and (3) comparing the level(s) of one or more biomarkers in the first sample to the level(s) of the one or more biomarkers in the second sample in order to assess the relative efficacy of the first and second compositions for treating inflammatory bowel disease. The results are indicative of the relative efficacy of the two compositions, and the results (or the levels of the one or more biomarkers in the first sample and/or the level(s) of the one or more biomarkers in the second sample) may be compared to inflammatory bowel disease-positive or inflammatory bowel disease-negative reference levels to aid in characterizing the relative efficacy.

Each of the methods of assessing efficacy may be conducted on one or more subjects or one or more groups of subjects (e.g., a first group being treated with a first composition and a second group being treated with a second composition).

As with the other methods described herein, the comparisons made in the methods of assessing efficacy (or relative efficacy) of compositions for treating inflammatory bowel disease may be carried out using various techniques, including simple comparisons, one or more statistical analyses, and combinations thereof. Any suitable method may be used to analyze the biological samples in order to determine the level(s) of the one or more biomarkers in the samples. In addition, the level(s) of one or more biomarkers, including a combination of all of the biomarkers in Tables 1A, 1B, 1C, 2, 3, 4B, 4D and/or 5B or any fraction thereof, may be determined and used in methods of assessing efficacy (or relative efficacy) of compositions for treating inflammatory bowel disease.

Finally, the methods of assessing efficacy (or relative efficacy) of one or more compositions for treating inflammatory bowel disease may further comprise analyzing the biological sample to determine the level(s) of one or more non-biomarker compounds. The non-biomarker compounds may then be compared to reference levels of non-biomarker compounds for subjects having (or not having) inflammatory bowel disease.

VI. Methods of Screening a Composition for Activity in Modulating Biomarkers Associated with Inflammatory Bowel Disease The identification of biomarkers for inflammatory bowel disease also allows for the screening of compositions for activity in modulating biomarkers associated with inflammatory bowel disease, which may be useful in treating inflammatory bowel disease. Methods of screening compositions useful for treatment of inflammatory bowel disease comprise assaying test compositions for activity in modulating the levels of one or more biomarkers in Tables 1, 2, 3, 4B, 4D, and/or 5B. Such screening assays may be conducted in vitro and/or in vivo, and may be in any form known in the art useful for assaying modulation of such biomarkers in the presence of a test composition such as, for example, cell culture assays, organ culture assays, and in vivo assays (e.g., assays involving animal models).

In one embodiment, a method for screening a composition for activity in modulating one or more biomarkers of inflammatory bowel disease comprises (1) contacting one or more cells with a composition, (2) analyzing at least a portion of the one or more cells or a biological sample associated with the cells to determine the level(s) of one or more biomarkers of inflammatory bowel disease selected from Tables 1A, 1B, 1C, 2, 3, 4B, 4D and/or 5B; and (3) comparing the level(s) of the one or more biomarkers with predetermined standard levels for the one or more biomarkers to determine whether the composition modulated the level(s) of the one or more biomarkers. As discussed above, the cells may be contacted with the composition in vitro and/or in vivo. The predetermined standard levels for the one or more biomarkers may be the levels of the one or more biomarkers in the one or more cells in the absence of the composition. The predetermined standard levels for the one or more biomarkers may also be the level(s) of the one or more biomarkers in control cells not contacted with the composition.

In addition, the methods may further comprise analyzing at least a portion of the one or more cells or a biological sample associated with the cells to determine the level(s) of one or more non-biomarker compounds of inflammatory bowel disease. The levels of the non-biomarker compounds may then be compared to predetermined standard levels of the one or more non-biomarker compounds.

Any suitable method may be used to analyze at least a portion of the one or more cells or a biological sample associated with the cells in order to determine the level(s) of the one or more biomarkers (or levels of non-biomarker compounds). Suitable methods include chromatography (e.g., HPLC, gas chromatograph, liquid chromatography), mass spectrometry (e.g., MS, MS-MS), ELISA, antibody linkage, other immunochemical techniques, and combinations thereof. Further, the level(s) of the one or more biomarkers (or levels of non-biomarker compounds) may be measured indirectly, for example, by using an assay that measures the level of a compound (or compounds) that correlates with the level of the biomarker(s) (or non-biomarker compounds) that are desired to be measured.

VII. Method of Identifying Potential Drug Targets

The identification of biomarkers for inflammatory bowel disease also allows for the identification of potential drug targets for inflammatory bowel disease. A method for identifying a potential drug target for inflammatory bowel disease comprises (1) identifying one or more biochemical pathways associated with one or more biomarkers for inflammatory bowel disease selected from Tables 1A, 1B, 1C, 2, 3, 4B, 4D and/or 5B and (2) identifying a protein (e.g., an enzyme) affecting at least one of the one or more identified biochemical pathways, the protein being a potential drug target for inflammatory bowel disease.

Another method for identifying a potential drug target for inflammatory bowel disease comprises (1) identifying one or more biochemical pathways associated with one or more biomarkers for inflammatory bowel disease selected from Tables 1A, 1B, 1C, 2, 3, 4B, 4D and/or 5B and one or more non-biomarker compounds of inflammatory bowel disease and (2) identifying a protein affecting at least one of the one or more identified biochemical pathways, the protein being a potential drug target for inflammatory bowel disease.

One or more biochemical pathways (e.g., biosynthetic and/or metabolic (catabolic) pathway) are identified that are associated with one or more biomarkers (or non-biomarker compounds). After the biochemical pathways are identified, one or more proteins affecting at least one of the pathways are identified. Preferably, those proteins affecting more than one of the pathways are identified.

A build-up of one metabolite (e.g., a pathway intermediate) may indicate the presence of a 'block' downstream of the metabolite and the block may result in a low/absent level of a downstream metabolite (e.g. product of a biosynthetic pathway). In a similar manner, the absence of a metabolite could indicate the presence of a 'block' in the pathway upstream of the metabolite resulting from inactive or non-functional enzyme(s) or from unavailability of biochemical intermediates that are required substrates to produce the product. Alternatively, an increase in the level of a metabolite could indicate a genetic mutation that produces an aberrant protein which results in the over-production and/or accumulation of a metabolite which then leads to an alteration of other related biochemical pathways and result in dysregulation of the normal flux through the pathway; further, the build-up of the biochemical intermediate metabolite may be toxic or may compromise the production of a necessary intermediate for a related pathway. It is possible that the relationship between pathways is currently unknown and this data could reveal such a relationship.

For example, several bile acids were differentially present in CD patients compared to the UC patients. Non-conjugated bile acids are increased in CD relative to UC and conjugated bile acids are decreased in UC relative to CD. These observations suggest that inflammatory bowel disease may be associated with alterations in the gut bacteria, mechanisms of re-absorption or differential liver interactions. The pathways leading to the production of any decreased biomarker would provide a number of potential targets for drug discovery.

The proteins identified as potential drug targets may then be used to identify compositions that may be potential candidates for treating inflammatory bowel disease, including compositions for gene therapy.

VIII. Methods of Treating Inflammatory Bowel Disease

The identification of biomarkers for inflammatory bowel disease also allows for the treatment of inflammatory bowel disease. For example, in order to treat a subject having inflammatory bowel disease, an effective amount of one or more inflammatory bowel disease biomarkers that are lowered in inflammatory bowel disease as compared to a healthy subject not having inflammatory bowel disease may be administered to the subject. The biomarkers that may be administered may comprise one or more of the biomarkers in Tables 1A, 1B, 1C, 2, 3, 4B, 4D and/or 5B that are decreased in inflammatory bowel disease. In some embodiments, the biomarkers that are administered are one or more biomarkers listed in Tables 1A, 1B, 1C, 2, 3, 4B, 4D and/or 5B that are decreased in inflammatory bowel disease and that have a p-value less than 0.10. In other embodiments, the biomarkers that are administered are one or biomarkers listed in Tables 1A, 1B, 1C, 2, 3, 4B, 4D and/or 5B that are decreased in inflammatory bowel disease by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent).

IX. Methods of Using the Inflammatory Bowel Disease Biomarkers for Inflammatory Bowel Disease Subtypes It is believed that some of the biomarkers for inflammatory bowel disease described herein may also be biomarkers for various subtypes of inflammatory bowel disease, including, for example, Crohn's Disease and Ulcerative Colitis which can be distinguished using the biomarkers described in Tables 1A, 1B, 1C, and 4B. Therefore, it is believed that at least some of the IBD biomarkers may be used in the methods described herein for subtypes of IBD. That is, the methods described herein with respect to inflammatory bowel disease may also be used for diagnosing (or aiding in the diagnosis of) any subtype of inflammatory bowel disease, methods of monitoring progression/regression of any subtype of inflammatory bowel disease, methods of assessing efficacy of compositions for treating any subtype of inflammatory bowel disease, methods of screening a composition for activity in modulating biomarkers associated with any subtype of inflammatory bowel disease, methods of identifying potential drug targets for any subtype of inflammatory bowel disease, and methods of treating any subtype of inflammatory bowel disease. Such methods could be conducted as described herein with respect to inflammatory bowel disease. For example, Crohn's disease symptoms and complications differ according to the location of the inflammation in the intestinal track. Common forms of Crohn's disease include, for example, ileocolitis, ileitis, gastroduodenal CD, jejunoileitis and granulomatous colitis. Ulcerative colitis subtypes include, for example, left-sided UC, and pancolitis UC.

X. Methods of Using the Inflammatory Bowel Disease Biomarkers to Distinguish Active from Inactive Inflammatory Bowel Disease and Subtypes It is believed that some of the biomarkers for inflammatory bowel disease described herein may also be biomarkers for distinguishing active from inactive subtypes of inflammatory bowel disease, including, for example, inactive Crohn's disease from inactive Ulcerative colitis, active Crohn's disease from active Ulcerative colitis, inactive from inactive Crohn's Disease and active from inactive Ulcerative Colitis which can be distinguished using the biomarkers described in Tables 1B, 1C, 4D, and 5B respectively. Therefore, it is believed that at least some of the IBD biomarkers may be used in the methods described herein for active and inactive forms of IBD. That is, the methods described herein with respect to inflammatory bowel disease may also be used for diagnosing (or aiding in the diagnosis of) inflammatory bowel disease that is active or in remission (inactive).

XI. Methods of Using the Inflammatory Bowel Disease Biomarkers for Other IBD Disorders It is believed that some of the biomarkers for inflammatory bowel disease described herein may also be biomarkers for inflammatory bowel disorders in general. Therefore, it is believed that at least some of the inflammatory bowel disease biomarkers may be used in the methods described herein for inflammatory bowel disorders in general. That is, the methods described herein with respect to inflammatory bowel disease may also be used for diagnosing (or aiding in the diagnosis of) an inflammatory bowel disorder, methods of monitoring progression/regression of an inflammatory bowel disorder, methods of assessing efficacy of compositions for treating an inflammatory bowel disorder, methods of screening a composition for activity in modulating biomarkers associated with an inflammatory bowel disorder, methods of identifying potential drug targets for inflammatory bowel disorder, and methods of treating a inflammatory bowel disorder. Such methods could be conducted as described herein with respect to inflammatory bowel disease.

XII. Other Methods

Other methods of using the biomarkers discussed herein are also contemplated. For example, the methods described in U.S. Pat. No. 7,005,255 and U.S. Pat. No. 7,329,489 may be conducted using a small molecule profile comprising one or more of the biomarkers disclosed herein and/or one or more of the non-biomarker compounds disclosed herein.

In any of the methods listed herein, the biomarkers that are used may be selected from those biomarkers in Tables 1A, 1B, 1C, 2, 3, 4B, 4D and/or 5B having p-values of less than 0.05 and/or q-values of less than 0.10. The biomarkers that are used in any of the methods described herein may also be selected from those biomarkers in Tables 1A, 1B, 1C, 2, 3, 4B, 4D and/or 5B that are decreased in inflammatory bowel disease (as compared to the control or remission) or that are decreased in remission (as compared to control or inflammatory bowel disease) by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent); and/or those biomarkers in Tables 1A, 1B, 1C, 2, 3, 4B, 4D and/or 5B that are increased in inflammatory bowel disease (as compared to the control or remission) or that are increased in remission (as compared to the control or inflammatory bowel disease) by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more.

EXAMPLES

The invention will be further explained by the following illustrative examples that are intended to be non-limiting.

General Methods

A. Identification of Metabolic Profiles for Inflammatory Bowel Disease

Each sample was analyzed to determine the concentration of several hundred metabolites. Analytical techniques such as GC-MS (gas chromatography-mass spectrometry) and LC-MS (liquid chromatography-mass spectrometry) were used to analyze the metabolites. Multiple aliquots were simultaneously, and in parallel, analyzed, and, after appropriate quality control (QC), the information derived from each analysis was recombined. Every sample was characterized according to several thousand characteristics, which ultimately amount to several hundred chemical species. The techniques used were able to identify both known metabolites and unnamed metabolites that are currently in our chemical library as well as novel, chemically unnamed compounds that are added to the library.

B. Statistical Analysis

The data were analyzed using T-tests to identify molecules (either known, named metabolites or unnamed metabolites) present at differential levels in a definable population or subpopulation (e.g., biomarkers for inflammatory bowel disease biological samples compared to control biological samples or compared to patients in remission from inflammatory bowel disease) useful for distinguishing between the definable populations (e.g., inflammatory bowel disease and control, inflammatory bowel disease and remission, remission and control). Other molecules (either known, named metabolites or unnamed metabolites) in the definable population or subpopulation were also identified.

C. Biomarker Identification

Various peaks identified in the analyses (e.g. GC-MS, LC-MS, MS-MS), including those identified as statistically significant, were subjected to a mass spectrometry based chemical identification process.

Example 1

Biomarker Metabolites for Crohn's Disease and Ulcerative Colitis

Biomarkers were discovered by (1) analyzing blood samples drawn from different groups of human subjects to determine the levels of metabolites in the samples and then (2) statistically analyzing the results to determine those metabolites that were differentially present in the two groups (i.e., Crohn's disease vs. Ulcerative colitis, active Crohn's disease vs. active Ulcerative Colitis, inactive Crohn's disease vs. inactive Ulcerative colitis).

T-tests were used to determine differences in the mean levels of metabolites between the two populations (i.e., Crohn's disease vs. Ulcerative colitis, active Crohn's disease vs. active Ulcerative Colitis, inactive Crohn's disease vs. inactive Ulcerative colitis). Random Forest analysis was performed to identify the metabolites that are most important to distinguish the two groups of subjects and thereby useful to identify a subject as having Crohn's disease or as having ulcerative colitis.

In a first experiment the blood samples used for the analysis were from subjects with Crohn's disease (N=101) and subjects with ulcerative colitis (N=73). In a second experiment the blood samples used for the analysis were from subjects with active Crohn's disease (N=50) and subjects with active ulcerative colitis (N=36). In a third experiment the blood samples used for the analysis were from subjects with inactive Crohn's disease (N=51) and subjects with inactive ulcerative colitis (N=37). After the levels of metabolites were determined, the data was analyzed using univariate T-tests (i.e., Welch's T-test).

Biomarkers

As listed below in Table 1 (including Tables 1A, 1B, and 1C), biomarkers were discovered that were differentially present between samples from Crohn's disease subjects and ulcerative colitis subjects, including patients in whom the disease was considered to be inactive (i.e., in remission) and patients with active disease. These biomarkers are listed in Table 1A. Table 1B lists biomarkers that were discovered that were differentially present between samples from subjects with Crohn's disease that is active and subjects with active Ulcerative colitis. Table 1C lists biomarkers that were discovered that were differentially present between samples from Crohn's disease subjects and Ulcerative colitis subjects in whom the diseases were determined to be inactive, (e.g., in remission from inflammatory bowel disease).

Table 1 includes, for each listed biomarker, the p-value and the q-value determined in the statistical analysis of the data concerning the biomarkers and the ratio between the mean in the Crohn's disease as compared to the ulcerative colitis mean. Library indicates the chemical library that was used to identify the compounds. The number 50 refers to the GC library and the numbers 200 and 201 refer to the LC library. "Comp ID" refers to the internal chemical database identification number for that compound.

TABLE 1

Biomarkers to Distinguish Crohn's Disease From Ulcerative Colitis

Table 1A. Biomarkers to Distinguish Crohn's Disease from Ulcerative Colitis, All (active & inactive)

| Comp ID | Library | Biomarker | CD All/ UC All | p-value | q-value |
|---|---|---|---|---|---|
| 36776 | 201 | 7-alpha-hydroxy-3-oxo-4-cholestenoate (7-HOCA) | 1.89 | 0.0000 | 0.0000 |
| 27531 | 201 | hyodeoxycholate | 6.32 | 0.0000 | 0.0000 |
| 33488 | 50 | lathosterol | 2.07 | 0.0000 | 0.0002 |
| 15753 | 200 | hippurate | 0.45 | 0.0000 | 0.0009 |
| 12261 | 201 | taurodeoxycholate | 0.47 | 0.0000 | 0.0012 |
| 33846 | 200 | indoleacetate | 1.63 | 0.0000 | 0.0017 |
| 33682 | 201 | Metabolite - 12260 | 0.34 | 0.0000 | 0.0018 |
| 18477 | 201 | glycodeoxycholate | 0.55 | 0.0000 | 0.0016 |
| 553 | 200 | cotinine | 2.14 | 0.0001 | 0.0024 |
| 32561 | 201 | Metabolite - 11244 | 1.54 | 0.0001 | 0.0028 |
| 32792 | 201 | Metabolite - 11475 | 1.58 | 0.0001 | 0.0028 |
| 32827 | 201 | Metabolite - 11510 | 1.62 | 0.0001 | 0.0026 |
| 33415 | 201 | Metabolite - 12063 | 1.91 | 0.0001 | 0.0024 |
| 33576 | 200 | Metabolite - 12159 | 0.40 | 0.0001 | 0.0034 |
| 33901 | 201 | Metabolite - 12456 | 1.46 | 0.0001 | 0.0028 |
| 36807 | 201 | 6-beta-hydroxylithocholate | 4.18 | 0.0002 | 0.0037 |
| 1670 | 50 | urea | 0.80 | 0.0003 | 0.0050 |
| 25459 | 50 | Metabolite - 10395 | 0.81 | 0.0003 | 0.0050 |
| 32620 | 201 | Metabolite - 11303 | 0.57 | 0.0003 | 0.0050 |
| 32757 | 201 | Metabolite - 11440 | 1.44 | 0.0004 | 0.0063 |
| 35688 | 201 | 2-palmitoylglycerophosphoethanolamine | 1.32 | 0.0004 | 0.0064 |
| 63 | 50 | cholesterol | 0.89 | 0.0006 | 0.0088 |
| 21011 | 50 | Metabolite - 07888 | 0.88 | 0.0007 | 0.0099 |
| 27278 | 50 | Metabolite - 10510 | 0.86 | 0.0008 | 0.0109 |
| 32808 | 201 | Metabolite - 11491 | 1.53 | 0.0008 | 0.0106 |
| 18929 | 50 | Metabolite - 05907 | 0.82 | 0.0009 | 0.0109 |
| 16866 | 50 | Metabolite - 04523 | 0.83 | 0.0010 | 0.0127 |
| 36850 | 201 | taurolithocholate 3-sulfate | 0.62 | 0.0012 | 0.0146 |
| 32558 | 201 | p-cresol sulfate | 0.83 | 0.0017 | 0.0191 |
| 27256 | 50 | Metabolite - 10500 | 0.90 | 0.0017 | 0.0191 |
| 32562 | 201 | Metabolite - 11245 | 1.31 | 0.0020 | 0.0212 |
| 32405 | 50 | 3-indolepropionate | 0.70 | 0.0023 | 0.0240 |
| 1563 | 201 | chenodeoxycholate | 1.30 | 0.0024 | 0.0241 |
| 32767 | 201 | Metabolite - 11450 | 1.29 | 0.0027 | 0.0266 |
| 31908 | 201 | 7-ketolithocholate | 2.48 | 0.0032 | 0.0275 |
| 11438 | 50 | phosphate | 0.92 | 0.0040 | 0.0375 |
| 15743 | 200 | dimethylarginine | 0.89 | 0.0044 | 0.0396 |
| 35832 | 50 | ornithine | 0.86 | 0.0049 | 0.0412 |
| 31522 | 200 | pyroglutamylglycine | 1.35 | 0.0050 | 0.0412 |
| 20675 | 201 | 1,5-anhydroglucitol (1,5-AG) | 0.90 | 0.0074 | 0.0599 |
| 32489 | 201 | caproate (6:0) | 1.10 | 0.0076 | 0.0601 |
| 18494 | 201 | taurochenodeoxycholate | 0.71 | 0.0086 | 0.0590 |
| 15749 | 201 | 3-phenylpropionate (hydrocinnamate) | 0.83 | 0.0087 | 0.0673 |
| 15990 | 200 | glycerophosphorylcholine (GPC) | 1.15 | 0.0105 | 0.0791 |
| 1644 | 201 | heptanoate (7:0) | 1.09 | 0.0115 | 0.0819 |
| 34368 | 200 | Metabolite - 12758 | 0.80 | 0.0116 | 0.0819 |
| 32425 | 201 | dehydroisoandrosterone sulfate (DHEA-S) | 1.31 | 0.0131 | 0.0887 |
| 34359 | 200 | Metabolite - 12749 | 0.91 | 0.0131 | 0.0887 |
| 33178 | 201 | Metabolite - 11833 | 0.48 | 0.0136 | 0.0900 |
| 32398 | 201 | sebacate | 1.38 | 0.0187 | 0.1189 |
| 33477 | 50 | erythronate | 0.90 | 0.0189 | 0.1189 |
| 33801 | 200 | ADpSGEGDFXAEGGGVR | 0.79 | 0.0190 | 0.1189 |
| 15778 | 201 | benzoate | 1.10 | 0.0203 | 0.1246 |
| 18357 | 200 | glycylvaline | 2.21 | 0.0213 | 0.1265 |
| 15335 | 50 | mannitol | 0.74 | 0.0213 | 0.1265 |
| 33221 | 201 | Metabolite - 11876 | 0.59 | 0.0220 | 0.1280 |

TABLE 1-continued

Biomarkers to Distinguish Crohn's Disease From Ulcerative Colitis

| | | | | | |
|---|---|---|---|---|---|
| 12035 | 201 | pelargonate (9:0) | 1.05 | 0.0228 | 0.1306 |
| 15630 | 200 | N-acetylornithine | 0.87 | 0.0241 | 0.1359 |
| 18497 | 201 | taurocholate | 0.85 | 0.0249 | 0.1380 |
| 19362 | 50 | Metabolite - 06226 | 0.92 | 0.0261 | 0.1422 |
| 1114 | 201 | deoxycholate | 1.21 | 0.0265 | 0.1292 |
| 22154 | 200 | bradykinin | 1.19 | 0.0272 | 0.1439 |
| 31787 | 201 | 3-carboxy-4-methyl-5-propyl-2-furanpropanoate (CMPF) | 1.22 | 0.0273 | 0.1439 |
| 32590 | 201 | Metabolite - 11273 | 1.33 | 0.0281 | 0.1454 |
| 25599 | 50 | Metabolite - 10429 | 0.84 | 0.0291 | 0.1454 |
| 32616 | 201 | Metabolite - 11299 | 0.59 | 0.0291 | 0.1454 |
| 15730 | 201 | suberate | 1.20 | 0.0293 | 0.1454 |
| 34366 | 200 | Metabolite - 12756 | 0.70 | 0.0315 | 0.1456 |
| 1303 | 50 | malate | 0.83 | 0.0317 | 0.1456 |
| 32709 | 200 | Metabolite - 03056 | 0.88 | 0.0317 | 0.1456 |
| 18281 | 201 | 2-hydroxyhippurate (salicylurate) | 0.11 | 0.0318 | 0.1456 |
| 15488 | 50 | acetylphosphate | 0.94 | 0.0320 | 0.1456 |
| 18476 | 200 | glycocholate | 0.78 | 0.0325 | 0.1456 |
| 34384 | 200 | stachydrine | 0.76 | 0.0327 | 0.1456 |
| 32877 | 201 | Metabolite - 11560 | 1.21 | 0.0333 | 0.1456 |
| 33165 | 200 | Metabolite - 11820 | 0.80 | 0.0344 | 0.1485 |
| 19576 | 50 | Metabolite - 06627 | 1.26 | 0.0370 | 0.1540 |
| 1361 | 201 | pentadecanoate (15:0) | 0.90 | 0.0371 | 0.1540 |
| 3147 | 201 | xanthine | 1.10 | 0.0385 | 0.1558 |
| 12774 | 50 | Metabolite - 03094 | 1.10 | 0.0397 | 0.1584 |
| 16823 | 50 | Metabolite - 04500 | 0.71 | 0.0401 | 0.1584 |
| 34244 | 201 | Metabolite - 12644 | 1.13 | 0.0408 | 0.1594 |
| 30282 | 50 | Metabolite - 10744 | 0.87 | 0.0465 | 0.1797 |
| 12129 | 201 | beta-hydroxyisovalerate | 1.13 | 0.0472 | 0.1803 |
| 33420 | 50 | gamma-tocopherol | 1.20 | 0.0489 | 0.1844 |
| 32735 | 200 | Metabolite - 01911 | 1.32 | 0.0517 | 0.1928 |
| 1110 | 201 | arachidonate (20:4(n-6)) | 1.08 | 0.0551 | 0.2015 |
| 2342 | 200 | serotonin (5HT) | 1.19 | 0.0554 | 0.2015 |
| 33173 | 201 | Metabolite - 11828 | 0.51 | 0.0558 | 0.2015 |
| 35153 | 200 | 1-docosahexaenoylglycerol (1-monodocosahexaenoin) | 0.87 | 0.0580 | 0.2073 |
| 3127 | 200 | hypoxanthine | 1.12 | 0.0625 | 0.2189 |
| 33353 | 201 | Metabolite - 12007 | 0.80 | 0.0626 | 0.2189 |
| 1564 | 50 | citrate | 0.91 | 0.0639 | 0.2192 |
| 33188 | 201 | Metabolite - 11843 | 0.53 | 0.0650 | 0.2192 |
| 32557 | 201 | Metabolite - 06126 | 1.09 | 0.0653 | 0.2192 |
| 18362 | 201 | azelate (nonanedioate) | 1.35 | 0.0654 | 0.2192 |
| 33195 | 201 | Metabolite - 11850 | 0.41 | 0.0690 | 0.2252 |
| 1572 | 50 | glycerate | 0.88 | 0.0692 | 0.2252 |
| 18467 | 201 | eicosapentaenoate (EPA; 20:5(n-3)) | 1.12 | 0.0728 | 0.2349 |
| 33509 | 200 | Metabolite - 12094 | 0.85 | 0.0741 | 0.2363 |
| 34214 | 201 | Metabolite - 12620 | 1.07 | 0.0747 | 0.2363 |
| 1769 | 200 | cortisone | 0.75 | 0.0760 | 0.2367 |
| 32740 | 201 | Metabolite - 11423 | 0.92 | 0.0763 | 0.2367 |
| 33773 | 200 | Metabolite - 12348 | 1.05 | 0.0783 | 0.2408 |
| 19934 | 50 | myo-inositol | 0.93 | 0.0847 | 0.2574 |
| 32807 | 201 | Metabolite - 11490 | 1.04 | 0.0865 | 0.2574 |
| 21630 | 50 | Metabolite - 08402 | 0.91 | 0.0868 | 0.2574 |
| 33423 | 201 | p-acetamidophenylglucuronide | 0.49 | 0.0882 | 0.2593 |
| 19414 | 50 | Metabolite - 06350 | 1.10 | 0.0915 | 0.2665 |
| 27718 | 200 | creatine | 1.11 | 0.0923 | 0.2667 |
| 27279 | 50 | Metabolite - 10511 | 0.89 | 0.0937 | 0.2682 |
| 32793 | 200 | Metabolite - 11476 | 1.03 | 0.0960 | 0.2726 |
| 599 | 50 | pyruvate | 0.91 | 0.0991 | 0.2790 |
| 22842 | 201 | cholate | 1.14 | 0.1008 | 0.2638 |
| 21631 | 50 | Metabolite - 08403 | 0.85 | 0.1010 | 0.2818 |
| 32388 | 201 | dodecanedioate | 1.24 | 0.1023 | 0.2830 |
| 32689 | 201 | Metabolite - 11372 | 1.10 | 0.1031 | 0.2830 |
| 59 | 201 | histidine | 1.06 | 0.1047 | 0.2841 |
| 34365 | 200 | Metabolite - 12755 | 0.64 | 0.1054 | 0.2841 |
| 19323 | 201 | docosahexaenoate (DHA; 22:6(n-3)) | 1.08 | 0.1066 | 0.2841 |
| 19396 | 50 | Metabolite - 06307 | 0.86 | 0.1069 | 0.2841 |
| 33073 | 200 | cysteine-glutathione disulfide | 0.92 | 0.1086 | 0.2849 |
| 27738 | 50 | threonate | 0.85 | 0.1089 | 0.2849 |
| 1592 | 50 | N-acetylneuraminate | 0.92 | 0.1114 | 0.2878 |
| 32815 | 201 | Metabolite - 11498 | 1.12 | 0.1126 | 0.2878 |
| 32760 | 201 | Metabolite - 11443 | 1.34 | 0.1127 | 0.2878 |
| 584 | 50 | mannose | 0.87 | 0.1164 | 0.2950 |
| 32762 | 201 | Metabolite - 11445 | 4.64 | 0.1174 | 0.2954 |
| 32836 | 200 | HWESASXX | 0.65 | 0.1212 | 0.3026 |
| 31555 | 201 | pyridoxate | 1.01 | 0.1279 | 0.3158 |
| 1659 | 50 | dehydroascorbate | 0.86 | 0.1284 | 0.3158 |
| 18446 | 50 | Metabolite - 05524 | 0.89 | 0.1315 | 0.3191 |

TABLE 1-continued

Biomarkers to Distinguish Crohn's Disease From Ulcerative Colitis

| | | | | | |
|---|---|---|---|---|---|
| 33937 | 201 | alpha-hydroxyisovalerate | 1.27 | 0.1316 | 0.3191 |
| 32769 | 201 | Metabolite - 11452 | 1.32 | 0.1352 | 0.3247 |
| 33939 | 200 | N-acetylthreonine | 1.04 | 0.1359 | 0.3247 |
| 32619 | 201 | Metabolite - 11302 | 1.24 | 0.1436 | 0.3406 |
| 34420 | 200 | (des-arg9) Bradykinin | 0.64 | 0.1521 | 0.3556 |
| 32867 | 201 | Metabolite - 11550 | 1.03 | 0.1524 | 0.3556 |
| 1494 | 200 | pyroglutamate (5-oxoproline) | 1.05 | 0.1541 | 0.3556 |
| 33852 | 200 | 1-myristoylglycerophosphocholine | 1.17 | 0.1542 | 0.3556 |
| 15365 | 50 | glycerol 3-phosphate (G3P) | 1.07 | 0.1597 | 0.3624 |
| 32830 | 200 | Metabolite - 11513 | 0.82 | 0.1604 | 0.3624 |
| 34314 | 201 | Metabolite - 12704 | 0.94 | 0.1604 | 0.3624 |
| 2132 | 200 | citrulline | 0.93 | 0.1640 | 0.3660 |
| 32553 | 201 | phenol sulfate | 1.52 | 0.1643 | 0.3660 |
| 20489 | 50 | glucose | 0.92 | 0.1653 | 0.3660 |
| 32644 | 200 | Metabolite - 11327 | 1.05 | 0.1673 | 0.3678 |
| 32675 | 200 | Metabolite - 03951 | 0.95 | 0.1683 | 0.3678 |
| 33510 | 200 | Metabolite - 12095 | 0.90 | 0.1721 | 0.3735 |
| 33961 | 200 | 1-stearoylglycerophosphocholine | 0.91 | 0.1753 | 0.3781 |
| 32458 | 200 | oleamide | 0.80 | 0.1779 | 0.3788 |
| 25607 | 50 | Metabolite - 10437 | 0.88 | 0.1779 | 0.3788 |
| 33389 | 201 | Metabolite - 12038 | 1.06 | 0.1813 | 0.3836 |
| 30805 | 50 | Metabolite - 10810 | 0.86 | 0.1868 | 0.3861 |
| 12067 | 201 | undecanoate (11:0) | 1.04 | 0.1871 | 0.3861 |
| 33935 | 200 | piperine | 1.39 | 0.1875 | 0.3861 |
| 32572 | 200 | Metabolite - 11255 | 0.93 | 0.1880 | 0.3861 |
| 33183 | 201 | Metabolite - 11838 | 0.96 | 0.1883 | 0.3861 |
| 1125 | 200 | isoleucine | 0.96 | 0.1916 | 0.3904 |
| 16666 | 50 | Metabolite - 04365 | 0.90 | 0.1941 | 0.3909 |
| 34201 | 201 | 1-stearoylglycerophosphoinositol | 1.07 | 0.1972 | 0.3924 |
| 31453 | 50 | cysteine | 0.88 | 0.1973 | 0.3924 |
| 32578 | 200 | Metabolite - 11261 | 0.85 | 0.2002 | 0.3957 |
| 33228 | 200 | Metabolite - 11883 | 0.91 | 0.2019 | 0.3959 |
| 15506 | 200 | choline | 1.04 | 0.2036 | 0.3959 |
| 32857 | 200 | Metabolite - 11540 | 1.09 | 0.2041 | 0.3959 |
| 22130 | 201 | phenyllactate (PLA) | 0.94 | 0.2050 | 0.3959 |
| 31534 | 200 | HXGXA | 0.43 | 0.2075 | 0.3984 |
| 33412 | 201 | Metabolite - 12060 | 0.94 | 0.2094 | 0.3996 |
| 32978 | 200 | Metabolite - 11656 | 1.01 | 0.2130 | 0.4042 |
| 1336 | 201 | palmitate (16:0) | 1.07 | 0.2183 | 0.4119 |
| 22649 | 50 | Metabolite - 09108 | 0.94 | 0.2223 | 0.4161 |
| 33955 | 200 | 1-palmitoylglycerophosphocholine | 1.06 | 0.2250 | 0.4161 |
| 37016 | 50 | arginine | 0.96 | 0.2254 | 0.4161 |
| 32795 | 201 | Metabolite - 11478 | 0.84 | 0.2264 | 0.4161 |
| 32501 | 201 | dihomo-alpha-linolenate (20:3(n-3)) | 1.03 | 0.2268 | 0.4161 |
| 22548 | 50 | Metabolite - 09026 | 0.90 | 0.2325 | 0.4242 |
| 34674 | 201 | Metabolite - 12990 | 1.06 | 0.2407 | 0.4364 |
| 25609 | 50 | Metabolite - 10439 | 0.87 | 0.2428 | 0.4364 |
| 2730 | 200 | gamma-glutamylglutamine | 0.95 | 0.2431 | 0.4364 |
| 17482 | 50 | Metabolite - 04874 | 0.94 | 0.2453 | 0.4381 |
| 32319 | 50 | trans-4-hydroxyproline | 1.09 | 0.2468 | 0.4383 |
| 16634 | 50 | Metabolite - 04357 | 0.93 | 0.2496 | 0.4409 |
| 32776 | 200 | 2-methylbutyroylcarnitine | 0.95 | 0.2521 | 0.4423 |
| 33969 | 201 | stearidonate (18:4(n-3)) | 1.10 | 0.2530 | 0.4423 |
| 22138 | 200 | homocitrulline | 0.96 | 0.2546 | 0.4426 |
| 1549 | 50 | 3-hydroxy-2-methylpropanoate | 0.98 | 0.2594 | 0.4453 |
| 64 | 200 | phenylalanine | 1.05 | 0.2596 | 0.4453 |
| 34419 | 200 | 1-linoleoylglycerophosphocholine | 0.93 | 0.2601 | 0.4453 |
| 1605 | 201 | ursodeoxycholate | 3.18 | 0.2614 | 0.4256 |
| 33782 | 201 | Metabolite - 10346 | 0.71 | 0.2616 | 0.4456 |
| 32548 | 201 | Metabolite - 11231 | 1.07 | 0.2656 | 0.4478 |
| 27710 | 50 | N-acetylglycine | 1.12 | 0.2684 | 0.4478 |
| 31912 | 201 | glycolithocholate | 0.97 | 0.2694 | 0.4478 |
| 15140 | 200 | kynurenine | 0.95 | 0.2697 | 0.4478 |
| 1561 | 50 | alpha-tocopherol | 0.94 | 0.2699 | 0.4478 |
| 31266 | 50 | fructose | 0.95 | 0.2719 | 0.4478 |
| 19368 | 50 | Metabolite - 06267 | 0.95 | 0.2724 | 0.4478 |
| 32586 | 200 | Metabolite - 01327 | 1.02 | 0.2765 | 0.4506 |
| 31530 | 200 | threonylphenylalanine | 0.85 | 0.2768 | 0.4506 |
| 33198 | 201 | Metabolite - 11853 | 1.03 | 0.2803 | 0.4542 |
| 21047 | 201 | 3-methyl-2-oxobutyrate | 0.97 | 0.2846 | 0.4589 |
| 32718 | 200 | phenylacetylglutamine | 1.20 | 0.2870 | 0.4605 |
| 24115 | 50 | Metabolite - 09752 | 0.95 | 0.2888 | 0.4611 |
| 16855 | 50 | Metabolite - 04515 | 0.66 | 0.2946 | 0.4682 |
| 32780 | 200 | Metabolite - 11463 | 0.83 | 0.3017 | 0.4734 |
| 16821 | 50 | Metabolite - 04498 | 0.92 | 0.3021 | 0.4734 |
| 32445 | 200 | 3-methylxanthine | 0.94 | 0.3022 | 0.4734 |
| 32504 | 201 | n-3 DPA (22:5(n-3)) | 1.09 | 0.3041 | 0.4741 |
| 1299 | 200 | tyrosine | 0.97 | 0.3060 | 0.4749 |

TABLE 1-continued

Biomarkers to Distinguish Crohn's Disease From Ulcerative Colitis

| | | | | | |
|---|---|---|---|---|---|
| 12593 | 50 | Metabolite - 02973 | 1.02 | 0.3078 | 0.4755 |
| 32595 | 200 | Metabolite - 08893 | 0.95 | 0.3124 | 0.4762 |
| 32348 | 200 | 2-aminobutyrate | 0.95 | 0.3132 | 0.4762 |
| 32328 | 200 | hexanoylcarnitine | 0.90 | 0.3137 | 0.4762 |
| 36099 | 201 | 4-ethylphenyl sulfate | 0.52 | 0.3155 | 0.4762 |
| 32315 | 50 | serine | 0.97 | 0.3160 | 0.4762 |
| 34481 | 200 | Metabolite - 12798 | 1.06 | 0.3169 | 0.4762 |
| 33968 | 201 | 5-dodecenoate (12:1(n-7)) | 0.96 | 0.3321 | 0.4927 |
| 1359 | 201 | oleate(18:1(n-9)) | 1.07 | 0.3364 | 0.4927 |
| 33132 | 200 | Metabolite - 11787 | 0.97 | 0.3376 | 0.4927 |
| 33254 | 201 | Metabolite - 11909 | 1.14 | 0.3386 | 0.4927 |
| 15996 | 50 | aspartate | 1.16 | 0.3395 | 0.4927 |
| 32863 | 201 | Metabolite - 11546 | 1.01 | 0.3395 | 0.4927 |
| 16829 | 50 | pyroglutamine | 0.88 | 0.3400 | 0.4927 |
| 1645 | 201 | laurate (12:0) | 1.07 | 0.3410 | 0.4927 |
| 34453 | 201 | Metabolite - 12776 | 0.93 | 0.3412 | 0.4927 |
| 34417 | 200 | 1-hexadecylglycerophosphocholine | 1.12 | 0.3459 | 0.4955 |
| 22175 | 200 | aspartylphenylalanine | 1.14 | 0.3489 | 0.4955 |
| 31396 | 50 | Metabolite - 10887 | 0.89 | 0.3506 | 0.4955 |
| 19363 | 50 | Metabolite - 06227 | 0.93 | 0.3516 | 0.4955 |
| 33403 | 200 | Metabolite - 12051 | 1.06 | 0.3529 | 0.4955 |
| 3141 | 200 | betaine | 0.96 | 0.3534 | 0.4955 |
| 33204 | 201 | Metabolite - 11859 | 1.03 | 0.3546 | 0.4955 |
| 34283 | 50 | asparagine | 0.96 | 0.3550 | 0.4955 |
| 1365 | 201 | myristate (14:0) | 1.06 | 0.3634 | 0.5024 |
| 31536 | 200 | N-(2-furoyl)glycine | 0.79 | 0.3638 | 0.5024 |
| 32497 | 201 | 10c-undecenoate | 1.03 | 0.3650 | 0.5024 |
| 33883 | 201 | Metabolite - 12441 | 0.85 | 0.3662 | 0.5024 |
| 1649 | 200 | valine | 0.98 | 0.3681 | 0.5024 |
| 32393 | 200 | glutamylvaline | 0.91 | 0.3701 | 0.5024 |
| 32654 | 200 | 3-dehydrocarnitine | 0.94 | 0.3719 | 0.5024 |
| 31548 | 200 | DSGEGDFXAEGGGVR | 1.06 | 0.3721 | 0.5024 |
| 33941 | 200 | decanoylcarnitine | 0.93 | 0.3757 | 0.5039 |
| 32748 | 201 | Metabolite - 11431 | 1.05 | 0.3763 | 0.5039 |
| 32346 | 201 | glycochenodeoxycholate | 0.72 | 0.3792 | 0.4847 |
| 33954 | 200 | glycylphenylalanine | 1.10 | 0.3792 | 0.5043 |
| 32338 | 50 | glycine | 0.96 | 0.3802 | 0.5043 |
| 2734 | 200 | gamma-glutamyltyrosine | 0.97 | 0.3818 | 0.5043 |
| 32753 | 201 | Metabolite - 09789 | 0.93 | 0.3839 | 0.5043 |
| 33675 | 201 | Metabolite - 12253 | 0.83 | 0.3842 | 0.5043 |
| 17627 | 50 | Metabolite - 04986 | 1.08 | 0.3899 | 0.5080 |
| 32716 | 200 | Metabolite - 11399 | 0.89 | 0.3900 | 0.5080 |
| 34329 | 201 | Metabolite - 12719 | 0.92 | 0.3940 | 0.5111 |
| 1301 | 200 | lysine | 1.03 | 0.3981 | 0.5145 |
| 32761 | 201 | Metabolite - 11444 | 1.11 | 0.4013 | 0.5166 |
| 33084 | 200 | ADSGEGDFXAEGGGVR | 0.97 | 0.4034 | 0.5173 |
| 31618 | 50 | Metabolite - 10964 | 1.06 | 0.4054 | 0.5175 |
| 32811 | 201 | Metabolite - 11494 | 1.04 | 0.4067 | 0.5175 |
| 1121 | 50 | margarate (17:0) | 0.96 | 0.4089 | 0.5184 |
| 35439 | 200 | glutaroyl carnitine | 1.04 | 0.4218 | 0.5318 |
| 21127 | 50 | 1-palmitoylglycerol (1-monopalmitin) | 1.07 | 0.4236 | 0.5318 |
| 1898 | 200 | proline | 1.03 | 0.4250 | 0.5318 |
| 27722 | 50 | erythrose | 0.94 | 0.4266 | 0.5318 |
| 33131 | 200 | Metabolite - 11786 | 0.96 | 0.4290 | 0.5318 |
| 16818 | 50 | Metabolite - 04495 | 0.96 | 0.4308 | 0.5318 |
| 1107 | 50 | allantoin | 0.93 | 0.4345 | 0.5330 |
| 33206 | 201 | Metabolite - 11861 | 0.97 | 0.4379 | 0.5330 |
| 32593 | 200 | heme | 0.96 | 0.4390 | 0.5330 |
| 32698 | 200 | Metabolite - 11381 | 1.00 | 0.4400 | 0.5330 |
| 32695 | 201 | Metabolite - 11378 | 0.80 | 0.4415 | 0.5330 |
| 33507 | 200 | Metabolite - 12092 | 1.11 | 0.4417 | 0.5330 |
| 33150 | 200 | Metabolite - 11805 | 0.93 | 0.4435 | 0.5330 |
| 32635 | 201 | Metabolite - 11318 | 1.08 | 0.4458 | 0.5330 |
| 32518 | 200 | Metabolite - 11204 | 1.03 | 0.4461 | 0.5330 |
| 33627 | 201 | Metabolite - 12206 | 0.97 | 0.4488 | 0.5342 |
| 21188 | 50 | stearoylglycerol (monostearin) | 0.95 | 0.4515 | 0.5355 |
| 1638 | 201 | arginine | 0.96 | 0.4590 | 0.5378 |
| 37015 | 50 | threonine | 0.98 | 0.4598 | 0.5378 |
| 32759 | 201 | Metabolite - 11442 | 0.99 | 0.4599 | 0.5378 |
| 32855 | 201 | Metabolite - 11538 | 0.96 | 0.4646 | 0.5409 |
| 34441 | 50 | Metabolite - 12771 | 1.03 | 0.4658 | 0.5409 |
| 587 | 50 | gluconate | 0.91 | 0.4686 | 0.5412 |
| 33633 | 201 | Metabolite - 12212 | 0.99 | 0.4693 | 0.5412 |
| 15500 | 200 | carnitine | 0.99 | 0.4753 | 0.5426 |
| 33515 | 200 | Metabolite - 12100 | 0.98 | 0.4788 | 0.5426 |
| 1642 | 201 | caprate (10:0) | 1.02 | 0.4805 | 0.5426 |
| 33225 | 201 | Metabolite - 11880 | 1.00 | 0.4810 | 0.5426 |
| 33190 | 201 | Metabolite - 11845 | 1.09 | 0.4813 | 0.5426 |

TABLE 1-continued

Biomarkers to Distinguish Crohn's Disease From Ulcerative Colitis

| | | | | | |
|---|---|---|---|---|---|
| 34456 | 200 | gamma-glutamylisoleucine | 0.97 | 0.4822 | 0.5426 |
| 32738 | 200 | Metabolite - 11421 | 0.94 | 0.4858 | 0.5426 |
| 32369 | 50 | Metabolite - 11175 | 1.05 | 0.4867 | 0.5426 |
| 18369 | 200 | gamma-glutamylleucine | 0.96 | 0.4868 | 0.5426 |
| 35844 | 50 | gamma, gamma-dimethylallyl pyrophosphate | 0.94 | 0.4868 | 0.5426 |
| 1481 | 50 | inositol 1-phosphate (I1P) | 0.93 | 0.4971 | 0.5466 |
| 32412 | 200 | butyrylcarnitine | 0.91 | 0.4976 | 0.5466 |
| 32758 | 201 | Metabolite - 11441 | 0.99 | 0.4991 | 0.5466 |
| 34395 | 201 | 1-methylurate | 1.11 | 0.4992 | 0.5466 |
| 35320 | 201 | catechol sulfate | 0.82 | 0.4992 | 0.5466 |
| 32847 | 201 | Metabolite - 11530 | 1.08 | 0.5018 | 0.5466 |
| 33453 | 50 | alpha-ketoglutarate | 0.84 | 0.5020 | 0.5466 |
| 32198 | 200 | acetylcarnitine | 0.97 | 0.5112 | 0.5530 |
| 33936 | 200 | octanoylcarnitine | 0.94 | 0.5224 | 0.5633 |
| 19503 | 50 | sphingomyelin | 0.95 | 0.5260 | 0.5635 |
| 1358 | 201 | stearate (18:0) | 1.03 | 0.5274 | 0.5635 |
| 32980 | 201 | adrenate (22:4(n-6)) | 1.06 | 0.5282 | 0.5635 |
| 33626 | 200 | Metabolite - 12205 | 1.04 | 0.5304 | 0.5635 |
| 36098 | 201 | 4-vinylphenol sulfate | 1.00 | 0.5313 | 0.5635 |
| 32632 | 200 | Metabolite - 11315 | 1.01 | 0.5327 | 0.5635 |
| 33447 | 201 | palmitoleate (16:1(n-7)) | 1.04 | 0.5378 | 0.5671 |
| 17805 | 201 | dihomolinolenate (20:2(n-6)) | 1.05 | 0.5396 | 0.5671 |
| 33142 | 200 | Metabolite - 11797 | 0.97 | 0.5423 | 0.5682 |
| 33972 | 201 | 10-nonadecenoate (19:1(n-9)) | 1.03 | 0.5498 | 0.5742 |
| 34253 | 200 | Metabolite - 12650 | 0.79 | 0.5528 | 0.5755 |
| 33390 | 201 | Metabolite - 12039 | 0.88 | 0.5557 | 0.5767 |
| 17064 | 50 | Metabolite - 04624 | 1.02 | 0.5643 | 0.5839 |
| 33821 | 200 | Metabolite - 12393 | 0.93 | 0.5677 | 0.5855 |
| 60 | 200 | leucine | 0.99 | 0.5720 | 0.5867 |
| 35127 | 200 | pro-hydroxy-pro | 0.97 | 0.5738 | 0.5867 |
| 18868 | 50 | Metabolite - 05847 | 1.07 | 0.5754 | 0.5867 |
| 22570 | 50 | Metabolite - 09033 | 0.96 | 0.5804 | 0.5867 |
| 12796 | 50 | Metabolite - 03114 | 0.94 | 0.5812 | 0.5867 |
| 35838 | 50 | beta-alanine | 1.02 | 0.5867 | 0.5867 |
| 33652 | 201 | Metabolite - 12230 | 1.01 | 0.5873 | 0.5867 |
| 33422 | 200 | gammaglutamylphenylalanine | 1.03 | 0.5896 | 0.5867 |
| 1444 | 200 | pipecolate | 1.00 | 0.5907 | 0.5867 |
| 31617 | 50 | Metabolite - 10963 | 1.05 | 0.5925 | 0.5867 |
| 33405 | 200 | Metabolite - 12053 | 0.78 | 0.5926 | 0.5867 |
| 33363 | 200 | gamma-glutamylmethionine | 1.05 | 0.5955 | 0.5867 |
| 33519 | 200 | Metabolite - 12104 | 0.99 | 0.5974 | 0.5867 |
| 33194 | 201 | Metabolite - 11849 | 1.43 | 0.5993 | 0.5867 |
| 35271 | 50 | Metabolite - 13497 | 1.06 | 0.6008 | 0.5867 |
| 34106 | 200 | Metabolite - 12542 | 1.11 | 0.6031 | 0.5867 |
| 34443 | 50 | Metabolite - 12773 | 1.04 | 0.6056 | 0.5867 |
| 33230 | 200 | 1-palmitoleoylglycerophosphocholine | 1.04 | 0.6065 | 0.5867 |
| 33089 | 50 | Metabolite - 11744 | 0.95 | 0.6065 | 0.5867 |
| 33103 | 50 | Metabolite - 11758 | 1.05 | 0.6078 | 0.5867 |
| 35831 | 50 | glutamine | 0.99 | 0.6094 | 0.5867 |
| 1123 | 201 | inosine | 1.01 | 0.6152 | 0.5879 |
| 33369 | 50 | Metabolite - 12023 | 0.96 | 0.6160 | 0.5879 |
| 527 | 50 | lactate | 0.99 | 0.6167 | 0.5879 |
| 25602 | 50 | Metabolite - 10432 | 1.00 | 0.6178 | 0.5879 |
| 31591 | 201 | androsterone sulfate | 0.91 | 0.6298 | 0.5976 |
| 1105 | 201 | linoleate (18:2(n-6)) | 1.02 | 0.6317 | 0.5977 |
| 32814 | 201 | Metabolite - 11497 | 0.99 | 0.6353 | 0.5977 |
| 4966 | 50 | xylitol | 1.03 | 0.6387 | 0.5977 |
| 35270 | 50 | Metabolite - 13496 | 0.99 | 0.6424 | 0.5977 |
| 12782 | 50 | Metabolite - 03100 | 0.97 | 0.6439 | 0.5977 |
| 12768 | 50 | Metabolite - 03088 | 0.90 | 0.6451 | 0.5977 |
| 33033 | 200 | Metabolite - 11689 | 0.70 | 0.6459 | 0.5977 |
| 33960 | 200 | 1-oleoylglycerophosphocholine | 1.00 | 0.6491 | 0.5977 |
| 542 | 50 | 3-hydroxybutyrate (BHBA) | 1.03 | 0.6492 | 0.5977 |
| 12789 | 50 | Metabolite - 03107 | 1.01 | 0.6496 | 0.5977 |
| 1508 | 200 | pantothenate | 0.98 | 0.6545 | 0.5981 |
| 32492 | 201 | caprylate (8:0) | 1.01 | 0.6555 | 0.5981 |
| 33140 | 200 | Metabolite - 11795 | 1.03 | 0.6579 | 0.5986 |
| 35252 | 50 | oxalacetic acid | 1.04 | 0.6678 | 0.6048 |
| 25532 | 50 | Metabolite - 10413 | 1.03 | 0.6703 | 0.6048 |
| 18394 | 201 | theophylline | 1.07 | 0.6704 | 0.6048 |
| 33396 | 201 | Metabolite - 12045 | 1.09 | 0.6719 | 0.6048 |
| 33666 | 200 | Metabolite - 12244 | 0.98 | 0.6752 | 0.6060 |
| 36747 | 200 | deoxycarnitine | 0.98 | 0.6813 | 0.6099 |
| 34516 | 201 | Metabolite - 12833 | 1.01 | 0.6861 | 0.6125 |
| 32587 | 201 | Metabolite - 02249 | 0.98 | 0.6914 | 0.6156 |
| 33408 | 200 | Metabolite - 12056 | 0.84 | 0.6942 | 0.6164 |
| 35160 | 200 | oleoylcarnitine | 0.98 | 0.6977 | 0.6179 |
| 19490 | 50 | Metabolite - 06488 | 1.04 | 0.6999 | 0.6181 |

TABLE 1-continued

Biomarkers to Distinguish Crohn's Disease From Ulcerative Colitis

| | | | | | |
|---|---|---|---|---|---|
| 15737 | 50 | glycolate (hydroxyacetate) | 1.02 | 0.7069 | 0.6181 |
| 27856 | 50 | Metabolite - 10597 | 0.94 | 0.7071 | 0.6181 |
| 1284 | 200 | threonine | 1.02 | 0.7078 | 0.6181 |
| 33971 | 201 | 10-heptadecenoate (17:1(n-7)) | 1.03 | 0.7090 | 0.6181 |
| 35433 | 200 | hydroxyisovaleroyl carnitine | 0.98 | 0.7090 | 0.6181 |
| 16837 | 50 | Metabolite - 04507 | 1.00 | 0.7209 | 0.6265 |
| 27672 | 201 | 3-indoxyl sulfate | 1.15 | 0.7224 | 0.6265 |
| 32869 | 200 | Metabolite - 11552 | 1.01 | 0.7270 | 0.6288 |
| 33638 | 201 | Metabolite - 12217 | 0.81 | 0.7308 | 0.6304 |
| 27273 | 50 | Metabolite - 10506 | 0.98 | 0.7352 | 0.6306 |
| 33386 | 50 | Metabolite - 12035 | 1.05 | 0.7352 | 0.6306 |
| 18335 | 50 | quinate | 0.99 | 0.7367 | 0.6306 |
| 36095 | 201 | thymol sulfate | 0.98 | 0.7429 | 0.6343 |
| 1712 | 200 | cortisol | 1.12 | 0.7537 | 0.6418 |
| 33884 | 201 | Metabolite - 12442 | 1.04 | 0.7555 | 0.6418 |
| 33441 | 200 | isobutyrylcarnitine | 1.03 | 0.7593 | 0.6425 |
| 32560 | 201 | Metabolite - 07765 | 1.02 | 0.7603 | 0.6425 |
| 30832 | 50 | Metabolite - 10814 | 0.98 | 0.7639 | 0.6432 |
| 34732 | 201 | isovalerate | 1.08 | 0.7650 | 0.6432 |
| 34035 | 201 | linolenate [alpha or gamma; (18:3(n-3 or 6))] | 0.99 | 0.7742 | 0.6494 |
| 569 | 200 | caffeine | 0.98 | 0.7799 | 0.6516 |
| 33138 | 200 | Metabolite - 11793 | 1.06 | 0.7809 | 0.6516 |
| 32452 | 200 | propionylcarnitine | 1.02 | 0.7896 | 0.6553 |
| 32418 | 201 | myristoleate (14:1(n-5)) | 1.03 | 0.7911 | 0.6553 |
| 27716 | 201 | bilirubin | 1.06 | 0.7927 | 0.6553 |
| 34223 | 200 | Metabolite - 12629 | 0.82 | 0.7951 | 0.6553 |
| 12781 | 50 | Metabolite - 03099 | 1.03 | 0.7952 | 0.6553 |
| 18349 | 50 | indolelactate | 0.96 | 0.7991 | 0.6569 |
| 36752 | 200 | N6-acetyllysine | 1.01 | 0.8047 | 0.6570 |
| 513 | 200 | creatinine | 1.01 | 0.8049 | 0.6570 |
| 1604 | 201 | urate | 1.02 | 0.8051 | 0.6570 |
| 32754 | 201 | Metabolite - 11437 | 0.66 | 0.8173 | 0.6643 |
| 18254 | 200 | paraxanthine | 1.05 | 0.8180 | 0.6643 |
| 21044 | 50 | 2-hydroxybutyrate (AHB) | 1.02 | 0.8224 | 0.6653 |
| 33587 | 201 | eicosenoate [9 or 11, cis or trans] | 0.98 | 0.8233 | 0.6653 |
| 36850 | 201 | octadecanedioate | 0.98 | 0.8276 | 0.6654 |
| 33442 | 201 | pseudouridine | 0.99 | 0.8299 | 0.6654 |
| 33237 | 201 | Metabolite - 11892 | 0.98 | 0.8304 | 0.6654 |
| 32339 | 50 | alanine | 1.01 | 0.8337 | 0.6654 |
| 22116 | 201 | 4-methyl-2-oxopentanoate | 1.00 | 0.8361 | 0.6654 |
| 33963 | 201 | acetoacetate | 1.08 | 0.8363 | 0.6654 |
| 32839 | 201 | Metabolite - 11522 | 1.02 | 0.8375 | 0.6654 |
| 18388 | 50 | Metabolite - 05491 | 1.01 | 0.8438 | 0.6688 |
| 15676 | 201 | 3-methyl-2-oxovalerate | 1.02 | 0.8466 | 0.6692 |
| 22601 | 50 | Metabolite - 09044 | 0.99 | 0.8483 | 0.6692 |
| 32401 | 200 | trigonelline (N'-methylnicotinate) | 1.00 | 0.8526 | 0.6704 |
| 32322 | 50 | glutamate | 1.03 | 0.8539 | 0.6704 |
| 54 | 200 | tryptophan | 1.01 | 0.8578 | 0.6719 |
| 1573 | 200 | guanosine | 1.01 | 0.8725 | 0.6815 |
| 32846 | 201 | Metabolite - 11529 | 0.89 | 0.8759 | 0.6815 |
| 33203 | 201 | Metabolite - 11858 | 0.91 | 0.8762 | 0.6815 |
| 34344 | 201 | Metabolite - 12734 | 0.79 | 0.8867 | 0.6869 |
| 32599 | 201 | Metabolite - 11282 | 0.95 | 0.8873 | 0.6869 |
| 34062 | 201 | Metabolite - 12524 | 1.00 | 0.8912 | 0.6883 |
| 34532 | 201 | Metabolite - 12849 | 0.95 | 0.8962 | 0.6906 |
| 34527 | 201 | Metabolite - 12844 | 0.96 | 0.9012 | 0.6929 |
| 19464 | 200 | testosterone | 0.90 | 0.9046 | 0.6938 |
| 32854 | 200 | Metabolite - 11537 | 0.96 | 0.9078 | 0.6947 |
| 16120 | 50 | Metabolite - 04055 | 1.02 | 0.9116 | 0.6960 |
| 15677 | 201 | 3-methylhistidine | 1.09 | 0.9146 | 0.6967 |
| 33822 | 200 | Metabolite - 12394 | 0.96 | 0.9174 | 0.6972 |
| 32197 | 201 | 3-(4-hydroxyphenyl)lactate | 0.99 | 0.9214 | 0.6980 |
| 32786 | 200 | Metabolite - 11469 | 0.79 | 0.9281 | 0.7006 |
| 33391 | 201 | Metabolite - 12040 | 0.97 | 0.9311 | 0.7012 |
| 34040 | 200 | Metabolite - 12510 | 0.94 | 0.9379 | 0.7015 |
| 35675 | 201 | 2-hydroxypalmitate | 0.99 | 0.9387 | 0.7015 |
| 606 | 201 | uridine | 1.01 | 0.9406 | 0.7015 |
| 18392 | 200 | theobromine | 0.89 | 0.9443 | 0.7015 |
| 33364 | 200 | gamma-glutamylthreonine | 1.01 | 0.9451 | 0.7015 |
| 17391 | 50 | Metabolite - 04807 | 1.08 | 0.9488 | 0.7015 |
| 15122 | 50 | glycerol | 0.99 | 0.9512 | 0.7015 |
| 32910 | 201 | Metabolite - 11593 | 0.99 | 0.9592 | 0.7015 |
| 34530 | 201 | Metabolite - 12847 | 0.92 | 0.9595 | 0.7015 |
| 36738 | 200 | gamma-glutamylglutamate | 0.98 | 0.9664 | 0.7015 |
| 36756 | 200 | leucylleucine | 0.83 | 0.9671 | 0.7015 |
| 1302 | 201 | methionine | 1.01 | 0.9718 | 0.7015 |
| 20699 | 50 | erythritol | 0.98 | 0.9784 | 0.7015 |
| 34407 | 200 | isovalerylcarnitine | 1.01 | 0.9791 | 0.7015 |

TABLE 1-continued

Biomarkers to Distinguish Crohn's Disease From Ulcerative Colitis

| 33973 | 201 | epiandrosterone sulfate | 1.04 | 0.9803 | 0.7015 |
| 32850 | 201 | Metabolite - 11533 | 1.00 | 0.9811 | 0.7015 |
| 2137 | 200 | biliverdin | 1.10 | 0.9825 | 0.7015 |
| 32549 | 201 | Metabolite - 02269 | 0.98 | 0.9832 | 0.7015 |
| 32625 | 201 | Metabolite - 11308 | 0.80 | 0.9835 | 0.7015 |
| 19402 | 50 | Metabolite - 06346 | 0.96 | 0.9862 | 0.7015 |
| 34400 | 201 | 1,7-dimethylurate | 1.00 | 0.9873 | 0.7015 |
| 18283 | 50 | Metabolite - 05426 | 0.93 | 0.9882 | 0.7015 |
| 34390 | 200 | 7-methylxanthine | 1.01 | 0.9884 | 0.7015 |
| 33957 | 200 | 1-heptadecanoylglycerophosphocholine | 1.07 | 0.9885 | 0.7015 |
| 22600 | 50 | Metabolite - 09043 | 0.99 | 0.9975 | 0.7064 |

Table 1B. Biomarkers to Distinguish Active Crohn's from Active Ulcerative Colitis

| Lib ID | Comp ID | Biomarker | CD Active/ UC Active | p | q |
|---|---|---|---|---|---|
| 201 | 36776 | 7-alpha-hydroxy-3-oxo-4-cholestenoate (7-Hoca) | 2.20 | 0.0000 | 0.0004 |
| 50 | 33488 | lathosterol | 2.81 | 0.0000 | 0.0027 |
| 201 | 27531 | hyodeoxycholate | 6.97 | 0.0000 | 0.0027 |
| 201 | 32558 | p-cresol sulfate | 0.47 | 0.0000 | 0.0034 |
| 200 | 553 | cotinine | 2.72 | 0.0001 | 0.0099 |
| 201 | 32620 | Metabolite - 11303 | 0.41 | 0.0003 | 0.0149 |
| 201 | 32792 | Metabolite - 11475 | 1.70 | 0.0004 | 0.0198 |
| 201 | 36850 | taurolithocholate 3-sulfate | 0.31 | 0.0006 | 0.0257 |
| 50 | 35832 | ornithine | 0.72 | 0.0008 | 0.0313 |
| 201 | 32827 | Metabolite - 11510 | 1.62 | 0.0009 | 0.0313 |
| 50 | 1670 | urea | 0.69 | 0.0010 | 0.0313 |
| 201 | 33682 | Metabolite - 12260 | 0.27 | 0.0011 | 0.0340 |
| 50 | 21011 | Metabolite - 07888 | 0.86 | 0.0017 | 0.0461 |
| 200 | 33576 | Metabolite - 12159 | 0.30 | 0.0019 | 0.0489 |
| 201 | 32561 | Metabolite - 11244 | 1.58 | 0.0022 | 0.0503 |
| 201 | 32489 | caproate (6:0) | 1.20 | 0.0023 | 0.0503 |
| 201 | 32757 | Metabolite - 11440 | 1.42 | 0.0040 | 0.0740 |
| 50 | 16823 | Metabolite - 04500 | 0.45 | 0.0045 | 0.0778 |
| 201 | 32767 | Metabolite - 11450 | 1.37 | 0.0047 | 0.0778 |
| 201 | 36807 | 6-beta-hydroxylithocholate | 3.52 | 0.0048 | 0.0778 |
| 200 | 33073 | cysteine-glutathione disulfide | 0.78 | 0.0060 | 0.0869 |
| 201 | 32425 | dehydroisoandrosterone sulfate (DHEA-S) | 1.44 | 0.0060 | 0.0869 |
| 200 | 34359 | Metabolite - 12749 | 0.86 | 0.0063 | 0.0869 |
| 50 | 16866 | Metabolite - 04523 | 0.80 | 0.0064 | 0.0869 |
| 201 | 18497 | taurocholate | 0.49 | 0.0066 | 0.0869 |
| 50 | 27256 | Metabolite - 10500 | 0.88 | 0.0069 | 0.0874 |
| 201 | 33415 | Metabolite - 12063 | 1.84 | 0.0077 | 0.0917 |
| 200 | 18476 | glycocholate | 0.64 | 0.0078 | 0.0917 |
| 200 | 32644 | Metabolite - 11327 | 1.15 | 0.0080 | 0.0917 |
| 201 | 32590 | Metabolite - 11273 | 1.50 | 0.0084 | 0.0917 |
| 201 | 32557 | Metabolite - 06126 | 0.64 | 0.0085 | 0.0917 |
| 50 | 18929 | Metabolite - 05907 | 0.82 | 0.0089 | 0.0926 |
| 201 | 32863 | Metabolite - 11546 | 0.69 | 0.0091 | 0.0926 |
| 201 | 1563 | chenodeoxycholate | 1.15 | 0.0097 | 0.0957 |
| 201 | 35688 | 2-palmitoylglycerophosphoethanolamine | 1.30 | 0.0100 | 0.0963 |
| 201 | 32808 | Metabolite - 11491 | 1.63 | 0.0111 | 0.1041 |
| 201 | 34314 | Metabolite - 12704 | 0.88 | 0.0136 | 0.1238 |
| 50 | 27738 | threonate | 0.66 | 0.0153 | 0.1333 |
| 200 | 34368 | Metabolite - 12758 | 0.73 | 0.0154 | 0.1333 |
| 200 | 34384 | stachydrine | 0.55 | 0.0162 | 0.1366 |
| 50 | 11438 | phosphate | 0.92 | 0.0167 | 0.1366 |
| 50 | 19934 | myo-inositol | 0.87 | 0.0169 | 0.1366 |
| 201 | 20675 | 1,5-anhydroglucitol (1,5-AG) | 0.85 | 0.0179 | 0.1411 |
| 200 | 15753 | hippurate | 0.56 | 0.0190 | 0.1468 |
| 50 | 27278 | Metabolite - 10510 | 0.85 | 0.0203 | 0.1536 |
| 200 | 2342 | serotonin (5HT) | 1.32 | 0.0222 | 0.1599 |
| 201 | 32815 | Metabolite - 11498 | 1.21 | 0.0222 | 0.1599 |
| 50 | 25459 | Metabolite - 10395 | 0.85 | 0.0225 | 0.1599 |
| 50 | 32405 | 3-indolepropionate | 0.77 | 0.0254 | 0.1770 |
| 201 | 32562 | Metabolite - 11245 | 1.28 | 0.0266 | 0.1812 |
| 200 | 32836 | HWESASXX | 0.40 | 0.0270 | 0.1812 |
| 50 | 32315 | serine | 0.89 | 0.0282 | 0.1857 |
| 201 | 32847 | Metabolite - 11530 | 1.30 | 0.0310 | 0.1925 |
| 50 | 31453 | cysteine | 0.75 | 0.0314 | 0.1925 |
| 201 | 36097 | 4-acetaminophen sulfate | 0.42 | 0.0314 | 0.1925 |
| 201 | 1110 | arachidonate (20:4(n-6)) | 1.13 | 0.0321 | 0.1925 |
| 200 | 18357 | glycylvaline | 2.38 | 0.0325 | 0.1925 |

TABLE 1-continued

Biomarkers to Distinguish Crohn's Disease From Ulcerative Colitis

| | | | | | |
|---|---|---|---|---|---|
| 50 | 12774 | Metabolite - 03094 | 1.14 | 0.0334 | 0.1947 |
| 201 | 32501 | dihomo-alpha-linolenate (20:3(n-3)) | 1.14 | 0.0370 | 0.2122 |
| 200 | 31522 | pyroglutamylglycine | 1.24 | 0.0387 | 0.2180 |
| 50 | 19362 | Metabolite - 06226 | 0.90 | 0.0421 | 0.2268 |
| 201 | 33353 | Metabolite - 12007 | 0.68 | 0.0425 | 0.2268 |
| 200 | 15630 | N-acetylornithine | 0.82 | 0.0438 | 0.2268 |
| 201 | 32807 | Metabolite - 11490 | 0.82 | 0.0438 | 0.2268 |
| 200 | 32830 | Metabolite - 11513 | 0.61 | 0.0440 | 0.2268 |
| 200 | 33509 | Metabolite - 12094 | 0.68 | 0.0443 | 0.2268 |
| 200 | 34366 | Metabolite - 12756 | 0.64 | 0.0447 | 0.2268 |
| 200 | 33846 | indoleacetate | 1.46 | 0.0457 | 0.2285 |
| 50 | 12032 | 4-acetamidophenol | 0.43 | 0.0465 | 0.2295 |
| 50 | 15488 | acetylphosphate | 0.92 | 0.0485 | 0.2359 |
| 201 | 1644 | heptanoate (7:0) | 1.10 | 0.0494 | 0.2368 |
| 200 | 32709 | Metabolite - 03056 | 0.83 | 0.0500 | 0.2368 |
| 201 | 32497 | 10c-undecenoate | 1.16 | 0.0525 | 0.2421 |
| 201 | 33195 | Metabolite - 11850 | 0.25 | 0.0525 | 0.2421 |
| 201 | 33901 | Metabolite - 12456 | 1.36 | 0.0543 | 0.2442 |
| 200 | 1769 | cortisone | 0.59 | 0.0550 | 0.2442 |
| 201 | 33178 | Metabolite - 11833 | 0.52 | 0.0550 | 0.2442 |
| 50 | 20489 | Glucose | 1.09 | 0.0556 | 0.4001 |
| 201 | 34201 | 1-stearoylglycerophosphoinositol | 1.16 | 0.0564 | 0.2474 |
| 200 | 32572 | Metabolite - 11255 | 0.71 | 0.0602 | 0.2608 |
| 201 | 32753 | Metabolite - 09789 | 0.77 | 0.0660 | 0.2823 |
| 200 | 22175 | aspartylphenylalanine | 1.28 | 0.0676 | 0.2857 |
| 201 | 33188 | Metabolite - 11843 | 0.39 | 0.0693 | 0.2895 |
| 50 | 63 | cholesterol | 0.93 | 0.0705 | 0.2911 |
| 201 | 34674 | Metabolite - 12990 | 1.15 | 0.0723 | 0.2949 |
| 201 | 15730 | suberate | 1.19 | 0.0734 | 0.2960 |
| 200 | 33939 | N-acetylthreonine | 1.10 | 0.0750 | 0.2989 |
| 201 | 33173 | Metabolite - 11828 | 0.40 | 0.0762 | 0.2989 |
| 201 | 33221 | Metabolite - 11876 | 0.49 | 0.0766 | 0.2989 |
| 201 | 31555 | pyridoxate | 0.71 | 0.0828 | 0.3156 |
| 201 | 32619 | Metabolite - 11302 | 1.38 | 0.0828 | 0.3156 |
| 201 | 31908 | 7-ketolithocholate | 1.37 | 0.0843 | 0.3156 |
| 201 | 33389 | Metabolite - 12038 | 1.13 | 0.0844 | 0.3156 |
| 50 | 19368 | Metabolite - 06267 | 0.87 | 0.0870 | 0.3216 |
| 201 | 35320 | catechol sulfate | 0.72 | 0.0889 | 0.3256 |
| 201 | 12261 | taurodeoxycholate | 0.42 | 0.0923 | 0.3275 |
| 201 | 32548 | Metabolite - 11231 | 1.15 | 0.0925 | 0.3275 |
| 50 | 22649 | Metabolite - 09108 | 0.87 | 0.0933 | 0.3275 |
| 50 | 33477 | erythronate | 0.88 | 0.0936 | 0.3275 |
| 200 | 15990 | glycerophosphorylcholine (GPC) | 1.13 | 0.0947 | 0.3275 |
| 201 | 32846 | Metabolite - 11529 | 0.58 | 0.0950 | 0.3275 |
| 201 | 1361 | pentadecanoate (15:0) | 0.90 | 0.0970 | 0.3284 |
| 50 | 1592 | N-acetylneuraminate | 0.87 | 0.0981 | 0.3284 |
| 200 | 33510 | Metabolite - 12095 | 0.79 | 0.0996 | 0.3284 |
| 200 | 32518 | Metabolite - 11204 | 1.08 | 0.1010 | 0.3284 |
| 201 | 18362 | azelate (nonanedioate) | 1.32 | 0.1011 | 0.3284 |
| 201 | 15778 | benzoate | 1.09 | 0.1018 | 0.3284 |
| 50 | 15335 | mannitol | 0.67 | 0.1021 | 0.3284 |
| 50 | 32338 | glycine | 0.89 | 0.1027 | 0.3284 |
| 50 | 16821 | Metabolite - 04498 | 0.85 | 0.1070 | 0.3371 |
| 201 | 33423 | p-acetamidophenylglucuronide | 0.38 | 0.1078 | 0.3371 |
| 50 | 28059 | dehydroascorbate | 0.78 | 0.1082 | 0.3371 |
| 50 | 33420 | gamma-tocopherol | 1.19 | 0.1106 | 0.3414 |
| 201 | 32398 | sebacate | 1.34 | 0.1129 | 0.3417 |
| 50 | 37016 | arginine | 0.93 | 0.1140 | 0.3417 |
| 200 | 34365 | Metabolite - 12755 | 0.54 | 0.1149 | 0.3417 |
| 50 | 34283 | asparagine | 0.88 | 0.1158 | 0.3417 |
| 201 | 32761 | Metabolite - 11444 | 1.29 | 0.1164 | 0.3417 |
| 50 | 19414 | Metabolite - 06350 | 1.13 | 0.1178 | 0.3417 |
| 201 | 32689 | Metabolite - 11372 | 1.14 | 0.1178 | 0.3417 |
| 50 | 37015 | threonine | 0.91 | 0.1186 | 0.3417 |
| 50 | 17064 | Metabolite - 04624 | 1.10 | 0.1193 | 0.3417 |
| 200 | 33422 | gammaglutamylphenylalanine | 1.11 | 0.1208 | 0.3423 |
| 50 | 16855 | Metabolite - 04515 | 0.39 | 0.1215 | 0.3423 |
| 50 | 16666 | Metabolite - 04365 | 0.82 | 0.1227 | 0.3431 |
| 200 | 33363 | gamma-glutamylmethionine | 1.15 | 0.1244 | 0.3450 |
| 201 | 32740 | Metabolite - 11423 | 0.89 | 0.1278 | 0.3504 |
| 201 | 59 | histidine | 1.07 | 0.1283 | 0.3504 |
| 200 | 32675 | Metabolite - 03951 | 0.91 | 0.1300 | 0.3508 |
| 201 | 32388 | dodecanedioate | 1.41 | 0.1304 | 0.3508 |
| 201 | 3147 | xanthine | 1.11 | 0.1318 | 0.3508 |
| 201 | 32616 | Metabolite - 11299 | 0.57 | 0.1324 | 0.3508 |
| 50 | 32369 | Metabolite - 11175 | 1.19 | 0.1349 | 0.3549 |
| 200 | 22154 | bradykinin | 1.18 | 0.1376 | 0.3568 |
| 200 | 32978 | Metabolite - 11656 | 1.01 | 0.1377 | 0.3568 |

TABLE 1-continued

Biomarkers to Distinguish Crohn's Disease From Ulcerative Colitis

| | | | | | |
|---|---|---|---|---|---|
| 201 | 33937 | alpha-hydroxyisovalerate | 1.40 | 0.1426 | 0.3668 |
| 201 | 32599 | Metabolite - 11282 | 0.82 | 0.1458 | 0.3724 |
| 200 | 1508 | pantothenate | 0.87 | 0.1476 | 0.3743 |
| 50 | 35836 | lysine | 0.86 | 0.1515 | 0.3816 |
| 201 | 32811 | Metabolite - 11494 | 1.08 | 0.1603 | 0.4000 |
| 201 | 32795 | Metabolite - 11478 | 0.73 | 0.1611 | 0.4000 |
| 200 | 513 | creatinine | 1.05 | 0.1629 | 0.4017 |
| 200 | 32735 | Metabolite - 01911 | 1.30 | 0.1662 | 0.4069 |
| 50 | 27710 | N-acetylglycine | 1.21 | 0.1675 | 0.4073 |
| 201 | 1114 | deoxycholate | 1.15 | 0.1688 | 0.4073 |
| 200 | 33403 | Metabolite - 12051 | 1.16 | 0.1707 | 0.4073 |
| 50 | 25607 | Metabolite - 10437 | 0.81 | 0.1709 | 0.4073 |
| 50 | 19576 | Metabolite - 06627 | 1.37 | 0.1723 | 0.4080 |
| 50 | 30282 | Metabolite - 10744 | 0.84 | 0.1740 | 0.4090 |
| 50 | 34443 | Metabolite - 12773 | 1.14 | 0.1786 | 0.4164 |
| 201 | 18281 | 2-hydroxyhippurate (salicylurate) | 0.08 | 0.1801 | 0.4164 |
| 50 | 20489 | glucose | 0.89 | 0.1811 | 0.4164 |
| 201 | 32748 | Metabolite - 11431 | 1.15 | 0.1818 | 0.4164 |
| 201 | 34214 | Metabolite - 12620 | 1.09 | 0.1857 | 0.4195 |
| 201 | 15749 | 3-phenylpropionate (hydrocinnamate) | 0.85 | 0.1867 | 0.4195 |
| 200 | 15743 | dimethylarginine | 0.91 | 0.1867 | 0.4195 |
| 200 | 3141 | betaine | 0.93 | 0.1884 | 0.4208 |
| 50 | 35838 | beta-alanine | 0.88 | 0.1970 | 0.4371 |
| 200 | 32793 | Metabolite - 11476 | 1.04 | 0.2004 | 0.4419 |
| 50 | 19396 | Metabolite - 06307 | 0.78 | 0.2037 | 0.4464 |
| 201 | 32855 | Metabolite - 11538 | 0.93 | 0.2063 | 0.4493 |
| 200 | 32698 | Metabolite - 11381 | 1.05 | 0.2087 | 0.4518 |
| 50 | 584 | mannose | 0.85 | 0.2111 | 0.4540 |
| 201 | 33183 | Metabolite - 11838 | 0.56 | 0.2125 | 0.4540 |
| 201 | 32980 | adrenate (22:4(n-6)) | 1.13 | 0.2136 | 0.4540 |
| 200 | 3127 | hypoxanthine | 1.12 | 0.2176 | 0.4572 |
| 200 | 32458 | oleamide | 0.75 | 0.2176 | 0.4572 |
| 50 | 34441 | Metabolite - 12771 | 1.10 | 0.2201 | 0.4598 |
| 200 | 33441 | isobutyrylcarnitine | 0.86 | 0.2223 | 0.4615 |
| 200 | 1299 | tyrosine | 0.94 | 0.2260 | 0.4661 |
| 50 | 21188 | stearoylglycerol (monostearin) | 0.91 | 0.2271 | 0.4661 |
| 201 | 22130 | phenyllactate (PLA) | 0.92 | 0.2311 | 0.4717 |
| 201 | 12035 | pelargonate (9:0) | 1.05 | 0.2369 | 0.4782 |
| 200 | 33773 | Metabolite - 12348 | 1.05 | 0.2371 | 0.4782 |
| 50 | 24115 | Metabolite - 09752 | 0.90 | 0.2417 | 0.4847 |
| 201 | 34244 | Metabolite - 12644 | 1.11 | 0.2430 | 0.4847 |
| 201 | 33884 | Metabolite - 12442 | 1.14 | 0.2456 | 0.4863 |
| 201 | 33206 | Metabolite - 11861 | 0.95 | 0.2465 | 0.4863 |
| 50 | 25599 | Metabolite - 10429 | 0.88 | 0.2494 | 0.4892 |
| 200 | 1494 | pyroglutamate (5-oxoproline) | 1.05 | 0.2543 | 0.4898 |
| 200 | 64 | phenylalanine | 1.06 | 0.2572 | 0.4898 |
| 50 | 18283 | Metabolite - 05426 | 0.69 | 0.2572 | 0.4898 |
| 201 | 12129 | beta-hydroxyisovalerate | 1.12 | 0.2588 | 0.4898 |
| 50 | 19490 | Metabolite - 06488 | 1.19 | 0.2596 | 0.4898 |
| 200 | 31536 | N-(2-furoyl)glycine | 0.65 | 0.2615 | 0.4898 |
| 50 | 12796 | Metabolite - 03114 | 1.28 | 0.2618 | 0.4898 |
| 200 | 33954 | glycylphenylalanine | 1.13 | 0.2622 | 0.4898 |
| 201 | 33675 | Metabolite - 12253 | 0.72 | 0.2657 | 0.4898 |
| 201 | 36095 | thymol sulfate | 0.44 | 0.2667 | 0.4898 |
| 201 | 34530 | Metabolite - 12847 | 0.66 | 0.2680 | 0.4898 |
| 201 | 31787 | 3-carboxy-4-methyl-5-propyl-2-furanpropanoate (CMPF) | 0.89 | 0.2685 | 0.4898 |
| 201 | 33391 | Metabolite - 12040 | 0.81 | 0.2694 | 0.4898 |
| 201 | 19323 | docosahexaenoate (DHA; 22:6(n-3)) | 1.06 | 0.2716 | 0.4898 |
| 50 | 21631 | Metabolite - 08403 | 0.84 | 0.2723 | 0.4898 |
| 200 | 27718 | creatine | 1.10 | 0.2725 | 0.4898 |
| 200 | 33852 | 1-myristoylglycerophosphocholine | 1.19 | 0.2824 | 0.4998 |
| 201 | 22116 | 4-methyl-2-oxopentanoate | 1.11 | 0.2847 | 0.4998 |
| 200 | 32401 | trigonelline (N'-methylnicotinate) | 0.85 | 0.2855 | 0.4998 |
| 200 | 31534 | HXGXA | 0.27 | 0.2858 | 0.4998 |
| 200 | 1712 | cortisol | 1.24 | 0.2870 | 0.4998 |
| 50 | 1561 | alpha-tocopherol | 0.92 | 0.2871 | 0.4998 |
| 201 | 1645 | laurate (12:0) | 1.14 | 0.2899 | 0.5021 |
| 201 | 32910 | Metabolite - 11593 | 0.93 | 0.2950 | 0.5048 |
| 201 | 15676 | 3-methyl-2-oxovalerate | 1.08 | 0.2954 | 0.5048 |
| 50 | 32339 | alanine | 0.94 | 0.2957 | 0.5048 |
| 200 | 33801 | ADpSGEGDFXAEGGGVR | 0.78 | 0.3021 | 0.5128 |
| 50 | 12593 | Metabolite - 02973 | 1.03 | 0.3033 | 0.5128 |
| 200 | 33936 | octanoylcarnitine | 1.10 | 0.3125 | 0.5258 |
| 201 | 32504 | n-3 DPA (22:5(n-3)) | 1.14 | 0.3149 | 0.5264 |
| 50 | 31396 | Metabolite - 10887 | 0.83 | 0.3158 | 0.5264 |
| 201 | 32760 | Metabolite - 11443 | 1.37 | 0.3220 | 0.5343 |
| 50 | 1107 | allantoin | 0.87 | 0.3259 | 0.5382 |

TABLE 1-continued

Biomarkers to Distinguish Crohn's Disease From Ulcerative Colitis

| | | | | | |
|---|---|---|---|---|---|
| 201 | 18467 | eicosapentaenoate (EPA; 20:5(n-3)) | 1.05 | 0.3314 | 0.5415 |
| 201 | 22842 | cholate | 0.86 | 0.3324 | 0.5415 |
| 201 | 12067 | undecanoate (11:0) | 1.04 | 0.3325 | 0.5415 |
| 201 | 1336 | palmitate (16:0) | 1.08 | 0.3346 | 0.5425 |
| 200 | 32198 | acetylcarnitine | 1.07 | 0.3375 | 0.5448 |
| 201 | 33627 | Metabolite - 12206 | 0.93 | 0.3394 | 0.5453 |
| 50 | 1564 | citrate | 0.94 | 0.3502 | 0.5579 |
| 200 | 33821 | Metabolite - 12393 | 1.04 | 0.3519 | 0.5579 |
| 50 | 30805 | Metabolite - 10810 | 0.83 | 0.3520 | 0.5579 |
| 201 | 1605 | ursodeoxycholate | 2.64 | 0.3586 | 0.5609 |
| 200 | 33150 | Metabolite - 11805 | 1.11 | 0.3588 | 0.5609 |
| 201 | 32492 | caprylate (8:0) | 1.05 | 0.3597 | 0.5609 |
| 201 | 15677 | 3-methylhistidine | 0.90 | 0.3619 | 0.5609 |
| 50 | 16120 | Metabolite - 04055 | 1.18 | 0.3650 | 0.5609 |
| 201 | 33782 | Metabolite - 10346 | 0.55 | 0.3661 | 0.5609 |
| 200 | 34481 | Metabolite - 12798 | 1.07 | 0.3677 | 0.5609 |
| 50 | 35270 | Metabolite - 13496 | 0.98 | 0.3677 | 0.5609 |
| 200 | 35439 | glutaroyl carnitine | 1.08 | 0.3696 | 0.5609 |
| 200 | 33364 | gamma-glutamylthreonine | 0.96 | 0.3697 | 0.5609 |
| 200 | 2132 | citrulline | 0.92 | 0.3724 | 0.5627 |
| 201 | 606 | uridine | 1.07 | 0.3781 | 0.5665 |
| 50 | 31618 | Metabolite - 10964 | 1.03 | 0.3781 | 0.5665 |
| 200 | 33228 | Metabolite - 11883 | 0.90 | 0.3816 | 0.5670 |
| 201 | 36098 | 4-vinylphenol sulfate | 0.68 | 0.3833 | 0.5670 |
| 201 | 34516 | Metabolite - 12833 | 0.84 | 0.3912 | 0.5693 |
| 201 | 17805 | dihomolinolenate (20:2(n-6)) | 1.12 | 0.3914 | 0.5693 |
| 200 | 32578 | Metabolite - 11261 | 0.84 | 0.3922 | 0.5693 |
| 201 | 33968 | 5-dodecenoate (12:1(n-7)) | 1.02 | 0.3932 | 0.5693 |
| 201 | 18494 | taurochenodeoxycholate | 0.61 | 0.3945 | 0.5693 |
| 200 | 34417 | 1-hexadecylglycerophosphocholine | 1.10 | 0.3963 | 0.5697 |
| 201 | 33883 | Metabolite - 12441 | 0.77 | 0.3994 | 0.5698 |
| 200 | 31548 | DSGEGDFXAEGGGVR | 0.95 | 0.4015 | 0.5698 |
| 201 | 36099 | 4-ethylphenyl sulfate | 0.48 | 0.4027 | 0.5698 |
| 201 | 32625 | Metabolite - 11308 | 0.95 | 0.4028 | 0.5698 |
| 200 | 32716 | Metabolite - 11399 | 0.80 | 0.4074 | 0.5740 |
| 200 | 54 | tryptophan | 1.04 | 0.4109 | 0.5744 |
| 50 | 25609 | Metabolite - 10439 | 0.84 | 0.4109 | 0.5744 |
| 200 | 32776 | 2-methylbutyroylcarnitine | 0.95 | 0.4147 | 0.5774 |
| 201 | 33225 | Metabolite - 11880 | 1.03 | 0.4196 | 0.5797 |
| 201 | 32346 | glycochenodeoxycholate | 0.66 | 0.4196 | 0.5797 |
| 200 | 33138 | Metabolite - 11793 | 1.10 | 0.4213 | 0.5799 |
| 50 | 599 | pyruvate | 0.93 | 0.4304 | 0.5874 |
| 200 | 33941 | decanoylcarnitine | 1.14 | 0.4317 | 0.5874 |
| 50 | 17627 | Metabolite - 04986 | 1.12 | 0.4318 | 0.5874 |
| 50 | 16818 | Metabolite - 04495 | 0.92 | 0.4357 | 0.5905 |
| 201 | 33633 | Metabolite - 12212 | 0.85 | 0.4388 | 0.5914 |
| 201 | 32877 | Metabolite - 11560 | 1.02 | 0.4397 | 0.5914 |
| 50 | 1572 | glycerate | 0.96 | 0.4423 | 0.5927 |
| 201 | 1358 | stearate (18:0) | 1.07 | 0.4442 | 0.5929 |
| 200 | 34419 | 1-linoleoylglycerophosphocholine | 0.91 | 0.4481 | 0.5959 |
| 200 | 34253 | Metabolite - 12650 | 0.68 | 0.4538 | 0.5970 |
| 201 | 31912 | glycolithocholate | 0.86 | 0.4581 | 0.5970 |
| 50 | 27279 | Metabolite - 10511 | 0.94 | 0.4583 | 0.5970 |
| 201 | 1359 | oleate(18:1(n-9)) | 1.07 | 0.4587 | 0.5970 |
| 200 | 32452 | propionylcarnitine | 1.10 | 0.4590 | 0.5970 |
| 201 | 33412 | Metabolite - 12060 | 0.94 | 0.4617 | 0.5983 |
| 200 | 32445 | 3-methylxanthine | 0.90 | 0.4706 | 0.6076 |
| 200 | 32595 | Metabolite - 08893 | 0.93 | 0.4727 | 0.6081 |
| 200 | 1125 | isoleucine | 0.98 | 0.4771 | 0.6090 |
| 50 | 18446 | Metabolite - 05524 | 1.11 | 0.4787 | 0.6090 |
| 201 | 32553 | phenol sulfate | 1.13 | 0.4788 | 0.6090 |
| 201 | 33254 | Metabolite - 11909 | 1.23 | 0.4817 | 0.6090 |
| 200 | 35160 | oleoylcarnitine | 1.11 | 0.4820 | 0.6090 |
| 201 | 33969 | stearidonate (18:4(n-3)) | 0.97 | 0.4866 | 0.6127 |
| 50 | 32322 | glutamate | 1.05 | 0.4920 | 0.6160 |
| 201 | 33447 | palmitoleate (16:1(n-7)) | 1.08 | 0.4927 | 0.6160 |
| 50 | 21127 | 1-palmitoylglycerol (1-monopalmitin) | 0.98 | 0.4968 | 0.6183 |
| 201 | 34532 | Metabolite - 12849 | 0.74 | 0.5029 | 0.6195 |
| 50 | 22548 | Metabolite - 09026 | 0.93 | 0.5035 | 0.6195 |
| 200 | 33230 | 1-palmitoleoylglycerophosphocholine | 1.10 | 0.5042 | 0.6195 |
| 201 | 32695 | Metabolite - 11378 | 0.84 | 0.5124 | 0.6238 |
| 50 | 31266 | fructose | 0.92 | 0.5131 | 0.6238 |
| 50 | 17391 | Metabolite - 04807 | 1.34 | 0.5155 | 0.6238 |
| 200 | 33955 | 1-palmitoylglycerophosphocholine | 1.03 | 0.5159 | 0.6238 |
| 201 | 1365 | myristate (14:0) | 1.07 | 0.5196 | 0.6238 |
| 50 | 12781 | Metabolite - 03099 | 1.10 | 0.5202 | 0.6238 |
| 200 | 36756 | leucylleucine | 0.59 | 0.5208 | 0.6238 |
| 201 | 32754 | Metabolite - 11437 | 0.30 | 0.5218 | 0.6238 |

TABLE 1-continued

Biomarkers to Distinguish Crohn's Disease From Ulcerative Colitis

| | | | | | |
|---|---|---|---|---|---|
| 200 | 33165 | Metabolite - 11820 | 0.86 | 0.5258 | 0.6244 |
| 201 | 33194 | Metabolite - 11849 | 1.44 | 0.5258 | 0.6244 |
| 50 | 35271 | Metabolite - 13497 | 1.06 | 0.5280 | 0.6249 |
| 50 | 31617 | Metabolite - 10963 | 1.11 | 0.5359 | 0.6290 |
| 200 | 2734 | gamma-glutamyltyrosine | 0.96 | 0.5364 | 0.6290 |
| 200 | 33935 | piperine | 1.23 | 0.5367 | 0.6290 |
| 50 | 15122 | glycerol | 1.05 | 0.5409 | 0.6299 |
| 201 | 33204 | Metabolite - 11859 | 1.04 | 0.5411 | 0.6299 |
| 50 | 35831 | glutamine | 0.97 | 0.5431 | 0.6301 |
| 200 | 32780 | Metabolite - 11463 | 0.73 | 0.5453 | 0.6306 |
| 50 | 20489 | Glucose | 1.09 | 0.0556 | 0.4001 |
| 50 | 20699 | erythritol | 0.94 | 0.5641 | 0.6503 |
| 200 | 33822 | Metabolite - 12394 | 0.96 | 0.5749 | 0.6557 |
| 200 | 33408 | Metabolite - 12056 | 0.93 | 0.5755 | 0.6557 |
| 50 | 21630 | Metabolite - 08402 | 0.95 | 0.5756 | 0.6557 |
| 201 | 32587 | Metabolite - 02249 | 0.96 | 0.5796 | 0.6557 |
| 201 | 33972 | 10-nonadecenoate (19:1(n-9)) | 1.10 | 0.5803 | 0.6557 |
| 201 | 34527 | Metabolite - 12844 | 1.01 | 0.5842 | 0.6557 |
| 201 | 32867 | Metabolite - 11550 | 1.02 | 0.5846 | 0.6557 |
| 200 | 32738 | Metabolite - 11421 | 1.07 | 0.5892 | 0.6557 |
| 200 | 31530 | threonylphenylalanine | 1.09 | 0.5902 | 0.6557 |
| 50 | 16634 | Metabolite - 04357 | 1.03 | 0.5902 | 0.6557 |
| 50 | 18388 | Metabolite - 05491 | 1.06 | 0.5904 | 0.6557 |
| 201 | 18394 | theophylline | 1.08 | 0.5912 | 0.6557 |
| 201 | 32635 | Metabolite - 11318 | 1.12 | 0.5928 | 0.6557 |
| 50 | 33386 | Metabolite - 12035 | 0.94 | 0.5965 | 0.6578 |
| 200 | 33961 | 1-stearoylglycerophosphocholine | 0.91 | 0.6067 | 0.6599 |
| 200 | 22138 | homocitrulline | 0.98 | 0.6079 | 0.6599 |
| 50 | 1303 | malate | 0.94 | 0.6114 | 0.6599 |
| 50 | 30832 | Metabolite - 10814 | 1.03 | 0.6134 | 0.6599 |
| 50 | 22601 | Metabolite - 09044 | 1.05 | 0.6137 | 0.6599 |
| 50 | 21044 | 2-hydroxybutyrate (AHB) | 1.11 | 0.6146 | 0.6599 |
| 200 | 34420 | (des-arg9) Bradykinin | 0.75 | 0.6152 | 0.6599 |
| 200 | 32718 | phenylacetylglutamine | 0.87 | 0.6175 | 0.6599 |
| 200 | 32412 | butyrylcarnitine | 0.88 | 0.6197 | 0.6599 |
| 201 | 32560 | Metabolite - 07765 | 1.13 | 0.6205 | 0.6599 |
| 50 | 35844 | gamma,gamma-dimethylallyl pyrophosphate | 1.03 | 0.6207 | 0.6599 |
| 50 | 18868 | Metabolite - 05847 | 1.13 | 0.6264 | 0.6640 |
| 50 | 1549 | 3-hydroxy-2-methylpropanoate | 0.99 | 0.6303 | 0.6645 |
| 201 | 32762 | Metabolite - 11445 | 3.11 | 0.6310 | 0.6645 |
| 50 | 18349 | indolelactate | 0.98 | 0.6326 | 0.6645 |
| 201 | 33190 | Metabolite - 11845 | 1.08 | 0.6359 | 0.6660 |
| 200 | 35127 | pro-hydroxy-pro | 0.95 | 0.6408 | 0.6661 |
| 50 | 12789 | Metabolite - 03107 | 1.01 | 0.6414 | 0.6661 |
| 200 | 15500 | carnitine | 1.01 | 0.6420 | 0.6661 |
| 200 | 33084 | ADSGEGDFXAEGGGVR | 0.93 | 0.6435 | 0.6661 |
| 201 | 33638 | Metabolite - 12217 | 0.70 | 0.6457 | 0.6664 |
| 201 | 32850 | Metabolite - 11533 | 1.02 | 0.6485 | 0.6668 |
| 201 | 32549 | Metabolite - 02269 | 0.75 | 0.6498 | 0.6668 |
| 201 | 33971 | 10-heptadecenoate (17:1(n-7)) | 1.08 | 0.6532 | 0.6683 |
| 200 | 18369 | gamma-glutamylleucine | 1.08 | 0.6560 | 0.6683 |
| 201 | 36850 | octadecanedioate | 1.08 | 0.6578 | 0.6683 |
| 200 | 33519 | Metabolite - 12104 | 0.99 | 0.6588 | 0.6683 |
| 201 | 33442 | pseudouridine | 0.97 | 0.6643 | 0.6686 |
| 201 | 1302 | methionine | 0.98 | 0.6655 | 0.6686 |
| 200 | 34390 | 7-methylxanthine | 1.02 | 0.6689 | 0.6686 |
| 200 | 33957 | 1-heptadecanoylglycerophosphocholine | 1.18 | 0.6703 | 0.6686 |
| 200 | 33033 | Metabolite - 11689 | 0.50 | 0.6719 | 0.6686 |
| 200 | 33666 | Metabolite - 12244 | 0.97 | 0.6723 | 0.6686 |
| 201 | 1642 | caprate (10:0) | 1.03 | 0.6766 | 0.6686 |
| 201 | 34329 | Metabolite - 12719 | 0.95 | 0.6769 | 0.6686 |
| 201 | 1123 | inosine | 0.88 | 0.6770 | 0.6686 |
| 200 | 33142 | Metabolite - 11797 | 0.79 | 0.6795 | 0.6686 |
| 50 | 22600 | Metabolite - 09043 | 1.07 | 0.6815 | 0.6686 |
| 201 | 27716 | bilirubin | 1.09 | 0.6816 | 0.6686 |
| 200 | 53 | glutamine | 1.02 | 0.6926 | 0.6735 |
| 201 | 32839 | Metabolite - 11522 | 1.05 | 0.6935 | 0.6735 |
| 50 | 16837 | Metabolite - 04507 | 0.86 | 0.6943 | 0.6735 |
| 201 | 33203 | Metabolite - 11858 | 0.77 | 0.6956 | 0.6735 |
| 200 | 33131 | Metabolite - 11786 | 0.98 | 0.7012 | 0.6735 |
| 201 | 27672 | 3-indoxyl sulfate | 0.99 | 0.7025 | 0.6735 |
| 200 | 35433 | hydroxyisovaleroyl carnitine | 1.01 | 0.7040 | 0.6735 |
| 50 | 587 | gluconate | 0.92 | 0.7065 | 0.6735 |
| 50 | 1121 | margarate (17:0) | 0.95 | 0.7087 | 0.6735 |
| 200 | 15506 | choline | 1.01 | 0.7093 | 0.6735 |
| 200 | 32869 | Metabolite - 11552 | 1.04 | 0.7093 | 0.6735 |
| 200 | 32328 | hexanoylcarnitine | 0.98 | 0.7094 | 0.6735 |
| 200 | 60 | leucine | 1.02 | 0.7135 | 0.6755 |

TABLE 1-continued

Biomarkers to Distinguish Crohn's Disease From Ulcerative Colitis

| | | | | | |
|---|---|---|---|---|---|
| 200 | 32654 | 3-dehydrocarnitine | 1.01 | 0.7184 | 0.6776 |
| 200 | 2137 | biliverdin | 1.16 | 0.7195 | 0.6776 |
| 201 | 33973 | epiandrosterone sulfate | 1.06 | 0.7230 | 0.6791 |
| 50 | 25532 | Metabolite - 10413 | 1.06 | 0.7273 | 0.6808 |
| 200 | 36747 | deoxycarnitine | 0.98 | 0.7286 | 0.6808 |
| 200 | 32786 | Metabolite - 11469 | 0.55 | 0.7333 | 0.6823 |
| 50 | 16829 | pyroglutamine | 0.98 | 0.7350 | 0.6823 |
| 200 | 35153 | 1-docosahexaenoylglycerol (1-monodocosahexaenoin) | 0.97 | 0.7367 | 0.6823 |
| 200 | 36738 | gamma-glutamylglutamate | 0.90 | 0.7418 | 0.6823 |
| 201 | 33587 | eicosenoate [9 or 11, cis or trans] | 0.95 | 0.7424 | 0.6823 |
| 200 | 2730 | gamma-glutamylglutamine | 1.02 | 0.7438 | 0.6823 |
| 50 | 27856 | Metabolite - 10597 | 0.96 | 0.7470 | 0.6823 |
| 50 | 27722 | erythrose | 0.96 | 0.7472 | 0.6823 |
| 201 | 32418 | myristoleate (14:1(n-5)) | 1.11 | 0.7479 | 0.6823 |
| 50 | 12768 | Metabolite - 03088 | 0.89 | 0.7508 | 0.6823 |
| 50 | 15996 | aspartate | 1.07 | 0.7514 | 0.6823 |
| 201 | 34453 | Metabolite - 12776 | 1.01 | 0.7607 | 0.6880 |
| 200 | 1444 | pipecolate | 0.99 | 0.7615 | 0.6880 |
| 200 | 33515 | Metabolite - 12100 | 0.99 | 0.7729 | 0.6937 |
| 201 | 34344 | Metabolite - 12734 | 0.88 | 0.7737 | 0.6937 |
| 50 | 15365 | glycerol 3-phosphate (G3P) | 1.01 | 0.7835 | 0.6996 |
| 201 | 1604 | urate | 1.02 | 0.7842 | 0.6996 |
| 50 | 33369 | Metabolite - 12023 | 1.04 | 0.7898 | 0.7014 |
| 200 | 1573 | guanosine | 0.99 | 0.7901 | 0.7014 |
| 50 | 12782 | Metabolite - 03100 | 1.03 | 0.7984 | 0.7031 |
| 200 | 1898 | proline | 0.98 | 0.8000 | 0.7031 |
| 200 | 32393 | glutamylvaline | 1.02 | 0.8028 | 0.7038 |
| 200 | 32593 | heme | 0.94 | 0.8056 | 0.7038 |
| 201 | 35675 | 2-hydroxypalmitate | 0.97 | 0.8082 | 0.7038 |
| 200 | 19464 | testosterone | 1.04 | 0.8087 | 0.7038 |
| 201 | 34732 | isovalerate | 1.04 | 0.8206 | 0.7124 |
| 201 | 32758 | Metabolite - 11441 | 0.99 | 0.8280 | 0.7170 |
| 201 | 33198 | Metabolite - 11853 | 1.02 | 0.8311 | 0.7180 |
| 50 | 27273 | Metabolite - 10506 | 0.97 | 0.8355 | 0.7200 |
| 201 | 33963 | acetoacetate | 1.30 | 0.8415 | 0.7235 |
| 50 | 527 | lactate | 1.03 | 0.8453 | 0.7242 |
| 200 | 34407 | isovalerylcarnitine | 0.98 | 0.8576 | 0.7294 |
| 50 | 35252 | oxalacetic acid | 1.18 | 0.8596 | 0.7294 |
| 201 | 32197 | 3-(4-hydroxyphenyl)lactate | 0.96 | 0.8607 | 0.7294 |
| 200 | 34040 | Metabolite - 12510 | 0.90 | 0.8615 | 0.7294 |
| 200 | 33405 | Metabolite - 12053 | 0.59 | 0.8628 | 0.7294 |
| 200 | 34456 | gamma-glutamylisoleucine | 1.00 | 0.8652 | 0.7297 |
| 201 | 1105 | linoleate (18:2(n-6)) | 1.00 | 0.8754 | 0.7347 |
| 200 | 1649 | valine | 1.00 | 0.8768 | 0.7347 |
| 201 | 34400 | 1,7-dimethylurate | 1.00 | 0.8773 | 0.7347 |
| 50 | 19402 | Metabolite - 06346 | 0.97 | 0.8851 | 0.7391 |
| 50 | 22570 | Metabolite - 09033 | 0.97 | 0.8867 | 0.7391 |
| 200 | 33626 | Metabolite - 12205 | 1.03 | 0.8906 | 0.7405 |
| 50 | 4966 | xylitol | 0.92 | 0.8927 | 0.7406 |
| 201 | 21047 | 3-methyl-2-oxobutyrate | 1.03 | 0.8977 | 0.7415 |
| 200 | 32348 | 2-aminobutyrate | 1.02 | 0.9001 | 0.7415 |
| 50 | 33103 | Metabolite - 11758 | 0.97 | 0.9001 | 0.7415 |
| 50 | 19503 | sphingomyelin | 0.96 | 0.9047 | 0.7420 |
| 50 | 19363 | Metabolite - 06227 | 0.97 | 0.9086 | 0.7420 |
| 50 | 33453 | alpha-ketoglutarate | 0.81 | 0.9108 | 0.7420 |
| 200 | 34106 | Metabolite - 12542 | 0.96 | 0.9131 | 0.7420 |
| 201 | 33396 | Metabolite - 12045 | 1.12 | 0.9142 | 0.7420 |
| 201 | 33390 | Metabolite - 12039 | 0.70 | 0.9145 | 0.7420 |
| 201 | 34035 | linolenate [alpha or gamma; (18:3(n-3 or 6))] | 0.99 | 0.9154 | 0.7420 |
| 201 | 34062 | Metabolite - 12524 | 1.00 | 0.9176 | 0.7421 |
| 50 | 15737 | glycolate (hydroxyacetate) | 1.00 | 0.9248 | 0.7447 |
| 50 | 1481 | inositol 1-phosphate (I1P) | 0.96 | 0.9260 | 0.7447 |
| 201 | 34395 | 1-methylurate | 0.97 | 0.9271 | 0.7447 |
| 50 | 33089 | Metabolite - 11744 | 1.00 | 0.9327 | 0.7448 |
| 50 | 25602 | Metabolite - 10432 | 1.04 | 0.9335 | 0.7448 |
| 200 | 18392 | theobromine | 0.88 | 0.9350 | 0.7448 |
| 200 | 36752 | N6-acetyllysine | 0.98 | 0.9355 | 0.7448 |
| 200 | 34223 | Metabolite - 12629 | 0.65 | 0.9397 | 0.7464 |
| 200 | 33960 | 1-oleoylglycerophosphocholine | 1.03 | 0.9423 | 0.7468 |
| 50 | 17482 | Metabolite - 04874 | 0.98 | 0.9478 | 0.7482 |
| 50 | 32319 | trans-4-hydroxyproline | 0.99 | 0.9483 | 0.7482 |
| 200 | 32632 | Metabolite - 11315 | 0.99 | 0.9528 | 0.7486 |
| 201 | 33237 | Metabolite - 11892 | 0.95 | 0.9529 | 0.7486 |
| 200 | 33132 | Metabolite - 11787 | 1.00 | 0.9616 | 0.7532 |
| 201 | 31591 | androsterone sulfate | 0.85 | 0.9647 | 0.7532 |
| 201 | 32759 | Metabolite - 11442 | 1.00 | 0.9652 | 0.7532 |
| 50 | 542 | 3-hydroxybutyrate (BHBA) | 1.12 | 0.9718 | 0.7562 |

TABLE 1-continued

Biomarkers to Distinguish Crohn's Disease From Ulcerative Colitis

| | | | | | |
|---|---|---|---|---|---|
| 201 | 32769 | Metabolite - 11452 | 1.00 | 0.9799 | 0.7562 |
| 200 | 569 | caffeine | 0.85 | 0.9813 | 0.7562 |
| 200 | 33140 | Metabolite - 11795 | 0.95 | 0.9815 | 0.7562 |
| 200 | 33507 | Metabolite - 12092 | 1.07 | 0.9842 | 0.7562 |
| 200 | 32586 | Metabolite - 01327 | 0.96 | 0.9863 | 0.7562 |
| 200 | 32854 | Metabolite - 11537 | 0.97 | 0.9868 | 0.7562 |
| 50 | 18335 | quinate | 0.86 | 0.9900 | 0.7562 |
| 200 | 32857 | Metabolite - 11540 | 1.05 | 0.9910 | 0.7562 |
| 200 | 18254 | paraxanthine | 0.91 | 0.9923 | 0.7562 |
| 200 | 15140 | kynurenine | 0.99 | 0.9925 | 0.7562 |
| 201 | 33652 | Metabolite - 12230 | 0.74 | 0.9969 | 0.7568 |
| 201 | 32814 | Metabolite - 11497 | 1.00 | 0.9981 | 0.7568 |

Table 1C. Biomarkers to Distinguish Inactive Crohn's Disease from Inactive Ulcerative Colitis

| Lib ID | Comp ID | Biomarker | CD inactive/ UC inactive | p-value | q-value |
|---|---|---|---|---|---|
| 201 | 33901 | Metabolite - 12456 | 1.1807 | 0.0001 | 0.0309 |
| 200 | 33846 | indoleacetate | 1.2842 | 0.0001 | 0.0309 |
| 200 | 15753 | hippurate | 0.4892 | 0.0002 | 0.0314 |
| 201 | 31908 | 7-ketolithocholate | 1.1427 | 0.0003 | 0.0353 |
| 201 | 36807 | 6-beta-hydroxylithocholate | 1.8223 | 0.0005 | 0.0462 |
| 201 | 27531 | hyodeoxycholate | 1.6388 | 0.001 | 0.075 |
| 201 | 36776 | 7-alpha-hydroxy-3-oxo-4-cholestenoate (7-Hoca) | 1.1382 | 0.0017 | 0.1074 |
| 201 | 33415 | Metabolite - 12063 | 1.4229 | 0.0028 | 0.1422 |
| 50 | 63 | cholesterol | 0.8945 | 0.0029 | 0.1422 |
| 50 | 25459 | Metabolite - 10395 | 0.8904 | 0.0032 | 0.1422 |
| 50 | 18446 | Metabolite - 05524 | 0.8123 | 0.0038 | 0.1489 |
| 200 | 15743 | dimethylarginine | 0.9071 | 0.004 | 0.1489 |
| 201 | 32553 | phenol sulfate | 1.3833 | 0.0051 | 0.1782 |
| 201 | 1605 | ursodeoxycholate | 1.2972 | 0.0099 | 0.3194 |
| 201 | 33682 | Metabolite - 12260 | 0.8969 | 0.0118 | 0.3465 |
| 200 | 35153 | 1-docosahexaenoylglycerol (1-monodocosahexaenoin) | 0.8686 | 0.0125 | 0.3465 |
| 200 | 33801 | ADpSGEGDFXAEGGGVR | 0.9553 | 0.0134 | 0.3465 |
| 50 | 33488 | lathosterol | 1.0529 | 0.0141 | 0.3465 |
| 50 | 27278 | Metabolite - 10510 | 0.8748 | 0.0151 | 0.3465 |
| 201 | 35688 | 2-palmitoylglycerophosphoethanolamine | 1.1660 | 0.0154 | 0.3465 |
| 200 | 33165 | Metabolite - 11820 | 0.7816 | 0.0166 | 0.3524 |
| 201 | 15749 | 3-phenylpropionate (hydrocinnamate) | 0.9309 | 0.0172 | 0.3524 |
| 201 | 32561 | Metabolite - 11244 | 1.1470 | 0.0196 | 0.3827 |
| 50 | 1303 | malate | 0.8485 | 0.0217 | 0.4076 |
| 201 | 32877 | Metabolite - 11560 | 1.2540 | 0.0249 | 0.4359 |
| 201 | 32808 | Metabolite - 11491 | 1.3119 | 0.0253 | 0.4359 |
| 201 | 32827 | Metabolite - 11510 | 1.2646 | 0.0262 | 0.4359 |
| 200 | 33576 | Metabolite - 12159 | 0.9755 | 0.0294 | 0.4727 |
| 50 | 32405 | indolepropionate | 0.9647 | 0.0328 | 0.4843 |
| 50 | 18929 | Metabolite - 05907 | 0.9158 | 0.0332 | 0.4843 |
| 201 | 32562 | Metabolite - 11245 | 1.1952 | 0.0334 | 0.4843 |
| 201 | 32757 | Metabolite - 11440 | 1.2491 | 0.0368 | 0.5119 |
| 200 | 32198 | acetylcarnitine | 0.8911 | 0.0376 | 0.5119 |
| 200 | 33941 | decanoylcarnitine | 0.7663 | 0.0395 | 0.5226 |
| 201 | 12035 | pelargonate (9:0) | 1.0205 | 0.0407 | 0.5236 |
| 201 | 18281 | 2-hydroxyhippurate (salicylurate) | 0.4456 | 0.0437 | 0.545 |
| 201 | 32769 | Metabolite - 11452 | 1.2307 | 0.0448 | 0.545 |
| 201 | 31787 | 3-carboxMetabolite - 4-methyl-5-propyl-2-furanpropanoate (CMPF) | 1.1328 | 0.0469 | 0.5461 |
| 200 | 2730 | gamma-glutamylglutamine | 0.9698 | 0.0474 | 0.5461 |
| 200 | 33821 | 1-eicosatrienoylglycerophosphocholine | 0.8328 | 0.0491 | 0.5493 |
| 200 | 31522 | pyroglutamylglycine | 1.1255 | 0.0511 | 0.5493 |
| 50 | 25599 | Metabolite - 10429 | 0.9026 | 0.0513 | 0.5493 |
| 200 | 15990 | glycerophosphorylcholine (GPC) | 1.1132 | 0.0546 | 0.5655 |
| 200 | 32328 | hexanoylcarnitine | 0.7712 | 0.0596 | 0.5655 |
| 50 | 16866 | Metabolite - 04523 | 0.9110 | 0.0608 | 0.5655 |
| 200 | 32718 | phenylacetylglutamine | 1.3657 | 0.062 | 0.5655 |
| 50 | 36532 | urea | 0.8871 | 0.0622 | 0.5655 |
| 200 | 33936 | octanoylcarnitine | 0.7501 | 0.0633 | 0.5655 |
| 200 | 31530 | threonylphenylalanine | 0.7969 | 0.0635 | 0.5655 |
| 50 | 21630 | Metabolite - 08402 | 0.8491 | 0.064 | 0.5655 |
| 201 | 36097 | 4-acetaminophen sulfate | 0.3978 | 0.065 | 0.5655 |
| 201 | 32792 | Metabolite - 11475 | 1.1462 | 0.0654 | 0.5655 |
| 200 | 33150 | Metabolite - 11805 | 0.8374 | 0.0672 | 0.5703 |
| 50 | 12796 | Metabolite - 03114 | 0.7411 | 0.0688 | 0.5729 |

TABLE 1-continued

Biomarkers to Distinguish Crohn's Disease From Ulcerative Colitis

| | | | | | |
|---|---|---|---|---|---|
| 200 | 553 | cotinine | 0.8600 | 0.0701 | 0.5736 |
| 200 | 32857 | Metabolite - 11540 | 1.0726 | 0.072 | 0.5781 |
| 50 | 1572 | glycerate | 1.0166 | 0.0791 | 0.6008 |
| 50 | 1564 | citrate | 0.9566 | 0.0795 | 0.6008 |
| 50 | 11438 | phosphate | 0.9478 | 0.0813 | 0.6008 |
| 201 | 32398 | sebacate | 1.1396 | 0.0853 | 0.6008 |
| 201 | 1563 | chenodeoxycholate | 0.7649 | 0.0854 | 0.6008 |
| 201 | 12129 | beta-hydroxyisovalerate | 1.0783 | 0.0858 | 0.6008 |
| 200 | 15140 | kynurenine | 0.9264 | 0.0866 | 0.6008 |
| 50 | 21011 | Metabolite - 07888 | 0.9482 | 0.0868 | 0.6008 |
| 50 | 27256 | Metabolite - 10500 | 0.9253 | 0.0872 | 0.6008 |
| 201 | 36098 | 4-vinylphenol sulfate | 1.1954 | 0.0897 | 0.6008 |
| 201 | 34244 | Metabolite - 12644 | 1.0290 | 0.0927 | 0.6008 |
| 200 | 32348 | 2-aminobutyrate | 0.8717 | 0.0931 | 0.6008 |
| 201 | 15778 | benzoate | 1.0907 | 0.0945 | 0.6008 |
| 50 | 15365 | glycerol 3-phosphate (G3P) | 1.0399 | 0.0952 | 0.6008 |
| 201 | 32762 | Metabolite - 11445 | 0.9978 | 0.0962 | 0.6008 |
| 200 | 32586 | Metabolite - 01327 | 1.1287 | 0.0989 | 0.6095 |
| 50 | 33477 | erythronate | 0.9930 | 0.1042 | 0.6209 |
| 201 | 36095 | thymol sulfate | 1.1921 | 0.1049 | 0.6209 |
| 200 | 22154 | bradykinin | 1.0616 | 0.1061 | 0.6209 |
| 200 | 32654 | 3-dehydrocarnitine | 0.9261 | 0.1088 | 0.6209 |
| 200 | 34420 | bradykinin, des-arg(9) | 0.7231 | 0.1089 | 0.6209 |
| 50 | 15335 | mannitol | 0.7819 | 0.1093 | 0.6209 |
| 201 | 1644 | heptanoate (7:0) | 1.0571 | 0.1112 | 0.6209 |
| 50 | 32319 | trans-4-hydroxyproline | 1.0537 | 0.1118 | 0.6209 |
| 201 | 32616 | Metabolite - 11299 | 0.8450 | 0.114 | 0.6241 |
| 201 | 22842 | cholate | 1.3437 | 0.1152 | 0.6241 |
| 201 | 1114 | deoxycholate | 1.3834 | 0.1167 | 0.625 |
| 50 | 19576 | Metabolite - 06627 | 0.9916 | 0.1193 | 0.6252 |
| 201 | 33178 | Metabolite - 11833 | 0.3197 | 0.1195 | 0.6252 |
| 201 | 18467 | eicosapentaenoate (EPA; 20:5n3) | 1.0077 | 0.1267 | 0.6369 |
| 200 | 18369 | gamma-glutamylleucine | 0.9398 | 0.127 | 0.6369 |
| 200 | 32393 | glutamylvaline | 1.0034 | 0.127 | 0.6369 |
| 201 | 21047 | 3-methyl-2-oxobutyrate | 0.8826 | 0.1275 | 0.6369 |
| 50 | 27279 | Metabolite - 10511 | 0.8393 | 0.1289 | 0.6369 |
| 50 | 599 | pyruvate | 0.9497 | 0.1327 | 0.6489 |
| 50 | 17482 | Metabolite - 04874 | 0.9319 | 0.141 | 0.6703 |
| 200 | 33961 | 1-stearoylglycerophosphocholine | 0.8579 | 0.1432 | 0.6703 |
| 200 | 32738 | Metabolite - 11421 | 0.8439 | 0.1437 | 0.6703 |
| 200 | 15506 | choline | 1.0354 | 0.1453 | 0.6703 |
| 201 | 33221 | Metabolite - 11876 | 0.8661 | 0.1459 | 0.6703 |
| 201 | 32620 | Metabolite - 11303 | 1.1441 | 0.1461 | 0.6703 |
| 50 | 30282 | Metabolite - 10744 | 0.9030 | 0.1521 | 0.6892 |
| 201 | 32847 | Metabolite - 11530 | 1.0377 | 0.1532 | 0.6892 |
| 201 | 3147 | xanthine | 1.0797 | 0.1599 | 0.7121 |
| 200 | 1898 | proline | 1.0512 | 0.1624 | 0.7122 |
| 200 | 3127 | hypoxanthine | 1.1895 | 0.165 | 0.7122 |
| 50 | 35844 | gamma,gamma-dimethylallyl pyrophosphate | 0.8436 | 0.1652 | 0.7122 |
| 201 | 32867 | Metabolite - 11550 | 1.0131 | 0.1669 | 0.7122 |
| 201 | 32346 | glycochenodeoxycholate | 0.8743 | 0.1679 | 0.7122 |
| 200 | 33132 | Metabolite - 11787 | 0.9416 | 0.1742 | 0.7266 |
| 200 | 35160 | oleoylcarnitine | 0.9332 | 0.1745 | 0.7266 |
| 200 | 32735 | Metabolite - 01911 | 1.0451 | 0.1772 | 0.7299 |
| 200 | 33773 | Metabolite - 12348-retired-Na adduct of X-11476 | 1.0315 | 0.1785 | 0.7299 |
| 201 | 22116 | 4-methyl-2-oxopentanoate | 0.8970 | 0.1827 | 0.7401 |
| 201 | 20675 | 1,5-anhydroglucitol (1,5-AG) | 0.9915 | 0.1844 | 0.7406 |
| 50 | 32339 | alanine | 1.1098 | 0.1897 | 0.7551 |
| 201 | 32846 | Metabolite - 11529 | 1.1817 | 0.1918 | 0.7568 |
| 201 | 33198 | Metabolite - 11853 | 0.9985 | 0.2048 | 0.7889 |
| 201 | 1361 | pentadecanoate (15:0) | 0.8656 | 0.2052 | 0.7889 |
| 200 | 15500 | carnitine | 0.9537 | 0.2052 | 0.7889 |
| 200 | 27718 | creatine | 1.0541 | 0.2078 | 0.792 |
| 50 | 18283 | Metabolite - 05426 | 1.0856 | 0.212 | 0.796 |
| 201 | 15730 | suberate | 1.1350 | 0.2152 | 0.796 |
| 201 | 32760 | Metabolite - 11443 | 1.3289 | 0.2173 | 0.796 |
| 201 | 12261 | taurodeoxycholate | 1.4665 | 0.2176 | 0.796 |
| 50 | 21631 | Metabolite - 08403 | 0.8723 | 0.2196 | 0.796 |
| 200 | 33935 | piperine | 1.2611 | 0.2213 | 0.796 |
| 201 | 32767 | Metabolite - 11450 | 1.1637 | 0.2215 | 0.796 |
| 50 | 19363 | Metabolite - 06227 | 0.9459 | 0.223 | 0.796 |
| 50 | 33420 | gamma-tocopherol | 0.8790 | 0.2274 | 0.8053 |
| 201 | 32599 | Metabolite - 11282 | 1.2469 | 0.2292 | 0.8053 |
| 201 | 34214 | Metabolite - 12620 | 0.9365 | 0.2342 | 0.8164 |
| 201 | 19323 | docosahexaenoate (DHA; 22:6n3) | 1.0070 | 0.239 | 0.8269 |
| 201 | 1123 | inosine | 1.2565 | 0.2439 | 0.8293 |
| 201 | 27672 | 3-indoxyl sulfate | 1.2715 | 0.2448 | 0.8293 |

TABLE 1-continued

Biomarkers to Distinguish Crohn's Disease From Ulcerative Colitis

| | | | | | |
|---|---|---|---|---|---|
| 200 | 60 | leucine | 0.9196 | 0.2453 | 0.8293 |
| 50 | 1549 | 3-hydroxy-2-methylpropanoate | 0.8093 | 0.2528 | 0.8486 |
| 200 | 15630 | N-acetylornithine | 1.0134 | 0.2623 | 0.8573 |
| 201 | 36850 | taurolithocholate 3-sulfate | 1.2624 | 0.2646 | 0.8573 |
| 200 | 1649 | valine | 0.9420 | 0.2657 | 0.8573 |
| 200 | 513 | creatinine | 0.9737 | 0.2667 | 0.8573 |
| 200 | 1125 | isoleucine | 0.9167 | 0.2698 | 0.8573 |
| 50 | 15488 | acetylphosphate | 0.9769 | 0.2705 | 0.8573 |
| 50 | 19362 | Metabolite - 06226 | 0.9736 | 0.2743 | 0.8573 |
| 50 | 16120 | Metabolite - 04055 | 0.8134 | 0.2747 | 0.8573 |
| 201 | 33412 | Metabolite - 12060 | 0.8601 | 0.2755 | 0.8573 |
| 201 | 34453 | Metabolite - 12776 | 0.8707 | 0.2783 | 0.8573 |
| 200 | 2132 | citrulline | 0.9688 | 0.2783 | 0.8573 |
| 200 | 33507 | Metabolite - 12092 | 1.1254 | 0.2783 | 0.8573 |
| 50 | 584 | mannose | 0.9089 | 0.2805 | 0.8581 |
| 200 | 18357 | glycylvaline | 1.3453 | 0.2855 | 0.8676 |
| 200 | 33955 | 1-palmitoylglycerophosphocholine | 1.0162 | 0.2878 | 0.8686 |
| 200 | 32709 | Metabolite - 03056 | 0.8692 | 0.2938 | 0.869 |
| 200 | 32793 | Metabolite - 11476 | 1.0319 | 0.2942 | 0.869 |
| 50 | 16829 | pyroglutamine | 0.9818 | 0.2944 | 0.869 |
| 50 | 16634 | Metabolite - 04357 | 0.9237 | 0.2956 | 0.869 |
| 50 | 15996 | aspartate | 1.0497 | 0.2987 | 0.8722 |
| 50 | 12032 | 4-acetamidophenol | 0.5510 | 0.304 | 0.8798 |
| 200 | 22138 | homocitrulline | 0.9433 | 0.3071 | 0.8798 |
| 201 | 34530 | Metabolite - 12847 | 1.1023 | 0.3071 | 0.8798 |
| 201 | 32754 | Metabolite - 11437 | 0.8674 | 0.3134 | 0.8805 |
| 50 | 19396 | Metabolite - 06307 | 0.9014 | 0.3153 | 0.8805 |
| 50 | 22548 | Metabolite - 09026 | 0.9940 | 0.3169 | 0.8805 |
| 201 | 33391 | Metabolite - 12040 | 0.9333 | 0.3205 | 0.8805 |
| 201 | 32863 | Metabolite - 11546 | 1.0723 | 0.3249 | 0.8805 |
| 201 | 32759 | Metabolite - 11442 | 1.0469 | 0.328 | 0.8805 |
| 50 | 35835 | histidine | 1.0696 | 0.3317 | 0.8805 |
| 201 | 18362 | azelate (nonanedioate) | 1.1376 | 0.3349 | 0.8805 |
| 50 | 33386 | Metabolite - 12035-decomposition product of uric acid | 1.1351 | 0.3353 | 0.8805 |
| 50 | 33369 | Metabolite - 12023 | 0.7433 | 0.3371 | 0.8805 |
| 200 | 34368 | Metabolite - 12758 | 0.9541 | 0.3396 | 0.8805 |
| 200 | 32578 | Metabolite - 11261 | 0.8797 | 0.3448 | 0.8805 |
| 50 | 22570 | Metabolite - 09033 | 0.9840 | 0.3463 | 0.8805 |
| 50 | 30805 | Metabolite - 10810 | 0.9336 | 0.3473 | 0.8805 |
| 200 | 34366 | Metabolite - 12756 | 0.8883 | 0.3499 | 0.8805 |
| 200 | 33852 | 1-myristoylglycerophosphocholine | 1.0294 | 0.3501 | 0.8805 |
| 200 | 33228 | 1-arachidonoylglycerophosphocholine | 0.9978 | 0.351 | 0.8805 |
| 50 | 21044 | 2-hydroxybutyrate (AHB) | 0.7896 | 0.3552 | 0.8805 |
| 50 | 16837 | Metabolite - 04507 | 0.9705 | 0.3555 | 0.8805 |
| 201 | 32740 | Metabolite - 11423 | 0.9791 | 0.3576 | 0.8805 |
| 201 | 12067 | undecanoate (11:0) | 0.9983 | 0.3616 | 0.8805 |
| 50 | 22601 | Metabolite - 09044 | 0.9124 | 0.3651 | 0.8805 |
| 200 | 32401 | trigonelline (N'-methylnicotinate) | 0.9617 | 0.3652 | 0.8805 |
| 201 | 33969 | stearidonate (18:4n3) | 1.0936 | 0.3668 | 0.8805 |
| 201 | 34395 | 1-methylurate | 0.9838 | 0.3722 | 0.8805 |
| 50 | 27856 | Metabolite - 10597 | 1.0075 | 0.3754 | 0.8805 |
| 50 | 31266 | fructose | 0.9907 | 0.3759 | 0.8805 |
| 200 | 1494 | pyroglutamate (5-oxoproline) | 1.0543 | 0.3807 | 0.8805 |
| 50 | 33453 | alpha-ketoglutarate | 0.8762 | 0.3878 | 0.8805 |
| 201 | 33173 | Metabolite - 11828 | 0.4694 | 0.3882 | 0.8805 |
| 200 | 1284 | threonine | 1.0788 | 0.3892 | 0.8805 |
| 200 | 32780 | Metabolite - 11463 | 0.9413 | 0.3942 | 0.8805 |
| 201 | 34532 | Metabolite - 12849 | 1.1740 | 0.3975 | 0.8805 |
| 200 | 34419 | 1-linoleoylglycerophosphocholine | 0.9907 | 0.3982 | 0.8805 |
| 201 | 36850 | octadecanedioate | 0.8708 | 0.3992 | 0.8805 |
| 200 | 35433 | hydroxyisovaleroyl carnitine | 0.9586 | 0.3997 | 0.8805 |
| 50 | 1481 | inositol 1-phosphate (I1P) | 0.9375 | 0.409 | 0.8805 |
| 50 | 25609 | Metabolite - 10439 | 0.7507 | 0.4091 | 0.8805 |
| 50 | 1121 | margarate (17:0) | 0.9458 | 0.4113 | 0.8805 |
| 201 | 31912 | glycolithocholate | 1.2985 | 0.419 | 0.8805 |
| 201 | 32625 | Metabolite - 11308 | 0.9864 | 0.4204 | 0.8805 |
| 201 | 33652 | Metabolite - 12230 | 0.9104 | 0.423 | 0.8805 |
| 50 | 27722 | erythrose | 0.9416 | 0.4241 | 0.8805 |
| 200 | 32593 | heme | 1.1373 | 0.4263 | 0.8805 |
| 201 | 606 | uridine | 0.9799 | 0.4267 | 0.8805 |
| 50 | 4966 | xylitol | 1.0179 | 0.4269 | 0.8805 |
| 200 | 32776 | 2-methylbutyroylcarnitine | 0.9295 | 0.4278 | 0.8805 |
| 50 | 19414 | Metabolite - 06350 | 0.9638 | 0.4286 | 0.8805 |
| 200 | 32632 | Metabolite - 11315 | 1.0699 | 0.4325 | 0.8805 |
| 200 | 34456 | gamma-glutamylisoleucine | 1.0121 | 0.4344 | 0.8805 |
| 201 | 33884 | Metabolite - 12442 | 0.9456 | 0.4361 | 0.8805 |
| 201 | 34329 | Metabolite - 12719 | 0.9962 | 0.4361 | 0.8805 |

TABLE 1-continued

Biomarkers to Distinguish Crohn's Disease From Ulcerative Colitis

| | | | | | |
|---|---|---|---|---|---|
| 50 | 12774 | Metabolite - 03094 | 0.9731 | 0.4371 | 0.8805 |
| 50 | 25602 | Metabolite - 10432 | 0.8328 | 0.4399 | 0.8805 |
| 50 | 32315 | serine | 1.0597 | 0.4413 | 0.8805 |
| 50 | 18388 | Metabolite - 05491 | 0.9192 | 0.4417 | 0.8805 |
| 50 | 19503 | sphingomyelin | 0.9571 | 0.4434 | 0.8805 |
| 200 | 33960 | 1-oleoylglycerophosphocholine | 0.9904 | 0.4451 | 0.8805 |
| 201 | 32497 | 10-undecenoate (11:1n1) | 0.8743 | 0.4483 | 0.8805 |
| 201 | 34527 | Metabolite - 12844 | 0.8784 | 0.4494 | 0.8805 |
| 201 | 1336 | palmitate (16:0) | 0.9463 | 0.4494 | 0.8805 |
| 200 | 32644 | Metabolite - 11327 | 0.9406 | 0.4507 | 0.8805 |
| 200 | 34359 | Metabolite - 12749 | 0.9966 | 0.4513 | 0.8805 |
| 201 | 33390 | Metabolite - 12039 | 0.8595 | 0.4517 | 0.8805 |
| 50 | 527 | lactate | 0.9405 | 0.4543 | 0.8805 |
| 201 | 32388 | dodecanedioate | 1.0576 | 0.4545 | 0.8805 |
| 200 | 33441 | isobutyrylcarnitine | 1.0485 | 0.4558 | 0.8805 |
| 50 | 17064 | Metabolite - 04624-breakdown/conversion product of creatine/creatinine | 1.0412 | 0.4578 | 0.8805 |
| 200 | 32445 | 3-methylxanthine | 0.9712 | 0.4583 | 0.8805 |
| 200 | 33084 | ADSGEGDFXAEGGGVR | 0.9508 | 0.4596 | 0.8805 |
| 50 | 35832 | ornithine | 0.9350 | 0.4607 | 0.8805 |
| 200 | 36756 | leucylleucine | 1.1052 | 0.4653 | 0.8805 |
| 201 | 32758 | Metabolite - 11441 | 1.0593 | 0.467 | 0.8805 |
| 200 | 33131 | Metabolite - 11786 | 0.9304 | 0.4685 | 0.8805 |
| 201 | 27716 | bilirubin | 1.0921 | 0.4758 | 0.8805 |
| 200 | 33515 | Metabolite - 12100 | 0.9348 | 0.4759 | 0.8805 |
| 201 | 32839 | Metabolite - 11522 | 1.0795 | 0.4764 | 0.8805 |
| 201 | 33423 | p-acetamidophenylglucuronide | 0.6204 | 0.4786 | 0.8805 |
| 201 | 32910 | Metabolite - 11593 | 1.0227 | 0.4786 | 0.8805 |
| 200 | 32595 | Metabolite - 08893 | 0.9926 | 0.4795 | 0.8805 |
| 50 | 15122 | glycerol | 0.8905 | 0.4799 | 0.8805 |
| 200 | 33626 | Metabolite - 12205 | 1.0002 | 0.4809 | 0.8805 |
| 201 | 32489 | caproate (6:0) | 1.0085 | 0.4813 | 0.8805 |
| 201 | 32689 | Metabolite - 11372 | 1.0168 | 0.4813 | 0.8805 |
| 50 | 32369 | Metabolite - 11175 | 0.8864 | 0.4835 | 0.8805 |
| 201 | 33204 | Metabolite - 11859 | 1.0221 | 0.4853 | 0.8805 |
| 200 | 31534 | HXGXA | 0.3770 | 0.4887 | 0.8805 |
| 200 | 33363 | gamma-glutamylmethionine | 1.0401 | 0.491 | 0.8805 |
| 50 | 35839 | lysine | 1.0433 | 0.491 | 0.8805 |
| 200 | 33422 | gammaglutamylphenylalanine | 0.9356 | 0.4943 | 0.8805 |
| 200 | 54 | tryptophan | 0.9728 | 0.4973 | 0.8805 |
| 200 | 32458 | oleamide | 0.8152 | 0.5021 | 0.8805 |
| 50 | 32338 | glycine | 1.0680 | 0.5022 | 0.8805 |
| 201 | 33782 | Metabolite - 10346 | 1.0576 | 0.5036 | 0.8805 |
| 200 | 32518 | Metabolite - 11204 | 0.9746 | 0.504 | 0.8805 |
| 201 | 32814 | Metabolite - 11497 | 1.0049 | 0.5088 | 0.8805 |
| 201 | 31591 | androsterone sulfate | 1.1993 | 0.5148 | 0.8805 |
| 50 | 17391 | Metabolite - 04807 | 0.9221 | 0.5183 | 0.8805 |
| 50 | 587 | gluconate | 0.8595 | 0.5205 | 0.8805 |
| 201 | 33937 | alpha-hydroxyisovalerate | 0.9069 | 0.5223 | 0.8805 |
| 201 | 33254 | Metabolite - 11909 | 0.8202 | 0.5237 | 0.8805 |
| 201 | 1365 | myristate (14:0) | 0.9335 | 0.5242 | 0.8805 |
| 200 | 33140 | Metabolite - 11795 | 1.0408 | 0.5268 | 0.8805 |
| 50 | 34443 | Metabolite - 12773 | 0.8801 | 0.5281 | 0.8805 |
| 50 | 33089 | Metabolite - 11744 | 1.1073 | 0.5304 | 0.8805 |
| 201 | 33188 | Metabolite - 11843 | 0.9794 | 0.5332 | 0.8805 |
| 50 | 542 | 3-hydroxybutyrate (BHBA) | 1.0875 | 0.5334 | 0.8805 |
| 200 | 1712 | cortisol | 1.0822 | 0.5336 | 0.8805 |
| 201 | 15676 | 3-methyl-2-oxovalerate | 0.9154 | 0.537 | 0.8805 |
| 50 | 33103 | Metabolite - 11758-decomposition product of uric acid | 1.0339 | 0.5391 | 0.8805 |
| 201 | 1359 | oleate(18:1(n-9)) | 0.9350 | 0.5422 | 0.8805 |
| 200 | 2734 | gamma-glutamyltyrosine | 0.9372 | 0.5426 | 0.8805 |
| 50 | 1592 | N-acetylneuraminate | 0.8637 | 0.5431 | 0.8805 |
| 200 | 33364 | gamma-glutamylthreonine | 1.1020 | 0.5436 | 0.8805 |
| 200 | 34106 | Metabolite - 12542 | 1.2605 | 0.5464 | 0.8805 |
| 200 | 34384 | stachydrine | 1.1684 | 0.5465 | 0.8805 |
| 50 | 20489 | glucose | 0.9650 | 0.5488 | 0.8805 |
| 200 | 33405 | Metabolite - 12053 | 1.1013 | 0.5509 | 0.8805 |
| 201 | 1110 | arachidonate (20:4n6) | 1.0207 | 0.5526 | 0.8805 |
| 50 | 37015 | threonine | 1.0525 | 0.5527 | 0.8805 |
| 200 | 33509 | Metabolite - 12094 | 1.0141 | 0.554 | 0.8805 |
| 201 | 36099 | 4-ethylphenyl sulfate | 1.1238 | 0.5662 | 0.8898 |
| 201 | 1642 | caprate (10:0) | 0.9892 | 0.5663 | 0.8898 |
| 200 | 34365 | Metabolite - 12755 | 0.8806 | 0.5716 | 0.8898 |
| 201 | 32980 | adrenate (22:4n6) | 0.8759 | 0.5721 | 0.8898 |
| 201 | 33183 | Metabolite - 11838 | 0.6107 | 0.5768 | 0.8898 |
| 200 | 53 | glutamine | 0.9850 | 0.5771 | 0.8898 |
| 50 | 19490 | Metabolite - 06488 | 0.7398 | 0.5841 | 0.8898 |

TABLE 1-continued

Biomarkers to Distinguish Crohn's Disease From Ulcerative Colitis

| | | | | | |
|---|---|---|---|---|---|
| 201 | 18497 | taurocholate | 1.1912 | 0.5845 | 0.8898 |
| 50 | 15737 | glycolate (hydroxyacetate) | 1.0485 | 0.5848 | 0.8898 |
| 201 | 32635 | Metabolite - 11318 | 0.9652 | 0.5852 | 0.8898 |
| 201 | 33968 | 5-dodecenoate (12:1n7) | 0.9466 | 0.5896 | 0.8898 |
| 50 | 1659 | dehydroascorbate | 1.0247 | 0.5903 | 0.8898 |
| 50 | 20699 | erythritol | 0.9901 | 0.5914 | 0.8898 |
| 201 | 32850 | Metabolite - 11533 | 0.9793 | 0.593 | 0.8898 |
| 201 | 32753 | Metabolite - 09789 | 1.1578 | 0.5992 | 0.8898 |
| 200 | 1508 | pantothenate | 1.1534 | 0.6004 | 0.8898 |
| 200 | 36738 | gamma-glutamylglutamate | 1.1471 | 0.6041 | 0.8898 |
| 201 | 15677 | 3-methylhistidine | 1.1927 | 0.6054 | 0.8898 |
| 201 | 1105 | linoleate (18:2n6) | 0.9493 | 0.6065 | 0.8898 |
| 201 | 33190 | Metabolite - 11845 | 1.0800 | 0.6068 | 0.8898 |
| 200 | 34481 | Metabolite - 12798 | 1.1146 | 0.6075 | 0.8898 |
| 201 | 22130 | phenyllactate (PLA) | 1.0167 | 0.6137 | 0.8898 |
| 201 | 32425 | dehydroisoandrosterone sulfate (DHEA-S) | 1.0612 | 0.6148 | 0.8898 |
| 200 | 1573 | guanosine | 1.0320 | 0.6178 | 0.8898 |
| 201 | 33396 | Metabolite - 12045 | 0.8623 | 0.622 | 0.8898 |
| 50 | 25607 | Metabolite - 10437 | 0.8842 | 0.6246 | 0.8898 |
| 50 | 18335 | quinate | 0.8497 | 0.6259 | 0.8898 |
| 50 | 1561 | alpha-tocopherol | 0.9576 | 0.627 | 0.8898 |
| 200 | 18476 | glycocholate | 1.1495 | 0.6316 | 0.8898 |
| 201 | 33883 | Metabolite - 12441 | 0.8124 | 0.6369 | 0.8898 |
| 200 | 34417 | 1-hexadecylglycerophosphocholine | 1.0956 | 0.6372 | 0.8898 |
| 200 | 33138 | Metabolite - 11793 | 1.0221 | 0.6388 | 0.8898 |
| 200 | 2342 | serotonin (5HT) | 0.9928 | 0.6405 | 0.8898 |
| 200 | 32786 | Metabolite - 11469 | 1.0142 | 0.6428 | 0.8898 |
| 200 | 32412 | butyrylcarnitine | 0.8626 | 0.6449 | 0.8898 |
| 201 | 33353 | Metabolite - 12007 | 1.0577 | 0.6465 | 0.8898 |
| 50 | 32322 | glutamate | 0.9871 | 0.6523 | 0.8898 |
| 200 | 22175 | aspartylphenylalanine | 1.0214 | 0.6535 | 0.8898 |
| 200 | 1444 | pipecolate | 1.0973 | 0.6547 | 0.8898 |
| 200 | 33142 | Metabolite - 11797 | 0.9243 | 0.6558 | 0.8898 |
| 200 | 36752 | N6-acetyllysine | 0.9765 | 0.659 | 0.8898 |
| 200 | 64 | phenylalanine | 0.9748 | 0.6655 | 0.8898 |
| 201 | 32549 | Metabolite - 02269 | 1.1950 | 0.669 | 0.8898 |
| 50 | 21127 | 1-palmitoylglycerol | 1.0653 | 0.6691 | 0.8898 |
| 201 | 1302 | methionine | 1.0101 | 0.6698 | 0.8898 |
| 201 | 32695 | Metabolite - 11378 | 0.7388 | 0.6711 | 0.8898 |
| 200 | 31548 | DSGEGDFXAEGGGVR | 0.9350 | 0.672 | 0.8898 |
| 201 | 31555 | pyridoxate | 1.3383 | 0.6723 | 0.8898 |
| 200 | 33822 | 1-docosahexaenoylglycerophosphocholine | 1.0456 | 0.6736 | 0.8898 |
| 200 | 1769 | cortisone | 0.7384 | 0.6745 | 0.8898 |
| 50 | 35252 | oxalacetic acid | 0.9946 | 0.6758 | 0.8898 |
| 50 | 34283 | asparagine | 1.0508 | 0.6763 | 0.8898 |
| 201 | 32807 | Metabolite - 11490 | 1.3554 | 0.6767 | 0.8898 |
| 50 | 17627 | Metabolite - 04986 | 1.0561 | 0.6773 | 0.8898 |
| 201 | 33237 | Metabolite - 11892 | 0.9977 | 0.6812 | 0.8898 |
| 200 | 33957 | 1-heptadecanoylglycerophosphocholine | 0.9733 | 0.6821 | 0.8898 |
| 200 | 569 | caffeine | 1.0446 | 0.6841 | 0.8898 |
| 201 | 32761 | Metabolite - 11444 | 0.8981 | 0.6873 | 0.8898 |
| 201 | 35320 | catechol sulfate | 0.9640 | 0.688 | 0.8898 |
| 50 | 12593 | Metabolite - 02973 | 1.0340 | 0.6898 | 0.8898 |
| 50 | 22600 | Metabolite - 09043 | 0.8450 | 0.6907 | 0.8898 |
| 201 | 32504 | docosapentaenoate (n3 DPA; 22:5n3) | 0.9041 | 0.6914 | 0.8898 |
| 200 | 32452 | propionylcarnitine | 0.9119 | 0.6919 | 0.8898 |
| 50 | 35838 | beta-alanine | 0.9804 | 0.6922 | 0.8898 |
| 201 | 33195 | Metabolite - 11850 | 1.1588 | 0.6925 | 0.8898 |
| 201 | 32590 | Metabolite - 11273 | 0.9949 | 0.6989 | 0.8932 |
| 200 | 2137 | biliverdin | 1.0809 | 0.6991 | 0.8932 |
| 50 | 12782 | Metabolite - 03100 | 0.7966 | 0.7013 | 0.8935 |
| 200 | 32716 | Metabolite - 11399 | 0.9561 | 0.7048 | 0.8944 |
| 200 | 32675 | Metabolite - 03951 | 0.9629 | 0.706 | 0.8944 |
| 200 | 32978 | Metabolite - 11656 | 1.0024 | 0.7103 | 0.8968 |
| 201 | 33633 | Metabolite - 12212 | 0.7863 | 0.7119 | 0.8968 |
| 200 | 33510 | Metabolite - 12095 | 1.0384 | 0.7213 | 0.9062 |
| 50 | 16818 | Metabolite - 04495 | 0.9683 | 0.7237 | 0.9067 |
| 50 | 12768 | Metabolite - 03088 | 0.8843 | 0.7336 | 0.9162 |
| 201 | 32619 | Metabolite - 11302 | 1.0717 | 0.7362 | 0.9162 |
| 200 | 18254 | paraxanthine | 1.0201 | 0.7375 | 0.9162 |
| 50 | 24115 | Metabolite - 09752 | 0.9765 | 0.7404 | 0.9173 |
| 200 | 19464 | testosterone | 0.9537 | 0.7455 | 0.9186 |
| 201 | 32811 | Metabolite - 11494 | 0.9522 | 0.7496 | 0.9197 |
| 200 | 35127 | pro-hydroxy-pro | 1.0251 | 0.7509 | 0.9197 |
| 200 | 34390 | 7-methylxanthine | 0.8884 | 0.7542 | 0.9197 |
| 50 | 31618 | Metabolite - 10964 | 1.0672 | 0.7559 | 0.9197 |
| 200 | 34040 | Metabolite - 12510 | 1.0636 | 0.7567 | 0.9197 |
| 201 | 33973 | epiandrosterone sulfate | 1.1123 | 0.7613 | 0.9226 |

TABLE 1-continued

Biomarkers to Distinguish Crohn's Disease From Ulcerative Colitis

| | | | | | |
|---|---|---|---|---|---|
| 200 | 34223 | Metabolite - 12629 | 1.0654 | 0.7631 | 0.9226 |
| 50 | 18868 | Metabolite - 05847 | 0.9788 | 0.768 | 0.926 |
| 200 | 33519 | Metabolite - 12104 | 0.9968 | 0.77 | 0.926 |
| 201 | 34035 | linolenate [alpha or gamma; (18:3n3 or 6)] | 0.8805 | 0.7735 | 0.9261 |
| 201 | 33972 | 10-nonadecenoate (19:1n9) | 0.8115 | 0.7788 | 0.9261 |
| 201 | 1645 | laurate (12:0) | 1.0121 | 0.779 | 0.9261 |
| 200 | 1299 | tyrosine | 0.9376 | 0.7798 | 0.9261 |
| 201 | 32795 | Metabolite - 11478 | 0.9894 | 0.7804 | 0.9261 |
| 50 | 27273 | Metabolite - 10506 | 0.9832 | 0.7841 | 0.928 |
| 50 | 12781 | Metabolite - 03099 | 0.9885 | 0.7864 | 0.9283 |
| 50 | 16666 | Metabolite - 04365 | 0.9305 | 0.7998 | 0.9416 |
| 50 | 25532 | Metabolite - 10413 | 0.9505 | 0.8032 | 0.9432 |
| 50 | 19368 | Metabolite - 06267 | 0.9933 | 0.8067 | 0.9435 |
| 50 | 19934 | myo-inositol | 0.9630 | 0.8083 | 0.9435 |
| 50 | 31396 | Metabolite - 10887 | 0.9838 | 0.8098 | 0.9435 |
| 200 | 36747 | deoxycarnitine | 0.9880 | 0.8186 | 0.9445 |
| 201 | 33675 | Metabolite - 12253 | 0.8285 | 0.827 | 0.9445 |
| 50 | 16823 | Metabolite - 04500 | 0.8983 | 0.8295 | 0.9445 |
| 201 | 32558 | p-cresol sulfate | 1.4554 | 0.8296 | 0.9445 |
| 200 | 33033 | Metabolite - 11689 | 1.0078 | 0.8311 | 0.9445 |
| 201 | 34516 | Metabolite - 12833 | 0.8390 | 0.8322 | 0.9445 |
| 201 | 34732 | isovalerate | 1.1939 | 0.8377 | 0.9445 |
| 201 | 33203 | Metabolite - 11858 | 1.0194 | 0.8444 | 0.9445 |
| 201 | 32557 | Metabolite - 06126 | 1.5304 | 0.8449 | 0.9445 |
| 200 | 18392 | theobromine | 0.8487 | 0.849 | 0.9445 |
| 201 | 34400 | 1,7-dimethylurate | 0.9676 | 0.8495 | 0.9445 |
| 50 | 12789 | Metabolite - 03107 | 0.9355 | 0.8569 | 0.9445 |
| 200 | 32854 | Metabolite - 11537 | 1.0100 | 0.8575 | 0.9445 |
| 201 | 33225 | Metabolite - 11880 | 0.9000 | 0.8579 | 0.9445 |
| 200 | 33666 | Metabolite - 12244 | 1.0189 | 0.8618 | 0.9445 |
| 201 | 33442 | pseudouridine | 0.9906 | 0.8629 | 0.9445 |
| 200 | 35439 | glutaroyl carnitine | 1.0558 | 0.8662 | 0.9445 |
| 201 | 35675 | 2-hydroxypalmitate | 1.0291 | 0.8692 | 0.9445 |
| 200 | 33073 | cysteine-glutathione disulfide | 1.1404 | 0.8713 | 0.9445 |
| 50 | 35270 | Metabolite - 13496 | 1.0118 | 0.8744 | 0.9445 |
| 200 | 33954 | glycylphenylalanine | 0.9279 | 0.8748 | 0.9445 |
| 201 | 32492 | caprylate (8:0) | 1.0265 | 0.8751 | 0.9445 |
| 50 | 27710 | N-acetylglycine | 0.9675 | 0.8776 | 0.9445 |
| 50 | 16821 | Metabolite - 04498 | 0.9702 | 0.8791 | 0.9445 |
| 201 | 33447 | palmitoleate (16:1n7) | 0.8464 | 0.8823 | 0.9445 |
| 201 | 18494 | taurochenodeoxycholate | 1.0646 | 0.8862 | 0.9445 |
| 200 | 34407 | isovalerylcarnitine | 0.9349 | 0.8871 | 0.9445 |
| 50 | 19402 | Metabolite - 06346 | 0.9753 | 0.8896 | 0.9445 |
| 50 | 31453 | cysteine | 0.9643 | 0.892 | 0.9445 |
| 201 | 32855 | Metabolite - 11538 | 1.0631 | 0.8932 | 0.9445 |
| 50 | 1107 | allantoin | 0.8521 | 0.894 | 0.9445 |
| 200 | 33939 | N-acetylthreonine | 1.0086 | 0.8941 | 0.9445 |
| 201 | 33627 | Metabolite - 12206 | 1.0595 | 0.8986 | 0.9445 |
| 50 | 27738 | threonate | 1.1310 | 0.8988 | 0.9445 |
| 201 | 33389 | Metabolite - 12038 | 0.9366 | 0.9016 | 0.9445 |
| 50 | 18349 | indolelactate | 1.0515 | 0.9024 | 0.9445 |
| 200 | 34253 | Metabolite - 12650 | 1.1334 | 0.9028 | 0.9445 |
| 200 | 32869 | Metabolite - 11552 | 0.9701 | 0.9093 | 0.9445 |
| 50 | 34441 | Metabolite - 12771 | 0.9363 | 0.9098 | 0.9445 |
| 50 | 21188 | 1-stearoylglycerol | 0.8702 | 0.9133 | 0.9445 |
| 201 | 1358 | stearate (18:0) | 0.9227 | 0.9138 | 0.9445 |
| 50 | 31617 | Metabolite - 10963 | 1.0403 | 0.915 | 0.9445 |
| 50 | 22649 | Metabolite - 09108 | 1.0701 | 0.915 | 0.9445 |
| 201 | 33206 | Metabolite - 11861 | 1.0126 | 0.9161 | 0.9445 |
| 50 | 35831 | glutamine-4 | 0.9929 | 0.9164 | 0.9445 |
| 201 | 32508 | Metabolite - 11231 | 0.9508 | 0.9192 | 0.9445 |
| 200 | 32836 | HWESASXX | 0.7941 | 0.9202 | 0.9445 |
| 201 | 34062 | Metabolite - 12524 | 0.9684 | 0.9222 | 0.9445 |
| 200 | 3141 | betaine | 0.9836 | 0.9245 | 0.9445 |
| 50 | 30832 | Metabolite - 10814 | 0.9095 | 0.9251 | 0.9445 |
| 201 | 33963 | acetoacetate | 0.8586 | 0.9266 | 0.9445 |
| 201 | 33194 | Metabolite - 11849 | 1.2499 | 0.9267 | 0.9445 |
| 201 | 32560 | Metabolite - 07765 | 0.8757 | 0.9283 | 0.9445 |
| 200 | 32698 | Metabolite - 11381 | 0.9421 | 0.9309 | 0.9451 |
| 201 | 1604 | urate | 1.0145 | 0.938 | 0.9497 |
| 50 | 37016 | arginine | 1.0101 | 0.9443 | 0.9497 |
| 50 | 35271 | Metabolite - 13497 | 1.0170 | 0.9472 | 0.9497 |
| 201 | 18394 | theophylline | 0.9775 | 0.9554 | 0.9497 |
| 200 | 33403 | Metabolite - 12051 | 0.9473 | 0.9557 | 0.9497 |
| 200 | 32572 | Metabolite - 11255 | 1.1527 | 0.9593 | 0.9497 |
| 201 | 33971 | 10-heptadecenoate (17:1n7) | 0.8664 | 0.9605 | 0.9497 |
| 201 | 32748 | Metabolite - 11431 | 0.8782 | 0.9605 | 0.9497 |
| 201 | 32501 | dihomo-alpha-linolenate (20:3n3) | 0.9378 | 0.9613 | 0.9497 |

TABLE 1-continued

Biomarkers to Distinguish Crohn's Disease From Ulcerative Colitis

| | | | | | |
|---|---|---|---|---|---|
| 201 | 34344 | Metabolite - 12734 | 1.0637 | 0.9635 | 0.9497 |
| 200 | 31536 | N-(2-furoyl)glycine | 0.9095 | 0.9663 | 0.9497 |
| 201 | 34674 | Metabolite - 12990 | 1.0031 | 0.9681 | 0.9497 |
| 200 | 33408 | Metabolite - 12056 | 0.8357 | 0.9688 | 0.9497 |
| 200 | 32830 | Metabolite - 11513 | 1.1112 | 0.9694 | 0.9497 |
| 201 | 34201 | 1-stearoylglycerophosphoinositol | 0.9672 | 0.9704 | 0.9497 |
| 201 | 32197 | 3-(4-hydroxyphenyl)lactate | 0.9040 | 0.9709 | 0.9497 |
| 50 | 16855 | Metabolite - 04515 | 1.3268 | 0.9714 | 0.9497 |
| 201 | 32418 | myristoleate (14:1n5) | 0.8202 | 0.979 | 0.9513 |
| 201 | 32815 | Metabolite - 11498 | 0.9654 | 0.9794 | 0.9513 |
| 201 | 34314 | Metabolite - 12704 | 0.9662 | 0.9892 | 0.9553 |
| 200 | 33230 | 1-palmitoleoylglycerophosphocholine | 0.9194 | 0.9898 | 0.9553 |
| 201 | 17805 | dihomo-linolenate (20:2n6) | 0.9351 | 0.9903 | 0.9553 |
| 201 | 33587 | eicosenoate (20:1n9 or 11) | 0.9286 | 0.992 | 0.9553 |
| 201 | 33638 | Metabolite - 12217 | 0.9539 | 0.9956 | 0.9566 |
| 201 | 32587 | Metabolite - 02249 | 0.9606 | 0.9975 | 0.9566 |

Example 2

Biomarker Metabolites for Active Vs. Inactive Crohn's Disease

Biomarkers were discovered by (1) analyzing blood samples drawn from different groups of human subjects to determine the levels of metabolites in the samples and then (2) statistically analyzing the results to determine those metabolites that were differentially present in the two groups.

The blood samples used for the analysis were from subjects with active Crohn's disease (N=50) and subjects with inactive Crohn's disease (N=51). After the levels of metabolites were determined, the data was analyzed using univariate T-tests (i.e., Welch's T-test).

T-tests were used to determine differences in the mean levels of metabolites between the two populations (i.e., active Crohn's disease vs. inactive Crohn's disease). Random Forest analysis was performed to identify the metabolites that are most important to distinguish the two groups of subjects and thereby useful to identify a subject as having active Crohn's disease or as having inactive Crohn's disease. These biomarkers are useful to track Crohn's disease progression/regression, to monitor treatment effects, to monitor clinical trials of therapeutic agents or Crohn's disease treatments.

Biomarkers

As listed below in Table 2, biomarkers were discovered that were differentially present between samples from Crohn's disease subjects and ulcerative colitis subjects. Table 2 lists biomarkers that were discovered that were differentially present between samples from inflammatory bowel disease subjects and subjects in remission from inflammatory bowel disease. Table 2 lists biomarkers that were discovered that were differentially present between samples from subjects with inactive (i.e., in remission) from Crohn's disease and subjects with active Crohn's disease.

Table 2 includes, includes, for each listed biomarker, the p-value and the q-value determined in the statistical analysis of the data concerning the biomarkers and the ratio between the mean in the active Crohn's disease as compared to inactive Crohn's disease mean. Library indicates the chemical library that was used to identify the compounds. The number 50 refers to the GC library and the numbers 200 and 201 refer to the LC library. "Comp ID" refers to the internal chemical database identification number for that compound.

TABLE 2

Biomarkers to Distinguish Active from Inactive Crohn's Disease

| Library | Comp ID | Biomarker | CD Active/ CD Inactive | p-value | q-value |
|---|---|---|---|---|---|
| 201 | 32558 | p-cresol sulfate | 0.42 | 0.0002 | 0.0690 |
| 50 | 584 | mannose | 1.30 | 0.0007 | 0.0963 |
| 50 | 1670 | urea | 0.79 | 0.0010 | 0.0963 |
| 200 | 32857 | Metabolite - 11540 | 0.75 | 0.0012 | 0.0963 |
| 50 | 25607 | Metabolite - 10437 | 0.78 | 0.0029 | 0.1762 |
| 200 | 33150 | Metabolite - 11805 | 1.43 | 0.0044 | 0.2306 |
| 201 | 15677 | 3-methylhistidine | 0.51 | 0.0057 | 0.2524 |
| 50 | 19934 | myo-inositol | 0.84 | 0.0066 | 0.2524 |
| 200 | 33441 | isobutyrylcarnitine | 0.67 | 0.0072 | 0.2524 |
| 50 | 16823 | Metabolite - 04500 | 0.48 | 0.0083 | 0.2524 |
| 201 | 32846 | Metabolite - 11529 | 0.55 | 0.0089 | 0.2524 |
| 201 | 33627 | Metabolite - 12206 | 0.82 | 0.0089 | 0.2524 |
| 201 | 27672 | 3-indoxyl sulfate | 0.70 | 0.0106 | 0.2675 |
| 50 | 35832 | ornithine | 0.72 | 0.0109 | 0.2675 |
| 50 | 19503 | sphingomyelin | 1.14 | 0.0125 | 0.2872 |
| 201 | 34314 | Metabolite - 12704 | 0.88 | 0.0141 | 0.3017 |
| 200 | 33073 | cysteine-glutathione disulfide | 0.72 | 0.0148 | 0.3017 |
| 200 | 32328 | hexanoylcarnitine | 1.24 | 0.0179 | 0.3274 |
| 201 | 32753 | Metabolite - 09789 | 0.70 | 0.0179 | 0.3274 |
| 201 | 32863 | Metabolite - 11546 | 0.52 | 0.0196 | 0.3274 |
| 201 | 36850 | taurolithocholate 3-sulfate | 0.40 | 0.0196 | 0.3274 |

TABLE 2-continued

Biomarkers to Distinguish Active from Inactive Crohn's Disease

| Library | Comp ID | Biomarker | CD Active/ CD Inactive | p-value | q-value |
|---|---|---|---|---|---|
| 201 | 32549 | Metabolite - 02269 | 0.48 | 0.0206 | 0.3278 |
| 200 | 15506 | choline | 0.92 | 0.0230 | 0.3435 |
| 201 | 32557 | Metabolite - 06126 | 0.39 | 0.0256 | 0.3435 |
| 50 | 33420 | gamma-tocopherol | 1.26 | 0.0261 | 0.3435 |
| 200 | 18392 | theobromine | 0.71 | 0.0278 | 0.3435 |
| 200 | 33936 | octanoylcarnitine | 1.25 | 0.0279 | 0.3435 |
| 200 | 1508 | pantothenate | 0.80 | 0.0280 | 0.3435 |
| 50 | 1564 | citrate | 0.87 | 0.0281 | 0.3435 |
| 50 | 27738 | threonate | 0.65 | 0.0317 | 0.3732 |
| 50 | 35270 | Metabolite - 13496 | 0.95 | 0.0360 | 0.3732 |
| 201 | 32553 | phenol sulfate | 0.72 | 0.0370 | 0.3732 |
| 201 | 33675 | Metabolite - 12253 | 0.68 | 0.0391 | 0.3732 |
| 200 | 32718 | phenylacetylglutamine | 0.61 | 0.0399 | 0.3732 |
| 200 | 32786 | Metabolite - 11469 | 0.55 | 0.0402 | 0.3732 |
| 201 | 59 | histidine | 0.90 | 0.0403 | 0.3732 |
| 50 | 16855 | Metabolite - 04515 | 0.49 | 0.0407 | 0.3732 |
| 50 | 32319 | trans-4-hydroxyproline | 0.82 | 0.0414 | 0.3732 |
| 200 | 32572 | Metabolite - 11255 | 0.60 | 0.0420 | 0.3732 |
| 201 | 33221 | Metabolite - 11876 | 0.76 | 0.0431 | 0.3732 |
| 201 | 33237 | Metabolite - 11892 | 1.10 | 0.0440 | 0.3732 |
| 200 | 33941 | decanoylcarnitine | 1.33 | 0.0443 | 0.3732 |
| 200 | 32445 | 3-methylxanthine | 0.88 | 0.0452 | 0.3732 |
| 50 | 27279 | Metabolite - 10511 | 1.12 | 0.0458 | 0.3732 |
| 201 | 36095 | thymol sulfate | 0.38 | 0.0485 | 0.3839 |
| 200 | 32854 | Metabolite - 11537 | 0.84 | 0.0492 | 0.3839 |
| 201 | 33225 | Metabolite - 11880 | 0.84 | 0.0527 | 0.4001 |
| 201 | 32769 | Metabolite - 11452 | 0.64 | 0.0552 | 0.4001 |
| 50 | 20489 | glucose | 1.09 | 0.0556 | 0.4001 |
| 50 | 15488 | acetylphosphate | 0.93 | 0.0576 | 0.4001 |
| 50 | 11438 | phosphate | 0.94 | 0.0578 | 0.4001 |
| 200 | 33422 | gammaglutamylphenylalanine | 1.11 | 0.0616 | 0.4082 |
| 200 | 32830 | Metabolite - 11513 | 0.69 | 0.0619 | 0.4082 |
| 50 | 15122 | glycerol | 1.17 | 0.0632 | 0.4082 |
| 201 | 34344 | Metabolite - 12734 | 0.70 | 0.0634 | 0.4082 |
| 201 | 32757 | Metabolite - 11440 | 1.25 | 0.0691 | 0.4308 |
| 50 | 35838 | beta-alanine | 0.64 | 0.0702 | 0.4308 |
| 201 | 35675 | 2-hydroxypalmitate | 0.91 | 0.0705 | 0.4308 |
| 50 | 25459 | Metabolite - 10395 | 0.90 | 0.0731 | 0.4396 |
| 200 | 34407 | isovalerylcarnitine | 0.83 | 0.0776 | 0.4539 |
| 50 | 31453 | cysteine | 0.77 | 0.0789 | 0.4539 |
| 201 | 34062 | Metabolite - 12524 | 0.93 | 0.0792 | 0.4539 |
| 201 | 33884 | Metabolite - 12442 | 1.25 | 0.0819 | 0.4618 |
| 200 | 34390 | 7-methylxanthine | 0.75 | 0.0834 | 0.4626 |
| 50 | 16821 | Metabolite - 04498 | 0.89 | 0.0845 | 0.4626 |
| 50 | 18283 | Metabolite - 05426 | 0.77 | 0.0858 | 0.4626 |
| 200 | 32738 | Metabolite - 11421 | 1.17 | 0.0888 | 0.4710 |
| 201 | 32758 | Metabolite - 11441 | 0.81 | 0.0899 | 0.4710 |
| 201 | 33633 | Metabolite - 12212 | 0.60 | 0.0938 | 0.4824 |
| 201 | 1605 | ursodeoxycholate | 0.91 | 0.0947 | 0.4824 |
| 201 | 1302 | methionine | 0.90 | 0.0967 | 0.4857 |
| 201 | 32620 | Metabolite - 11303 | 0.66 | 0.1028 | 0.5040 |
| 201 | 31555 | pyridoxate | 0.66 | 0.1032 | 0.5040 |
| 200 | 34384 | stachydrine | 0.62 | 0.1045 | 0.5040 |
| 200 | 36747 | deoxycarnitine | 0.94 | 0.1062 | 0.5058 |
| 201 | 34732 | isovalerate | 0.85 | 0.1087 | 0.5112 |
| 200 | 54 | tryptophan | 0.93 | 0.1129 | 0.5182 |
| 201 | 33198 | Metabolite - 11853 | 0.95 | 0.1134 | 0.5182 |
| 201 | 36807 | 6-beta-hydroxylithocholate | 0.49 | 0.1176 | 0.5182 |
| 200 | 33509 | Metabolite - 12094 | 0.68 | 0.1180 | 0.5182 |
| 200 | 33510 | Metabolite - 12095 | 0.78 | 0.1184 | 0.5182 |
| 200 | 34253 | Metabolite - 12650 | 0.79 | 0.1187 | 0.5182 |
| 200 | 33084 | ADSGEGDFXAEGGGVR | 1.17 | 0.1225 | 0.5284 |
| 200 | 34419 | 1-linoleoylglycerophosphocholine | 0.88 | 0.1278 | 0.5314 |
| 201 | 31787 | 3-carboxy-4-methyl-5-propyl-2-furanpropanoate (CMPF) | 0.59 | 0.1285 | 0.5314 |
| 201 | 606 | uridine | 1.11 | 0.1322 | 0.5314 |
| 50 | 12593 | Metabolite - 02973 | 1.04 | 0.1344 | 0.5314 |
| 50 | 19363 | Metabolite - 06227 | 0.93 | 0.1352 | 0.5314 |
| 201 | 33447 | palmitoleate (16:1(n-7)) | 1.33 | 0.1372 | 0.5314 |
| 200 | 32836 | HWESASXX | 0.61 | 0.1386 | 0.5314 |
| 201 | 15778 | benzoate | 0.92 | 0.1410 | 0.5314 |
| 50 | 12768 | Metabolite - 03088 | 1.13 | 0.1419 | 0.5314 |
| 50 | 1561 | alpha-tocopherol | 0.89 | 0.1429 | 0.5314 |
| 50 | 587 | gluconate | 1.11 | 0.1440 | 0.5314 |

TABLE 2-continued

Biomarkers to Distinguish Active from Inactive Crohn's Disease

| Library | Comp ID | Biomarker | CD Active/ CD Inactive | p-value | q-value |
|---|---|---|---|---|---|
| 50 | 25599 | Metabolite - 10429 | 0.92 | 0.1470 | 0.5314 |
| 201 | 32561 | Metabolite - 11244 | 1.20 | 0.1506 | 0.5314 |
| 201 | 32759 | Metabolite - 11442 | 0.81 | 0.1516 | 0.5314 |
| 200 | 32593 | heme | 0.74 | 0.1540 | 0.5314 |
| 200 | 32869 | Metabolite - 11552 | 0.92 | 0.1540 | 0.5314 |
| 200 | 1573 | guanosine | 1.19 | 0.1564 | 0.5314 |
| 201 | 32689 | Metabolite - 11372 | 0.87 | 0.1569 | 0.5314 |
| 50 | 37015 | threonine | 0.92 | 0.1570 | 0.5314 |
| 50 | 33386 | Metabolite - 12035 | 0.81 | 0.1570 | 0.5314 |
| 201 | 33391 | Metabolite - 12040 | 0.82 | 0.1574 | 0.5314 |
| 200 | 22175 | aspartylphenylalanine | 1.13 | 0.1589 | 0.5314 |
| 200 | 33822 | Metabolite - 12394 | 0.81 | 0.1591 | 0.5314 |
| 50 | 18349 | indolelactate | 0.89 | 0.1617 | 0.5314 |
| 201 | 20675 | 1,5-anhydroglucitol (1,5-AG) | 0.89 | 0.1628 | 0.5314 |
| 50 | 1572 | glycerate | 0.86 | 0.1651 | 0.5314 |
| 50 | 25609 | Metabolite - 10439 | 0.86 | 0.1669 | 0.5314 |
| 201 | 32980 | adrenate (22:4(n-6)) | 1.16 | 0.1703 | 0.5314 |
| 200 | 15630 | N-acetylornithine | 0.89 | 0.1710 | 0.5314 |
| 50 | 27278 | Metabolite - 10510 | 0.89 | 0.1714 | 0.5314 |
| 201 | 32418 | myristoleate (14:1(n-5)) | 1.37 | 0.1752 | 0.5314 |
| 201 | 32754 | Metabolite - 11437 | 0.50 | 0.1754 | 0.5314 |
| 50 | 15365 | glycerol 3-phosphate (G3P) | 0.90 | 0.1755 | 0.5314 |
| 200 | 33364 | gamma-glutamylthreonine | 0.91 | 0.1766 | 0.5314 |
| 200 | 15500 | carnitine | 1.04 | 0.1777 | 0.5314 |
| 201 | 32839 | Metabolite - 11522 | 0.84 | 0.1784 | 0.5314 |
| 201 | 34530 | Metabolite - 12847 | 0.68 | 0.1792 | 0.5314 |
| 201 | 36098 | 4-vinylphenol sulfate | 0.66 | 0.1840 | 0.5314 |
| 201 | 33971 | 10-heptadecenoate (17:1(n-7)) | 1.35 | 0.1845 | 0.5314 |
| 50 | 19402 | Metabolite - 06346 | 0.92 | 0.1864 | 0.5314 |
| 201 | 36850 | octadecanedioate | 1.25 | 0.1865 | 0.5314 |
| 201 | 32616 | Metabolite - 11299 | 0.73 | 0.1889 | 0.5314 |
| 201 | 32855 | Metabolite - 11538 | 0.87 | 0.1889 | 0.5314 |
| 201 | 12035 | pelargonate (9:0) | 0.97 | 0.1903 | 0.5314 |
| 201 | 33353 | Metabolite - 12007 | 0.90 | 0.1929 | 0.5314 |
| 201 | 1361 | pentadecanoate (15:0) | 0.92 | 0.1931 | 0.5314 |
| 50 | 33103 | Metabolite - 11758 | 0.82 | 0.1989 | 0.5314 |
| 50 | 35836 | lysine | 0.83 | 0.1991 | 0.5314 |
| 200 | 33935 | piperine | 0.68 | 0.2005 | 0.5314 |
| 201 | 34532 | Metabolite - 12849 | 0.72 | 0.2006 | 0.5314 |
| 200 | 33846 | indoleacetate | 0.87 | 0.2012 | 0.5314 |
| 200 | 1649 | valine | 0.95 | 0.2017 | 0.5314 |
| 50 | 27273 | Metabolite - 10506 | 1.05 | 0.2029 | 0.5314 |
| 201 | 32795 | Metabolite - 11478 | 0.84 | 0.2051 | 0.5334 |
| 201 | 18281 | 2-hydroxyhippurate (salicylurate) | 2.02 | 0.2086 | 0.5388 |
| 201 | 32587 | Metabolite - 02249 | 0.89 | 0.2109 | 0.5409 |
| 50 | 21011 | Metabolite - 07888 | 0.94 | 0.2148 | 0.5471 |
| 200 | 34365 | Metabolite - 12755 | 1.26 | 0.2181 | 0.5482 |
| 50 | 18446 | Metabolite - 05524 | 1.12 | 0.2187 | 0.5482 |
| 201 | 32815 | Metabolite - 11498 | 1.09 | 0.2198 | 0.5482 |
| 201 | 32590 | Metabolite - 11273 | 1.14 | 0.2235 | 0.5493 |
| 50 | 32405 | 3-indolepropionate | 0.79 | 0.2246 | 0.5493 |
| 50 | 30805 | Metabolite - 10810 | 0.94 | 0.2261 | 0.5493 |
| 200 | 33228 | Metabolite - 11883 | 0.91 | 0.2269 | 0.5493 |
| 200 | 36752 | N6-acetyllysine | 0.91 | 0.2300 | 0.5493 |
| 201 | 32562 | Metabolite - 11245 | 1.16 | 0.2303 | 0.5493 |
| 50 | 599 | pyruvate | 1.09 | 0.2307 | 0.5493 |
| 201 | 17805 | dihomolinolenate (20:2(n-6)) | 1.17 | 0.2371 | 0.5569 |
| 200 | 33666 | Metabolite - 12244 | 0.93 | 0.2384 | 0.5569 |
| 201 | 1359 | oleate(18:1(n-9)) | 1.14 | 0.2402 | 0.5575 |
| 201 | 12067 | undecanoate (11:0) | 0.95 | 0.2432 | 0.5575 |
| 50 | 19396 | Metabolite - 06307 | 1.12 | 0.2432 | 0.5575 |
| 201 | 32497 | 10c-undecenoate | 1.08 | 0.2460 | 0.5576 |
| 200 | 32672 | pyroglutamine | 1.28 | 0.2463 | 0.5576 |
| 201 | 19323 | docosahexaenoate (DHA; 22:6(n-3)) | 0.86 | 0.2504 | 0.5633 |
| 201 | 32548 | Metabolite - 11231 | 1.08 | 0.2617 | 0.5841 |
| 201 | 18497 | taurocholate | 0.47 | 0.2633 | 0.5841 |
| 201 | 18467 | eicosapentaenoate (EPA; 20:5(n-3)) | 0.84 | 0.2661 | 0.5841 |
| 50 | 16818 | Metabolite - 04495 | 0.89 | 0.2666 | 0.5841 |
| 50 | 31396 | Metabolite - 10887 | 0.94 | 0.2676 | 0.5841 |
| 201 | 33412 | Metabolite - 12060 | 1.13 | 0.2706 | 0.5871 |
| 200 | 32632 | Metabolite - 11315 | 0.92 | 0.2722 | 0.5871 |
| 201 | 32635 | Metabolite - 11318 | 0.93 | 0.2799 | 0.5965 |
| 50 | 18388 | Metabolite - 05491 | 1.07 | 0.2807 | 0.5965 |
| 50 | 33477 | erythronate | 0.94 | 0.2836 | 0.5965 |

TABLE 2-continued

Biomarkers to Distinguish Active from Inactive Crohn's Disease

| Library | Comp ID | Biomarker | CD Active/CD Inactive | p-value | q-value |
|---|---|---|---|---|---|
| 50 | 24115 | Metabolite - 09752 | 0.90 | 0.2850 | 0.5965 |
| 50 | 35252 | oxalacetic acid | 1.33 | 0.2860 | 0.5965 |
| 50 | 12796 | Metabolite - 03114 | 1.24 | 0.2865 | 0.5965 |
| 50 | 21631 | Metabolite - 08403 | 0.94 | 0.2879 | 0.5965 |
| 200 | 36756 | leucylleucine | 0.74 | 0.2902 | 0.5977 |
| 200 | 32518 | Metabolite - 11204 | 1.05 | 0.2951 | 0.6045 |
| 200 | 33142 | Metabolite - 11797 | 0.57 | 0.2993 | 0.6075 |
| 200 | 1299 | tyrosine | 0.93 | 0.2998 | 0.6075 |
| 200 | 34481 | Metabolite - 12798 | 1.07 | 0.3079 | 0.6109 |
| 201 | 33194 | Metabolite - 11849 | 0.91 | 0.3082 | 0.6109 |
| 200 | 569 | caffeine | 0.93 | 0.3117 | 0.6109 |
| 200 | 31548 | DSGEGDFXAEGGGVR | 1.34 | 0.3118 | 0.6109 |
| 200 | 553 | cotinine | 1.23 | 0.3119 | 0.6109 |
| 201 | 32807 | Metabolite - 11490 | 0.73 | 0.3132 | 0.6109 |
| 50 | 25602 | Metabolite - 10432 | 0.85 | 0.3166 | 0.6112 |
| 201 | 12261 | taurodeoxycholate | 0.57 | 0.3203 | 0.6112 |
| 200 | 31530 | threonylphenylalanine | 1.20 | 0.3204 | 0.6112 |
| 201 | 32847 | Metabolite - 11530 | 0.86 | 0.3217 | 0.6112 |
| 201 | 1336 | palmitate (16:0) | 1.09 | 0.3219 | 0.6112 |
| 200 | 2132 | citrulline | 0.94 | 0.3234 | 0.6112 |
| 201 | 27716 | bilirubin | 0.64 | 0.3287 | 0.6181 |
| 200 | 32793 | Metabolite - 11476 | 1.03 | 0.3311 | 0.6194 |
| 50 | 32315 | serine | 0.94 | 0.3360 | 0.6237 |
| 201 | 1365 | myristate (14:0) | 1.14 | 0.3367 | 0.6237 |
| 50 | 27856 | Metabolite - 10597 | 1.04 | 0.3409 | 0.6270 |
| 200 | 31522 | pyroglutamylglycine | 0.75 | 0.3420 | 0.6270 |
| 200 | 35127 | pro-hydroxy-pro | 0.92 | 0.3476 | 0.6342 |
| 201 | 33203 | Metabolite - 11858 | 1.02 | 0.3516 | 0.6382 |
| 201 | 31908 | 7-ketolithocholate | 0.92 | 0.3548 | 0.6409 |
| 50 | 1121 | margarate (17:0) | 1.08 | 0.3633 | 0.6432 |
| 200 | 34359 | Metabolite - 12749 | 0.96 | 0.3677 | 0.6432 |
| 200 | 53 | Glutamine | 1.03 | 0.3656 | 0.6432 |
| 201 | 33415 | Metabolite - 12063 | 1.12 | 0.3678 | 0.6432 |
| 201 | 33389 | Metabolite - 12038 | 0.95 | 0.3691 | 0.6432 |
| 200 | 32698 | Metabolite - 11381 | 1.03 | 0.3694 | 0.6432 |
| 200 | 1898 | proline | 0.96 | 0.3755 | 0.6432 |
| 201 | 33901 | Metabolite - 12456 | 1.14 | 0.3761 | 0.6432 |
| 50 | 30832 | Metabolite - 10814 | 0.95 | 0.3780 | 0.6432 |
| 200 | 1444 | pipecolate | 0.87 | 0.3786 | 0.6432 |
| 50 | 34283 | asparagine | 0.94 | 0.3806 | 0.6432 |
| 50 | 19414 | Metabolite - 06350 | 1.07 | 0.3835 | 0.6432 |
| 201 | 1123 | inosine | 1.16 | 0.3883 | 0.6432 |
| 200 | 32198 | acetylcarnitine | 1.06 | 0.3899 | 0.6432 |
| 200 | 32348 | 2-aminobutyrate | 0.94 | 0.3908 | 0.6432 |
| 50 | 27710 | N-acetylglycine | 1.14 | 0.3908 | 0.6432 |
| 50 | 19368 | Metabolite - 06267 | 0.94 | 0.3924 | 0.6432 |
| 200 | 33519 | Metabolite - 12104 | 1.03 | 0.3925 | 0.6432 |
| 200 | 32644 | Metabolite - 11327 | 1.04 | 0.3929 | 0.6432 |
| 201 | 36099 | 4-ethylphenyl sulfate | 0.89 | 0.3978 | 0.6440 |
| 201 | 3147 | xanthine | 1.06 | 0.3982 | 0.6440 |
| 201 | 33178 | Metabolite - 11833 | 2.48 | 0.3987 | 0.6440 |
| 200 | 32654 | 3-dehydrocarnitine | 1.05 | 0.4056 | 0.6503 |
| 200 | 1494 | pyroglutamate (5-oxoproline) | 0.96 | 0.4086 | 0.6503 |
| 50 | 27256 | Metabolite - 10500 | 0.96 | 0.4086 | 0.6503 |
| 200 | 3141 | betaine | 0.94 | 0.4113 | 0.6503 |
| 200 | 2730 | gamma-glutamylglutamine | 1.05 | 0.4114 | 0.6503 |
| 201 | 33968 | 5-dodecenoate (12:1(n-7)) | 1.14 | 0.4144 | 0.6513 |
| 201 | 32748 | Metabolite - 11431 | 1.07 | 0.4172 | 0.6513 |
| 200 | 3127 | hypoxanthine | 1.06 | 0.4174 | 0.6513 |
| 201 | 34453 | Metabolite - 12776 | 0.97 | 0.4260 | 0.6619 |
| 201 | 32808 | Metabolite - 11491 | 0.89 | 0.4286 | 0.6631 |
| 50 | 16866 | Metabolite - 04523 | 0.94 | 0.4351 | 0.6704 |
| 201 | 32811 | Metabolite - 11494 | 0.94 | 0.4396 | 0.6728 |
| 201 | 33972 | 10-nonadecenoate (19:1(n-9)) | 1.23 | 0.4403 | 0.6728 |
| 50 | 1549 | 3-hydroxy-2-methylpropanoate | 0.92 | 0.4443 | 0.6748 |
| 201 | 34244 | Metabolite - 12644 | 0.94 | 0.4453 | 0.6748 |
| 201 | 32867 | Metabolite - 11550 | 0.98 | 0.4473 | 0.6751 |
| 50 | 12782 | Metabolite - 03100 | 0.92 | 0.4499 | 0.6761 |
| 201 | 1358 | stearate (18:0) | 1.08 | 0.4551 | 0.6798 |
| 200 | 33852 | 1-myristoylglycerophosphocholine | 0.99 | 0.4561 | 0.6798 |
| 201 | 34035 | linolenate [alpha or gamma; (18:3(n-3 or 6))] | 1.09 | 0.4599 | 0.6827 |
| 201 | 1105 | linoleate (18:2(n-6)) | 1.07 | 0.4622 | 0.6834 |
| 50 | 12789 | Metabolite - 03107 | 0.87 | 0.4657 | 0.6835 |

TABLE 2-continued

Biomarkers to Distinguish Active from Inactive Crohn's Disease

| Library | Comp ID | Biomarker | CD Active/ CD Inactive | p-value | q-value |
|---|---|---|---|---|---|
| 50 | 1303 | malate | 0.99 | 0.4662 | 0.6835 |
| 50 | 22570 | Metabolite - 09033 | 1.04 | 0.4693 | 0.6835 |
| 201 | 33206 | Metabolite - 11861 | 0.98 | 0.4697 | 0.6835 |
| 201 | 34674 | Metabolite - 12990 | 1.01 | 0.4743 | 0.6837 |
| 50 | 22601 | Metabolite - 09044 | 0.94 | 0.4764 | 0.6837 |
| 201 | 33195 | Metabolite - 11850 | 0.86 | 0.4766 | 0.6837 |
| 201 | 1114 | deoxycholate | 0.87 | 0.4773 | 0.6837 |
| 201 | 33423 | p-acetamidophenylglucuronide | 1.29 | 0.4837 | 0.6881 |
| 200 | 33801 | ADpSGEGDFXAEGGGVR | 1.18 | 0.4890 | 0.6881 |
| 200 | 33939 | N-acetylthreonine | 0.98 | 0.4903 | 0.6881 |
| 50 | 33488 | lathosterol | 1.23 | 0.4906 | 0.6881 |
| 50 | 4966 | xylitol | 0.89 | 0.4923 | 0.6881 |
| 200 | 1712 | cortisol | 0.85 | 0.4934 | 0.6881 |
| 201 | 34516 | Metabolite - 12833 | 0.75 | 0.4935 | 0.6881 |
| 50 | 18929 | Metabolite - 05907 | 0.94 | 0.5019 | 0.6954 |
| 201 | 33682 | Metabolite - 12260 | 0.70 | 0.5043 | 0.6954 |
| 200 | 32776 | 2-methylbutyroylcarnitine | 0.96 | 0.5049 | 0.6954 |
| 50 | 15335 | mannitol | 0.79 | 0.5065 | 0.6954 |
| 200 | 32412 | butyrylcarnitine | 1.13 | 0.5114 | 0.6954 |
| 50 | 35844 | gamma,gamma-dimethylallyl pyrophosphate | 1.05 | 0.5119 | 0.6954 |
| 200 | 32401 | trigonelline (N'-methylnicotinate) | 0.97 | 0.5121 | 0.6954 |
| 201 | 32560 | Metabolite - 07765 | 1.22 | 0.5173 | 0.7000 |
| 200 | 32452 | propionylcarnitine | 0.97 | 0.5271 | 0.7105 |
| 201 | 1644 | heptanoate (7:0) | 0.98 | 0.5297 | 0.7105 |
| 201 | 33587 | eicosenoate [9 or 11, cis or trans] | 1.13 | 0.5309 | 0.7105 |
| 200 | 35160 | oleoylcarnitine | 1.11 | 0.5352 | 0.7110 |
| 50 | 18868 | Metabolite - 05847 | 0.99 | 0.5379 | 0.7110 |
| 201 | 1645 | laurate (12:0) | 1.09 | 0.5423 | 0.7110 |
| 200 | 33576 | Metabolite - 12159 | 0.84 | 0.5423 | 0.7110 |
| 200 | 18357 | glycylvaline | 1.21 | 0.5428 | 0.7110 |
| 201 | 31912 | glycolithocholate | 0.77 | 0.5462 | 0.7110 |
| 200 | 31534 | HXGXA | 0.67 | 0.5474 | 0.7110 |
| 201 | 33204 | Metabolite - 11859 | 0.99 | 0.5478 | 0.7110 |
| 200 | 32675 | Metabolite - 03951 | 0.98 | 0.5487 | 0.7110 |
| 200 | 2342 | serotonin (5HT) | 1.05 | 0.5556 | 0.7135 |
| 50 | 27722 | erythrose | 0.96 | 0.5657 | 0.7135 |
| 200 | 33507 | Metabolite - 12092 | 0.98 | 0.5663 | 0.7135 |
| 200 | 33961 | 1-stearoylglycerophosphocholine | 1.07 | 0.5719 | 0.7135 |
| 50 | 33453 | alpha-ketoglutarate | 1.06 | 0.5748 | 0.7135 |
| 200 | 513 | creatinine | 1.02 | 0.5753 | 0.7135 |
| 200 | 33403 | Metabolite - 12051 | 1.00 | 0.5766 | 0.7135 |
| 201 | 27531 | hyodeoxycholate | 0.82 | 0.5766 | 0.7135 |
| 201 | 33190 | Metabolite - 11845 | 0.94 | 0.5770 | 0.7135 |
| 50 | 31617 | Metabolite - 10963 | 0.99 | 0.5771 | 0.7135 |
| 200 | 32978 | Metabolite - 11656 | 1.00 | 0.5777 | 0.7135 |
| 50 | 33089 | Metabolite - 11744 | 0.96 | 0.5788 | 0.7135 |
| 50 | 22600 | Metabolite - 09043 | 0.96 | 0.5809 | 0.7135 |
| 201 | 22130 | phenyllactate (PLA) | 1.03 | 0.5810 | 0.7135 |
| 50 | 34441 | Metabolite - 12771 | 0.90 | 0.5852 | 0.7135 |
| 201 | 32767 | Metabolite - 11450 | 1.03 | 0.5877 | 0.7135 |
| 201 | 32761 | Metabolite - 11444 | 1.07 | 0.5895 | 0.7135 |
| 201 | 34527 | Metabolite - 12844 | 1.05 | 0.5914 | 0.7135 |
| 201 | 32695 | Metabolite - 11378 | 1.01 | 0.5925 | 0.7135 |
| 201 | 32762 | Metabolite - 11445 | 0.63 | 0.5941 | 0.7135 |
| 200 | 2137 | biliverdin | 0.93 | 0.5976 | 0.7135 |
| 201 | 1642 | caprate (10:0) | 0.98 | 0.5981 | 0.7135 |
| 200 | 1769 | cortisone | 1.04 | 0.5982 | 0.7135 |
| 201 | 32814 | Metabolite - 11497 | 1.02 | 0.5994 | 0.7135 |
| 201 | 34329 | Metabolite - 12719 | 1.01 | 0.6030 | 0.7135 |
| 200 | 34040 | Metabolite - 12510 | 0.97 | 0.6092 | 0.7135 |
| 201 | 35320 | catechol sulfate | 0.85 | 0.6128 | 0.7135 |
| 50 | 22548 | Metabolite - 09026 | 0.96 | 0.6134 | 0.7135 |
| 200 | 33773 | Metabolite - 12348 | 0.99 | 0.6144 | 0.7135 |
| 201 | 32877 | Metabolite - 11560 | 0.90 | 0.6145 | 0.7135 |
| 200 | 1125 | isoleucine | 0.97 | 0.6157 | 0.7135 |
| 50 | 21630 | Metabolite - 08402 | 0.95 | 0.6161 | 0.7135 |
| 201 | 21047 | 3-methyl-2-oxobutyrate | 1.02 | 0.6185 | 0.7135 |
| 200 | 22138 | homocitrulline | 0.99 | 0.6211 | 0.7135 |
| 201 | 22842 | cholate | 0.59 | 0.6221 | 0.7135 |
| 200 | 33033 | Metabolite - 11689 | 0.81 | 0.6222 | 0.7135 |
| 201 | 32619 | Metabolite - 11302 | 1.04 | 0.6226 | 0.7135 |
| 200 | 33138 | Metabolite - 11793 | 1.04 | 0.6299 | 0.7163 |
| 200 | 35433 | hydroxyisovaleroyl carnitine | 0.98 | 0.6305 | 0.7163 |

TABLE 2-continued

Biomarkers to Distinguish Active from Inactive Crohn's Disease

| Library | Comp ID | Biomarker | CD Active/ CD Inactive | p-value | q-value |
|---|---|---|---|---|---|
| 50 | 542 | 3-hydroxybutyrate (BHBA) | 1.16 | 0.6332 | 0.7163 |
| 200 | 15990 | glycerophosphorylcholine (GPC) | 1.02 | 0.6380 | 0.7163 |
| 50 | 21188 | stearoylglycerol (monostearin) | 0.97 | 0.6382 | 0.7163 |
| 200 | 33408 | Metabolite - 12056 | 0.88 | 0.6392 | 0.7163 |
| 200 | 35153 | 1-docosahexaenoylglycerol (1-monodocosahexaenoin) | 1.10 | 0.6407 | 0.7163 |
| 201 | 32501 | dihomo-alpha-linolenate (20:3(n-3)) | 0.96 | 0.6419 | 0.7163 |
| 201 | 18394 | theophylline | 0.93 | 0.6451 | 0.7163 |
| 200 | 32578 | Metabolite - 11261 | 0.96 | 0.6465 | 0.7163 |
| 200 | 34366 | Metabolite - 12756 | 1.05 | 0.6466 | 0.7163 |
| 201 | 32850 | Metabolite - 11533 | 0.99 | 0.6491 | 0.7167 |
| 50 | 16666 | Metabolite - 04365 | 0.95 | 0.6520 | 0.7167 |
| 201 | 34201 | 1-stearoylglycerophosphoinositol | 1.03 | 0.6531 | 0.7167 |
| 50 | 1107 | allantoin | 1.03 | 0.6567 | 0.7167 |
| 201 | 34214 | Metabolite - 12620 | 0.99 | 0.6603 | 0.7185 |
| 201 | 33652 | Metabolite - 12230 | 0.80 | 0.6629 | 0.7190 |
| 201 | 33782 | Metabolite - 10346 | 0.93 | 0.6646 | 0.7190 |
| 201 | 35688 | 2-palmitoylglycerophosphoethanolamine | 0.95 | 0.6671 | 0.7195 |
| 200 | 33132 | Metabolite - 11787 | 0.99 | 0.6696 | 0.7201 |
| 200 | 34106 | Metabolite - 12542 | 0.73 | 0.6762 | 0.7229 |
| 200 | 27718 | creatine | 0.91 | 0.6827 | 0.7265 |
| 200 | 33230 | 1-palmitoleoylglycerophosphocholine | 1.13 | 0.6855 | 0.7265 |
| 200 | 33955 | 1-palmitoylglycerophosphocholine | 0.97 | 0.6855 | 0.7265 |
| 201 | 18362 | azelate (nonanedioate) | 1.00 | 0.6892 | 0.7283 |
| 201 | 32792 | Metabolite - 11475 | 0.98 | 0.6918 | 0.7290 |
| 201 | 32625 | Metabolite - 11308 | 0.96 | 0.6972 | 0.7295 |
| 201 | 33390 | Metabolite - 12039 | 1.02 | 0.6973 | 0.7295 |
| 201 | 32492 | caprylate (8:0) | 0.97 | 0.6983 | 0.7295 |
| 201 | 32599 | Metabolite - 11282 | 1.03 | 0.7046 | 0.7341 |
| 50 | 17064 | Metabolite - 04624 | 1.01 | 0.7086 | 0.7347 |
| 200 | 32709 | Metabolite - 03056 | 1.03 | 0.7092 | 0.7347 |
| 200 | 32780 | Metabolite - 11463 | 0.97 | 0.7114 | 0.7349 |
| 201 | 33173 | Metabolite - 11828 | 1.14 | 0.7135 | 0.7350 |
| 201 | 32425 | dehydroisoandrosterone sulfate (DHEA-S) | 0.97 | 0.7163 | 0.7352 |
| 200 | 60 | leucine | 0.98 | 0.7178 | 0.7352 |
| 50 | 22649 | Metabolite - 09108 | 0.98 | 0.7201 | 0.7355 |
| 201 | 34400 | 1,7-dimethylurate | 1.01 | 0.7221 | 0.7356 |
| 50 | 17391 | Metabolite - 04807 | 1.14 | 0.7257 | 0.7363 |
| 200 | 15140 | kynurenine | 0.99 | 0.7274 | 0.7363 |
| 201 | 1638 | arginine | 1.00 | 0.7289 | 0.7363 |
| 200 | 15743 | dimethylarginine | 1.03 | 0.7333 | 0.7363 |
| 200 | 34417 | 1-hexadecylglycerophosphocholine | 0.99 | 0.7380 | 0.7363 |
| 201 | 36776 | 7-alpha-hydroxy-3-oxo-4-cholestenoate (7-Hoca) | 1.06 | 0.7392 | 0.7363 |
| 200 | 33131 | Metabolite - 11786 | 1.04 | 0.7403 | 0.7363 |
| 50 | 32338 | glycine | 1.00 | 0.7424 | 0.7363 |
| 50 | 18335 | quinate | 1.08 | 0.7458 | 0.7363 |
| 201 | 32504 | n-3 DPA (22:5(n-3)) | 1.09 | 0.7472 | 0.7363 |
| 200 | 33515 | Metabolite - 12100 | 0.99 | 0.7474 | 0.7363 |
| 201 | 33188 | Metabolite - 11843 | 0.95 | 0.7483 | 0.7363 |
| 200 | 22154 | bradykinin | 0.96 | 0.7497 | 0.7363 |
| 200 | 64 | phenylalanine | 0.98 | 0.7510 | 0.7363 |
| 50 | 63 | cholesterol | 0.98 | 0.7568 | 0.7378 |
| 200 | 33363 | gamma-glutamylmethionine | 1.01 | 0.7590 | 0.7378 |
| 201 | 32760 | Metabolite - 11443 | 1.08 | 0.7670 | 0.7378 |
| 201 | 1110 | arachidonate (20:4(n-6)) | 1.01 | 0.7671 | 0.7378 |
| 50 | 16837 | Metabolite - 04507 | 1.01 | 0.7715 | 0.7378 |
| 201 | 1563 | chenodeoxycholate | 0.71 | 0.7718 | 0.7378 |
| 201 | 33883 | Metabolite - 12441 | 0.62 | 0.7732 | 0.7378 |
| 50 | 19576 | Metabolite - 06627 | 1.02 | 0.7743 | 0.7378 |
| 50 | 20699 | erythritol | 0.99 | 0.7763 | 0.7378 |
| 200 | 33960 | 1-oleoylglycerophosphocholine | 1.05 | 0.7768 | 0.7378 |
| 50 | 35271 | Metabolite - 13497 | 0.96 | 0.7781 | 0.7378 |
| 201 | 33969 | stearidonate (18:4(n-3)) | 0.93 | 0.7782 | 0.7378 |
| 200 | 32595 | Metabolite - 08893 | 0.99 | 0.7786 | 0.7378 |
| 201 | 33638 | Metabolite - 12217 | 0.91 | 0.7852 | 0.7421 |
| 200 | 31536 | N-(2-furoyl)glycine | 1.03 | 0.7890 | 0.7438 |
| 50 | 17482 | Metabolite - 04874 | 0.99 | 0.7988 | 0.7486 |
| 50 | 17627 | Metabolite - 04986 | 1.00 | 0.8013 | 0.7486 |
| 200 | 32735 | Metabolite - 01911 | 0.95 | 0.8023 | 0.7486 |
| 200 | 33165 | Metabolite - 11820 | 0.93 | 0.8043 | 0.7486 |
| 50 | 12781 | Metabolite - 03099 | 1.00 | 0.8109 | 0.7509 |

TABLE 2-continued

Biomarkers to Distinguish Active from Inactive Crohn's Disease

| Library | Comp ID | Biomarker | CD Active/ CD Inactive | p-value | q-value |
|---|---|---|---|---|---|
| 200 | 15753 | hippurate | 0.98 | 0.8152 | 0.7509 |
| 200 | 36738 | gamma-glutamylglutamate | 0.97 | 0.8199 | 0.7509 |
| 200 | 32393 | glutamylvaline | 1.04 | 0.8241 | 0.7509 |
| 201 | 15730 | suberate | 0.95 | 0.8247 | 0.7509 |
| 200 | 18369 | gamma-glutamylleucine | 1.02 | 0.8263 | 0.7509 |
| 50 | 32369 | Metabolite - 11175 | 1.05 | 0.8267 | 0.7509 |
| 201 | 33183 | Metabolite - 11838 | 0.70 | 0.8274 | 0.7509 |
| 50 | 31618 | Metabolite - 10964 | 0.93 | 0.8309 | 0.7509 |
| 200 | 18254 | paraxanthine | 0.99 | 0.8310 | 0.7509 |
| 50 | 32322 | glutamate | 0.99 | 0.8325 | 0.7509 |
| 200 | 32586 | Metabolite - 01327 | 0.82 | 0.8329 | 0.7509 |
| 200 | 32458 | oleamide | 0.94 | 0.8348 | 0.7509 |
| 50 | 12032 | 4-acetamidophenol | 0.84 | 0.8381 | 0.7509 |
| 200 | 19464 | testosterone | 1.01 | 0.8419 | 0.7509 |
| 201 | 34395 | 1-methylurate | 0.90 | 0.8424 | 0.7509 |
| 201 | 31591 | androsterone sulfate | 0.92 | 0.8437 | 0.7509 |
| 201 | 18494 | taurochenodeoxycholate | 0.74 | 0.8478 | 0.7509 |
| 50 | 31266 | fructose | 0.96 | 0.8520 | 0.7509 |
| 50 | 15996 | aspartate | 0.94 | 0.8531 | 0.7509 |
| 201 | 32489 | caproate (6:0) | 1.03 | 0.8592 | 0.7509 |
| 200 | 34456 | gamma-glutamylisoleucine | 0.99 | 0.8600 | 0.7509 |
| 50 | 30282 | Metabolite - 10744 | 0.97 | 0.8607 | 0.7509 |
| 200 | 33957 | 1-heptadecanoylglycerophosphocholine | 1.06 | 0.8610 | 0.7509 |
| 200 | 2734 | gamma-glutamyltyrosine | 0.97 | 0.8638 | 0.7509 |
| 201 | 32910 | Metabolite - 11593 | 0.97 | 0.8658 | 0.7509 |
| 201 | 32827 | Metabolite - 11510 | 0.92 | 0.8659 | 0.7509 |
| 201 | 33442 | pseudouridine | 0.99 | 0.8662 | 0.7509 |
| 201 | 32398 | sebacate | 1.01 | 0.8662 | 0.7509 |
| 201 | 32346 | glycochenodeoxycholate | 0.82 | 0.8740 | 0.7522 |
| 50 | 19362 | Metabolite - 06226 | 1.01 | 0.8741 | 0.7522 |
| 50 | 32339 | alanine | 0.99 | 0.8752 | 0.7522 |
| 50 | 1659 | dehydroascorbate | 0.95 | 0.8776 | 0.7522 |
| 201 | 15676 | 3-methyl-2-oxovalerate | 0.98 | 0.8836 | 0.7522 |
| 201 | 32740 | Metabolite - 11423 | 1.01 | 0.8840 | 0.7522 |
| 200 | 34420 | (des-arg9) Bradykinin | 1.53 | 0.8906 | 0.7542 |
| 200 | 33821 | Metabolite - 12393 | 0.98 | 0.8949 | 0.7544 |
| 201 | 15749 | 3-phenylpropionate (hydrocinnamate) | 1.01 | 0.8978 | 0.7544 |
| 200 | 34368 | Metabolite - 12758 | 1.00 | 0.9035 | 0.7544 |
| 201 | 33254 | Metabolite - 11909 | 1.26 | 0.9040 | 0.7544 |
| 201 | 1604 | urate | 0.98 | 0.9069 | 0.7544 |
| 200 | 33140 | Metabolite - 11795 | 0.96 | 0.9069 | 0.7544 |
| 201 | 36097 | 4-acetaminophen sulfate | 1.49 | 0.9073 | 0.7544 |
| 201 | 33973 | epiandrosterone sulfate | 0.89 | 0.9111 | 0.7550 |
| 200 | 33405 | Metabolite - 12053 | 0.93 | 0.9128 | 0.7550 |
| 50 | 25532 | Metabolite - 10413 | 1.04 | 0.9142 | 0.7550 |
| 50 | 1592 | N-acetylneuraminate | 0.98 | 0.9275 | 0.7611 |
| 200 | 35439 | glutaroyl carnitine | 1.02 | 0.9285 | 0.7611 |
| 200 | 32716 | Metabolite - 11399 | 0.94 | 0.9293 | 0.7611 |
| 201 | 32388 | dodecanedioate | 1.18 | 0.9298 | 0.7611 |
| 201 | 33937 | alpha-hydroxyisovalerate | 1.10 | 0.9323 | 0.7614 |
| 201 | 33963 | acetoacetate | 1.17 | 0.9376 | 0.7640 |
| 50 | 21044 | 2-hydroxybutyrate (AHB) | 1.05 | 0.9411 | 0.7652 |
| 50 | 16634 | Metabolite - 04357 | 1.05 | 0.9463 | 0.7677 |
| 50 | 16120 | Metabolite - 04055 | 1.01 | 0.9520 | 0.7697 |
| 50 | 527 | lactate | 0.98 | 0.9553 | 0.7697 |
| 50 | 34443 | Metabolite - 12773 | 0.97 | 0.9568 | 0.7697 |
| 50 | 21127 | 1-palmitoylglycerol (1-monopalmitin) | 0.94 | 0.9571 | 0.7697 |
| 200 | 33954 | glycylphenylalanine | 0.94 | 0.9616 | 0.7707 |
| 201 | 32197 | 3-(4-hydroxyphenyl)lactate | 0.98 | 0.9636 | 0.7707 |
| 50 | 12774 | Metabolite - 03094 | 0.98 | 0.9655 | 0.7707 |
| 200 | 34223 | Metabolite - 12629 | 0.95 | 0.9676 | 0.7707 |
| 201 | 33396 | Metabolite - 12045 | 1.19 | 0.9689 | 0.7707 |
| 50 | 1481 | inositol 1-phosphate (I1P) | 0.95 | 0.9724 | 0.7718 |
| 201 | 12129 | beta-hydroxyisovalerate | 1.03 | 0.9805 | 0.7765 |
| 200 | 18476 | glycocholate | 0.90 | 0.9844 | 0.7766 |
| 50 | 19490 | Metabolite - 06488 | 0.95 | 0.9847 | 0.7766 |
| 50 | 33369 | Metabolite - 12023 | 1.00 | 0.9902 | 0.7775 |
| 201 | 22116 | 4-methyl-2-oxopentanoate | 1.00 | 0.9920 | 0.7775 |
| 50 | 15737 | glycolate (hydroxyacetate) | 0.98 | 0.9930 | 0.7775 |
| 200 | 33626 | Metabolite - 12205 | 1.00 | 0.9944 | 0.7775 |

Example 3

Biomarker Metabolites Specific for Active Vs. Inactive Ulcerative Colitis

Biomarkers were discovered by (1) analyzing blood samples drawn from different groups of human subjects to determine the levels of metabolites in the samples and then (2) statistically analyzing the results to determine those metabolites that were differentially present in the two groups.

The blood samples used for the analysis were from subjects with active ulcerative colitis (N=36) and subjects with inactive ulcerative colitis (N=37). After the levels of metabolites were determined, the data was analyzed using univariate T-tests (i.e., Welch's T-test).

T-tests were used to determine differences in the mean levels of metabolites between the two populations (i.e., active ulcerative colitis vs. inactive ulcerative colitis). Random Forest analysis was performed to identify the metabolites that are most important to distinguish the two groups of subjects and thereby useful to identify a subject as having active ulcerative colitis or as having inactive ulcerative colitis.

Biomarkers

As listed below in Table 3, biomarkers were discovered that were differentially present between samples from inactive (i.e., in remission) ulcerative colitis subjects and active ulcerative colitis subjects. Table 3 lists biomarkers that were discovered that were differentially present between samples from active ulcerative colitis subjects and subjects in remission from ulcerative colitis. These biomarkers are useful to track Crohn's disease progression/regression, to monitor treatment effects, to monitor clinical trials of therapeutic agents or Crohn's disease treatments.

Table 3 includes, for each listed biomarker, the p-value and the q-value determined in the statistical analysis of the data concerning the biomarkers and the ratio between the mean in the active Ulcerative colitis as compared to the inactive ulcerative colitis mean. Library indicates the chemical library that was used to identify the compounds. The number 50 refers to the GC library and the numbers 200 and 201 refer to the LC library. "Comp ID" refers to the internal chemical database identification number for that compound.

TABLE 3

| | | Biomarkers to Distinguish Active from Inactive Ulcerative Colitis | | | |
|---|---|---|---|---|---|
| Library | Comp ID | Biomarker | UC Active/ UC Inactive | p-value | q-value |
| 201 | 32847 | Metabolite - 11530 | 0.62 | 0.0000 | 0.0119 |
| 200 | 54 | tryptophan | 0.87 | 0.0063 | 0.5313 |
| 50 | 584 | mannose | 1.37 | 0.0068 | 0.5313 |
| 201 | 33901 | Metabolite - 12456 | 1.33 | 0.0079 | 0.5313 |
| 201 | 32599 | Metabolite - 11282 | 1.41 | 0.0088 | 0.5313 |
| 50 | 1564 | citrate | 0.82 | 0.0107 | 0.5313 |
| 201 | 59 | histidine | 0.89 | 0.0127 | 0.5313 |
| 201 | 32811 | Metabolite - 11494 | 0.88 | 0.0143 | 0.5313 |
| 200 | 32644 | Metabolite - 11327 | 0.87 | 0.0149 | 0.5313 |
| 200 | 32348 | 2-aminobutyrate | 0.83 | 0.0154 | 0.5313 |
| 50 | 1572 | glycerate | 0.74 | 0.0174 | 0.5313 |
| 201 | 22116 | 4-methyl-2-oxopentanoate | 0.83 | 0.0186 | 0.5313 |
| 200 | 33821 | Metabolite - 12393 | 0.79 | 0.0203 | 0.5313 |
| 200 | 1712 | cortisol | 0.71 | 0.0205 | 0.5313 |
| 50 | 18446 | Metabolite - 05524 | 0.74 | 0.0220 | 0.5313 |
| 201 | 32839 | Metabolite - 11522 | 0.80 | 0.0226 | 0.5313 |
| 201 | 32759 | Metabolite - 11442 | 0.80 | 0.0230 | 0.5313 |
| 200 | 1649 | valine | 0.91 | 0.0277 | 0.5313 |
| 201 | 33389 | Metabolite - 12038 | 0.84 | 0.0292 | 0.5313 |
| 200 | 34390 | 7-methylxanthine | 0.75 | 0.0302 | 0.5313 |
| 201 | 1123 | inosine | 1.62 | 0.0302 | 0.5313 |
| 201 | 32758 | Metabolite - 11441 | 0.82 | 0.0334 | 0.5313 |
| 50 | 25459 | Metabolite - 10395 | 0.83 | 0.0367 | 0.5313 |
| 201 | 32425 | dehydroisoandrosterone sulfate (DHEA-S) | 0.81 | 0.0384 | 0.5313 |
| 201 | 32489 | caproate (6:0) | 0.87 | 0.0403 | 0.5313 |
| 200 | 33939 | N-acetylthreonine | 0.89 | 0.0438 | 0.5313 |
| 50 | 32339 | alanine | 1.14 | 0.0441 | 0.5313 |
| 50 | 32315 | serine | 1.12 | 0.0442 | 0.5313 |
| 200 | 32198 | acetylcarnitine | 0.88 | 0.0464 | 0.5313 |
| 201 | 27716 | bilirubin | 0.62 | 0.0468 | 0.5313 |
| 50 | 32338 | glycine | 1.18 | 0.0471 | 0.5313 |
| 200 | 18369 | gamma-glutamylleucine | 0.81 | 0.0482 | 0.5313 |
| 200 | 18476 | glycocholate | 1.33 | 0.0512 | 0.5313 |
| 200 | 1573 | guanosine | 1.26 | 0.0515 | 0.5313 |
| 200 | 1769 | cortisone | 1.83 | 0.0527 | 0.5313 |
| 201 | 32501 | dihomo-alpha-linolenate (20:3(n-3)) | 0.80 | 0.0543 | 0.5313 |
| 201 | 32689 | Metabolite - 11372 | 0.81 | 0.0550 | 0.5313 |
| 200 | 33822 | Metabolite - 12394 | 0.81 | 0.0562 | 0.5313 |
| 200 | 34365 | Metabolite - 12755 | 1.96 | 0.0563 | 0.5313 |
| 201 | 33225 | Metabolite - 11880 | 0.79 | 0.0577 | 0.5313 |
| 50 | 34443 | Metabolite - 12773 | 0.82 | 0.0593 | 0.5313 |
| 50 | 22601 | Metabolite - 09044 | 0.84 | 0.0603 | 0.5313 |
| 201 | 36776 | 7-alpha-hydroxy-3-oxo-4-cholestenoate (7-Hoca) | 0.79 | 0.0625 | 0.5313 |
| 50 | 32369 | Metabolite - 11175 | 0.83 | 0.0628 | 0.5313 |
| 200 | 513 | creatinine | 0.93 | 0.0638 | 0.5313 |

TABLE 3-continued

Biomarkers to Distinguish Active from Inactive Ulcerative Colitis

| Library | Comp ID | Biomarker | UC Active/ UC Inactive | p-value | q-value |
|---|---|---|---|---|---|
| 50 | 20489 | glucose | 1.16 | 0.0642 | 0.5313 |
| 50 | 12796 | Metabolite - 03114 | 0.68 | 0.0670 | 0.5313 |
| 50 | 19363 | Metabolite - 06227 | 0.86 | 0.0674 | 0.5313 |
| 200 | 33363 | gamma-glutamylmethionine | 0.84 | 0.0680 | 0.5313 |
| 50 | 16120 | Metabolite - 04055 | 0.77 | 0.0688 | 0.5313 |
| 201 | 32346 | glycochenodeoxycholate | 1.25 | 0.0688 | 0.5313 |
| 200 | 60 | leucine | 0.92 | 0.0715 | 0.5313 |
| 200 | 32593 | heme | 0.78 | 0.0716 | 0.5313 |
| 50 | 37016 | arginine | 1.11 | 0.0729 | 0.5313 |
| 50 | 25602 | Metabolite - 10432 | 0.79 | 0.0735 | 0.5313 |
| 50 | 17064 | Metabolite - 04624 | 0.88 | 0.0748 | 0.5313 |
| 200 | 33165 | Metabolite - 11820 | 0.80 | 0.0767 | 0.5313 |
| 50 | 63 | cholesterol | 0.91 | 0.0778 | 0.5313 |
| 200 | 15140 | kynurenine | 0.90 | 0.0782 | 0.5313 |
| 50 | 21630 | Metabolite - 08402 | 0.87 | 0.0803 | 0.5360 |
| 201 | 15676 | 3-methyl-2-oxovalerate | 0.88 | 0.0851 | 0.5542 |
| 201 | 27531 | hyodeoxycholate | 0.61 | 0.0858 | 0.5542 |
| 200 | 32586 | Metabolite - 01327 | 0.92 | 0.0887 | 0.5643 |
| 50 | 25599 | Metabolite - 10429 | 0.84 | 0.0978 | 0.6082 |
| 50 | 27278 | Metabolite - 10510 | 0.90 | 0.0987 | 0.6082 |
| 201 | 32625 | Metabolite - 11308 | 0.71 | 0.1013 | 0.6149 |
| 200 | 32452 | propionylcarnitine | 0.84 | 0.1075 | 0.6317 |
| 201 | 33237 | Metabolite - 11892 | 1.18 | 0.1094 | 0.6317 |
| 50 | 34441 | Metabolite - 12771 | 0.80 | 0.1121 | 0.6317 |
| 201 | 34732 | isovalerate | 0.92 | 0.1144 | 0.6317 |
| 201 | 33415 | Metabolite - 12063 | 1.23 | 0.1158 | 0.6317 |
| 200 | 32854 | Metabolite - 11537 | 0.82 | 0.1164 | 0.6317 |
| 201 | 32497 | 10c-undecenoate | 0.86 | 0.1167 | 0.6317 |
| 200 | 33132 | Metabolite - 11787 | 0.92 | 0.1209 | 0.6420 |
| 201 | 32792 | Metabolite - 11475 | 0.85 | 0.1273 | 0.6420 |
| 50 | 19490 | Metabolite - 06488 | 0.74 | 0.1288 | 0.6420 |
| 201 | 33423 | p-acetamidophenylglucuronide | 2.62 | 0.1308 | 0.6420 |
| 50 | 22649 | Metabolite - 09108 | 1.16 | 0.1319 | 0.6420 |
| 201 | 15778 | benzoate | 0.93 | 0.1321 | 0.6420 |
| 201 | 33627 | Metabolite - 12206 | 0.88 | 0.1326 | 0.6420 |
| 201 | 32767 | Metabolite - 11450 | 0.92 | 0.1360 | 0.6420 |
| 201 | 32827 | Metabolite - 11510 | 0.92 | 0.1373 | 0.6420 |
| 200 | 34368 | Metabolite - 12758 | 1.21 | 0.1393 | 0.6420 |
| 200 | 31530 | threonylphenylalanine | 0.74 | 0.1427 | 0.6420 |
| 50 | 19396 | Metabolite - 06307 | 1.38 | 0.1432 | 0.6420 |
| 200 | 32445 | 3-methylxanthine | 0.95 | 0.1511 | 0.6420 |
| 50 | 35839 | lysine | 0.84 | 0.1521 | 0.6420 |
| 201 | 34062 | Metabolite - 12524 | 0.93 | 0.1521 | 0.6420 |
| 50 | 16837 | Metabolite - 04507 | 1.38 | 0.1531 | 0.6420 |
| 200 | 35433 | hydroxyisovaleroyl carnitine | 0.92 | 0.1541 | 0.6420 |
| 200 | 2730 | gamma-glutamylglutamine | 0.91 | 0.1553 | 0.6420 |
| 200 | 18392 | theobromine | 0.73 | 0.1585 | 0.6420 |
| 201 | 32761 | Metabolite - 11444 | 0.81 | 0.1594 | 0.6420 |
| 200 | 553 | cotinine | 0.77 | 0.1601 | 0.6420 |
| 201 | 34201 | 1-stearoylglycerophoinositol | 0.88 | 0.1602 | 0.6420 |
| 200 | 31548 | DSGEGDFXAEGGGVR | 1.78 | 0.1603 | 0.6420 |
| 200 | 32393 | glutamylvaline | 0.84 | 0.1625 | 0.6420 |
| 200 | 35153 | 1-docosahexaenoylglycerol (1-monodocosahexaenoin) | 0.89 | 0.1660 | 0.6420 |
| 50 | 18349 | indolelactate | 0.86 | 0.1662 | 0.6420 |
| 50 | 1549 | 3-hydroxy-2-methylpropanoate | 0.90 | 0.1664 | 0.6420 |
| 201 | 32910 | Metabolite - 11593 | 1.09 | 0.1671 | 0.6420 |
| 200 | 15753 | hippurate | 0.66 | 0.1685 | 0.6420 |
| 200 | 32869 | Metabolite - 11552 | 0.88 | 0.1693 | 0.6420 |
| 50 | 1303 | malate | 0.79 | 0.1701 | 0.6420 |
| 201 | 34453 | Metabolite - 12776 | 0.84 | 0.1715 | 0.6420 |
| 50 | 33420 | gamma-tocopherol | 1.30 | 0.1734 | 0.6431 |
| 200 | 35160 | oleoylcarnitine | 0.88 | 0.1750 | 0.6431 |
| 201 | 32850 | Metabolite - 11533 | 0.96 | 0.1900 | 0.6562 |
| 50 | 21044 | 2-hydroxybutyrate (AHB) | 0.89 | 0.1911 | 0.6562 |
| 50 | 32405 | 3-indolepropionate | 0.68 | 0.1916 | 0.6562 |
| 200 | 32518 | Metabolite - 11204 | 0.94 | 0.1929 | 0.6562 |
| 201 | 35320 | catechol sulfate | 1.10 | 0.1931 | 0.6562 |
| 201 | 32553 | phenol sulfate | 1.29 | 0.1943 | 0.6562 |
| 200 | 32709 | Metabolite - 03056 | 1.16 | 0.1952 | 0.6562 |
| 200 | 34366 | Metabolite - 12756 | 1.24 | 0.1953 | 0.6562 |
| 201 | 36098 | 4-vinylphenol sulfate | 1.37 | 0.1986 | 0.6562 |
| 201 | 21047 | 3-methyl-2-oxobutyrate | 0.91 | 0.1992 | 0.6562 |
| 200 | 31536 | N-(2-furoyl)glycine | 1.57 | 0.2011 | 0.6562 |

TABLE 3-continued

Biomarkers to Distinguish Active from Inactive Ulcerative Colitis

| Library | Comp ID | Biomarker | UC Active/ UC Inactive | p-value | q-value |
|---|---|---|---|---|---|
| 200 | 32401 | trigonelline (N'-methylnicotinate) | 1.34 | 0.2013 | 0.6562 |
| 201 | 1644 | heptanoate (7:0) | 0.95 | 0.2021 | 0.6562 |
| 200 | 33084 | ADSGEGDFXAEGGGVR | 1.29 | 0.2034 | 0.6562 |
| 201 | 33173 | Metabolite - 11828 | 2.08 | 0.2067 | 0.6562 |
| 201 | 33633 | Metabolite - 12212 | 0.78 | 0.2106 | 0.6562 |
| 201 | 33178 | Metabolite - 11833 | 1.93 | 0.2113 | 0.6562 |
| 200 | 2137 | biliverdin | 0.83 | 0.2139 | 0.6562 |
| 50 | 17482 | Metabolite - 04874 | 0.91 | 0.2143 | 0.6562 |
| 200 | 34419 | 1-linoleoylglycerophosphocholine | 0.92 | 0.2151 | 0.6562 |
| 50 | 33488 | lathosterol | 0.69 | 0.2155 | 0.6562 |
| 50 | 19503 | sphingomyelin | 1.11 | 0.2181 | 0.6562 |
| 50 | 12774 | Metabolite - 03094 | 0.92 | 0.2184 | 0.6562 |
| 50 | 25607 | Metabolite - 10437 | 0.91 | 0.2235 | 0.6562 |
| 200 | 34407 | isovalerylcarnitine | 0.87 | 0.2264 | 0.6562 |
| 50 | 22600 | Metabolite - 09043 | 0.83 | 0.2307 | 0.6562 |
| 201 | 32590 | Metabolite - 11273 | 0.91 | 0.2321 | 0.6562 |
| 50 | 35844 | gamma,gamma-dimethylallyl pyrophosphate | 0.89 | 0.2323 | 0.6562 |
| 50 | 34283 | asparagine | 1.12 | 0.2324 | 0.6562 |
| 201 | 32616 | Metabolite - 11299 | 0.78 | 0.2346 | 0.6562 |
| 201 | 32863 | Metabolite - 11546 | 1.00 | 0.2350 | 0.6562 |
| 201 | 12067 | undecanoate (11:0) | 0.96 | 0.2351 | 0.6562 |
| 50 | 1107 | allantoin | 1.18 | 0.2382 | 0.6562 |
| 50 | 30832 | Metabolite - 10814 | 0.87 | 0.2387 | 0.6562 |
| 201 | 33195 | Metabolite - 11850 | 3.10 | 0.2393 | 0.6562 |
| 201 | 32492 | caprylate (8:0) | 0.90 | 0.2406 | 0.6562 |
| 200 | 2342 | serotonin (5HT) | 0.86 | 0.2436 | 0.6562 |
| 50 | 19368 | Metabolite - 06267 | 1.12 | 0.2437 | 0.6562 |
| 50 | 33369 | Metabolite - 12023 | 0.87 | 0.2453 | 0.6562 |
| 201 | 15677 | 3-methylhistidine | 0.69 | 0.2457 | 0.6562 |
| 200 | 34359 | Metabolite - 12749 | 1.07 | 0.2527 | 0.6705 |
| 201 | 1110 | arachidonate (20:4(n-6)) | 0.92 | 0.2581 | 0.6803 |
| 200 | 64 | phenylalanine | 0.96 | 0.2631 | 0.6842 |
| 50 | 19402 | Metabolite - 06346 | 0.91 | 0.2655 | 0.6842 |
| 200 | 32654 | 3-dehydrocarnitine | 0.91 | 0.2667 | 0.6842 |
| 201 | 22130 | phenyllactate (PLA) | 1.09 | 0.2674 | 0.6842 |
| 201 | 32815 | Metabolite - 11498 | 0.92 | 0.2692 | 0.6842 |
| 201 | 33188 | Metabolite - 11843 | 2.00 | 0.2699 | 0.6842 |
| 200 | 15506 | choline | 0.96 | 0.2766 | 0.6938 |
| 200 | 36747 | deoxycarnitine | 0.93 | 0.2771 | 0.6938 |
| 201 | 27672 | 3-indoxyl sulfate | 0.92 | 0.2831 | 0.7045 |
| 50 | 12768 | Metabolite - 03088 | 1.17 | 0.2858 | 0.7068 |
| 50 | 527 | lactate | 0.92 | 0.2898 | 0.7109 |
| 50 | 1592 | N-acetylneuraminate | 1.11 | 0.2917 | 0.7109 |
| 50 | 12781 | Metabolite - 03099 | 0.88 | 0.2939 | 0.7109 |
| 201 | 32549 | Metabolite - 02269 | 0.73 | 0.3048 | 0.7109 |
| 201 | 34344 | Metabolite - 12734 | 0.59 | 0.3048 | 0.7109 |
| 201 | 18494 | taurochenodeoxycholate | 1.21 | 0.3066 | 0.7109 |
| 201 | 34674 | Metabolite - 12990 | 0.86 | 0.3068 | 0.7109 |
| 200 | 33519 | Metabolite - 12104 | 1.04 | 0.3084 | 0.7109 |
| 200 | 33852 | 1-myristoylglycerophosphocholine | 0.96 | 0.3085 | 0.7109 |
| 50 | 19362 | Metabolite - 06226 | 1.05 | 0.3091 | 0.7109 |
| 200 | 32836 | HWESASXX | 1.60 | 0.3110 | 0.7109 |
| 50 | 31617 | Metabolite - 10963 | 0.89 | 0.3138 | 0.7109 |
| 200 | 33957 | 1-heptadecanoylglycerophosphocholine | 0.87 | 0.3167 | 0.7109 |
| 200 | 1494 | pyroglutamate (5-oxoproline) | 0.95 | 0.3188 | 0.7109 |
| 50 | 11438 | phosphate | 0.95 | 0.3286 | 0.7109 |
| 201 | 15730 | suberate | 0.97 | 0.3318 | 0.7109 |
| 201 | 18497 | taurocholate | 1.21 | 0.3320 | 0.7109 |
| 50 | 25609 | Metabolite - 10439 | 0.92 | 0.3320 | 0.7109 |
| 200 | 1125 | isoleucine | 0.94 | 0.3371 | 0.7109 |
| 201 | 33968 | 5-dodecenoate (12:1(n-7)) | 1.02 | 0.3375 | 0.7109 |
| 200 | 33142 | Metabolite - 11797 | 0.80 | 0.3383 | 0.7109 |
| 201 | 32635 | Metabolite - 11318 | 0.86 | 0.3424 | 0.7109 |
| 50 | 33089 | Metabolite - 11744 | 0.88 | 0.3444 | 0.7109 |
| 200 | 33228 | Metabolite - 11883 | 0.93 | 0.3474 | 0.7109 |
| 201 | 35675 | 2-hydroxypalmitate | 0.94 | 0.3482 | 0.7109 |
| 50 | 17391 | Metabolite - 04807 | 0.76 | 0.3503 | 0.7109 |
| 200 | 33954 | glycylphenylalanine | 0.89 | 0.3523 | 0.7109 |
| 200 | 34106 | Metabolite - 12542 | 0.95 | 0.3525 | 0.7109 |
| 201 | 32740 | Metabolite - 11423 | 1.09 | 0.3526 | 0.7109 |
| 50 | 27273 | Metabolite - 10506 | 1.07 | 0.3566 | 0.7109 |
| 200 | 33941 | decanoylcarnitine | 0.88 | 0.3568 | 0.7109 |

TABLE 3-continued

Biomarkers to Distinguish Active from Inactive Ulcerative Colitis

| Library | Comp ID | Biomarker | UC Active/ UC Inactive | p-value | q-value |
|---|---|---|---|---|---|
| 201 | 36095 | thymol sulfate | 1.60 | 0.3570 | 0.7109 |
| 200 | 22138 | homocitrulline | 0.94 | 0.3616 | 0.7109 |
| 200 | 35439 | glutaroyl carnitine | 0.96 | 0.3626 | 0.7109 |
| 201 | 32388 | dodecanedioate | 0.90 | 0.3649 | 0.7109 |
| 50 | 32322 | glutamate | 0.95 | 0.3654 | 0.7109 |
| 50 | 35271 | Metabolite - 13497 | 0.96 | 0.3691 | 0.7109 |
| 201 | 1105 | linoleate (18:2(n-6)) | 1.12 | 0.3711 | 0.7109 |
| 201 | 33675 | Metabolite - 12253 | 0.86 | 0.3715 | 0.7109 |
| 200 | 3127 | hypoxanthine | 1.06 | 0.3728 | 0.7109 |
| 200 | 15990 | glycerophosphorylcholine (GPC) | 1.05 | 0.3731 | 0.7109 |
| 201 | 33937 | alpha-hydroxyisovalerate | 0.90 | 0.3767 | 0.7109 |
| 201 | 32619 | Metabolite - 11302 | 0.86 | 0.3769 | 0.7109 |
| 200 | 32857 | Metabolite - 11540 | 0.81 | 0.3778 | 0.7109 |
| 201 | 33587 | eicosenoate [9 or 11, cis or trans] | 1.22 | 0.3779 | 0.7109 |
| 201 | 32808 | Metabolite - 11491 | 0.80 | 0.3779 | 0.7109 |
| 201 | 1114 | deoxycholate | 0.78 | 0.3794 | 0.7109 |
| 50 | 16666 | Metabolite - 04365 | 1.14 | 0.3816 | 0.7109 |
| 50 | 27722 | erythrose | 0.93 | 0.3832 | 0.7109 |
| 50 | 15488 | acetylphosphate | 0.96 | 0.3848 | 0.7109 |
| 201 | 34530 | Metabolite - 12847 | 1.28 | 0.3866 | 0.7109 |
| 50 | 1659 | dehydroascorbate | 1.15 | 0.3872 | 0.7109 |
| 201 | 31908 | 7-ketolithocholate | 1.14 | 0.3904 | 0.7109 |
| 201 | 33412 | Metabolite - 12060 | 1.11 | 0.3905 | 0.7109 |
| 201 | 32877 | Metabolite - 11560 | 1.26 | 0.3913 | 0.7109 |
| 201 | 18394 | theophylline | 0.92 | 0.3932 | 0.7109 |
| 200 | 33403 | Metabolite - 12051 | 0.86 | 0.3945 | 0.7109 |
| 50 | 35270 | Metabolite - 13496 | 0.97 | 0.3952 | 0.7109 |
| 50 | 12032 | 4-acetamidophenol | 0.84 | 0.3966 | 0.7109 |
| 201 | 1361 | pentadecanoate (15:0) | 0.92 | 0.3970 | 0.7109 |
| 201 | 33390 | Metabolite - 12039 | 1.73 | 0.3999 | 0.7109 |
| 200 | 32786 | Metabolite - 11469 | 1.03 | 0.4050 | 0.7109 |
| 201 | 18281 | 2-hydroxyhippurate (salicylurate) | 15.07 | 0.4066 | 0.7109 |
| 200 | 2132 | citrulline | 0.95 | 0.4069 | 0.7109 |
| 200 | 22175 | aspartylphenylalanine | 0.91 | 0.4073 | 0.7109 |
| 200 | 33936 | octanoylcarnitine | 0.90 | 0.4114 | 0.7109 |
| 201 | 33221 | Metabolite - 11876 | 1.06 | 0.4128 | 0.7109 |
| 50 | 12789 | Metabolite - 03107 | 0.88 | 0.4133 | 0.7109 |
| 50 | 37015 | threonine | 1.06 | 0.4135 | 0.7109 |
| 201 | 32418 | myristoleate (14:1(n-5)) | 1.16 | 0.4147 | 0.7109 |
| 50 | 21188 | stearoylglycerol (monostearin) | 1.06 | 0.4152 | 0.7109 |
| 50 | 12782 | Metabolite - 03100 | 0.81 | 0.4177 | 0.7122 |
| 200 | 33138 | Metabolite - 11793 | 0.97 | 0.4218 | 0.7155 |
| 201 | 32620 | Metabolite - 11303 | 1.23 | 0.4233 | 0.7155 |
| 201 | 1359 | oleate(18:1(n-9)) | 1.13 | 0.4276 | 0.7195 |
| 201 | 33353 | Metabolite - 12007 | 1.22 | 0.4324 | 0.7195 |
| 201 | 33391 | Metabolite - 12040 | 1.16 | 0.4335 | 0.7195 |
| 200 | 33576 | Metabolite - 12159 | 1.49 | 0.4339 | 0.7195 |
| 50 | 18283 | Metabolite - 05426 | 1.42 | 0.4364 | 0.7195 |
| 50 | 587 | gluconate | 1.09 | 0.4368 | 0.7195 |
| 50 | 18868 | Metabolite - 05847 | 0.89 | 0.4395 | 0.7195 |
| 200 | 1898 | proline | 1.05 | 0.4447 | 0.7235 |
| 200 | 34456 | gamma-glutamylisoleucine | 0.93 | 0.4488 | 0.7235 |
| 50 | 20699 | erythritol | 1.06 | 0.4508 | 0.7235 |
| 201 | 33973 | epiandrosterone sulfate | 0.86 | 0.4528 | 0.7235 |
| 50 | 1561 | alpha-tocopherol | 0.94 | 0.4549 | 0.7235 |
| 201 | 32762 | Metabolite - 11445 | 1.36 | 0.4550 | 0.7235 |
| 50 | 22548 | Metabolite - 09026 | 0.90 | 0.4570 | 0.7235 |
| 201 | 34527 | Metabolite - 12844 | 0.95 | 0.4581 | 0.7235 |
| 201 | 1302 | methionine | 0.95 | 0.4618 | 0.7235 |
| 50 | 35252 | oxalacetic acid | 1.02 | 0.4639 | 0.7235 |
| 200 | 33666 | Metabolite - 12244 | 0.94 | 0.4639 | 0.7235 |
| 201 | 34035 | linolenate [alpha or gamma; (18:3(n-3 or 6))] | 1.10 | 0.4641 | 0.7235 |
| 50 | 12593 | Metabolite - 02973 | 1.03 | 0.4702 | 0.7251 |
| 201 | 19323 | docosahexaenoate (DHA; 22:6(n-3)) | 0.90 | 0.4711 | 0.7251 |
| 200 | 33140 | Metabolite - 11795 | 1.12 | 0.4720 | 0.7251 |
| 201 | 32548 | Metabolite - 11231 | 0.93 | 0.4742 | 0.7251 |
| 200 | 34420 | (des-arg9) Bradykinin | 1.06 | 0.4801 | 0.7314 |
| 201 | 33971 | 10-heptadecenoate (17:1(n-7)) | 1.22 | 0.4860 | 0.7347 |
| 200 | 15743 | dimethylarginine | 0.99 | 0.4864 | 0.7347 |
| 200 | 33515 | Metabolite - 12100 | 0.96 | 0.4890 | 0.7347 |
| 201 | 15749 | 3-phenylpropionate (hydrocinnamate) | 0.96 | 0.4896 | 0.7347 |
| 201 | 32846 | Metabolite - 11529 | 1.18 | 0.4921 | 0.7356 |
| 50 | 21631 | Metabolite - 08403 | 0.96 | 0.4972 | 0.7356 |

TABLE 3-continued

Biomarkers to Distinguish Active from Inactive Ulcerative Colitis

| Library | Comp ID | Biomarker | UC Active/ UC Inactive | p-value | q-value |
|---|---|---|---|---|---|
| 201 | 34400 | 1,7-dimethylurate | 1.02 | 0.4974 | 0.7356 |
| 50 | 1481 | inositol 1-phosphate (I1P) | 0.91 | 0.4976 | 0.7356 |
| 201 | 36807 | 6-beta-hydroxylithocholate | 0.72 | 0.5029 | 0.7357 |
| 200 | 33773 | Metabolite - 12348 | 0.98 | 0.5036 | 0.7357 |
| 200 | 33441 | isobutyrylcarnitine | 0.93 | 0.5047 | 0.7357 |
| 50 | 35833 | ornithine | 1.05 | 0.5062 | 0.7357 |
| 201 | 1365 | myristate (14:0) | 1.11 | 0.5069 | 0.7357 |
| 200 | 35127 | pro-hydroxy-pro | 0.97 | 0.5098 | 0.7364 |
| 200 | 32458 | oleamide | 1.09 | 0.5110 | 0.7364 |
| 201 | 36097 | 4-acetaminophen sulfate | 1.59 | 0.5132 | 0.7370 |
| 200 | 32675 | Metabolite - 03951 | 1.04 | 0.5180 | 0.7412 |
| 201 | 31912 | glycolithocholate | 0.96 | 0.5203 | 0.7416 |
| 200 | 32412 | butyrylcarnitine | 1.21 | 0.5229 | 0.7416 |
| 50 | 33103 | Metabolite - 11758 | 0.97 | 0.5274 | 0.7416 |
| 50 | 15737 | glycolate (hydroxyacetate) | 1.02 | 0.5292 | 0.7416 |
| 50 | 27279 | Metabolite - 10511 | 1.01 | 0.5293 | 0.7416 |
| 50 | 35831 | glutamine | 1.03 | 0.5311 | 0.7416 |
| 50 | 33477 | erythronate | 0.97 | 0.5313 | 0.7416 |
| 201 | 33206 | Metabolite - 11861 | 1.03 | 0.5340 | 0.7423 |
| 201 | 33447 | palmitoleate (16:1(n-7)) | 1.22 | 0.5365 | 0.7423 |
| 200 | 33935 | piperine | 0.85 | 0.5373 | 0.7423 |
| 201 | 3147 | xanthine | 1.04 | 0.5431 | 0.7448 |
| 50 | 30805 | Metabolite - 10810 | 0.99 | 0.5461 | 0.7448 |
| 200 | 18357 | glycylvaline | 1.04 | 0.5463 | 0.7448 |
| 201 | 32587 | Metabolite - 02249 | 0.93 | 0.5468 | 0.7448 |
| 201 | 32980 | adrenate (22:4(n-6)) | 1.00 | 0.5499 | 0.7448 |
| 50 | 17627 | Metabolite - 04986 | 0.93 | 0.5503 | 0.7448 |
| 201 | 33183 | Metabolite - 11838 | 2.24 | 0.5542 | 0.7457 |
| 201 | 34329 | Metabolite - 12719 | 0.95 | 0.5559 | 0.7457 |
| 200 | 33626 | Metabolite - 12205 | 1.02 | 0.5572 | 0.7457 |
| 200 | 31522 | pyroglutamylglycine | 0.88 | 0.5591 | 0.7457 |
| 201 | 32748 | Metabolite - 11431 | 0.91 | 0.5603 | 0.7457 |
| 201 | 32807 | Metabolite - 11490 | 1.16 | 0.5700 | 0.7561 |
| 50 | 16818 | Metabolite - 04495 | 0.96 | 0.5746 | 0.7586 |
| 200 | 1444 | pipecolate | 0.89 | 0.5795 | 0.7586 |
| 201 | 33204 | Metabolite - 11859 | 0.98 | 0.5798 | 0.7586 |
| 50 | 31453 | cysteine | 1.03 | 0.5830 | 0.7586 |
| 200 | 32698 | Metabolite - 11381 | 0.94 | 0.5846 | 0.7586 |
| 200 | 32776 | 2-methylbutyroylcarnitine | 0.96 | 0.5857 | 0.7586 |
| 200 | 36738 | gamma-glutamylglutamate | 1.16 | 0.5878 | 0.7586 |
| 50 | 15335 | mannitol | 0.95 | 0.5887 | 0.7586 |
| 200 | 36752 | N6-acetyllysine | 0.97 | 0.5895 | 0.7586 |
| 201 | 34395 | 1-methylurate | 1.19 | 0.5908 | 0.7586 |
| 200 | 34253 | Metabolite - 12650 | 1.06 | 0.5941 | 0.7589 |
| 201 | 33190 | Metabolite - 11845 | 0.96 | 0.5948 | 0.7589 |
| 50 | 19934 | myo-inositol | 0.96 | 0.6047 | 0.7626 |
| 201 | 1336 | palmitate (16:0) | 1.08 | 0.6065 | 0.7626 |
| 200 | 569 | caffeine | 1.27 | 0.6067 | 0.7626 |
| 50 | 16634 | Metabolite - 04357 | 0.86 | 0.6069 | 0.7626 |
| 50 | 27738 | threonate | 1.04 | 0.6073 | 0.7626 |
| 200 | 34481 | Metabolite - 12798 | 1.04 | 0.6093 | 0.7627 |
| 200 | 32718 | phenylacetylglutamine | 1.08 | 0.6111 | 0.7627 |
| 200 | 15500 | carnitine | 0.98 | 0.6131 | 0.7628 |
| 50 | 15996 | aspartate | 1.11 | 0.6186 | 0.7648 |
| 200 | 33960 | 1-oleoylglycerophosphocholine | 0.98 | 0.6197 | 0.7648 |
| 50 | 36534 | urea | 0.99 | 0.6211 | 0.7648 |
| 201 | 32562 | Metabolite - 11245 | 1.21 | 0.6223 | 0.7648 |
| 200 | 32716 | Metabolite - 11399 | 1.18 | 0.6268 | 0.7667 |
| 201 | 32760 | Metabolite - 11443 | 1.03 | 0.6285 | 0.7667 |
| 201 | 35688 | 2-palmitoylglycerophosphoethanolamine | 0.97 | 0.6310 | 0.7667 |
| 50 | 1121 | margarate (17:0) | 1.10 | 0.6315 | 0.7667 |
| 201 | 33969 | stearidonate (18:4(n-3)) | 1.19 | 0.6448 | 0.7794 |
| 200 | 33422 | gammaglutamylphenylalanine | 0.96 | 0.6459 | 0.7794 |
| 200 | 33507 | Metabolite - 12092 | 1.05 | 0.6480 | 0.7796 |
| 200 | 32738 | Metabolite - 11421 | 0.91 | 0.6554 | 0.7835 |
| 200 | 32793 | Metabolite - 11476 | 1.02 | 0.6591 | 0.7835 |
| 50 | 27710 | N-acetylglycine | 0.97 | 0.6609 | 0.7835 |
| 200 | 32830 | Metabolite - 11513 | 1.20 | 0.6662 | 0.7835 |
| 200 | 33846 | indoleacetate | 1.08 | 0.6674 | 0.7835 |
| 201 | 1563 | chenodeoxycholate | 0.89 | 0.6675 | 0.7835 |
| 201 | 33194 | Metabolite - 11849 | 0.90 | 0.6691 | 0.7835 |
| 201 | 33442 | pseudouridine | 1.03 | 0.6704 | 0.7835 |
| 201 | 32754 | Metabolite - 11437 | 2.77 | 0.6713 | 0.7835 |

TABLE 3-continued

Biomarkers to Distinguish Active from Inactive Ulcerative Colitis

| Library | Comp ID | Biomarker | UC Active/ UC Inactive | p-value | q-value |
|---|---|---|---|---|---|
| 200 | 36756 | leucylleucine | 1.49 | 0.6729 | 0.7835 |
| 201 | 12035 | pelargonate (9:0) | 0.98 | 0.6734 | 0.7835 |
| 200 | 32978 | Metabolite - 11656 | 1.00 | 0.6748 | 0.7835 |
| 200 | 33405 | Metabolite - 12053 | 1.76 | 0.6783 | 0.7854 |
| 50 | 18929 | Metabolite - 05907 | 0.94 | 0.6813 | 0.7865 |
| 50 | 16823 | Metabolite - 04500 | 1.03 | 0.6881 | 0.7902 |
| 201 | 32504 | n-3 DPA (22:5(n-3)) | 0.99 | 0.6884 | 0.7902 |
| 201 | 33682 | Metabolite - 12260 | 1.08 | 0.7067 | 0.7942 |
| 201 | 34516 | Metabolite - 12833 | 1.07 | 0.7086 | 0.7942 |
| 50 | 599 | pyruvate | 1.05 | 0.7111 | 0.7942 |
| 50 | 22570 | Metabolite - 09033 | 1.02 | 0.7121 | 0.7942 |
| 201 | 31591 | androsterone sulfate | 1.03 | 0.7125 | 0.7942 |
| 50 | 27856 | Metabolite - 10597 | 1.00 | 0.7128 | 0.7942 |
| 201 | 33198 | Metabolite - 11853 | 0.98 | 0.7128 | 0.7942 |
| 201 | 33396 | Metabolite - 12045 | 1.13 | 0.7142 | 0.7942 |
| 201 | 34214 | Metabolite - 12620 | 0.96 | 0.7146 | 0.7942 |
| 50 | 16821 | Metabolite - 04498 | 1.04 | 0.7179 | 0.7942 |
| 200 | 32578 | Metabolite - 11261 | 0.97 | 0.7193 | 0.7942 |
| 201 | 33972 | 10-nonadecenoate (19:1(n-9)) | 1.07 | 0.7227 | 0.7942 |
| 200 | 19464 | testosterone | 0.78 | 0.7227 | 0.7942 |
| 201 | 33884 | Metabolite - 12442 | 1.04 | 0.7236 | 0.7942 |
| 201 | 34532 | Metabolite - 12849 | 1.18 | 0.7286 | 0.7945 |
| 201 | 31787 | 3-carboxy-4-methyl-5-propyl-2-furanpropanoate (CMPF) | 1.03 | 0.7297 | 0.7945 |
| 200 | 3141 | betaine | 1.01 | 0.7306 | 0.7945 |
| 200 | 32735 | Metabolite - 01911 | 0.97 | 0.7338 | 0.7945 |
| 201 | 32558 | p-cresol sulfate | 1.07 | 0.7357 | 0.7945 |
| 201 | 33652 | Metabolite - 12230 | 1.53 | 0.7361 | 0.7945 |
| 201 | 12261 | taurodeoxycholate | 1.10 | 0.7460 | 0.8012 |
| 200 | 33230 | 1-palmitoleoylglycerophosphocholine | 1.00 | 0.7518 | 0.8041 |
| 50 | 31618 | Metabolite - 10964 | 0.98 | 0.7532 | 0.8041 |
| 201 | 1604 | urate | 0.98 | 0.7580 | 0.8043 |
| 201 | 12129 | beta-hydroxyisovalerate | 1.06 | 0.7589 | 0.8043 |
| 200 | 33073 | cysteine-glutathione disulfide | 0.97 | 0.7611 | 0.8046 |
| 50 | 15122 | glycerol | 1.03 | 0.7643 | 0.8058 |
| 50 | 4966 | xylitol | 1.09 | 0.7804 | 0.8153 |
| 201 | 36099 | 4-ethylphenyl sulfate | 1.04 | 0.7812 | 0.8153 |
| 201 | 1642 | caprate (10:0) | 0.97 | 0.7821 | 0.8153 |
| 200 | 34384 | stachydrine | 1.11 | 0.7821 | 0.8153 |
| 201 | 36850 | taurolithocholate 3-sulfate | 1.27 | 0.7845 | 0.8153 |
| 50 | 21127 | 1-palmitoylglycerol (1-monopalmitin) | 1.12 | 0.7860 | 0.8153 |
| 200 | 33801 | ADpSGEGDFXAEGGGVR | 1.21 | 0.7875 | 0.8153 |
| 200 | 32572 | Metabolite - 11255 | 0.96 | 0.7953 | 0.8206 |
| 50 | 18388 | Metabolite - 05491 | 0.98 | 0.7972 | 0.8206 |
| 201 | 18467 | eicosapentaenoate (EPA; 20:5(n-3)) | 0.94 | 0.7988 | 0.8206 |
| 201 | 606 | uridine | 0.98 | 0.8017 | 0.8214 |
| 201 | 32867 | Metabolite - 11550 | 1.00 | 0.8037 | 0.8214 |
| 200 | 15630 | N-acetylornithine | 0.99 | 0.8121 | 0.8250 |
| 201 | 33203 | Metabolite - 11858 | 1.49 | 0.8137 | 0.8250 |
| 50 | 32319 | trans-4-hydroxyproline | 0.98 | 0.8172 | 0.8250 |
| 200 | 22154 | bradykinin | 0.99 | 0.8175 | 0.8250 |
| 201 | 18362 | azelate (nonanedioate) | 1.04 | 0.8211 | 0.8265 |
| 201 | 33638 | Metabolite - 12217 | 1.21 | 0.8270 | 0.8279 |
| 50 | 16866 | Metabolite - 04523 | 1.02 | 0.8274 | 0.8279 |
| 201 | 31555 | pyridoxate | 1.29 | 0.8307 | 0.8279 |
| 50 | 16829 | pyroglutamine | 1.02 | 0.8336 | 0.8279 |
| 200 | 33961 | 1-stearoylglycerophosphocholine | 1.08 | 0.8361 | 0.8279 |
| 200 | 34223 | Metabolite - 12629 | 1.56 | 0.8363 | 0.8279 |
| 50 | 27256 | Metabolite - 10500 | 1.01 | 0.8369 | 0.8279 |
| 201 | 1645 | laurate (12:0) | 0.95 | 0.8403 | 0.8291 |
| 50 | 33453 | alpha-ketoglutarate | 1.15 | 0.8480 | 0.8302 |
| 201 | 20675 | 1,5-anhydroglucitol (1,5-AG) | 1.00 | 0.8497 | 0.8302 |
| 201 | 22842 | cholate | 1.20 | 0.8570 | 0.8302 |
| 50 | 33386 | Metabolite - 12035 | 1.00 | 0.8572 | 0.8302 |
| 201 | 17805 | dihomolinolenate (20:2(n-6)) | 1.03 | 0.8602 | 0.8302 |
| 50 | 25532 | Metabolite - 10413 | 0.98 | 0.8617 | 0.8302 |
| 201 | 32757 | Metabolite - 11440 | 1.27 | 0.8622 | 0.8302 |
| 201 | 32398 | sebacate | 1.07 | 0.8643 | 0.8302 |
| 50 | 24115 | Metabolite - 09752 | 0.99 | 0.8656 | 0.8302 |
| 201 | 32695 | Metabolite - 11378 | 0.94 | 0.8657 | 0.8302 |
| 200 | 2734 | gamma-glutamyltyrosine | 1.00 | 0.8663 | 0.8302 |
| 201 | 32753 | Metabolite - 09789 | 1.00 | 0.8700 | 0.8319 |
| 200 | 33510 | Metabolite - 12095 | 1.00 | 0.8723 | 0.8320 |
| 201 | 32197 | 3-(4-hydroxyphenyl)lactate | 1.04 | 0.8743 | 0.8320 |

TABLE 3-continued

Biomarkers to Distinguish Active from Inactive Ulcerative Colitis

| Library | Comp ID | Biomarker | UC Active/ UC Inactive | p-value | q-value |
|---|---|---|---|---|---|
| 200 | 32328 | hexanoylcarnitine | 1.03 | 0.8877 | 0.8387 |
| 50 | 16855 | Metabolite - 04515 | 1.25 | 0.8899 | 0.8387 |
| 200 | 33033 | Metabolite - 11689 | 1.64 | 0.8920 | 0.8387 |
| 200 | 33150 | Metabolite - 11805 | 0.97 | 0.8941 | 0.8387 |
| 50 | 18335 | quinate | 1.48 | 0.8976 | 0.8387 |
| 200 | 1299 | tyrosine | 0.99 | 0.9001 | 0.8387 |
| 200 | 1508 | pantothenate | 1.01 | 0.9011 | 0.8387 |
| 201 | 32814 | Metabolite - 11497 | 1.00 | 0.9023 | 0.8387 |
| 201 | 1605 | ursodeoxycholate | 0.94 | 0.9043 | 0.8387 |
| 50 | 15365 | glycerol 3-phosphate (G3P) | 1.02 | 0.9058 | 0.8387 |
| 50 | 21011 | Metabolite - 07888 | 1.00 | 0.9092 | 0.8387 |
| 200 | 32780 | Metabolite - 11463 | 1.26 | 0.9102 | 0.8387 |
| 200 | 32632 | Metabolite - 11315 | 0.95 | 0.9127 | 0.8387 |
| 201 | 32769 | Metabolite - 11452 | 1.05 | 0.9144 | 0.8387 |
| 201 | 32561 | Metabolite - 11244 | 1.13 | 0.9148 | 0.8387 |
| 50 | 542 | 3-hydroxybutyrate (BHBA) | 0.98 | 0.9189 | 0.8392 |
| 200 | 33509 | Metabolite - 12094 | 1.03 | 0.9196 | 0.8392 |
| 200 | 18254 | paraxanthine | 1.36 | 0.9241 | 0.8395 |
| 201 | 33782 | Metabolite - 10346 | 1.58 | 0.9249 | 0.8395 |
| 201 | 32795 | Metabolite - 11478 | 1.09 | 0.9261 | 0.8395 |
| 50 | 30282 | Metabolite - 10744 | 1.04 | 0.9316 | 0.8415 |
| 201 | 34314 | Metabolite - 12704 | 0.98 | 0.9327 | 0.8415 |
| 200 | 33364 | gamma-glutamylthreonine | 1.00 | 0.9359 | 0.8425 |
| 50 | 31396 | Metabolite - 10887 | 1.08 | 0.9410 | 0.8437 |
| 201 | 32855 | Metabolite - 11538 | 0.94 | 0.9413 | 0.8437 |
| 200 | 34417 | 1-hexadecylglycerophosphocholine | 1.02 | 0.9450 | 0.8451 |
| 200 | 33408 | Metabolite - 12056 | 0.74 | 0.9538 | 0.8456 |
| 201 | 36850 | octadecanedioate | 1.02 | 0.9570 | 0.8456 |
| 200 | 27718 | creatine | 0.92 | 0.9571 | 0.8456 |
| 201 | 33254 | Metabolite - 11909 | 1.07 | 0.9620 | 0.8456 |
| 200 | 34040 | Metabolite - 12510 | 1.06 | 0.9633 | 0.8456 |
| 50 | 31266 | fructose | 1.03 | 0.9645 | 0.8456 |
| 50 | 35838 | beta-alanine | 0.84 | 0.9699 | 0.8456 |
| 200 | 32595 | Metabolite - 08893 | 1.03 | 0.9729 | 0.8456 |
| 201 | 32557 | Metabolite - 06126 | 0.89 | 0.9731 | 0.8456 |
| 201 | 32560 | Metabolite - 07765 | 0.98 | 0.9745 | 0.8456 |
| 201 | 33963 | acetoacetate | 0.82 | 0.9750 | 0.8456 |
| 201 | 34244 | Metabolite - 12644 | 0.97 | 0.9800 | 0.8456 |
| 200 | 33131 | Metabolite - 11786 | 0.99 | 0.9830 | 0.8456 |
| 50 | 19414 | Metabolite - 06350 | 1.00 | 0.9841 | 0.8456 |
| 200 | 31534 | HXGXA | 1.79 | 0.9852 | 0.8456 |
| 50 | 19576 | Metabolite - 06627 | 0.87 | 0.9871 | 0.8456 |
| 201 | 1358 | stearate (18:0) | 1.00 | 0.9873 | 0.8456 |
| 200 | 33955 | 1-palmitoylglycerophosphocholine | 1.03 | 0.9878 | 0.8456 |
| 201 | 33883 | Metabolite - 12441 | 0.73 | 0.9968 | 0.8514 |

Example 4

Classification of Subjects Using Biomarkers

Random forest analyses were used for classification of samples into groups (e.g. Crohn's disease or Ulcerative colitis, active CD or inactive CD, active or inactive UC). Random forests give an estimate of how well we can classify individuals in a new data set into each group, in contrast to a t-test, which tests whether the unknown means for two populations are different or not. Random forests create a set of classification trees based on continual sampling of the experimental units and compounds. Then each observation is classified based on the majority votes from all the classification trees.

Random forest results show that the samples can be classified correctly with varying degrees of accuracy using the biomarkers. The confusion matrices demonstrate that using blood samples CD subjects can be distinguished from UC subjects (Table 4A), active CD subjects from inactive CD subjects (Table 4C) and active UC subjects from inactive UC subjects (Table 5A). The "Out-of-Bag" (OOB) Error rate gives an estimate of how accurately new observations can be predicted using the random forest model (e.g., whether a sample is from a subject having CD or a UC subject).

The biomarkers that are most important to making the classification are also identified. Listed in Table 4B are the most important biomarkers to classify subjects as having CD or UC. Listed in Table 4D are the most important biomarkers to classify subjects as having active or inactive CD. Listed in Table 5B are the most important biomarkers to classify subjects as having active or inactive UC.

TABLE 4A

RF Confusion Matrix, Distinguish Crohn's Disease from Ulcerative Colitis
The two disease types UC and CD - OOB error rate 25.29%

| CD all vs UC all | CD | UC | err |
|---|---|---|---|
| CD | 71 | 30 | 0.30 |
| UC | 14 | 59 | 0.19 |

Based on the OOB Error rate of 25.29%, the Random Forest model that was created could be used to distinguish a subject having Crohn's disease from Ulcerative colitis with about 75% accuracy from analysis of the levels of the biomarkers in samples from the subject.

TABLE 4B

Most important biomarkers to distinguish CD from UC based upon RF analysis

| LIB | ID | Biomarker |
|---|---|---|
| 201 | 27531 | Hyodeoxycholate |
| 201 | 36776 | 7-alpha-hydroxy-3-oxo-4-cholestenoate (7-Hoca) |
| 50 | 33488 | Lathosterol |
| 200 | 15753 | Hippurate |
| 201 | 36807 | 6-beta-hydroxylithocholate |
| 201 | 33682 | Metabolite - 12260 |
| 201 | 32562 | Metabolite - 11245 |
| 201 | 32827 | Metabolite - 11510 |
| 201 | 32561 | Metabolite - 11244 |
| 50 | 21011 | Metabolite - 07888 |
| 201 | 33415 | Metabolite - 12063 |
| 50 | 18929 | Metabolite - 05907 |
| 50 | 27278 | Metabolite - 10510 |
| 200 | 33846 | Indoleacetate |
| 200 | 33576 | Metabolite - 12159 |
| 201 | 32620 | Metabolite - 11303 |
| 201 | 36850 | taurolithocholate 3-sulfate |
| 200 | 553 | Cotinine |
| 50 | 36532 | Urea |
| 201 | 33901 | Metabolite - 12456 |
| 201 | 32757 | Metabolite - 11440 |
| 50 | 25459 | Metabolite - 10395 |
| 201 | 32792 | Metabolite - 11475 |
| 50 | 16866 | Metabolite - 04523 |
| 201 | 35688 | 2-palmitoylglycerophosphoethanolamine |
| 200 | 15743 | Dimethylarginine |
| 201 | 36097 | 4-acetaminophen sulfate |
| 201 | 32558 | p-cresol sulfate |
| 201 | 31787 | 3-carbox-4-methyl-5-propyl-2-furanpropanoate (CMPF) |
| 201 | 31908 | 7-ketolithocholate |
| 50 | 32405 | 3-indolepropionate |
| 201 | 32489 | caproate (6:0) |
| 50 | 15488 | Acetylphosphate |
| 201 | 18467 | eicosapentaenoate-EPA-20-5-n-3- |
| 200 | 18357 | Glycylvaline |
| 201 | 34244 | Metabolite - 12644 |
| 200 | 32735 | Metabolite - 01911 |
| 201 | 32808 | Metabolite - 11491 |
| 201 | 15749 | 3-phenylpropionate (hydrocinnamate) |
| 50 | 33477 | Erythronate |
| 201 | 1563 | chenodeoxycholate |
| 50 | 11438 | Phosphate |
| 201 | 19323 | docosahexaenoate (DHA; 22:6(n-3)) |
| 200 | 33165 | Metabolite - 11820 |
| 50 | 27256 | Metabolite - 10500 |
| 50 | 1493 | Ornithine |
| 201 | 18362 | azelate (nonanedioate) |
| 200 | 27718 | Creatine |

TABLE 4C

RF Confusion Matrix, Distinguish Active from Inactive Crohn's Disease Active and Inactive within CD - OOB error rate 38.36%

| CD Act vs Inact | Active | Inactive | err |
|---|---|---|---|
| Active | 27 | 23 | 0.46 |
| Inactive | 24 | 27 | 0.47 |

Based on the OOB Error rate of 38.36%, the Random Forest model that was created could be used to distinguish active Crohn's disease from inactive Crohn's disease with about 62% accuracy from analysis of the levels of the biomarkers in samples from the subject.

TABLE 4D

Most important biomarkers to distinguish Active from Inactive CD, based upon RF analysis

| LIB | ID | Biomarker |
|---|---|---|
| 50 | 36534 | Urea |
| 200 | 32857 | Metabolite - 11540 |
| 201 | 32558 | p-cresol sulfate |
| 50 | 25607 | Metabolite - 10437 |
| 50 | 584 | Mannose |
| 201 | 15677 | 3-methylhistidine |
| 201 | 27672 | 3-indoxyl-sulfate |
| 50 | 19503 | Sphingomyelin |
| 200 | 33936 | Octanoylcarnitine |
| 200 | 33422 | Gammaglutamylphenylalanine |
| 50 | 31453 | Cysteine |
| 50 | 15488 | Acetylphosphate |
| 201 | 32846 | Metabolite - 11529 |
| 201 | 33627 | Metabolite - 12206 |
| 50 | 35838 | beta-alanine |
| 200 | 33150 | Metabolite - 11805 |
| 50 | 19934 | myo-inositol |
| 201 | 1302 | Methionine |
| 200 | 33510 | Metabolite - 12095 |
| 200 | 32572 | Metabolite - 11255 |
| 200 | 33441 | Isobutyrylcarnitine |
| 201 | 32753 | Metabolite - 09789 |
| 50 | 16823 | Metabolite - 04500 |
| 201 | 12035 | pelargonate (9:0) |
| 200 | 18392 | Theobromine |
| 50 | 1564 | Citrate |
| 200 | 32445 | 3-methylxanthine |
| 200 | 32854 | Metabolite - 11537 |
| 50 | 35270 | Metabolite - 13496 |
| 201 | 34314 | Metabolite - 12704 |
| 201 | 32497 | 10c-undecenoate |
| 200 | 33509 | Metabolite - 12094 |
| 200 | 33073 | cysteine-glutathione-disulfide- |
| 201 | 606 | Uridine |
| 50 | 18349 | Indolelactate |
| 50 | 35832 | Ornithine |
| 50 | 32319 | trans-4-hydroxyproline |
| 201 | 32863 | Metabolite - 11546 |
| 50 | 11438 | Phosphate |
| 200 | 22175 | Aspartylphenylalanine |
| 200 | 33822 | Metabolite - 12394 |
| 200 | 33084 | ADSGEGDFXAEGGGVR- |
| 201 | 33412 | Metabolite - 12060 |
| 50 | 33420 | gamma-tocopherol |
| 201 | 35675 | 2-hydroxypalmitate |
| 200 | 32328 | Hexanoylcarnitine |
| 201 | 32557 | Metabolite - 06126 |
| 201 | 36850 | taurolithocholate 3-sulfate |

TABLE 5A

RF Confusion Matrix, Distinguish Active from Inactive Ulcerative Colitis Active and Inactive within UC - OOB error rate 46.53%

| UC Act vs Inact | Active | Inactive | err |
|---|---|---|---|
| Active | 22 | 14 | 0.39 |
| Inactive | 14 | 23 | 0.38 |

Based on the OOB Error rate of 46.53%, the Random Forest model that was created could be used to distinguish active from inactive Ulcerative colitis with about 53% accuracy from analysis of the levels of the biomarkers in samples from the subject.

TABLE 5B

Most important biomarkers to distinguish Active from Inactive Ulcerative Colitis based upon RF analysis

| LIB | ID | Biomarker |
|---|---|---|
| 201 | 32847 | Metabolite - 11530 |
| 50 | 19396 | Metabolite - 06307 |
| 201 | 32839 | Metabolite - 11522 |
| 50 | 1564 | Citrate |
| 200 | 54 | Tryptophan |
| 200 | 33939 | N-acetylthreonine |
| 200 | 33822 | Metabolite - 12394 |
| 200 | 33084 | ADSGEGDFXAEGGGVR- |
| 50 | 63 | Cholesterol |
| 201 | 59 | Histidine |
| 200 | 32348 | 2-aminobutyrate |
| 50 | 1572 | Glycerate |
| 201 | 33225 | Metabolite - 11880 |
| 200 | 31548 | DSGEGDFXAEGGGVR- |
| 200 | 1712 | Cortisol |
| 201 | 1123 | Inosine |
| 201 | 33901 | Metabolite - 12456 |
| 201 | 1638 | Arginine |
| 200 | 15140 | Kynurenine |
| 200 | 32445 | 3-methylxanthine |
| 50 | 35259 | Glucose |
| 50 | 22649 | Metabolite - 09108 |
| 200 | 32644 | Metabolite - 11327 |
| 50 | 21044 | 2-hydroxybutyrate (AHB) |
| 201 | 32811 | Metabolite - 11494 |
| 50 | 32405 | 3-indolepropionate |
| 201 | 32501 | dihomo-alpha-linolenate (20:3(n-3)) |
| 200 | 32586 | Metabolite - 01327 |
| 200 | 33801 | ADpSGEGDFXAEGGGVR- |
| 50 | 32315 | Serine |
| 201 | 32599 | Metabolite - 11282 |
| 200 | 34390 | 7-methylxanthine |
| 200 | 32198 | Acetylcarnitine |
| 50 | 32338 | Glycine |
| 50 | 18446 | Metabolite - 05524 |
| 200 | 1649 | Valine |
| 200 | 60 | Leucine |
| 201 | 33415 | Metabolite - 12063 |
| 200 | 33852 | 1-myristoylglycerophosphocholine- |
| 201 | 32863 | Metabolite - 11546 |
| 201 | 15676 | 3-methyl-2-oxovalerate |
| 200 | 1573 | Guanosine |
| 201 | 33389 | Metabolite - 12038 |

TABLE 5B-continued

Most important biomarkers to distinguish Active from Inactive Ulcerative Colitis based upon RF analysis

| LIB | ID | Biomarker |
|---|---|---|
| 201 | 32758 | Metabolite - 11441 |
| 200 | 35433 | hydroxyisovaleroyl carnitine |
| 201 | 32759 | Metabolite - 11442 |
| 50 | 1670 | Urea |
| 201 | 32767 | Metabolite - 11450 |
| 50 | 584 | Mannose |

Example 5

Metabolites Specific for Distinguishing CD Subtypes

Based upon our analysis there appears to be a sub-set (~50%) of CD which may represent a specific form of the disease (e.g. ileal involvement). Two compounds, hyodeoxycholate and 7-alpha-hydroxy-3-oxo-4-cholestenoate (7-HOCA) (formerly Metabolite-11908), indicate the presence of a CD subtype in the population. High levels of hyodeoxycholate indicate a high chance of CD, but many false negatives were observed at the low end which is likely an indication of a subpopulation within CD. Detailed diagnosis metadata may further confirm this result. The results are shown in FIG. 1.

Example 6

Quantitative Biomarker Assays to Distinguish Subjects with Ulcerative Colitis from Crohn's Disease Quantitative assays were developed for the selected set of biomarkers listed in Table 6B and the measured levels were used to:

Measure the biomarker levels in plasma from subjects, all included (i.e., those with and those without an ileal resection).

Measure the biomarker levels in plasma from subjects without an ileal resection (i.e., ileal resection subjects excluded from analysis).

TABLE 6

Cohort Disease Groups and Subgroups:

| Disease Type | N | Ileal Resection | No Ileal Resection | Colectomy | Colon Disease | Ileum Disease |
|---|---|---|---|---|---|---|
| Crohn's Disease (CD)- Active | 75 | 35 | 40 | 8 | 48 | 58 |
| Crohn's Disease (CD)- Inactive | 77 | 30 | 47 | 2 | 53 | 58 |
| Crohn's Disease (Total) | 152 | 65 | 87 | 10 | 101 | 116 |
| Ulcerative Colitis (UC)- Active | 61 | 0 | 61 | 2 | 61 | 0 |
| Ulcerative Colitis (UC)- Inactive | 62 | 0 | 62 | 0 | 62 | 0 |
| Ulcerative Colitis (Total) | 123 | 0 | 123 | 2 | 123 | 0 |
| Healthy Control | 50 | NA | NA | NA | NA | NA |

TABLE 6A

Cohort Demographics:

| Group | Total | Males/Females | Age Range (years) |
|---|---|---|---|
| Crohn's Disease, CD | 152 | 76/76 | 19.9-79 |
| Ulcerative Colitis, UC | 123 | 59/64 | 18.6-79 |
| Healthy Control, HC | 50 | 23/27 | 23-75 |

TABLE 6B

Quantitative assays specific for the following biomarkers were developed.

| Compound ID | Biomarker | HMDB ID |
|---|---|---|
| 36807 | 6-beta-hydroxylithocholate (beta.OH.lithocholate) | 00811 |
| 36776 | 7-alpha-hydroxy-3-oxo-4-cholestenoate (7-hydroxy-cholestenoic acid, 7-HOCA, HOCA) | 12458 |
| 31908 | 7-ketolithocholic acid (7-oxolithocholic acid, ketolithocholic.acid) | 00467 |
| 1563 | Chenodeoxycholic acid | 00518 |
| 22842 | Cholic acid | 00619 |
| 1114 | Deoxycholic acid | 00626 |
| 18476 | Glycocholic acid | 00138 |
| 18477 | Glycodeoxycholic acid | 00631 |
| 27531 | Hyodeoxycholic acid | 00733 |
| 1605 | Ursodeoxycholic acid | 00946 |

LC-MS Method for the Determination of Biomarkers

Calibration spiking solutions were prepared in acetonitrile/water (1:1) and used to prepare fortified calibration standards in 100 µl de-lipidized serum. Calibration standards and subject samples were spiked with a solution of isotopically labelled internal standards in acetonitrile/water (1:1). After acidifying with 200 µl of 0.1% formic acid in water, the sample was extracted with 2 mL of ethyl acetate/cyclohexane (9:1). Following centrifugation, the organic supernatant was removed, evaporated and reconstituted in 0.100 mL acetonitrile/water (1:1).

This solution was injected onto a Waters Acquity/Thermo Quantum Ultra LC MS system equipped with a HESI probe and analyzed in negative mode.

Chromatographic conditions: Acquit), C 18 BEH, 1.7 micron 2.1×100 mm, (Waters) reversed phase column isocratic elution with acetonitrile/methanol (3:1) and water/0.01% formic acid in a ratio of 85:15.

The peak areas of the respective parent ions were measured against the peak area of the respective internal standard parent ions (Table 6C). Quantitation was performed using a weighted linear least squares regression analysis generated from fortified calibration standards prepared immediately prior to each run. The range of quantitation for each compound is listed in Table 6C.

TABLE 6C

Assay Details.

| Biomarker Compound | Ion monitored | Calibration range [ng/mL] | Internal Standard | Ion monitored |
|---|---|---|---|---|
| cholic acid | 407.3 | 20.0-4000 | cholic acid-d4 | 411.3 |
| deoxycholic acid | 391.3 | 100-20000 | deoxycholic acid-d4 | 395.3 |
| hyodeoxycholic acid | 391.3 | 10.0-2000 | ursodeoxycholic acid-d4 | 395.3 |
| ursodeoxycholic acid | 391.3 | 100-20000 | ursodeoxycholic acid-d4 | 395.3 |
| chenodeoxycholic acid | 391.3 | 20.0-4000 | chenodeoxycholic acid-d4 | 395.3 |
| glycocholic acid | 464.3 | 20.0-4000 | glycocholic acid-d4 | 468.3 |
| glycodeoxycholic acid | 448.3 | 100-20000 | glycodeoxycholic acid-d4 | 452.3 |
| 7-oxolithocholic acid | 389.3 | 2.00-400 | ursodeoxycholic acid-d4 | 395.3 |
| 7-hydroxy-cholestenoic acid (7-HOCA) | 429.3 | 4.00-800 | deoxycholic acid-d4 | 395.3 |

Paired t-tests were performed on the data to determine if the biomarkers were present at differential levels in a definable population or subpopulation (e.g., Crohn's disease vs. Ulcerative colitis, or active Crohn's disease vs. inactive Crohn's disease, or Crohn's disease patients without a surgical resection of the ileum vs. Ulcerative colitis patients without a surgical resection of the ileum, etc.). The comparisons and results are shown in Tables 6D, 6E, and 6F. The biomarkers that were statistically significantly changed in each comparison are presented in bold and marked with asterisks. It can be seen that the pattern of the significant biomarkers varies with the comparison and is useful to discriminate the populations and subpopulations. For example, the biomarkers that distinguish UC from CD include 6-beta-OH-lithocholate, 7-HOCA, deoxy cholic acid, glycodeoxycholic acid, and hyodeoxycholic acid while a subset of these biomarkers that does not include 6-beta-OH-lithocholate distinguishes active UC from active CD.

TABLE 6D

Pairwise T-Test Analysis, All patients included in the analysis:

| BIOMARKER | ALL UC vs. ALL CD Pair 1 | UC Active vs. CD Active Pair 2 | UC Inact vs. CD Inact Pair 3 | UC Active vs. UC Inact Pair 4 | CD Act vs. CD Inact Pair 5 | ILIUM DZ Y vs. N Pair 6 | ILIUM DZ Y vs. N w/o Resection Pair 7 |
|---|---|---|---|---|---|---|---|
| 6-beta-OH-lithocholate | 0.0006* | 0.1455 | 0.0007* | 0.9027 | 0.0466* | 1.41E−08* | 0.0352* |
| 7-HOCA | 1.02E−13* | 1.04E−09* | 1.47E−05* | 0.3482 | 0.1454 | 1.35E−16* | 0.0011* |
| 7-ketolithocholic acid | 0.6465 | 0.8995 | 0.4357 | 0.9439 | 0.4039 | 0.0003* | 0.0366* |
| chenodeoxycholic acid | 0.0626 | 0.1456 | 0.1900 | 0.0635 | 0.1242 | 7.71E−07* | 0.0043* |
| Cholic acid | 0.2120 | 0.8326 | 0.1735 | 0.0561 | 0.4016 | 4.98E−06* | 0.0013* |
| Deoxycholic acid | 1.65E−06* | 2.08E−05* | 0.0116* | 0.5764 | 0.0244* | 0.0001* | 0.0013* |
| Glycocholic acid | 0.3473 | 0.4099 | 0.6325 | 0.1042 | 0.0531 | 0.7590 | 0.4498 |

TABLE 6D-continued

Pairwise T-Test Analysis, All patients included in the analysis:

| BIOMARKER | ALL UC vs. ALL CD Pair 1 | UC Active vs. CD Active Pair 2 | UC Inact vs. CD Inact Pair 3 | UC Active vs. UC Inact Pair 4 | CD Act vs. CD Inact Pair 5 | ILIUM DZ Y vs. N Pair 6 | ILIUM DZ Y vs. N w/o Resection Pair 7 |
|---|---|---|---|---|---|---|---|
| Glycodeoxycholic acid | 5.75E−10* | 1.69E−08* | 0.0019* | 0.7591 | 0.0208* | 2.66E−08* | 9.21E−05* |
| Hyodeoxycholic acid | 0.0007* | 0.0007* | 0.1442 | 0.9963 | 0.0577 | 1.77E−06* | 0.0039* |
| Ursodeoxycholic acid | 0.7788 | 0.2420 | 0.1260 | 0.7121 | 0.0178* | 0.0022* | 0.1787 |

Pairwise T-TESTS KEY:
Pair 1: UC vs. CD (ALL)
Pair 2: UC-Active vs. CD-Active
Pair 3: UC-Inactive vs. CD-Inactive
Pair 4: UC-Inactive vs. UC-Active
Pair 5: CD-Inactive vs. CD-Active
Pair 6: ILEUM_Disease: YES vs. NO, All (i.e., ileum disease vs. no ileum involvement, including all subjects)
Pair 7: ILEUM_Disease: YES vs. NO, No Resection (i.e., ileum disease vs. no ileum involvement, excluding resection subjects)
UC, Ulcerative colitis
CD, Crohn's Disease

TABLE 6E

Disease vs. Healthy

| BIOMARKER | CD vs. HC | UC vs. HC | CD-active vs. HC | UC-active vs. HC | CD-inactive vs. HC | UC-inactive vs. HC |
|---|---|---|---|---|---|---|
| 6-beta-OH- lithocholate | 0.2025 | 0.3299 | 0.9781 | 0.4203 | 0.0415* | 0.3804 |
| 7-HOCA | 0.8779 | 0.0005* | 0.8103 | 0.0008* | 0.6338 | 0.0142* |
| 7-ketolithocholic acid | 0.0448* | 0.0045* | 0.1116 | 0.0098* | 0.0696 | 0.0119* |
| chenodeoxycholic acid | 0.1984 | 0.1586 | 0.0964 | 0.0206* | 0.4817 | 0.6678 |
| Cholic acid | 0.0207* | 0.0170* | 0.0342* | 0.0017* | 0.0372* | 0.1687 |
| Deoxycholic acid | 0.0048* | 0.6483 | 0.0060* | 0.8823 | 0.0495* | 0.5084 |
| Glycocholic acid | 0.1914 | 0.1624 | 0.0250* | 0.0676 | 0.7519 | 0.6183 |
| Glycodeoxycholic acid | 0.0011* | 0.6611 | 0.0026* | 0.5948 | 0.0162* | 0.7966 |
| Hyodeoxycholic acid | 0.0080* | 0.1658 | 0.0061* | 0.2187 | 0.0637 | 0.2250 |
| Ursodeoxycholic acid | 0.1842 | 0.0194* | 0.6566 | 0.0267* | 0.0912 | 0.0633 |

TABLE 6F

CD vs. UC and Active vs. Inactive

| BIOMARKER | UC vs. CD | UC-active vs. CD-active | UC-inactive vs. CD-inactive | UC-active vs. UC-inactive | CD-active vs. CD-inactive |
|---|---|---|---|---|---|
| 6-beta-OH-lithocholate | 0.5811 | 0.5633 | 0.1932 | 0.9027 | 0.1102 |
| 7-HOCA | 0.0102* | 0.0227* | 0.2024 | 0.3482 | 0.5871 |
| 7-ketolithocholic acid | 0.3945 | 0.4774 | 0.6205 | 0.9439 | 0.8734 |
| chenodeoxycholic acid | 0.9494 | 0.6527 | 0.7667 | 0.0635 | 0.3828 |
| Cholic acid | 0.9538 | 0.3045 | 0.4440 | 0.0561 | 0.9560 |
| Deoxycholic acid | 0.0001* | 0.0028* | 0.0080* | 0.5764 | 0.3767 |
| Glycocholic acid | 0.8229 | 0.9966 | 0.8440 | 0.1042 | 0.0258* |
| Glycodeoxycholic acid | 0.0000* | 0.0003* | 0.0055* | 0.7591 | 0.4687 |
| Hyodeoxycholic acid | 0.0804 | 0.0768 | 0.4432 | 0.9963 | 0.3487 |
| Ursodeoxycholic acid | 0.3062 | 0.1237 | 0.9898 | 0.7121 | 0.2575 |

CD, Crohn's Disease
UC, Ulcerative colitis
HC, Healthy control

Example 7

Logistic Regression Analysis and Biomarker Models

Logistic regression analysis was used to generate model algorithms using the levels of one or more of the biomarkers (6-beta-hydroxylithocholate (beta.OH.lithocholate); 7-alpha-hydroxy-3-oxo-4-cholestenoate (7-HOCA, HOCA); 7-ketolithocholic acid (ketolithocholic.acid); Chenodeoxycholic acid; Cholic acid; Deoxycholic acid; Glycocholic acid; Glycodeoxycholic acid; Hyodeoxycholic acid; and Ursodeoxycholic acid) measured using the targeted assays described above on plasma samples from the subjects described in Tables 6 and 6A. The results are presented in Tables 7 and 7A. Receiver Operator Characteristics (ROC) graphs were constructed and the area under the curve (AUC) was used to estimate the discriminative power of the model or test. The AUC is an indicator of the goodness of the test and can have any value between 0 and 1. A perfect diagnostic test has an AUC of 1.0. The biomarker models generated attain an AUC of 0.72 when only subjects that have not undergone a surgical resection of the ileum were analyzed (Table 7) and an AUC of 0.82 when all of the subjects were included (Table 7A). In Table 7 the biomarker models were developed and tested using the levels of the biomarkers measured in the cohort that included only those subjects without a surgical resection of the ileum.

TABLE 7

Biomarker Models for Determination of IBD Developed Using Logistic Regression Analysis of Non-resectioned Subjects with Crohn's Disease or Ulcerative Colitis Using the Listed Biomarkers

| AUC | Biomarkers used in logistic regression analysis | NUMBER_OF_Biomarkers |
|---|---|---|
| 0.72 | beta.OH.lithocholate, HOCA, Glycodeoxycholic.Acid | 3 |
| 0.71 | beta.OH.lithocholate, HOCA, Glycocholic.Acid, Glycodeoxycholic.Acid | 4 |
| 0.71 | beta.OH.lithocholate, HOCA, Glycodeoxycholic.Acid, Ursodeoxycholic.Acid | 4 |
| 0.71 | beta.OH.lithocholate, HOCA, chenodeoxycholic.acid, Glycodeoxycholic.Acid | 4 |
| 0.70 | HOCA, Glycodeoxycholic.Acid, Ursodeoxycholic.Acid | 3 |
| 0.70 | HOCA, Cholic.Acid, Glycodeoxycholic.Acid, Ursodeoxycholic.Acid | 4 |
| 0.70 | beta.OH.lithocholate, Glycodeoxycholic.Acid, Ursodeoxycholic.Acid | 3 |
| 0.70 | beta.OH.lithocholate, Glycodeoxycholic.Acid | 2 |
| 0.70 | beta.OH.lithocholate, HOCA, Cholic.Acid, Glycodeoxycholic.Acid | 4 |
| 0.70 | beta.OH.lithocholate, HOCA, ketolithocholic.acid, Glycodeoxycholic.Acid | 4 |
| 0.70 | beta.OH.lithocholate, HOCA, Cholic.Acid, Glycocholic.Acid | 4 |
| 0.70 | HOCA, ketolithocholic.acid, Cholic.Acid, Glycodeoxycholic.Acid | 4 |
| 0.70 | HOCA, ketolithocholic.acid, Glycodeoxycholic.Acid | 3 |
| 0.69 | HOCA, Glycocholic.Acid, Glycodeoxycholic.Acid, Ursodeoxycholic.Acid | 4 |
| 0.69 | beta.OH.lithocholate, Glycocholic.Acid, Glycodeoxycholic.Acid | 3 |
| 0.69 | HOCA, Deoxycholic.Acid, Glycodeoxycholic.Acid | 3 |
| 0.69 | HOCA, ketolithocholic.acid, Glycodeoxycholic.Acid, Ursodeoxycholic.Acid | 4 |
| 0.69 | HOCA, Glycodeoxycholic.Acid | 2 |
| 0.69 | Glycodeoxycholic.Acid, Ursodeoxycholic.Acid | 2 |
| 0.69 | HOCA, chenodeoxycholic.acid, Glycodeoxycholic.Acid | 3 |
| 0.69 | beta.OH.lithocholate, HOCA, Glycodeoxycholic.Acid, Hyodeoxycholic.Acid | 4 |
| 0.69 | beta.OH.lithocholate, Cholic.Acid, Glycocholic.Acid, Glycodeoxycholic.Acid | 4 |
| 0.69 | beta.OH.lithocholate, HOCA, Deoxycholic.Acid, Glycodeoxycholic.Acid | 4 |
| 0.69 | beta.OH.lithocholate, Glycodeoxycholic.Acid, Hyodeoxycholic.Acid, Ursodeoxycholic.Acid | 4 |
| 0.69 | HOCA, chenodeoxycholic.acid, Glycodeoxycholic.Acid, Ursodeoxycholic.Acid | 4 |
| 0.69 | HOCA, ketolithocholic.acid, Glycocholic.Acid, Glycodeoxycholic.Acid | 4 |
| 0.69 | beta.OH.lithocholate, HOCA, Glycocholic.Acid | 3 |
| 0.69 | HOCA, chenodeoxycholic.acid, Cholic.Acid, Glycodeoxycholic.Acid | 4 |
| 0.69 | HOCA, Cholic.Acid, Glycodeoxycholic.Acid | 3 |
| 0.69 | HOCA, ketolithocholic.acid, chenodeoxycholic.acid, Glycodeoxycholic.Acid | 4 |
| 0.69 | beta.OH.lithocholate, Glycocholic.Acid, Glycodeoxycholic.Acid, Hyodeoxycholic.Acid | 4 |
| 0.69 | beta.OH.lithocholate, HOCA, Glycocholic.Acid, Ursodeoxycholic.Acid | 4 |
| 0.69 | HOCA, Cholic.Acid, Glycodeoxycholic.Acid, Hyodeoxycholic.Acid | 4 |
| 0.68 | ketolithocholic.acid, Glycodeoxycholic.Acid | 2 |
| 0.68 | beta.OH.lithocholate, Cholic.Acid, Glycodeoxycholic.Acid, Ursodeoxycholic.Acid | 4 |
| 0.68 | beta.OH.lithocholate, Deoxycholic.Acid, Glycocholic.Acid, Glycodeoxycholic.Acid | 4 |
| 0.68 | beta.OH.lithocholate, Glycocholic.Acid, Glycodeoxycholic.Acid, Ursodeoxycholic.Acid | 4 |
| 0.68 | HOCA, ketolithocholic.acid, Glycodeoxycholic.Acid, Hyodeoxycholic.Acid | 4 |
| 0.68 | beta.OH.lithocholate, HOCA, Cholic.Acid, Hyodeoxycholic.Acid | 4 |
| 0.68 | HOCA, Cholic.Acid, Deoxycholic.Acid, Glycodeoxycholic.Acid | 4 |
| 0.68 | beta.OH.lithocholate, HOCA, Cholic.Acid | 3 |
| 0.68 | HOCA, Glycodeoxycholic.Acid, Hyodeoxycholic.Acid, Ursodeoxycholic.Acid | 4 |
| 0.68 | beta.OH.lithocholate, HOCA | 2 |
| 0.68 | beta.OH.lithocholate, HOCA, Glycocholic.Acid, Hyodeoxycholic.Acid | 4 |
| 0.68 | beta.OH.lithocholate, chenodeoxycholic.acid, Glycodeoxycholic.Acid, Ursodeoxycholic.Acid | 4 |
| 0.68 | beta.OH.lithocholate, HOCA, Deoxycholic.Acid | 3 |
| 0.68 | Cholic.Acid, Glycocholic.Acid, Glycodeoxycholic.Acid, Ursodeoxycholic.Acid | 4 |
| 0.68 | HOCA, Glycodeoxycholic.Acid, Hyodeoxycholic.Acid | 3 |
| 0.68 | beta.OH.lithocholate, HOCA, ketolithocholic.acid, Cholic.Acid | 4 |
| 0.68 | HOCA, ketolithocholic.acid, Deoxycholic.Acid, Glycodeoxycholic.Acid | 4 |
| 0.68 | beta.OH.lithocholate, HOCA, chenodeoxycholic.acid, Glycocholic.Acid | 4 |
| 0.68 | beta.OH.lithocholate, HOCA, Deoxycholic.Acid, Ursodeoxycholic.Acid | 4 |
| 0.68 | beta.OH.lithocholate, HOCA, ketolithocholic.acid, Glycocholic.Acid | 4 |

TABLE 7-continued

Biomarker Models for Determination of IBD Developed Using Logistic
Regression Analysis of Non-resectioned Subjects with Crohn's Disease or
Ulcerative Colitis Using the Listed Biomarkers

| AUC | Biomarkers used in logistic regression analysis | NUMBER_OF_Biomarkers |
|---|---|---|
| 0.68 | beta.OH.lithocholate, Cholic.Acid, Glycodeoxycholic.Acid | 3 |
| 0.68 | beta.OH.lithocholate, HOCA, Ursodeoxycholic.Acid | 3 |
| 0.68 | beta.OH.lithocholate, chenodeoxycholic.acid, Glycocholic.Acid, Glycodeoxycholic.Acid | 4 |
| 0.68 | beta.OH.lithocholate, HOCA, chenodeoxycholic.acid, Cholic.Acid | 4 |
| 0.68 | Glycodeoxycholic.Acid, Hyodeoxycholic.Acid, Ursodeoxycholic.Acid | 3 |
| 0.68 | HOCA, chenodeoxycholic.acid, Glycocholic.Acid, Glycodeoxycholic.Acid | 4 |
| 0.68 | beta.OH.lithocholate, chenodeoxycholic.acid, Cholic.Acid, Glycodeoxycholic.Acid | 4 |
| 0.68 | beta.OH.lithocholate, Glycodeoxycholic.Acid, Hyodeoxycholic.Acid | 3 |
| 0.68 | beta.OH.lithocholate, ketolithocholic.acid, chenodeoxycholic.acid, Glycodeoxycholic.Acid | 4 |
| 0.68 | beta.OH.lithocholate, HOCA, Deoxycholic.Acid, Glycocholic.Acid | 4 |
| 0.68 | beta.OH.lithocholate, HOCA, Cholic.Acid, Ursodeoxycholic.Acid | 4 |
| 0.68 | HOCA, Glycocholic.Acid, Glycodeoxycholic.Acid | 3 |
| 0.68 | HOCA, chenodeoxycholic.acid, Glycodeoxycholic.Acid, Hyodeoxycholic.Acid | 4 |
| 0.68 | HOCA, ketolithocholic.acid, Cholic.Acid, Glycocholic.Acid | 4 |
| 0.67 | beta.OH.lithocholate, HOCA, chenodeoxycholic.acid, Ursodeoxycholic.Acid | 4 |
| 0.67 | beta.OH.lithocholate, ketolithocholic.acid, Glycodeoxycholic.Acid, Hyodeoxycholic.Acid | 4 |
| 0.67 | beta.OH.lithocholate, Cholic.Acid, Glycodeoxycholic.Acid, Hyodeoxycholic.Acid | 4 |
| 0.67 | chenodeoxycholic.acid, Glycodeoxycholic.Acid | 2 |
| 0.67 | Glycocholic.Acid, Glycodeoxycholic.Acid, Hyodeoxycholic.Acid, Ursodeoxycholic.Acid | 4 |
| 0.67 | beta.OH.lithocholate, HOCA, ketolithocholic.acid, chenodeoxycholic.acid | 4 |
| 0.67 | beta.OH.lithocholate, HOCA, Deoxycholic.Acid, Hyodeoxycholic.Acid | 4 |
| 0.67 | HOCA, Glycocholic.Acid, Glycodeoxycholic.Acid, Hyodeoxycholic.Acid | 4 |
| 0.67 | beta.OH.lithocholate, ketolithocholic.acid, Glycodeoxycholic.Acid, Ursodeoxycholic.Acid | 4 |
| 0.67 | beta.OH.lithocholate, ketolithocholic.acid, Glycodeoxycholic.Acid | 3 |
| 0.67 | HOCA, Cholic.Acid, Glycocholic.Acid, Glycodeoxycholic.Acid | 4 |
| 0.67 | beta.OH.lithocholate, ketolithocholic.acid, Glycocholic.Acid, Glycodeoxycholic.Acid | 4 |
| 0.67 | Deoxycholic.Acid, Glycocholic.Acid, Glycodeoxycholic.Acid, Ursodeoxycholic.Acid | 4 |
| 0.67 | beta.OH.lithocholate, HOCA, ketolithocholic.acid, Hyodeoxycholic.Acid | 4 |
| 0.67 | Glycocholic.Acid, Glycodeoxycholic.Acid, Ursodeoxycholic.Acid | 3 |
| 0.67 | beta.OH.lithocholate, HOCA, Hyodeoxycholic.Acid, Ursodeoxycholic.Acid | 4 |
| 0.67 | Deoxycholic.Acid, Glycodeoxycholic.Acid, Ursodeoxycholic.Acid | 3 |
| 0.67 | chenodeoxycholic.acid, Cholic.Acid, Glycodeoxycholic.Acid, Hyodeoxycholic.Acid | 4 |
| 0.67 | ketolithocholic.acid, Glycodeoxycholic.Acid, Hyodeoxycholic.Acid | 3 |
| 0.67 | Glycocholic.Acid, Glycodeoxycholic.Acid | 2 |
| 0.67 | ketolithocholic.acid, Cholic.Acid, Glycodeoxycholic.Acid | 3 |
| 0.67 | beta.OH.lithocholate, HOCA, Cholic.Acid, Deoxycholic.Acid | 4 |
| 0.67 | HOCA, Hyodeoxycholic.Acid, Ursodeoxycholic.Acid | 3 |
| 0.67 | HOCA, Deoxycholic.Acid, Glycocholic.Acid, Glycodeoxycholic.Acid | 4 |
| 0.67 | HOCA, ketolithocholic.acid, Glycocholic.Acid | 3 |
| 0.67 | Cholic.Acid, Deoxycholic.Acid, Glycodeoxycholic.Acid, Ursodeoxycholic.Acid | 4 |
| 0.67 | Cholic.Acid, Glycodeoxycholic.Acid, Ursodeoxycholic.Acid | 3 |
| 0.67 | HOCA, Cholic.Acid, Hyodeoxycholic.Acid, Ursodeoxycholic.Acid | 4 |
| 0.67 | HOCA, Deoxycholic.Acid, Glycodeoxycholic.Acid, Ursodeoxycholic.Acid | 4 |
| 0.67 | beta.OH.lithocholate, Deoxycholic.Acid, Glycodeoxycholic.Acid, Hyodeoxycholic.Acid | 4 |
| 0.67 | Deoxycholic.Acid, Glycodeoxycholic.Acid, Hyodeoxycholic.Acid, Ursodeoxycholic.Acid | 4 |
| 0.67 | beta.OH.lithocholate, HOCA, Hyodeoxycholic.Acid | 3 |
| 0.66 | beta.OH.lithocholate, HOCA, chenodeoxycholic.acid | 3 |
| 0.66 | beta.OH.lithocholate, ketolithocholic.acid, Deoxycholic.Acid, Glycodeoxycholic.Acid | 4 |
| 0.66 | chenodeoxycholic.acid, Cholic.Acid, Glycodeoxycholic.Acid | 3 |
| 0.66 | ketolithocholic.acid, chenodeoxycholic.acid, Glycodeoxycholic.Acid | 3 |
| 0.66 | HOCA, ketolithocholic.acid, Glycocholic.Acid, Ursodeoxycholic.Acid | 4 |
| 0.66 | beta.OH.lithocholate, chenodeoxycholic.acid, Glycodeoxycholic.Acid | 3 |
| 0.66 | chenodeoxycholic.acid, Glycodeoxycholic.Acid, Hyodeoxycholic.Acid | 3 |

TABLE 7-continued

Biomarker Models for Determination of IBD Developed Using Logistic
Regression Analysis of Non-resectioned Subjects with Crohn's Disease or
Ulcerative Colitis Using the Listed Biomarkers

| AUC | Biomarkers used in logistic regression analysis | NUMBER_OF_Biomarkers |
|---|---|---|
| 0.66 | beta.OH.lithocholate, chenodeoxycholic.acid, Deoxycholic.Acid, Glycodeoxycholic.Acid | 4 |
| 0.66 | ketolithocholic.acid, Glycocholic.Acid, Glycodeoxycholic.Acid | 3 |
| 0.66 | chenodeoxycholic.acid, Cholic.Acid, Glycocholic.Acid, Glycodeoxycholic.Acid | 4 |
| 0.66 | HOCA, Cholic.Acid, Glycocholic.Acid, Ursodeoxycholic.Acid | 4 |
| 0.66 | beta.OH.lithocholate, Deoxycholic.Acid, Glycodeoxycholic.Acid, Ursodeoxycholic.Acid | 4 |
| 0.66 | chenodeoxycholic.acid, Glycodeoxycholic.Acid, Ursodeoxycholic.Acid | 3 |
| 0.66 | HOCA, ketolithocholic.acid | 2 |
| 0.66 | Cholic.Acid, Deoxycholic.Acid, Glycocholic.Acid, Glycodeoxycholic.Acid | 4 |
| 0.66 | HOCA, ketolithocholic.acid, Cholic.Acid | 3 |
| 0.66 | beta.OH.lithocholate, Deoxycholic.Acid, Glycodeoxycholic.Acid | 3 |
| 0.66 | HOCA, Deoxycholic.Acid, Glycodeoxycholic.Acid, Hyodeoxycholic.Acid | 4 |
| 0.66 | Glycodeoxycholic.Acid | 1 |
| 0.66 | beta.OH.lithocholate, HOCA, chenodeoxycholic.acid, Hyodeoxycholic.Acid | 4 |
| 0.66 | beta.OH.lithocholate, ketolithocholic.acid, Cholic.Acid, Glycodeoxycholic.Acid | 4 |
| 0.66 | HOCA, Cholic.Acid, Ursodeoxycholic.Acid | 3 |
| 0.66 | ketolithocholic.acid, Glycocholic.Acid, Glycodeoxycholic.Acid, Ursodeoxycholic.Acid | 4 |
| 0.66 | chenodeoxycholic.acid, Glycocholic.Acid, Glycodeoxycholic.Acid, Ursodeoxycholic.Acid | 4 |
| 0.66 | HOCA, ketolithocholic.acid, Hyodeoxycholic.Acid | 3 |
| 0.66 | ketolithocholic.acid, chenodeoxycholic.acid, Cholic.Acid, Glycodeoxycholic.Acid | 4 |
| 0.66 | ketolithocholic.acid, Glycocholic.Acid, Glycodeoxycholic.Acid, Hyodeoxycholic.Acid | 4 |
| 0.66 | HOCA, Deoxycholic.Acid, Ursodeoxycholic.Acid | 3 |
| 0.66 | HOCA, ketolithocholic.acid, Glycocholic.Acid, Hyodeoxycholic.Acid | 4 |
| 0.66 | Cholic.Acid, Glycocholic.Acid, Glycodeoxycholic.Acid | 3 |
| 0.66 | HOCA, Glycocholic.Acid, Ursodeoxycholic.Acid | 3 |
| 0.66 | Glycocholic.Acid, Glycodeoxycholic.Acid, Hyodeoxycholic.Acid | 3 |
| 0.66 | HOCA, chenodeoxycholic.acid, Deoxycholic.Acid, Glycodeoxycholic.Acid | 4 |
| 0.66 | beta.OH.lithocholate, HOCA, ketolithocholic.acid, Ursodeoxycholic.Acid | 4 |
| 0.66 | beta.OH.lithocholate, chenodeoxycholic.acid, Glycodeoxycholic.Acid, Hyodeoxycholic.Acid | 4 |
| 0.66 | ketolithocholic.acid, Glycodeoxycholic.Acid, Ursodeoxycholic.Acid | 3 |
| 0.66 | chenodeoxycholic.acid, Glycocholic.Acid, Glycodeoxycholic.Acid | 3 |
| 0.66 | ketolithocholic.acid, Deoxycholic.Acid, Glycodeoxycholic.Acid | 3 |
| 0.66 | ketolithocholic.acid, Cholic.Acid, Deoxycholic.Acid, Glycodeoxycholic.Acid | 4 |
| 0.66 | HOCA, Ursodeoxycholic.Acid | 2 |
| 0.66 | HOCA, chenodeoxycholic.acid, Glycocholic.Acid | 3 |
| 0.66 | Deoxycholic.Acid, Glycodeoxycholic.Acid, Hyodeoxycholic.Acid | 3 |
| 0.66 | Cholic.Acid, Glycodeoxycholic.Acid | 2 |
| 0.65 | beta.OH.lithocholate, ketolithocholic.acid, Hyodeoxycholic.Acid, Ursodeoxycholic.Acid | 4 |
| 0.65 | HOCA, Cholic.Acid, Deoxycholic.Acid, Ursodeoxycholic.Acid | 4 |
| 0.65 | chenodeoxycholic.acid, Deoxycholic.Acid, Glycodeoxycholic.Acid, Ursodeoxycholic.Acid | 4 |
| 0.65 | chenodeoxycholic.acid, Deoxycholic.Acid, Glycodeoxycholic.Acid, Hyodeoxycholic.Acid | 4 |
| 0.65 | ketolithocholic.acid, Deoxycholic.Acid, Glycodeoxycholic.Acid, Ursodeoxycholic.Acid | 4 |
| 0.65 | beta.OH.lithocholate, HOCA, ketolithocholic.acid | 3 |
| 0.65 | HOCA, chenodeoxycholic.acid | 2 |
| 0.65 | HOCA, chenodeoxycholic.acid, Hyodeoxycholic.Acid, Ursodeoxycholic.Acid | 4 |
| 0.65 | chenodeoxycholic.acid, Cholic.Acid, Glycodeoxycholic.Acid, Ursodeoxycholic.Acid | 4 |
| 0.65 | HOCA, ketolithocholic.acid, Deoxycholic.Acid | 3 |
| 0.65 | HOCA, chenodeoxycholic.acid, Cholic.Acid, Deoxycholic.Acid | 4 |
| 0.65 | ketolithocholic.acid, chenodeoxycholic.acid, Glycocholic.Acid, Glycodeoxycholic.Acid | 4 |
| 0.65 | HOCA, Glycocholic.Acid, Hyodeoxycholic.Acid, Ursodeoxycholic.Acid | 4 |
| 0.65 | ketolithocholic.acid, chenodeoxycholic.acid, Glycodeoxycholic.Acid, Ursodeoxycholic.Acid | 4 |
| 0.65 | Deoxycholic.Acid, Glycodeoxycholic.Acid | 2 |

TABLE 7-continued

Biomarker Models for Determination of IBD Developed Using Logistic
Regression Analysis of Non-resectioned Subjects with Crohn's Disease or
Ulcerative Colitis Using the Listed Biomarkers

| AUC | Biomarkers used in logistic regression analysis | NUMBER_OF_Biomarkers |
|---|---|---|
| 0.65 | chenodeoxycholic.acid, Glycodeoxycholic.Acid, Hyodeoxycholic.Acid, Ursodeoxycholic.Acid | 4 |
| 0.65 | chenodeoxycholic.acid, Deoxycholic.Acid, Glycodeoxycholic.Acid | 3 |
| 0.65 | HOCA, chenodeoxycholic.acid, Deoxycholic.Acid, Ursodeoxycholic.Acid | 4 |
| 0.65 | beta.OH.lithocholate, chenodeoxycholic.acid, Hyodeoxycholic.Acid | 3 |
| 0.65 | HOCA, ketolithocholic.acid, Cholic.Acid, Ursodeoxycholic.Acid | 4 |
| 0.65 | HOCA, chenodeoxycholic.acid, Ursodeoxycholic.Acid | 3 |
| 0.65 | HOCA, Cholic.Acid, Hyodeoxycholic.Acid | 3 |
| 0.65 | Deoxycholic.Acid, Glycocholic.Acid, Glycodeoxycholic.Acid | 3 |
| 0.65 | chenodeoxycholic.acid, Deoxycholic.Acid, Glycocholic.Acid, Glycodeoxycholic.Acid | 4 |
| 0.65 | Cholic.Acid, Glycodeoxycholic.Acid, Hyodeoxycholic.Acid, Ursodeoxycholic.Acid | 4 |
| 0.65 | HOCA, chenodeoxycholic.acid, Cholic.Acid | 3 |
| 0.65 | HOCA, ketolithocholic.acid, Ursodeoxycholic.Acid | 3 |
| 0.65 | HOCA, Glycocholic.Acid | 2 |
| 0.65 | HOCA | 1 |
| 0.65 | HOCA, ketolithocholic.acid, chenodeoxycholic.acid, Cholic.Acid | 4 |
| 0.65 | HOCA, ketolithocholic.acid, Hyodeoxycholic.Acid, Ursodeoxycholic.Acid | 4 |
| 0.65 | chenodeoxycholic.acid, Glycocholic.Acid, Glycodeoxycholic.Acid, Hyodeoxycholic.Acid | 4 |
| 0.65 | HOCA, ketolithocholic.acid, Cholic.Acid, Deoxycholic.Acid | 4 |
| 0.65 | ketolithocholic.acid, Deoxycholic.Acid, Glycocholic.Acid, Glycodeoxycholic.Acid | 4 |
| 0.65 | HOCA, ketolithocholic.acid, chenodeoxycholic.acid | 3 |
| 0.65 | ketolithocholic.acid, chenodeoxycholic.acid, Deoxycholic.Acid, Glycodeoxycholic.Acid | 4 |
| 0.65 | HOCA, Deoxycholic.Acid, Hyodeoxycholic.Acid | 3 |
| 0.65 | ketolithocholic.acid, Cholic.Acid, Glycodeoxycholic.Acid, Ursodeoxycholic.Acid | 4 |
| 0.65 | HOCA, Cholic.Acid, Glycocholic.Acid | 3 |
| 0.65 | HOCA, Hyodeoxycholic.Acid | 2 |
| 0.65 | Cholic.Acid, Deoxycholic.Acid, Glycodeoxycholic.Acid, Hyodeoxycholic.Acid | 4 |
| 0.65 | HOCA, chenodeoxycholic.acid, Cholic.Acid, Ursodeoxycholic.Acid | 4 |
| 0.65 | HOCA, ketolithocholic.acid, Deoxycholic.Acid, Glycocholic.Acid | 4 |
| 0.64 | beta.OH.lithocholate, Hyodeoxycholic.Acid | 2 |
| 0.64 | beta.OH.lithocholate, Hyodeoxycholic.Acid, Ursodeoxycholic.Acid | 3 |
| 0.64 | HOCA, Deoxycholic.Acid, Glycocholic.Acid, Ursodeoxycholic.Acid | 4 |
| 0.64 | HOCA, Deoxycholic.Acid, Hyodeoxycholic.Acid, Ursodeoxycholic.Acid | 4 |
| 0.64 | Glycodeoxycholic.Acid, Hyodeoxycholic.Acid | 2 |
| 0.64 | HOCA, Cholic.Acid | 2 |
| 0.64 | beta.OH.lithocholate, HOCA, chenodeoxycholic.acid, Deoxycholic.Acid | 4 |
| 0.64 | HOCA, chenodeoxycholic.acid, Hyodeoxycholic.Acid | 3 |
| 0.64 | HOCA, chenodeoxycholic.acid, Glycocholic.Acid, Hyodeoxycholic.Acid | 4 |
| 0.64 | beta.OH.lithocholate, Deoxycholic.Acid, Hyodeoxycholic.Acid, Ursodeoxycholic.Acid | 4 |
| 0.64 | HOCA, chenodeoxycholic.acid, Glycocholic.Acid, Ursodeoxycholic.Acid | 4 |
| 0.64 | HOCA, chenodeoxycholic.acid, Deoxycholic.Acid | 3 |
| 0.64 | HOCA, ketolithocholic.acid, chenodeoxycholic.acid, Glycocholic.Acid | 4 |
| 0.64 | ketolithocholic.acid, Cholic.Acid, Glycocholic.Acid, Glycodeoxycholic.Acid | 4 |
| 0.64 | ketolithocholic.acid, Cholic.Acid, Glycodeoxycholic.Acid, Hyodeoxycholic.Acid | 4 |
| 0.64 | HOCA, chenodeoxycholic.acid, Cholic.Acid, Hyodeoxycholic.Acid | 4 |
| 0.64 | Cholic.Acid, Deoxycholic.Acid, Glycodeoxycholic.Acid | 3 |
| 0.64 | HOCA, ketolithocholic.acid, chenodeoxycholic.acid, Hyodeoxycholic.Acid | 4 |
| 0.64 | HOCA, Cholic.Acid, Deoxycholic.Acid, Hyodeoxycholic.Acid | 4 |
| 0.64 | HOCA, Deoxycholic.Acid, Glycocholic.Acid | 3 |
| 0.64 | HOCA, chenodeoxycholic.acid, Deoxycholic.Acid, Hyodeoxycholic.Acid | 4 |
| 0.64 | beta.OH.lithocholate, HOCA, ketolithocholic.acid, Deoxycholic.Acid | 4 |
| 0.64 | ketolithocholic.acid, Glycodeoxycholic.Acid, Hyodeoxycholic.Acid, Ursodeoxycholic.Acid | 4 |
| 0.64 | beta.OH.lithocholate, Cholic.Acid, Hyodeoxycholic.Acid | 3 |
| 0.64 | beta.OH.lithocholate, Cholic.Acid, Deoxycholic.Acid, Glycodeoxycholic.Acid | 4 |
| 0.64 | HOCA, Glycocholic.Acid, Hyodeoxycholic.Acid | 3 |
| 0.64 | HOCA, ketolithocholic.acid, Deoxycholic.Acid, Ursodeoxycholic.Acid | 4 |

TABLE 7-continued

Biomarker Models for Determination of IBD Developed Using Logistic
Regression Analysis of Non-resectioned Subjects with Crohn's Disease or
Ulcerative Colitis Using the Listed Biomarkers

| AUC | Biomarkers used in logistic regression analysis | NUMBER_OF_Biomarkers |
|---|---|---|
| 0.64 | beta.OH.lithocholate, Deoxycholic.Acid | 2 |
| 0.64 | ketolithocholic.acid, Deoxycholic.Acid, Glycodeoxycholic.Acid, Hyodeoxycholic.Acid | 4 |
| 0.64 | Deoxycholic.Acid, Glycocholic.Acid, Glycodeoxycholic.Acid, Hyodeoxycholic.Acid | 4 |
| 0.63 | Deoxycholic.Acid, Glycocholic.Acid, Hyodeoxycholic.Acid, Ursodeoxycholic.Acid | 4 |
| 0.63 | HOCA, Cholic.Acid, Deoxycholic.Acid, Glycocholic.Acid | 4 |
| 0.63 | Cholic.Acid, Glycocholic.Acid, Glycodeoxycholic.Acid, Hyodeoxycholic.Acid | 4 |
| 0.63 | chenodeoxycholic.acid, Cholic.Acid, Deoxycholic.Acid, Glycodeoxycholic.Acid | 4 |
| 0.63 | ketolithocholic.acid, chenodeoxycholic.acid, Glycodeoxycholic.Acid, Hyodeoxycholic.Acid | 4 |
| 0.63 | beta.OH.lithocholate, Deoxycholic.Acid, Ursodeoxycholic.Acid | 3 |
| 0.63 | HOCA, Cholic.Acid, Deoxycholic.Acid | 3 |
| 0.63 | HOCA, ketolithocholic.acid, Cholic.Acid, Hyodeoxycholic.Acid | 4 |
| 0.63 | HOCA, Deoxycholic.Acid, Glycocholic.Acid, Hyodeoxycholic.Acid | 4 |
| 0.63 | Cholic.Acid, Glycodeoxycholic.Acid, Hyodeoxycholic.Acid | 3 |
| 0.63 | HOCA, ketolithocholic.acid, chenodeoxycholic.acid, Deoxycholic.Acid | 4 |
| 0.63 | beta.OH.lithocholate, chenodeoxycholic.acid, Glycocholic.Acid, Hyodeoxycholic.Acid | 4 |
| 0.63 | HOCA, Deoxycholic.Acid | 2 |
| 0.63 | beta.OH.lithocholate, Deoxycholic.Acid, Glycocholic.Acid | 3 |
| 0.62 | chenodeoxycholic.acid, Deoxycholic.Acid, Ursodeoxycholic.Acid | 3 |
| 0.62 | beta.OH.lithocholate, ketolithocholic.acid, Deoxycholic.Acid, Ursodeoxycholic.Acid | 4 |
| 0.62 | HOCA, Cholic.Acid, Glycocholic.Acid, Hyodeoxycholic.Acid | 4 |
| 0.62 | Deoxycholic.Acid, Hyodeoxycholic.Acid, Ursodeoxycholic.Acid | 3 |
| 0.62 | beta.OH.lithocholate, chenodeoxycholic.acid, Hyodeoxycholic.Acid, Ursodeoxycholic.Acid | 4 |
| 0.62 | beta.OH.lithocholate, Cholic.Acid, Deoxycholic.Acid, Hyodeoxycholic.Acid | 4 |
| 0.62 | Glycocholic.Acid, Hyodeoxycholic.Acid, Ursodeoxycholic.Acid | 3 |
| 0.62 | Cholic.Acid, Deoxycholic.Acid, Hyodeoxycholic.Acid, Ursodeoxycholic.Acid | 4 |
| 0.62 | beta.OH.lithocholate, chenodeoxycholic.acid, Deoxycholic.Acid, Ursodeoxycholic.Acid | 4 |
| 0.62 | Cholic.Acid, Hyodeoxycholic.Acid, Ursodeoxycholic.Acid | 3 |
| 0.62 | beta.OH.lithocholate, chenodeoxycholic.acid, Deoxycholic.Acid, Hyodeoxycholic.Acid | 4 |
| 0.62 | beta.OH.lithocholate, Glycocholic.Acid, Hyodeoxycholic.Acid | 3 |
| 0.62 | HOCA, ketolithocholic.acid, chenodeoxycholic.acid, Ursodeoxycholic.Acid | 4 |
| 0.62 | beta.OH.lithocholate, Glycocholic.Acid, Hyodeoxycholic.Acid, Ursodeoxycholic.Acid | 4 |
| 0.62 | Hyodeoxycholic.Acid, Ursodeoxycholic.Acid | 2 |
| 0.62 | beta.OH.lithocholate, ketolithocholic.acid, Hyodeoxycholic.Acid | 3 |
| 0.62 | beta.OH.lithocholate, Cholic.Acid, Deoxycholic.Acid, Ursodeoxycholic.Acid | 4 |
| 0.62 | beta.OH.lithocholate, Deoxycholic.Acid, Glycocholic.Acid, Ursodeoxycholic.Acid | 4 |
| 0.62 | beta.OH.lithocholate, Deoxycholic.Acid, Hyodeoxycholic.Acid | 3 |
| 0.62 | HOCA, ketolithocholic.acid, Deoxycholic.Acid, Hyodeoxycholic.Acid | 4 |
| 0.61 | beta.OH.lithocholate, chenodeoxycholic.acid, Cholic.Acid, Hyodeoxycholic.Acid | 4 |
| 0.61 | ketolithocholic.acid, Glycocholic.Acid, Hyodeoxycholic.Acid, Ursodeoxycholic.Acid | 4 |
| 0.61 | chenodeoxycholic.acid | 1 |
| 0.61 | Deoxycholic.Acid, Ursodeoxycholic.Acid | 2 |
| 0.61 | chenodeoxycholic.acid, Hyodeoxycholic.Acid, Ursodeoxycholic.Acid | 3 |
| 0.61 | ketolithocholic.acid, Deoxycholic.Acid, Hyodeoxycholic.Acid, Ursodeoxycholic.Acid | 4 |
| 0.61 | beta.OH.lithocholate, ketolithocholic.acid, chenodeoxycholic.acid, Hyodeoxycholic.Acid | 4 |
| 0.61 | beta.OH.lithocholate, chenodeoxycholic.acid | 2 |
| 0.61 | beta.OH.lithocholate, Cholic.Acid, Hyodeoxycholic.Acid, Ursodeoxycholic.Acid | 4 |
| 0.61 | ketolithocholic.acid, Hyodeoxycholic.Acid, Ursodeoxycholic.Acid | 3 |
| 0.61 | ketolithocholic.acid, chenodeoxycholic.acid, Cholic.Acid, Hyodeoxycholic.Acid | 4 |
| 0.61 | HOCA, chenodeoxycholic.acid, Cholic.Acid, Glycocholic.Acid | 4 |
| 0.61 | Hyodeoxycholic.Acid | 1 |

TABLE 7-continued

Biomarker Models for Determination of IBD Developed Using Logistic
Regression Analysis of Non-resectioned Subjects with Crohn's Disease or
Ulcerative Colitis Using the Listed Biomarkers

| AUC | Biomarkers used in logistic regression analysis | NUMBER_OF_Biomarkers |
|---|---|---|
| 0.60 | ketolithocholic.acid, Cholic.Acid, Hyodeoxycholic.Acid, Ursodeoxycholic.Acid | 4 |
| 0.60 | Cholic.Acid, Deoxycholic.Acid, Ursodeoxycholic.Acid | 3 |
| 0.60 | beta.OH.lithocholate, chenodeoxycholic.acid, Deoxycholic.Acid, Glycocholic.Acid | 4 |
| 0.60 | chenodeoxycholic.acid, Deoxycholic.Acid, Hyodeoxycholic.Acid, Ursodeoxycholic.Acid | 4 |
| 0.60 | Deoxycholic.Acid, Glycocholic.Acid, Ursodeoxycholic.Acid | 3 |
| 0.60 | beta.OH.lithocholate, chenodeoxycholic.acid, Deoxycholic.Acid | 3 |
| 0.60 | beta.OH.lithocholate, chenodeoxycholic.acid, Glycocholic.Acid | 3 |
| 0.60 | ketolithocholic.acid, chenodeoxycholic.acid | 2 |
| 0.60 | beta.OH.lithocholate, ketolithocholic.acid | 2 |
| 0.60 | beta.OH.lithocholate, Cholic.Acid, Glycocholic.Acid, Hyodeoxycholic.Acid | 4 |
| 0.60 | beta.OH.lithocholate, ketolithocholic.acid, chenodeoxycholic.acid | 3 |
| 0.60 | beta.OH.lithocholate, chenodeoxycholic.acid, Cholic.Acid | 3 |
| 0.59 | beta.OH.lithocholate, chenodeoxycholic.acid, Cholic.Acid, Deoxycholic.Acid | 4 |
| 0.59 | ketolithocholic.acid, chenodeoxycholic.acid, Deoxycholic.Acid | 3 |
| 0.59 | chenodeoxycholic.acid, Cholic.Acid, Hyodeoxycholic.Acid, Ursodeoxycholic.Acid | 4 |
| 0.59 | ketolithocholic.acid, chenodeoxycholic.acid, Deoxycholic.Acid, Ursodeoxycholic.Acid | 4 |
| 0.59 | beta.OH.lithocholate | 1 |
| 0.59 | beta.OH.lithocholate, Cholic.Acid | 2 |
| 0.59 | beta.OH.lithocholate, ketolithocholic.acid, Glycocholic.Acid, Hyodeoxycholic.Acid | 4 |
| 0.59 | Cholic.Acid, Glycocholic.Acid, Hyodeoxycholic.Acid, Ursodeoxycholic.Acid | 4 |
| 0.59 | chenodeoxycholic.acid, Glycocholic.Acid, Hyodeoxycholic.Acid, Ursodeoxycholic.Acid | 4 |
| 0.59 | ketolithocholic.acid, Cholic.Acid, Deoxycholic.Acid, Glycocholic.Acid | 4 |
| 0.59 | ketolithocholic.acid, chenodeoxycholic.acid, Hyodeoxycholic.Acid, Ursodeoxycholic.Acid | 4 |
| 0.59 | beta.OH.lithocholate, ketolithocholic.acid, chenodeoxycholic.acid, Cholic.Acid | 4 |
| 0.59 | beta.OH.lithocholate, ketolithocholic.acid, Glycocholic.Acid, Ursodeoxycholic.Acid | 4 |
| 0.59 | beta.OH.lithocholate, ketolithocholic.acid, Deoxycholic.Acid, Hyodeoxycholic.Acid | 4 |
| 0.59 | beta.OH.lithocholate, ketolithocholic.acid, Glycocholic.Acid | 3 |
| 0.59 | beta.OH.lithocholate, ketolithocholic.acid, Cholic.Acid, Hyodeoxycholic.Acid | 4 |
| 0.59 | beta.OH.lithocholate, Deoxycholic.Acid, Glycocholic.Acid, Hyodeoxycholic.Acid | 4 |
| 0.58 | ketolithocholic.acid, Deoxycholic.Acid, Ursodeoxycholic.Acid | 3 |
| 0.58 | beta.OH.lithocholate, ketolithocholic.acid, chenodeoxycholic.acid, Deoxycholic.Acid | 4 |
| 0.58 | beta.OH.lithocholate, Ursodeoxycholic.Acid | 2 |
| 0.58 | beta.OH.lithocholate, ketolithocholic.acid, Cholic.Acid, Deoxycholic.Acid | 4 |
| 0.58 | ketolithocholic.acid, Hyodeoxycholic.Acid | 2 |
| 0.58 | ketolithocholic.acid, chenodeoxycholic.acid, Deoxycholic.Acid, Hyodeoxycholic.Acid | 4 |
| 0.58 | ketolithocholic.acid, Cholic.Acid, Deoxycholic.Acid, Hyodeoxycholic.Acid | 4 |
| 0.58 | HOCA, chenodeoxycholic.acid, Deoxycholic.Acid, Glycocholic.Acid | 4 |
| 0.58 | ketolithocholic.acid, Glycocholic.Acid, Hyodeoxycholic.Acid | 3 |
| 0.58 | chenodeoxycholic.acid, Hyodeoxycholic.Acid | 2 |
| 0.58 | beta.OH.lithocholate, Glycocholic.Acid | 2 |
| 0.58 | ketolithocholic.acid, chenodeoxycholic.acid, Hyodeoxycholic.Acid | 3 |
| 0.58 | Cholic.Acid, Deoxycholic.Acid, Glycocholic.Acid, Ursodeoxycholic.Acid | 4 |
| 0.58 | ketolithocholic.acid | 1 |
| 0.58 | ketolithocholic.acid, Deoxycholic.Acid, Glycocholic.Acid, Ursodeoxycholic.Acid | 4 |
| 0.58 | ketolithocholic.acid, Cholic.Acid, Hyodeoxycholic.Acid | 3 |
| 0.57 | beta.OH.lithocholate, ketolithocholic.acid, Cholic.Acid | 3 |
| 0.57 | chenodeoxycholic.acid, Deoxycholic.Acid, Glycocholic.Acid, Ursodeoxycholic.Acid | 4 |
| 0.57 | beta.OH.lithocholate, Cholic.Acid, Ursodeoxycholic.Acid | 3 |
| 0.57 | beta.OH.lithocholate, ketolithocholic.acid, Ursodeoxycholic.Acid | 3 |
| 0.57 | ketolithocholic.acid, chenodeoxycholic.acid, Cholic.Acid | 3 |
| 0.57 | chenodeoxycholic.acid, Cholic.Acid, Deoxycholic.Acid | 3 |

TABLE 7-continued

Biomarker Models for Determination of IBD Developed Using Logistic
Regression Analysis of Non-resectioned Subjects with Crohn's Disease or
Ulcerative Colitis Using the Listed Biomarkers

| AUC | Biomarkers used in logistic regression analysis | NUMBER_OF_Biomarkers |
|---|---|---|
| 0.57 | beta.OH.lithocholate, ketolithocholic.acid, Cholic.Acid, Ursodeoxycholic.Acid | 4 |
| 0.57 | beta.OH.lithocholate, Glycocholic.Acid, Ursodeoxycholic.Acid | 3 |
| 0.57 | beta.OH.lithocholate, Cholic.Acid, Deoxycholic.Acid, Glycocholic.Acid | 4 |
| 0.57 | ketolithocholic.acid, chenodeoxycholic.acid, Glycocholic.Acid, Hyodeoxycholic.Acid | 4 |
| 0.57 | chenodeoxycholic.acid, Cholic.Acid, Hyodeoxycholic.Acid | 3 |
| 0.57 | chenodeoxycholic.acid, Deoxycholic.Acid, Hyodeoxycholic.Acid | 3 |
| 0.57 | ketolithocholic.acid, Cholic.Acid, Deoxycholic.Acid, Ursodeoxycholic.Acid | 4 |
| 0.57 | ketolithocholic.acid, Deoxycholic.Acid | 2 |
| 0.57 | beta.OH.lithocholate, Cholic.Acid, Glycocholic.Acid | 3 |
| 0.57 | beta.OH.lithocholate, ketolithocholic.acid, Deoxycholic.Acid, Glycocholic.Acid | 4 |
| 0.57 | chenodeoxycholic.acid, Cholic.Acid, Deoxycholic.Acid, Ursodeoxycholic.Acid | 4 |
| 0.57 | beta.OH.lithocholate, Cholic.Acid, Deoxycholic.Acid | 3 |
| 0.57 | chenodeoxycholic.acid, Cholic.Acid | 2 |
| 0.57 | ketolithocholic.acid, Deoxycholic.Acid, Glycocholic.Acid, Hyodeoxycholic.Acid | 4 |
| 0.57 | beta.OH.lithocholate, ketolithocholic.acid, Deoxycholic.Acid | 3 |
| 0.57 | ketolithocholic.acid, Deoxycholic.Acid, Glycocholic.Acid | 3 |
| 0.56 | ketolithocholic.acid, chenodeoxycholic.acid, Cholic.Acid, Deoxycholic.Acid | 4 |
| 0.56 | ketolithocholic.acid, chenodeoxycholic.acid, Cholic.Acid, Glycocholic.Acid | 4 |
| 0.56 | beta.OH.lithocholate, chenodeoxycholic.acid, Ursodeoxycholic.Acid | 3 |
| 0.56 | Glycocholic.Acid, Ursodeoxycholic.Acid | 2 |
| 0.56 | chenodeoxycholic.acid, Deoxycholic.Acid | 2 |
| 0.56 | ketolithocholic.acid, Cholic.Acid, Glycocholic.Acid | 3 |
| 0.56 | chenodeoxycholic.acid, Glycocholic.Acid, Hyodeoxycholic.Acid | 3 |
| 0.56 | ketolithocholic.acid, Cholic.Acid | 2 |
| 0.56 | ketolithocholic.acid, Glycocholic.Acid | 2 |
| 0.56 | chenodeoxycholic.acid, Cholic.Acid, Glycocholic.Acid, Hyodeoxycholic.Acid | 4 |
| 0.56 | beta.OH.lithocholate, chenodeoxycholic.acid, Cholic.Acid, Glycocholic.Acid | 4 |
| 0.56 | beta.OH.lithocholate, chenodeoxycholic.acid, Glycocholic.Acid, Ursodeoxycholic.Acid | 4 |
| 0.56 | beta.OH.lithocholate, ketolithocholic.acid, chenodeoxycholic.acid, Glycocholic.Acid | 4 |
| 0.56 | Ursodeoxycholic.Acid | 1 |
| 0.56 | ketolithocholic.acid, Cholic.Acid, Glycocholic.Acid, Hyodeoxycholic.Acid | 4 |
| 0.55 | chenodeoxycholic.acid, Cholic.Acid, Glycocholic.Acid | 3 |
| 0.55 | ketolithocholic.acid, chenodeoxycholic.acid, Glycocholic.Acid | 3 |
| 0.55 | ketolithocholic.acid, chenodeoxycholic.acid, Deoxycholic.Acid, Glycocholic.Acid | 4 |
| 0.55 | chenodeoxycholic.acid, Deoxycholic.Acid, Glycocholic.Acid, Hyodeoxycholic.Acid | 4 |
| 0.55 | ketolithocholic.acid, Glycocholic.Acid, Ursodeoxycholic.Acid | 3 |
| 0.55 | ketolithocholic.acid, Deoxycholic.Acid, Hyodeoxycholic.Acid | 3 |
| 0.55 | beta.OH.lithocholate, ketolithocholic.acid, Cholic.Acid, Glycocholic.Acid | 4 |
| 0.55 | chenodeoxycholic.acid, Cholic.Acid, Deoxycholic.Acid, Hyodeoxycholic.Acid | 4 |
| 0.55 | ketolithocholic.acid, Ursodeoxycholic.Acid | 2 |
| 0.54 | Cholic.Acid, Glycocholic.Acid, Ursodeoxycholic.Acid | 3 |
| 0.54 | beta.OH.lithocholate, ketolithocholic.acid, chenodeoxycholic.acid, Ursodeoxycholic.Acid | 4 |
| 0.54 | beta.OH.lithocholate, Cholic.Acid, Glycocholic.Acid, Ursodeoxycholic.Acid | 4 |
| 0.54 | ketolithocholic.acid, Cholic.Acid, Deoxycholic.Acid | 3 |
| 0.54 | Cholic.Acid, Deoxycholic.Acid, Hyodeoxycholic.Acid | 3 |
| 0.53 | chenodeoxycholic.acid, Deoxycholic.Acid, Glycocholic.Acid | 3 |
| 0.53 | ketolithocholic.acid, Cholic.Acid, Ursodeoxycholic.Acid | 3 |
| 0.53 | Deoxycholic.Acid, Hyodeoxycholic.Acid | 2 |
| 0.53 | Cholic.Acid, Ursodeoxycholic.Acid | 2 |
| 0.53 | ketolithocholic.acid, chenodeoxycholic.acid, Ursodeoxycholic.Acid | 3 |
| 0.53 | chenodeoxycholic.acid, Glycocholic.Acid | 2 |
| 0.53 | chenodeoxycholic.acid, Ursodeoxycholic.Acid | 2 |
| 0.53 | beta.OH.lithocholate, chenodeoxycholic.acid, Cholic.Acid, Ursodeoxycholic.Acid | 4 |

TABLE 7-continued

Biomarker Models for Determination of IBD Developed Using Logistic Regression Analysis of Non-resectioned Subjects with Crohn's Disease or Ulcerative Colitis Using the Listed Biomarkers

| AUC | Biomarkers used in logistic regression analysis | NUMBER_OF_Biomarkers |
|---|---|---|
| 0.53 | chenodeoxycholic.acid, Cholic.Acid, Deoxycholic.Acid, Glycocholic.Acid | 4 |
| 0.52 | Cholic.Acid, Deoxycholic.Acid, Glycocholic.Acid, Hyodeoxycholic.Acid | 4 |
| 0.52 | chenodeoxycholic.acid, Cholic.Acid, Glycocholic.Acid, Ursodeoxycholic.Acid | 4 |
| 0.52 | Cholic.Acid, Glycocholic.Acid, Hyodeoxycholic.Acid | 3 |
| 0.52 | chenodeoxycholic.acid, Cholic.Acid, Ursodeoxycholic.Acid | 3 |
| 0.52 | chenodeoxycholic.acid, Glycocholic.Acid, Ursodeoxycholic.Acid | 3 |
| 0.51 | Deoxycholic.Acid, Glycocholic.Acid, Hyodeoxycholic.Acid | 3 |
| 0.51 | ketolithocholic.acid, chenodeoxycholic.acid, Cholic.Acid, Ursodeoxycholic.Acid | 4 |
| 0.50 | Cholic.Acid, Hyodeoxycholic.Acid | 2 |
| 0.50 | ketolithocholic.acid, Cholic.Acid, Glycocholic.Acid, Ursodeoxycholic.Acid | 4 |
| 0.49 | ketolithocholic.acid, chenodeoxycholic.acid, Glycocholic.Acid, Ursodeoxycholic.Acid | 4 |
| 0.49 | Glycocholic.Acid, Hyodeoxycholic.Acid | 2 |
| 0.46 | Glycocholic.Acid | 1 |
| 0.43 | Deoxycholic.Acid, Glycocholic.Acid | 2 |
| 0.43 | Cholic.Acid, Deoxycholic.Acid | 2 |
| 0.42 | Deoxycholic.Acid | 1 |
| 0.42 | Cholic.Acid, Deoxycholic.Acid, Glycocholic.Acid | 3 |
| 0.41 | Cholic.Acid, Glycocholic.Acid | 2 |
| 0.39 | Cholic.Acid | 1 |

In Table 7A the biomarker models were developed and tested using the levels of the biomarkers measured in the cohort that included all of the subjects, both those with and those without a surgical resection of the ileum.

TABLE 7A

Biomarker Models for Determination of IBD Developed Using Logistic Regression Analysis of All Subjects with Crohn's Disease or Ulcerative Colitis Using the Listed Biomarkers

| AUC | Biomarkers used in logistic regression analysis | NUMBER OF Biomarkers |
|---|---|---|
| 0.82 | beta.OH.lithocholate, HOCA, Glycodeoxycholic.Acid, Ursodeoxycholic.Acid | 4 |
| 0.82 | beta.OH.lithocholate, HOCA, Deoxycholic.Acid, Glycodeoxycholic.Acid | 4 |
| 0.82 | beta.OH.lithocholate, HOCA, Glycocholic.Acid, Glycodeoxycholic.Acid | 4 |
| 0.82 | beta.OH.lithocholate, HOCA, Glycodeoxycholic.Acid | 3 |
| 0.82 | beta.OH.lithocholate, HOCA, chenodeoxycholic.acid, Glycodeoxycholic.Acid | 4 |
| 0.82 | beta.OH.lithocholate, HOCA, ketolithocholic.acid, Glycodeoxycholic.Acid | 4 |
| 0.81 | beta.OH.lithocholate, HOCA, Glycocholic.Acid | 3 |
| 0.81 | beta.OH.lithocholate, HOCA, Cholic.Acid, Glycodeoxycholic.Acid | 4 |
| 0.81 | beta.OH.lithocholate, HOCA, chenodeoxycholic.acid, Glycocholic.Acid | 4 |
| 0.81 | beta.OH.lithocholate, HOCA, Glycocholic.Acid, Ursodeoxycholic.Acid | 4 |
| 0.81 | beta.OH.lithocholate, HOCA, Glycocholic.Acid, Hyodeoxycholic.Acid | 4 |
| 0.81 | beta.OH.lithocholate, HOCA, Glycodeoxycholic.Acid, Hyodeoxycholic.Acid | 4 |
| 0.81 | beta.OH.lithocholate, HOCA, ketolithocholic.acid, Glycocholic.Acid | 4 |
| 0.81 | HOCA, Cholic.Acid, Deoxycholic.Acid, Glycodeoxycholic.Acid | 4 |
| 0.81 | beta.OH.lithocholate, HOCA | 2 |
| 0.81 | beta.OH.lithocholate, HOCA, chenodeoxycholic.acid | 3 |
| 0.81 | beta.OH.lithocholate, HOCA, Deoxycholic.Acid, Glycocholic.Acid | 4 |
| 0.80 | beta.OH.lithocholate, HOCA, ketolithocholic.acid | 3 |
| 0.80 | beta.OH.lithocholate, HOCA, Cholic.Acid, Glycocholic.Acid | 4 |
| 0.80 | beta.OH.lithocholate, HOCA, ketolithocholic.acid, Deoxycholic.Acid | 4 |

TABLE 7A-continued

Biomarker Models for Determination of IBD Developed Using
Logistic Regression Analysis of All Subjects with Crohn's
Disease or Ulcerative Colitis Using the Listed Biomarkers

| AUC | Biomarkers used in logistic regression analysis | NUMBER OF Biomarkers |
|---|---|---|
| 0.80 | beta.OH.lithocholate, HOCA, Ursodeoxycholic.Acid | 3 |
| 0.80 | beta.OH.lithocholate, HOCA, ketolithocholic.acid, Ursodeoxycholic.Acid | 4 |
| 0.80 | beta.OH.lithocholate, HOCA, ketolithocholic.acid, chenodeoxycholic.acid | 4 |
| 0.80 | HOCA, chenodeoxycholic.acid, Deoxycholic.Acid, Glycodeoxycholic.Acid | 4 |
| 0.80 | HOCA, ketolithocholic.acid, Deoxycholic.Acid, Glycodeoxycholic.Acid | 4 |
| 0.80 | beta.OH.lithocholate, HOCA, Deoxycholic.Acid, Ursodeoxycholic.Acid | 4 |
| 0.80 | beta.OH.lithocholate, HOCA, Deoxycholic.Acid, Hyodeoxycholic.Acid | 4 |
| 0.80 | HOCA, Deoxycholic.Acid, Glycocholic.Acid, Glycodeoxycholic.Acid | 4 |
| 0.80 | HOCA, ketolithocholic.acid, chenodeoxycholic.acid, Glycodeoxycholic.Acid | 4 |
| 0.80 | beta.OH.lithocholate, HOCA, ketolithocholic.acid, Cholic.Acid | 4 |
| 0.80 | HOCA, Glycodeoxycholic.Acid, Ursodeoxycholic.Acid | 3 |
| 0.80 | beta.OH.lithocholate, HOCA, Deoxycholic.Acid | 3 |
| 0.80 | HOCA, ketolithocholic.acid, Cholic.Acid, Glycodeoxycholic.Acid | 4 |
| 0.80 | beta.OH.lithocholate, HOCA, chenodeoxycholic.acid, Ursodeoxycholic.Acid | 4 |
| 0.80 | beta.OH.lithocholate, HOCA, Cholic.Acid, Deoxycholic.Acid | 4 |
| 0.80 | beta.OH.lithocholate, HOCA, ketolithocholic.acid, Hyodeoxycholic.Acid | 4 |
| 0.80 | beta.OH.lithocholate, HOCA, chenodeoxycholic.acid, Hyodeoxycholic.Acid | 4 |
| 0.80 | HOCA, ketolithocholic.acid, Glycodeoxycholic.Acid, Ursodeoxycholic.Acid | 4 |
| 0.80 | HOCA, Glycocholic.Acid, Glycodeoxycholic.Acid, Ursodeoxycholic.Acid | 4 |
| 0.80 | HOCA, Deoxycholic.Acid, Glycodeoxycholic.Acid, Ursodeoxycholic.Acid | 4 |
| 0.80 | HOCA, ketolithocholic.acid, Glycodeoxycholic.Acid | 3 |
| 0.80 | beta.OH.lithocholate, HOCA, chenodeoxycholic.acid, Cholic.Acid | 4 |
| 0.80 | HOCA, Deoxycholic.Acid, Glycodeoxycholic.Acid, Hyodeoxycholic.Acid | 4 |
| 0.80 | HOCA, ketolithocholic.acid, Glycodeoxycholic.Acid, Hyodeoxycholic.Acid | 4 |
| 0.80 | HOCA, ketolithocholic.acid, Glycocholic.Acid | 3 |
| 0.80 | beta.OH.lithocholate, HOCA, Cholic.Acid, Ursodeoxycholic.Acid | 4 |
| 0.79 | HOCA, chenodeoxycholic.acid, Glycodeoxycholic.Acid, Ursodeoxycholic.Acid | 4 |
| 0.79 | beta.OH.lithocholate, HOCA, Hyodeoxycholic.Acid | 3 |
| 0.79 | beta.OH.lithocholate, HOCA, Cholic.Acid | 3 |
| 0.79 | beta.OH.lithocholate, HOCA, Hyodeoxycholic.Acid, Ursodeoxycholic.Acid | 4 |
| 0.79 | HOCA, Glycodeoxycholic.Acid, Hyodeoxycholic.Acid, Ursodeoxycholic.Acid | 4 |
| 0.79 | HOCA, Deoxycholic.Acid, Glycodeoxycholic.Acid | 3 |
| 0.79 | HOCA, Glycodeoxycholic.Acid | 2 |
| 0.79 | HOCA, ketolithocholic.acid, chenodeoxycholic.acid, Glycocholic.Acid | 4 |
| 0.79 | beta.OH.lithocholate, HOCA, Cholic.Acid, Hyodeoxycholic.Acid | 4 |
| 0.79 | HOCA, Glycocholic.Acid, Hyodeoxycholic.Acid, Ursodeoxycholic.Acid | 4 |
| 0.79 | HOCA, Glycocholic.Acid, Ursodeoxycholic.Acid | 3 |
| 0.79 | HOCA, Cholic.Acid, Glycodeoxycholic.Acid, Ursodeoxycholic.Acid | 4 |
| 0.79 | HOCA, ketolithocholic.acid, Glycocholic.Acid, Ursodeoxycholic.Acid | 4 |
| 0.79 | HOCA, chenodeoxycholic.acid, Glycodeoxycholic.Acid | 3 |
| 0.79 | HOCA, ketolithocholic.acid | 2 |
| 0.79 | HOCA, chenodeoxycholic.acid, Glycodeoxycholic.Acid, Hyodeoxycholic.Acid | 4 |
| 0.79 | beta.OH.lithocholate, HOCA, chenodeoxycholic.acid, Deoxycholic.Acid | 4 |

TABLE 7A-continued

Biomarker Models for Determination of IBD Developed Using
Logistic Regression Analysis of All Subjects with Crohn's
Disease or Ulcerative Colitis Using the Listed Biomarkers

| AUC | Biomarkers used in logistic regression analysis | NUMBER OF Biomarkers |
|---|---|---|
| 0.79 | HOCA, Ursodeoxycholic.Acid | 2 |
| 0.79 | HOCA, ketolithocholic.acid, Glycocholic.Acid, Glycodeoxycholic.Acid | 4 |
| 0.79 | HOCA, Glycocholic.Acid | 2 |
| 0.79 | HOCA, Deoxycholic.Acid, Ursodeoxycholic.Acid | 3 |
| 0.79 | HOCA, ketolithocholic.acid, Glycocholic.Acid, Hyodeoxycholic.Acid | 4 |
| 0.79 | HOCA, Deoxycholic.Acid, Glycocholic.Acid, Ursodeoxycholic.Acid | 4 |
| 0.79 | HOCA, Cholic.Acid, Glycodeoxycholic.Acid | 3 |
| 0.79 | HOCA, ketolithocholic.acid, Deoxycholic.Acid, Glycocholic.Acid | 4 |
| 0.79 | HOCA, Glycocholic.Acid, Glycodeoxycholic.Acid | 3 |
| 0.79 | HOCA, Cholic.Acid, Glycocholic.Acid, Ursodeoxycholic.Acid | 4 |
| 0.79 | HOCA, chenodeoxycholic.acid, Deoxycholic.Acid, Glycocholic.Acid | 4 |
| 0.79 | HOCA, ketolithocholic.acid, chenodeoxycholic.acid, Cholic.Acid | 4 |
| 0.79 | HOCA, ketolithocholic.acid, Cholic.Acid | 3 |
| 0.79 | HOCA, Cholic.Acid, Ursodeoxycholic.Acid | 3 |
| 0.79 | HOCA, ketolithocholic.acid, Ursodeoxycholic.Acid | 3 |
| 0.79 | HOCA, ketolithocholic.acid, Hyodeoxycholic.Acid | 3 |
| 0.79 | HOCA, chenodeoxycholic.acid, Glycocholic.Acid, Ursodeoxycholic.Acid | 4 |
| 0.79 | HOCA, Cholic.Acid, Deoxycholic.Acid, Glycocholic.Acid | 4 |
| 0.79 | HOCA, chenodeoxycholic.acid, Ursodeoxycholic.Acid | 3 |
| 0.78 | HOCA, Deoxycholic.Acid, Glycocholic.Acid | 3 |
| 0.78 | HOCA, chenodeoxycholic.acid, Cholic.Acid, Glycodeoxycholic.Acid | 4 |
| 0.78 | HOCA, chenodeoxycholic.acid, Hyodeoxycholic.Acid, Ursodeoxycholic.Acid | 4 |
| 0.78 | HOCA, Hyodeoxycholic.Acid, Ursodeoxycholic.Acid | 3 |
| 0.78 | HOCA, chenodeoxycholic.acid, Deoxycholic.Acid, Ursodeoxycholic.Acid | 4 |
| 0.78 | HOCA, chenodeoxycholic.acid, Cholic.Acid, Ursodeoxycholic.Acid | 4 |
| 0.78 | HOCA, ketolithocholic.acid, Deoxycholic.Acid | 3 |
| 0.78 | HOCA, ketolithocholic.acid, Cholic.Acid, Glycocholic.Acid | 4 |
| 0.78 | HOCA, Deoxycholic.Acid, Glycocholic.Acid, Hyodeoxycholic.Acid | 4 |
| 0.78 | HOCA, ketolithocholic.acid, Hyodeoxycholic.Acid, Ursodeoxycholic.Acid | 4 |
| 0.78 | HOCA | 1 |
| 0.78 | HOCA, ketolithocholic.acid, Cholic.Acid, Ursodeoxycholic.Acid | 4 |
| 0.78 | HOCA, chenodeoxycholic.acid | 2 |
| 0.78 | HOCA, Deoxycholic.Acid | 2 |
| 0.78 | HOCA, ketolithocholic.acid, Cholic.Acid, Hyodeoxycholic.Acid | 4 |
| 0.78 | HOCA, Glycodeoxycholic.Acid, Hyodeoxycholic.Acid | 3 |
| 0.78 | HOCA, Cholic.Acid, Glycodeoxycholic.Acid, Hyodeoxycholic.Acid | 4 |
| 0.78 | HOCA, chenodeoxycholic.acid, Glycocholic.Acid, Glycodeoxycholic.Acid | 4 |
| 0.78 | HOCA, ketolithocholic.acid, chenodeoxycholic.acid | 3 |
| 0.78 | HOCA, Deoxycholic.Acid, Hyodeoxycholic.Acid, Ursodeoxycholic.Acid | 4 |
| 0.78 | HOCA, ketolithocholic.acid, chenodeoxycholic.acid, Ursodeoxycholic.Acid | 4 |
| 0.78 | HOCA, chenodeoxycholic.acid, Glycocholic.Acid | 3 |
| 0.78 | HOCA, Cholic.Acid, Hyodeoxycholic.Acid, Ursodeoxycholic.Acid | 4 |
| 0.78 | HOCA, ketolithocholic.acid, Deoxycholic.Acid, Ursodeoxycholic.Acid | 4 |
| 0.78 | HOCA, chenodeoxycholic.acid, Cholic.Acid | 3 |
| 0.78 | HOCA, Hyodeoxycholic.Acid | 2 |
| 0.78 | HOCA, Cholic.Acid, Deoxycholic.Acid, Ursodeoxycholic.Acid | 4 |
| 0.78 | HOCA, Cholic.Acid, Deoxycholic.Acid | 3 |
| 0.78 | HOCA, Glycocholic.Acid, Hyodeoxycholic.Acid | 3 |
| 0.78 | HOCA, ketolithocholic.acid, Deoxycholic.Acid, Hyodeoxycholic.Acid | 4 |

TABLE 7A-continued

Biomarker Models for Determination of IBD Developed Using
Logistic Regression Analysis of All Subjects with Crohn's
Disease or Ulcerative Colitis Using the Listed Biomarkers

| AUC | Biomarkers used in logistic regression analysis | NUMBER OF Biomarkers |
|---|---|---|
| 0.78 | HOCA, Cholic.Acid, Glycocholic.Acid, Hyodeoxycholic.Acid | 4 |
| 0.78 | HOCA, Cholic.Acid, Glycocholic.Acid | 3 |
| 0.78 | HOCA, Cholic.Acid | 2 |
| 0.78 | HOCA, ketolithocholic.acid, Cholic.Acid, Deoxycholic.Acid | 4 |
| 0.78 | beta.OH.lithocholate, Deoxycholic.Acid, Glycocholic.Acid, Glycodeoxycholic.Acid | 4 |
| 0.78 | HOCA, chenodeoxycholic.acid, Cholic.Acid, Glycocholic.Acid | 4 |
| 0.78 | HOCA, chenodeoxycholic.acid, Cholic.Acid, Deoxycholic.Acid | 4 |
| 0.78 | HOCA, chenodeoxycholic.acid, Deoxycholic.Acid | 3 |
| 0.78 | HOCA, Deoxycholic.Acid, Hyodeoxycholic.Acid | 3 |
| 0.78 | HOCA, ketolithocholic.acid, chenodeoxycholic.acid, Hyodeoxycholic.Acid | 4 |
| 0.78 | HOCA, Cholic.Acid, Deoxycholic.Acid, Hyodeoxycholic.Acid | 4 |
| 0.78 | HOCA, Cholic.Acid, Glycocholic.Acid, Glycodeoxycholic.Acid | 4 |
| 0.78 | HOCA, Glycocholic.Acid, Glycodeoxycholic.Acid, Hyodeoxycholic.Acid | 4 |
| 0.77 | HOCA, chenodeoxycholic.acid, Hyodeoxycholic.Acid | 3 |
| 0.77 | HOCA, chenodeoxycholic.acid, Glycocholic.Acid, Hyodeoxycholic.Acid | 4 |
| 0.77 | HOCA, chenodeoxycholic.acid, Deoxycholic.Acid, Hyodeoxycholic.Acid | 4 |
| 0.77 | beta.OH.lithocholate, Deoxycholic.Acid, Glycodeoxycholic.Acid | 3 |
| 0.77 | HOCA, ketolithocholic.acid, chenodeoxycholic.acid, Deoxycholic.Acid | 4 |
| 0.77 | HOCA, Cholic.Acid, Hyodeoxycholic.Acid | 3 |
| 0.77 | beta.OH.lithocholate, chenodeoxycholic.acid, Deoxycholic.Acid, Glycodeoxycholic.Acid | 4 |
| 0.77 | HOCA, chenodeoxycholic.acid, Cholic.Acid, Hyodeoxycholic.Acid | 4 |
| 0.77 | beta.OH.lithocholate, ketolithocholic.acid, Deoxycholic.Acid, Glycodeoxycholic.Acid | 4 |
| 0.76 | beta.OH.lithocholate, Deoxycholic.Acid, Glycodeoxycholic.Acid, Ursodeoxycholic.Acid | 4 |
| 0.76 | beta.OH.lithocholate, Cholic.Acid, Deoxycholic.Acid, Glycodeoxycholic.Acid | 4 |
| 0.76 | beta.OH.lithocholate, Deoxycholic.Acid, Glycodeoxycholic.Acid, Hyodeoxycholic.Acid | 4 |
| 0.76 | beta.OH.lithocholate, chenodeoxycholic.acid, Glycodeoxycholic.Acid, Ursodeoxycholic.Acid | 4 |
| 0.76 | beta.OH.lithocholate, chenodeoxycholic.acid, Cholic.Acid, Glycodeoxycholic.Acid | 4 |
| 0.75 | chenodeoxycholic.acid, Cholic.Acid, Deoxycholic.Acid, Glycodeoxycholic.Acid | 4 |
| 0.75 | beta.OH.lithocholate, Cholic.Acid, Glycodeoxycholic.Acid | 3 |
| 0.75 | beta.OH.lithocholate, Glycodeoxycholic.Acid, Ursodeoxycholic.Acid | 3 |
| 0.75 | beta.OH.lithocholate, chenodeoxycholic.acid, Glycodeoxycholic.Acid | 3 |
| 0.75 | beta.OH.lithocholate, chenodeoxycholic.acid, Glycodeoxycholic.Acid, Hyodeoxycholic.Acid | 4 |
| 0.75 | beta.OH.lithocholate, Cholic.Acid, Glycodeoxycholic.Acid, Ursodeoxycholic.Acid | 4 |
| 0.75 | beta.OH.lithocholate, ketolithocholic.acid, Glycocholic.Acid, Glycodeoxycholic.Acid | 4 |
| 0.75 | beta.OH.lithocholate, ketolithocholic.acid, Glycodeoxycholic.Acid | 3 |
| 0.75 | beta.OH.lithocholate, Glycodeoxycholic.Acid | 2 |
| 0.75 | chenodeoxycholic.acid, Deoxycholic.Acid, Glycodeoxycholic.Acid | 3 |
| 0.75 | beta.OH.lithocholate, ketolithocholic.acid, chenodeoxycholic.acid, Glycodeoxycholic.Acid | 4 |
| 0.75 | beta.OH.lithocholate, ketolithocholic.acid, Glycodeoxycholic.Acid, Ursodeoxycholic.Acid | 4 |
| 0.75 | beta.OH.lithocholate, chenodeoxycholic.acid, Glycocholic.Acid, Glycodeoxycholic.Acid | 4 |

TABLE 7A-continued

Biomarker Models for Determination of IBD Developed Using
Logistic Regression Analysis of All Subjects with Crohn's
Disease or Ulcerative Colitis Using the Listed Biomarkers

| AUC | Biomarkers used in logistic regression analysis | NUMBER OF Biomarkers |
|---|---|---|
| 0.75 | beta.OH.lithocholate, Glycocholic.Acid, Glycodeoxycholic.Acid | 3 |
| 0.74 | beta.OH.lithocholate, Glycocholic.Acid, Glycodeoxycholic.Acid, Ursodeoxycholic.Acid | 4 |
| 0.74 | chenodeoxycholic.acid, Deoxycholic.Acid, Glycocholic.Acid, Glycodeoxycholic.Acid | 4 |
| 0.74 | ketolithocholic.acid, chenodeoxycholic.acid, Deoxycholic.Acid, Glycodeoxycholic.Acid | 4 |
| 0.74 | beta.OH.lithocholate, Glycodeoxycholic.Acid, Hyodeoxycholic.Acid | 3 |
| 0.74 | beta.OH.lithocholate, Cholic.Acid, Glycocholic.Acid, Glycodeoxycholic.Acid | 4 |
| 0.74 | chenodeoxycholic.acid, Cholic.Acid, Glycodeoxycholic.Acid, Ursodeoxycholic.Acid | 4 |
| 0.74 | beta.OH.lithocholate, Cholic.Acid, Glycodeoxycholic.Acid, Hyodeoxycholic.Acid | 4 |
| 0.74 | beta.OH.lithocholate, Glycocholic.Acid, Glycodeoxycholic.Acid, Hyodeoxycholic.Acid | 4 |
| 0.74 | beta.OH.lithocholate, ketolithocholic.acid, Cholic.Acid, Glycodeoxycholic.Acid | 4 |
| 0.74 | ketolithocholic.acid, Deoxycholic.Acid, Glycodeoxycholic.Acid | 3 |
| 0.74 | Deoxycholic.Acid, Glycocholic.Acid, Glycodeoxycholic.Acid, Ursodeoxycholic.Acid | 4 |
| 0.74 | beta.OH.lithocholate, chenodeoxycholic.acid, Glycocholic.Acid, Hyodeoxycholic.Acid | 4 |
| 0.74 | ketolithocholic.acid, Cholic.Acid, Deoxycholic.Acid, Glycodeoxycholic.Acid | 4 |
| 0.74 | chenodeoxycholic.acid, Deoxycholic.Acid, Glycodeoxycholic.Acid, Hyodeoxycholic.Acid | 4 |
| 0.73 | Deoxycholic.Acid, Glycodeoxycholic.Acid, Ursodeoxycholic.Acid | 3 |
| 0.73 | Cholic.Acid, Deoxycholic.Acid, Glycodeoxycholic.Acid, Ursodeoxycholic.Acid | 4 |
| 0.73 | ketolithocholic.acid, chenodeoxycholic.acid, Glycodeoxycholic.Acid | 3 |
| 0.73 | ketolithocholic.acid, chenodeoxycholic.acid, Cholic.Acid, Glycodeoxycholic.Acid | 4 |
| 0.73 | chenodeoxycholic.acid, Deoxycholic.Acid, Glycodeoxycholic.Acid, Ursodeoxycholic.Acid | 4 |
| 0.73 | beta.OH.lithocholate, chenodeoxycholic.acid, Hyodeoxycholic.Acid, Ursodeoxycholic.Acid | 4 |
| 0.73 | ketolithocholic.acid, Deoxycholic.Acid, Glycocholic.Acid, Glycodeoxycholic.Acid | 4 |
| 0.73 | ketolithocholic.acid, Deoxycholic.Acid, Glycodeoxycholic.Acid, Hyodeoxycholic.Acid | 4 |
| 0.73 | ketolithocholic.acid, Deoxycholic.Acid, Glycodeoxycholic.Acid, Ursodeoxycholic.Acid | 4 |
| 0.73 | Deoxycholic.Acid, Glycodeoxycholic.Acid, Hyodeoxycholic.Acid, Ursodeoxycholic.Acid | 4 |
| 0.73 | ketolithocholic.acid, Cholic.Acid, Glycodeoxycholic.Acid | 3 |
| 0.72 | beta.OH.lithocholate, chenodeoxycholic.acid, Cholic.Acid, Ursodeoxycholic.Acid | 4 |
| 0.72 | beta.OH.lithocholate, ketolithocholic.acid, Glycodeoxycholic.Acid, Hyodeoxycholic.Acid | 4 |
| 0.72 | ketolithocholic.acid, chenodeoxycholic.acid, Glycodeoxycholic.Acid, Hyodeoxycholic.Acid | 4 |
| 0.72 | ketolithocholic.acid, Glycodeoxycholic.Acid | 2 |
| 0.72 | chenodeoxycholic.acid, Glycodeoxycholic.Acid, Ursodeoxycholic.Acid | 3 |
| 0.72 | beta.OH.lithocholate, chenodeoxycholic.acid, Deoxycholic.Acid, Hyodeoxycholic.Acid | 4 |
| 0.72 | beta.OH.lithocholate, chenodeoxycholic.acid, Cholic.Acid, Hyodeoxycholic.Acid | 4 |
| 0.72 | ketolithocholic.acid, Glycodeoxycholic.Acid, Ursodeoxycholic.Acid | 3 |
| 0.72 | ketolithocholic.acid, chenodeoxycholic.acid, Glycocholic.Acid, Glycodeoxycholic.Acid | 4 |
| 0.72 | beta.OH.lithocholate, chenodeoxycholic.acid, Ursodeoxycholic.Acid | 3 |
| 0.72 | ketolithocholic.acid, Cholic.Acid, Glycodeoxycholic.Acid, Hyodeoxycholic.Acid | 4 |
| 0.72 | Deoxycholic.Acid, Glycocholic.Acid, Glycodeoxycholic.Acid | 3 |

TABLE 7A-continued

Biomarker Models for Determination of IBD Developed Using
Logistic Regression Analysis of All Subjects with Crohn's
Disease or Ulcerative Colitis Using the Listed Biomarkers

| AUC | Biomarkers used in logistic regression analysis | NUMBER OF Biomarkers |
|---|---|---|
| 0.72 | beta.OH.lithocholate, chenodeoxycholic.acid, Hyodeoxycholic.Acid | 3 |
| 0.72 | ketolithocholic.acid, chenodeoxycholic.acid, Glycodeoxycholic.Acid, Ursodeoxycholic.Acid | 4 |
| 0.72 | beta.OH.lithocholate, chenodeoxycholic.acid, Glycocholic.Acid | 3 |
| 0.72 | beta.OH.lithocholate, ketolithocholic.acid, chenodeoxycholic.acid, Hyodeoxycholic.Acid | 4 |
| 0.72 | ketolithocholic.acid, Glycocholic.Acid, Glycodeoxycholic.Acid | 3 |
| 0.72 | chenodeoxycholic.acid, Glycodeoxycholic.Acid, Hyodeoxycholic.Acid, Ursodeoxycholic.Acid | 4 |
| 0.72 | beta.OH.lithocholate, ketolithocholic.acid, Hyodeoxycholic.Acid | 3 |
| 0.72 | beta.OH.lithocholate, chenodeoxycholic.acid, Glycocholic.Acid, Ursodeoxycholic.Acid | 4 |
| 0.72 | beta.OH.lithocholate, chenodeoxycholic.acid, Cholic.Acid, Glycocholic.Acid | 4 |
| 0.72 | ketolithocholic.acid, Glycodeoxycholic.Acid, Hyodeoxycholic.Acid | 3 |
| 0.72 | beta.OH.lithocholate, chenodeoxycholic.acid, Cholic.Acid | 3 |
| 0.72 | chenodeoxycholic.acid, Glycodeoxycholic.Acid | 2 |
| 0.72 | ketolithocholic.acid, Glycodeoxycholic.Acid, Hyodeoxycholic.Acid, Ursodeoxycholic.Acid | 4 |
| 0.72 | ketolithocholic.acid, Cholic.Acid, Glycocholic.Acid, Glycodeoxycholic.Acid | 4 |
| 0.72 | ketolithocholic.acid, Glycocholic.Acid, Glycodeoxycholic.Acid, Ursodeoxycholic.Acid | 4 |
| 0.72 | beta.OH.lithocholate, Glycodeoxycholic.Acid, Hyodeoxycholic.Acid, Ursodeoxycholic.Acid | 4 |
| 0.72 | beta.OH.lithocholate, Hyodeoxycholic.Acid, Ursodeoxycholic.Acid | 3 |
| 0.72 | ketolithocholic.acid, Cholic.Acid, Glycodeoxycholic.Acid, Ursodeoxycholic.Acid | 4 |
| 0.72 | chenodeoxycholic.acid, Glycocholic.Acid, Glycodeoxycholic.Acid | 3 |
| 0.72 | beta.OH.lithocholate, Glycocholic.Acid, Hyodeoxycholic.Acid, Ursodeoxycholic.Acid | 4 |
| 0.72 | beta.OH.lithocholate, Deoxycholic.Acid, Hyodeoxycholic.Acid | 3 |
| 0.72 | beta.OH.lithocholate, ketolithocholic.acid, Glycocholic.Acid, Hyodeoxycholic.Acid | 4 |
| 0.71 | beta.OH.lithocholate, Glycocholic.Acid, Hyodeoxycholic.Acid | 3 |
| 0.71 | ketolithocholic.acid, Glycocholic.Acid, Glycodeoxycholic.Acid, Hyodeoxycholic.Acid | 4 |
| 0.71 | beta.OH.lithocholate, ketolithocholic.acid, chenodeoxycholic.acid, Cholic.Acid | 4 |
| 0.71 | Glycocholic.Acid, Glycodeoxycholic.Acid, Ursodeoxycholic.Acid | 3 |
| 0.71 | Glycodeoxycholic.Acid, Ursodeoxycholic.Acid | 2 |
| 0.71 | chenodeoxycholic.acid, Glycocholic.Acid, Glycodeoxycholic.Acid, Ursodeoxycholic.Acid | 4 |
| 0.71 | chenodeoxycholic.acid, Cholic.Acid, Glycodeoxycholic.Acid | 3 |
| 0.71 | chenodeoxycholic.acid, Cholic.Acid, Glycocholic.Acid, Glycodeoxycholic.Acid | 4 |
| 0.71 | beta.OH.lithocholate, chenodeoxycholic.acid | 2 |
| 0.71 | beta.OH.lithocholate, ketolithocholic.acid, chenodeoxycholic.acid, Glycocholic.Acid | 4 |
| 0.71 | beta.OH.lithocholate, Deoxycholic.Acid, Glycocholic.Acid, Hyodeoxycholic.Acid | 4 |
| 0.71 | beta.OH.lithocholate, ketolithocholic.acid, Cholic.Acid, Hyodeoxycholic.Acid | 4 |
| 0.71 | beta.OH.lithocholate, chenodeoxycholic.acid, Cholic.Acid, Deoxycholic.Acid | 4 |
| 0.71 | beta.OH.lithocholate, ketolithocholic.acid, chenodeoxycholic.acid, Ursodeoxycholic.Acid | 4 |
| 0.71 | chenodeoxycholic.acid, Cholic.Acid, Glycodeoxycholic.Acid, Hyodeoxycholic.Acid | 4 |
| 0.71 | beta.OH.lithocholate, Cholic.Acid, Glycocholic.Acid, Hyodeoxycholic.Acid | 4 |

TABLE 7A-continued

Biomarker Models for Determination of IBD Developed Using
Logistic Regression Analysis of All Subjects with Crohn's
Disease or Ulcerative Colitis Using the Listed Biomarkers

| AUC | Biomarkers used in logistic regression analysis | NUMBER OF Biomarkers |
|---|---|---|
| 0.71 | beta.OH.lithocholate, Cholic.Acid, Hyodeoxycholic.Acid, Ursodeoxycholic.Acid | 4 |
| 0.71 | Deoxycholic.Acid, Glycodeoxycholic.Acid | 2 |
| 0.71 | Cholic.Acid, Deoxycholic.Acid, Glycocholic.Acid, Glycodeoxycholic.Acid | 4 |
| 0.71 | Glycodeoxycholic.Acid, Hyodeoxycholic.Acid, Ursodeoxycholic.Acid | 3 |
| 0.71 | beta.OH.lithocholate, chenodeoxycholic.acid, Deoxycholic.Acid, Ursodeoxycholic.Acid | 4 |
| 0.70 | beta.OH.lithocholate, Hyodeoxycholic.Acid | 2 |
| 0.70 | beta.OH.lithocholate, ketolithocholic.acid, Deoxycholic.Acid, Hyodeoxycholic.Acid | 4 |
| 0.70 | Deoxycholic.Acid, Glycocholic.Acid, Glycodeoxycholic.Acid, Hyodeoxycholic.Acid | 4 |
| 0.70 | beta.OH.lithocholate, Cholic.Acid, Deoxycholic.Acid, Hyodeoxycholic.Acid | 4 |
| 0.70 | Glycocholic.Acid, Glycodeoxycholic.Acid, Hyodeoxycholic.Acid, Ursodeoxycholic.Acid | 4 |
| 0.70 | beta.OH.lithocholate, ketolithocholic.acid, Hyodeoxycholic.Acid, Ursodeoxycholic.Acid | 4 |
| 0.70 | Deoxycholic.Acid, Glycodeoxycholic.Acid, Hyodeoxycholic.Acid | 3 |
| 0.70 | chenodeoxycholic.acid, Glycocholic.Acid, Glycodeoxycholic.Acid, Hyodeoxycholic.Acid | 4 |
| 0.70 | chenodeoxycholic.acid, Glycodeoxycholic.Acid, Hyodeoxycholic.Acid | 3 |
| 0.70 | chenodeoxycholic.acid, Hyodeoxycholic.Acid | 2 |
| 0.70 | beta.OH.lithocholate, Cholic.Acid, Hyodeoxycholic.Acid | 3 |
| 0.70 | beta.OH.lithocholate, ketolithocholic.acid, chenodeoxycholic.acid | 3 |
| 0.70 | beta.OH.lithocholate, chenodeoxycholic.acid, Deoxycholic.Acid | 3 |
| 0.70 | beta.OH.lithocholate, chenodeoxycholic.acid, Deoxycholic.Acid, Glycocholic.Acid | 4 |
| 0.70 | ketolithocholic.acid, chenodeoxycholic.acid, Hyodeoxycholic.Acid | 3 |
| 0.70 | Cholic.Acid, Glycodeoxycholic.Acid, Ursodeoxycholic.Acid | 3 |
| 0.70 | ketolithocholic.acid, chenodeoxycholic.acid, Deoxycholic.Acid, Hyodeoxycholic.Acid | 4 |
| 0.69 | beta.OH.lithocholate, ketolithocholic.acid, Glycocholic.Acid | 3 |
| 0.69 | chenodeoxycholic.acid, Cholic.Acid, Hyodeoxycholic.Acid, Ursodeoxycholic.Acid | 4 |
| 0.69 | chenodeoxycholic.acid, Cholic.Acid, Ursodeoxycholic.Acid | 3 |
| 0.69 | beta.OH.lithocholate, ketolithocholic.acid, chenodeoxycholic.acid, Deoxycholic.Acid | 4 |
| 0.69 | Cholic.Acid, Deoxycholic.Acid, Glycodeoxycholic.Acid, Hyodeoxycholic.Acid | 4 |
| 0.69 | chenodeoxycholic.acid, Hyodeoxycholic.Acid, Ursodeoxycholic.Acid | 3 |
| 0.69 | Cholic.Acid, Glycocholic.Acid, Glycodeoxycholic.Acid, Ursodeoxycholic.Acid | 4 |
| 0.69 | ketolithocholic.acid, chenodeoxycholic.acid, Cholic.Acid, Ursodeoxycholic.Acid | 4 |
| 0.69 | ketolithocholic.acid, chenodeoxycholic.acid, Cholic.Acid, Hyodeoxycholic.Acid | 4 |
| 0.69 | chenodeoxycholic.acid | 1 |
| 0.69 | beta.OH.lithocholate | 1 |
| 0.69 | beta.OH.lithocholate, Glycocholic.Acid, Ursodeoxycholic.Acid | 3 |
| 0.69 | Cholic.Acid, Deoxycholic.Acid, Glycodeoxycholic.Acid | 3 |
| 0.69 | beta.OH.lithocholate, ketolithocholic.acid | 2 |
| 0.69 | chenodeoxycholic.acid, Cholic.Acid, Hyodeoxycholic.Acid | 3 |
| 0.69 | ketolithocholic.acid, chenodeoxycholic.acid, Cholic.Acid, Deoxycholic.Acid | 4 |
| 0.69 | chenodeoxycholic.acid, Cholic.Acid, Glycocholic.Acid, Ursodeoxycholic.Acid | 4 |
| 0.69 | Cholic.Acid, Glycodeoxycholic.Acid, Hyodeoxycholic.Acid, Ursodeoxycholic.Acid | 4 |
| 0.69 | ketolithocholic.acid, Hyodeoxycholic.Acid, Ursodeoxycholic.Acid | 3 |

TABLE 7A-continued

Biomarker Models for Determination of IBD Developed Using
Logistic Regression Analysis of All Subjects with Crohn's
Disease or Ulcerative Colitis Using the Listed Biomarkers

| AUC | Biomarkers used in logistic regression analysis | NUMBER OF Biomarkers |
|---|---|---|
| 0.69 | ketolithocholic.acid, chenodeoxycholic.acid, Cholic.Acid, Glycocholic.Acid | 4 |
| 0.69 | beta.OH.lithocholate, Deoxycholic.Acid, Hyodeoxycholic.Acid, Ursodeoxycholic.Acid | 4 |
| 0.69 | chenodeoxycholic.acid, Cholic.Acid, Deoxycholic.Acid, Ursodeoxycholic.Acid | 4 |
| 0.69 | ketolithocholic.acid, chenodeoxycholic.acid, Cholic.Acid | 3 |
| 0.68 | beta.OH.lithocholate, ketolithocholic.acid, Deoxycholic.Acid, Glycocholic.Acid | 4 |
| 0.68 | beta.OH.lithocholate, ketolithocholic.acid, Cholic.Acid | 3 |
| 0.68 | beta.OH.lithocholate, Cholic.Acid, Glycocholic.Acid | 3 |
| 0.68 | ketolithocholic.acid, Glycocholic.Acid, Hyodeoxycholic.Acid, Ursodeoxycholic.Acid | 4 |
| 0.68 | beta.OH.lithocholate, Glycocholic.Acid | 2 |
| 0.68 | beta.OH.lithocholate, ketolithocholic.acid, Deoxycholic.Acid | 3 |
| 0.68 | beta.OH.lithocholate, ketolithocholic.acid, Ursodeoxycholic.Acid | 3 |
| 0.68 | Glycodeoxycholic.Acid, Hyodeoxycholic.Acid | 2 |
| 0.68 | chenodeoxycholic.acid, Cholic.Acid, Deoxycholic.Acid, Hyodeoxycholic.Acid | 4 |
| 0.68 | beta.OH.lithocholate, Ursodeoxycholic.Acid | 2 |
| 0.68 | ketolithocholic.acid, chenodeoxycholic.acid, Deoxycholic.Acid | 3 |
| 0.68 | beta.OH.lithocholate, ketolithocholic.acid, Cholic.Acid, Glycocholic.Acid | 4 |
| 0.68 | ketolithocholic.acid, chenodeoxycholic.acid | 2 |
| 0.68 | beta.OH.lithocholate, Cholic.Acid, Glycocholic.Acid, Ursodeoxycholic.Acid | 4 |
| 0.68 | ketolithocholic.acid, chenodeoxycholic.acid, Glycocholic.Acid, Hyodeoxycholic.Acid | 4 |
| 0.68 | chenodeoxycholic.acid, Cholic.Acid, Glycocholic.Acid, Hyodeoxycholic.Acid | 4 |
| 0.68 | chenodeoxycholic.acid, Deoxycholic.Acid, Hyodeoxycholic.Acid, Ursodeoxycholic.Acid | 4 |
| 0.68 | chenodeoxycholic.acid, Deoxycholic.Acid, Hyodeoxycholic.Acid | 3 |
| 0.68 | beta.OH.lithocholate, Deoxycholic.Acid | 2 |
| 0.68 | beta.OH.lithocholate, ketolithocholic.acid, Glycocholic.Acid, Ursodeoxycholic.Acid | 4 |
| 0.68 | Hyodeoxycholic.Acid, Ursodeoxycholic.Acid | 2 |
| 0.68 | Glycodeoxycholic.Acid | 1 |
| 0.68 | chenodeoxycholic.acid, Cholic.Acid | 2 |
| 0.67 | beta.OH.lithocholate, Deoxycholic.Acid, Glycocholic.Acid | 3 |
| 0.67 | ketolithocholic.acid, Deoxycholic.Acid, Hyodeoxycholic.Acid, Ursodeoxycholic.Acid | 4 |
| 0.67 | chenodeoxycholic.acid, Cholic.Acid, Deoxycholic.Acid | 3 |
| 0.67 | beta.OH.lithocholate, Cholic.Acid, Deoxycholic.Acid, Glycocholic.Acid | 4 |
| 0.67 | beta.OH.lithocholate, ketolithocholic.acid, Cholic.Acid, Ursodeoxycholic.Acid | 4 |
| 0.67 | ketolithocholic.acid, Cholic.Acid, Hyodeoxycholic.Acid, Ursodeoxycholic.Acid | 4 |
| 0.67 | ketolithocholic.acid, Deoxycholic.Acid, Hyodeoxycholic.Acid | 3 |
| 0.67 | Glycocholic.Acid, Hyodeoxycholic.Acid, Ursodeoxycholic.Acid | 3 |
| 0.67 | chenodeoxycholic.acid, Cholic.Acid, Glycocholic.Acid | 3 |
| 0.67 | chenodeoxycholic.acid, Deoxycholic.Acid | 2 |
| 0.67 | ketolithocholic.acid, Hyodeoxycholic.Acid | 2 |
| 0.67 | beta.OH.lithocholate, Cholic.Acid | 2 |
| 0.67 | ketolithocholic.acid, Glycocholic.Acid, Hyodeoxycholic.Acid | 3 |
| 0.67 | chenodeoxycholic.acid, Cholic.Acid, Deoxycholic.Acid, Glycocholic.Acid | 4 |
| 0.67 | beta.OH.lithocholate, Deoxycholic.Acid, Glycocholic.Acid, Ursodeoxycholic.Acid | 4 |
| 0.67 | Cholic.Acid, Glycodeoxycholic.Acid | 2 |
| 0.67 | ketolithocholic.acid, Cholic.Acid, Hyodeoxycholic.Acid | 3 |
| 0.67 | chenodeoxycholic.acid, Glycocholic.Acid, Hyodeoxycholic.Acid | 3 |
| 0.67 | Glycocholic.Acid, Glycodeoxycholic.Acid | 2 |

TABLE 7A-continued

Biomarker Models for Determination of IBD Developed Using
Logistic Regression Analysis of All Subjects with Crohn's
Disease or Ulcerative Colitis Using the Listed Biomarkers

| AUC | Biomarkers used in logistic regression analysis | NUMBER OF Biomarkers |
|---|---|---|
| 0.66 | chenodeoxycholic.acid, Glycocholic.Acid, Hyodeoxycholic.Acid, Ursodeoxycholic.Acid | 4 |
| 0.66 | chenodeoxycholic.acid, Glycocholic.Acid | 2 |
| 0.66 | beta.OH.lithocholate, Cholic.Acid, Deoxycholic.Acid | 3 |
| 0.66 | Deoxycholic.Acid, Hyodeoxycholic.Acid, Ursodeoxycholic.Acid | 3 |
| 0.66 | ketolithocholic.acid, chenodeoxycholic.acid, Hyodeoxycholic.Acid, Ursodeoxycholic.Acid | 4 |
| 0.66 | Cholic.Acid, Glycodeoxycholic.Acid, Hyodeoxycholic.Acid | 3 |
| 0.66 | ketolithocholic.acid, Cholic.Acid, Glycocholic.Acid, Hyodeoxycholic.Acid | 4 |
| 0.66 | beta.OH.lithocholate, Cholic.Acid, Ursodeoxycholic.Acid | 3 |
| 0.66 | chenodeoxycholic.acid, Deoxycholic.Acid, Glycocholic.Acid, Hyodeoxycholic.Acid | 4 |
| 0.66 | Cholic.Acid, Hyodeoxycholic.Acid, Ursodeoxycholic.Acid | 3 |
| 0.66 | beta.OH.lithocholate, ketolithocholic.acid, Cholic.Acid, Deoxycholic.Acid | 4 |
| 0.66 | beta.OH.lithocholate, ketolithocholic.acid, Deoxycholic.Acid, Ursodeoxycholic.Acid | 4 |
| 0.66 | ketolithocholic.acid, chenodeoxycholic.acid, Deoxycholic.Acid, Glycocholic.Acid | 4 |
| 0.66 | Deoxycholic.Acid, Glycocholic.Acid, Hyodeoxycholic.Acid, Ursodeoxycholic.Acid | 4 |
| 0.66 | ketolithocholic.acid, Ursodeoxycholic.Acid | 2 |
| 0.66 | ketolithocholic.acid, chenodeoxycholic.acid, Glycocholic.Acid | 3 |
| 0.65 | Glycocholic.Acid, Glycodeoxycholic.Acid, Hyodeoxycholic.Acid | 3 |
| 0.65 | Cholic.Acid, Glycocholic.Acid, Glycodeoxycholic.Acid | 3 |
| 0.65 | ketolithocholic.acid, Glycocholic.Acid | 2 |
| 0.65 | ketolithocholic.acid, chenodeoxycholic.acid, Glycocholic.Acid, Ursodeoxycholic.Acid | 4 |
| 0.65 | ketolithocholic.acid | 1 |
| 0.65 | Cholic.Acid, Deoxycholic.Acid, Hyodeoxycholic.Acid, Ursodeoxycholic.Acid | 4 |
| 0.65 | ketolithocholic.acid, Deoxycholic.Acid, Glycocholic.Acid, Ursodeoxycholic.Acid | 4 |
| 0.65 | ketolithocholic.acid, Deoxycholic.Acid, Glycocholic.Acid, Hyodeoxycholic.Acid | 4 |
| 0.65 | beta.OH.lithocholate, Cholic.Acid, Deoxycholic.Acid, Ursodeoxycholic.Acid | 4 |
| 0.65 | ketolithocholic.acid, Deoxycholic.Acid, Glycocholic.Acid | 3 |
| 0.65 | Cholic.Acid, Glycocholic.Acid, Hyodeoxycholic.Acid, Ursodeoxycholic.Acid | 4 |
| 0.65 | chenodeoxycholic.acid, Ursodeoxycholic.Acid | 2 |
| 0.65 | ketolithocholic.acid, Glycocholic.Acid, Ursodeoxycholic.Acid | 3 |
| 0.65 | ketolithocholic.acid, Cholic.Acid, Deoxycholic.Acid, Hyodeoxycholic.Acid | 4 |
| 0.65 | ketolithocholic.acid, Cholic.Acid, Glycocholic.Acid | 3 |
| 0.64 | chenodeoxycholic.acid, Glycocholic.Acid, Ursodeoxycholic.Acid | 3 |
| 0.64 | chenodeoxycholic.acid, Deoxycholic.Acid, Ursodeoxycholic.Acid | 3 |
| 0.64 | beta.OH.lithocholate, Deoxycholic.Acid, Ursodeoxycholic.Acid | 3 |
| 0.64 | ketolithocholic.acid, Cholic.Acid, Glycocholic.Acid, Ursodeoxycholic.Acid | 4 |
| 0.64 | ketolithocholic.acid, Deoxycholic.Acid | 2 |
| 0.64 | ketolithocholic.acid, chenodeoxycholic.acid, Deoxycholic.Acid, Ursodeoxycholic.Acid | 4 |
| 0.64 | ketolithocholic.acid, chenodeoxycholic.acid, Ursodeoxycholic.Acid | 3 |
| 0.64 | chenodeoxycholic.acid, Deoxycholic.Acid, Glycocholic.Acid | 3 |
| 0.64 | Cholic.Acid, Glycocholic.Acid, Glycodeoxycholic.Acid, Hyodeoxycholic.Acid | 4 |
| 0.63 | ketolithocholic.acid, Cholic.Acid | 2 |
| 0.63 | ketolithocholic.acid, Cholic.Acid, Ursodeoxycholic.Acid | 3 |
| 0.63 | ketolithocholic.acid, Cholic.Acid, Deoxycholic.Acid | 3 |
| 0.63 | ketolithocholic.acid, Cholic.Acid, Deoxycholic.Acid, Glycocholic.Acid | 4 |

TABLE 7A-continued

Biomarker Models for Determination of IBD Developed Using
Logistic Regression Analysis of All Subjects with Crohn's
Disease or Ulcerative Colitis Using the Listed Biomarkers

| AUC | Biomarkers used in logistic regression analysis | NUMBER OF Biomarkers |
|---|---|---|
| 0.63 | chenodeoxycholic.acid, Deoxycholic.Acid, Glycocholic.Acid, Ursodeoxycholic.Acid | 4 |
| 0.62 | ketolithocholic.acid, Cholic.Acid, Deoxycholic.Acid, Ursodeoxycholic.Acid | 4 |
| 0.62 | Glycocholic.Acid, Ursodeoxycholic.Acid | 2 |
| 0.62 | ketolithocholic.acid, Deoxycholic.Acid, Ursodeoxycholic.Acid | 3 |
| 0.62 | Cholic.Acid, Glycocholic.Acid, Ursodeoxycholic.Acid | 3 |
| 0.61 | Deoxycholic.Acid, Glycocholic.Acid, Ursodeoxycholic.Acid | 3 |
| 0.61 | Hyodeoxycholic.Acid | 1 |
| 0.60 | Cholic.Acid, Deoxycholic.Acid, Glycocholic.Acid, Ursodeoxycholic.Acid | 4 |
| 0.60 | Cholic.Acid, Hyodeoxycholic.Acid | 2 |
| 0.60 | Ursodeoxycholic.Acid | 1 |
| 0.59 | Deoxycholic.Acid, Hyodeoxycholic.Acid | 2 |
| 0.59 | Deoxycholic.Acid, Ursodeoxycholic.Acid | 2 |
| 0.58 | Cholic.Acid, Ursodeoxycholic.Acid | 2 |
| 0.58 | Cholic.Acid, Deoxycholic.Acid, Ursodeoxycholic.Acid | 3 |
| 0.57 | Deoxycholic.Acid, Glycocholic.Acid, Hyodeoxycholic.Acid | 3 |
| 0.57 | Cholic.Acid, Deoxycholic.Acid, Glycocholic.Acid, Hyodeoxycholic.Acid | 4 |
| 0.56 | Cholic.Acid, Deoxycholic.Acid, Hyodeoxycholic.Acid | 3 |
| 0.56 | Cholic.Acid, Glycocholic.Acid, Hyodeoxycholic.Acid | 3 |
| 0.56 | Glycocholic.Acid, Hyodeoxycholic.Acid | 2 |
| 0.51 | Glycocholic.Acid | 1 |
| 0.49 | Deoxycholic.Acid, Glycocholic.Acid | 2 |
| 0.49 | Cholic.Acid, Glycocholic.Acid | 2 |
| 0.48 | Cholic.Acid, Deoxycholic.Acid, Glycocholic.Acid | 3 |
| 0.47 | Cholic.Acid | 1 |
| 0.42 | Deoxycholic.Acid | 1 |
| 0.40 | Cholic.Acid, Deoxycholic.Acid | 2 |

Example 8

Analytical Characterization of Unnamed Biomarkers Compounds

Table 8 below includes analytical characteristics of each of the unnamed metabolites listed in the Tables above. Methods for the analysis of metabolites using LC-MS techniques are provided in U.S. Pat. Nos. 7,433,787 and 7,561,975, U.S. Patent Publication 20090017464 and using GC-MS techniques are provided in Lawton, et al. Pharmacogenomics 9(4): 383-397 (2008). The table includes, for each listed Metabolite, the retention time (RT), retention index (RI), mass, and polarity obtained using the analytical methods described above. "Mass" refers to the mass of the C12 isotope of the parent ion used in quantification of the compound. "Polarity" indicates the polarity of the quantitative ion as being either positive (+) or negative (−). Library indicates GC-MS (50) or LC-MS (200, 201).

TABLE 8

Analytical characteristics of unnamed metabolites.

| Lib ID | Comp ID | Name | MASS | Polarity | RT | RI |
|---|---|---|---|---|---|---|
| 200 | 32586 | Metabolite - 01327 | 585.2 | + | 4.6 | 4625 |
| 200 | 32735 | Metabolite - 01911 | 464.1 | + | 4.26 | 4275 |
| 201 | 32587 | Metabolite - 02249 | 267.2 | − | 4.03 | 4025 |
| 201 | 32549 | Metabolite - 02269 | 255.1 | − | 1.55 | 1551 |
| 201 | 32550 | Metabolite - 02272 has been identified as catechol sulfate Compound ID 35320 | 189 | − | 1.97 | 1958 |
| 201 | 32756 | Metabolite - 02276 has been identified as 4-vinylphenol sulfate Compound ID 36098 | 199.1 | − | 3.35 | 3339 |
| 201 | 32952 | Metabolite - 02277 has been identified as 4-ethylphenyl sulfate Compound ID 36099 | 201.1 | − | 3.61 | 3604 |
| 50 | 12593 | Metabolite - 02973 | 281 | + | 4.74 | 1210.5 |
| 200 | 32709 | Metabolite - 03056 | 185.2 | + | 2.21 | 2264 |

TABLE 8-continued

Analytical characteristics of unnamed metabolites.

| Lib ID | Comp ID | Name | MASS | Polarity | RT | RI |
|---|---|---|---|---|---|---|
| 50 | 12757 | Metabolite - 03078 has been identified as glutamine Compound ID 35831 | 203.1 | + | 10.65 | 1884.5 |
| 50 | 12767 | Metabolite - 03087 has been identified as orinithine Compound ID 35832 | 174.1 | + | 11.19 | 1940.3 |
| 50 | 12768 | Metabolite - 03088 | 372.2 | + | 11.23 | 1944.1 |
| 50 | 12774 | Metabolite - 03094 | 299 | + | 11.55 | 1978.7 |
| 50 | 12781 | Metabolite - 03099 | 204 | + | 11.77 | 2002.3 |
| 50 | 12782 | Metabolite - 03100 | 204 | + | 11.85 | 2010.7 |
| 50 | 12789 | Metabolite - 03107 | 204.1 | + | 12.21 | 2049 |
| 50 | 12796 | Metabolite - 03114 | 204 | + | 12.79 | 2119.2 |
| 200 | 32675 | Metabolite - 03951 | 367.1 | + | 1.87 | 1912 |
| 50 | 16120 | Metabolite - 04055 | 304.1 | + | 12.04 | 2021.4 |
| 50 | 16511 | Metabolite - 4274 has been identified as ornithine Compound ID 35833 | 158.1 | + | 10.37 | 1854.7 |
| 50 | 16634 | Metabolite - 04357 | 216 | + | 8 | 1540.5 |
| 50 | 16650 | Metabolite - 04360 has been identified as oxalacetic acid Compound ID 35252 | 347.2 | + | 9.15 | 1678.4 |
| 50 | 16666 | Metabolite - 04365 | 204 | + | 11.05 | 1893.1 |
| 50 | 16818 | Metabolite - 04495 | 117 | + | 6.59 | 1381 |
| 50 | 16821 | Metabolite - 04498 | 103 | + | 7.06 | 1434.9 |
| 50 | 16823 | Metabolite - 04500 | 172 | + | 7.3 | 1462 |
| 50 | 16837 | Metabolite - 04507 | 245 | + | 8.89 | 1644.9 |
| 50 | 16855 | Metabolite - 04515 | 318.1 | + | 10.69 | 1854.9 |
| 50 | 16866 | Metabolite - 04523 | 258.1 | + | 12.46 | 2048.1 |
| 50 | 17064 | Metabolite - 04624 | 342.2 | + | 10.01 | 1779.2 |
| 50 | 17391 | Metabolite - 04807 | 143 | + | 4.24 | 1126.1 |
| 50 | 17482 | Metabolite - 04874 | 103 | + | 11.73 | 1975.8 |
| 50 | 17627 | Metabolite - 04986 | 204.1 | + | 11.56 | 1956.4 |
| 50 | 18232 | Metabolite - 05403 has been identified as urea Compound ID 36532 | 319 | + | 5.92 | 1301.2 |
| 50 | 18283 | Metabolite - 05426 | 245.1 | + | 10.15 | 1792.1 |
| 50 | 18388 | Metabolite - 05491 | 129 | + | 8.3 | 1575.3 |
| 50 | 18446 | Metabolite - 05524 | 203.9 | + | 13.6 | 2191.4 |
| 50 | 18868 | Metabolite - 05847 | 288.2 | + | 12.35 | 2039.3 |
| 50 | 18929 | Metabolite - 05907 | 229.1 | + | 8.69 | 1643.2 |
| 201 | 32557 | Metabolite - 06126 | 203.1 | − | 2.69 | 2684 |
| 50 | 19362 | Metabolite - 06226 | 154 | + | 4.38 | 1137.4 |
| 50 | 19363 | Metabolite - 06227 | 196.1 | + | 5 | 1210.5 |
| 50 | 19368 | Metabolite - 06267 | 257.1 | + | 9.32 | 1702.7 |
| 50 | 19370 | Metabolite - 06268 has been identified as arginine Compound ID 37016 | 271.1 | + | 9.91 | 1773.3 |
| 50 | 19374 | Metabolite - 06270 has been identified as Glucose Compound ID 35258 | 320.2 | + | 11.35 | 1928.5 |
| 50 | 19396 | Metabolite - 06307 | 257.1 | + | 7.58 | 1502.3 |
| 50 | 19402 | Metabolite - 06346 | 263.2 | + | 8 | 1550.1 |
| 50 | 19414 | Metabolite - 06350 | 169 | + | 11.41 | 1936.4 |
| 50 | 19478 | Metabolite - 06467 has been identified as Glucose Compound ID 35259 | 320.1 | + | 11.09 | 1893.4 |
| 50 | 19490 | Metabolite - 06488 | 204.1 | + | 12.25 | 2021.7 |
| 50 | 19576 | Metabolite - 06627 | 304.2 | + | 11.96 | 1990.7 |
| 201 | 32560 | Metabolite - 07765 | 245.1 | − | 3.71 | 3705 |
| 50 | 21011 | Metabolite - 07888 | 311.3 | + | 15.96 | 2513.3 |
| 50 | 21421 | Metabolite - 08214 has been identified as sphingomyelin Compound ID 19503 | 311.186 | + | 17.13 | 2645 |
| 50 | 21630 | Metabolite - 08402 | 283.1 | + | 15.27 | 2427.7 |
| 50 | 21631 | Metabolite - 08403 | 309.2 | + | 15.96 | 2520.6 |
| 200 | 32595 | Metabolite - 08893 | 431.9 | + | 5.19 | 5200 |
| 50 | 22548 | Metabolite - 09026 | 156 | + | 8.45 | 1599.5 |
| 50 | 22570 | Metabolite - 09033 | 217.1 | + | 9.61 | 1735.6 |
| 50 | 22600 | Metabolite - 09043 | 204.1 | + | 11.75 | 1974.5 |
| 50 | 22601 | Metabolite - 09044 | 204.1 | + | 13.38 | 2168.3 |
| 50 | 22649 | Metabolite - 09108 | 156 | + | 11.2 | 1895.9 |
| 50 | 24076 | Metabolite - 09726 has been identified as urea Compound ID 36534 | 245 | + | 4.91 | 1167.5 |

TABLE 8-continued

Analytical characteristics of unnamed metabolites.

| Lib ID | Comp ID | Name | MASS | Polarity | RT | RI |
|---|---|---|---|---|---|---|
| 50 | 24077 | Metabolite - 09727 has been identified as 3-hydroxy-2-methylpropanoate Compound ID 1549 | 177 | + | 5.24 | 1203.9 |
| 50 | 24115 | Metabolite - 09752 | 229 | + | 7.34 | 1441 |
| 201 | 32753 | Metabolite - 09789 | 153.1 | − | 2.62 | 2613 |
| 201 | 33782 | Metabolite - 10346 | 259.1 | − | 3.93 | 3989 |
| 50 | 25459 | Metabolite - 10395 | 156 | + | 9.94 | 1769 |
| 50 | 25532 | Metabolite - 10413 | 204.1 | + | 12.53 | 2042.7 |
| 50 | 25599 | Metabolite - 10429 | 265 | + | 11.6 | 1952.6 |
| 50 | 25602 | Metabolite - 10432 | 204 | + | 12.29 | 2031.5 |
| 50 | 25607 | Metabolite - 10437 | 331.1 | + | 8.43 | 1596.4 |
| 50 | 25609 | Metabolite - 10439 | 331.1 | + | 8.84 | 1644 |
| 50 | 27256 | Metabolite - 10500 | 211 | + | 5.3 | 1229.9 |
| 50 | 27273 | Metabolite - 10506 | 218.1 | + | 11.3 | 1915.1 |
| 50 | 27275 | Metabolite - 10507 has been identified as histidine Compound ID 35835 | 370.2 | + | 11.97 | 1988.1 |
| 50 | 27278 | Metabolite - 10510 | 297.2 | + | 15.77 | 2470 |
| 50 | 27279 | Metabolite - 10511 | 309.3 | + | 17.12 | 2645 |
| 50 | 27856 | Metabolite - 10597 | 218 | + | 7.19 | 1447 |
| 50 | 28059 | Metabolite - 10650 has been identified as dehydroascorbate Compound ID 1659 | 345.1 | + | 10.26 | 1800.6 |
| 50 | 30282 | Metabolite - 10744 | 311.2 | + | 15.75 | 2503 |
| 50 | 30805 | Metabolite - 10810 | 232.1 | + | 9.44 | 1710 |
| 50 | 30821 | Metabolite - 10812 has been identified as lysine Compound ID 35836 | 172.1 | + | 11.2 | 1910 |
| 50 | 30832 | Metabolite - 10814 | 204.1 | + | 12.84 | 2094 |
| 50 | 31016 | Metabolite - 10827 has been identified as beta-alanine Compound ID 35838 | 334.1 | + | 8.36 | 1582.3 |
| 50 | 31396 | Metabolite - 10887 | 358.2 | + | 10.66 | 1868 |
| 50 | 31492 | Metabolite - 10917 has been identified as gamma, gamma-dimethylallyl pyrophosphate Compound ID 35844 | 211.1 | + | 7.72 | 1491 |
| 50 | 31509 | Metabolite - 10931 has been identified as lysine Compound ID 35839 | 174.1 | + | 12.02 | 1984 |
| 50 | 31617 | Metabolite - 10963 | 204.1 | + | 11.97 | 1988 |
| 50 | 31618 | Metabolite - 10964 | 261.2 | + | 12.3 | 2025 |
| 50 | 32110 | Metabolite - 11086 has been identified as threonine Compound ID 37015 | 116.9 | + | 6.54 | 1403.6 |
| 50 | 32369 | Metabolite - 11175 | 204.1 | + | 13.43 | 2149 |
| 200 | 32518 | Metabolite - 11204 | 229.2 | + | 5.26 | 5263 |
| 201 | 32548 | Metabolite - 11231 | 330 | − | 1.47 | 1471 |
| 201 | 32561 | Metabolite - 11244 | 224.2 | − | 3.78 | 3771 |
| 201 | 32562 | Metabolite - 11245 | 238.3 | − | 3.91 | 3902 |
| 201 | 32563 | Metabolite - 11246 has been identified as 2-propylpentanoate (valproate) Compound ID 22290 | 143.2 | − | 3.94 | 3930 |
| 200 | 32572 | Metabolite - 11255 | 247.1 | + | 2.38 | 2442 |
| 200 | 32578 | Metabolite - 11261 | 286.2 | + | 3.69 | 3600 |
| 201 | 32590 | Metabolite - 11273 | 369.2 | − | 4.56 | 4552 |
| 201 | 32599 | Metabolite - 11282 | 254.8 | − | 4.77 | 4763 |
| 201 | 32616 | Metabolite - 11299 | 507.2 | − | 4.9 | 4893 |
| 201 | 32619 | Metabolite - 11302 | 397.3 | − | 5.01 | 4998 |
| 201 | 32620 | Metabolite - 11303 | 512.3 | − | 5.02 | 5015 |
| 201 | 32625 | Metabolite - 11308 | 365.3 | − | 5.15 | 5133 |
| 200 | 32632 | Metabolite - 11315 | 130.2 | + | 1.19 | 1210 |
| 201 | 32635 | Metabolite - 11318 | 476.3 | − | 5.81 | 5699 |
| 200 | 32644 | Metabolite - 11327 | 269.2 | + | 5.16 | 5176 |
| 200 | 32652 | Metabolite - 11335 has been identified as pro-hydroxy-pro Compound ID 35127 | 229.2 | + | 0.97 | 991 |
| 200 | 32671 | Metabolite - 11354 has been identified as deoxycarnitine Compound ID 36747 | 146.2 | + | 0.76 | 770 |
| 201 | 32689 | Metabolite - 11372 | 467.4 | − | 5.35 | 5303 |
| 201 | 32695 | Metabolite - 11378 | 445.4 | − | 5.37 | 5325 |
| 200 | 32698 | Metabolite - 11381 | 186.2 | + | 1.11 | 1126 |

TABLE 8-continued

Analytical characteristics of unnamed metabolites.

| Lib ID | Comp ID | Name | MASS | Polarity | RT | RI |
|---|---|---|---|---|---|---|
| 200 | 32716 | Metabolite - 11399 | 344.1 | + | 2.79 | 2826 |
| 200 | 32738 | Metabolite - 11421 | 314.2 | + | 4.54 | 4575 |
| 201 | 32740 | Metabolite - 11423 | 260.1 | − | 1.05 | 1038 |
| 201 | 32748 | Metabolite - 11431 | 330 | − | 1.58 | 1575 |
| 201 | 32754 | Metabolite - 11437 | 231 | − | 2.89 | 2888 |
| 201 | 32757 | Metabolite - 11440 | 246.3 | − | 3.58 | 3571 |
| 201 | 32758 | Metabolite - 11441 | 331.1 | − | 3.78 | 3773 |
| 201 | 32759 | Metabolite - 11442 | 331.1 | − | 3.91 | 3902 |
| 201 | 32760 | Metabolite - 11443 | 225.3 | − | 3.92 | 3910 |
| 201 | 32761 | Metabolite - 11444 | 541.2 | − | 3.99 | 3983 |
| 201 | 32762 | Metabolite - 11445 | 239.3 | − | 4.01 | 3995 |
| 201 | 32767 | Metabolite - 11450 | 224.2 | − | 4.11 | 4103 |
| 201 | 32769 | Metabolite - 11452 | 352.1 | − | 4.12 | 4109 |
| 200 | 32780 | Metabolite - 11463 | 388.2 | + | 2.96 | 3014 |
| 200 | 32786 | Metabolite - 11469 | 239.1 | + | 3.82 | 3874 |
| 201 | 32792 | Metabolite - 11475 | 383.2 | − | 4.25 | 4240 |
| 200 | 32793 | Metabolite - 11476 | 189.1 | + | 4.52 | 4525 |
| 201 | 32795 | Metabolite - 11478 | 165.2 | − | 4.3 | 4286 |
| 201 | 32797 | Metabolite - 11480 has been identified as thymol sulfate Compound ID 36095 | 229 | − | 4.42 | 4406 |
| 201 | 32807 | Metabolite - 11490 | 279.8 | − | 4.77 | 4762 |
| 201 | 32808 | Metabolite - 11491 | 567.3 | − | 4.85 | 4846 |
| 201 | 32811 | Metabolite - 11494 | 473.3 | − | 5.73 | 5631 |
| 201 | 32813 | Metabolite - 11496 has been identified as 2-hydroxypalmitate Compound ID 35675 | 271.3 | − | 5.58 | 5508 |
| 201 | 32814 | Metabolite - 11497 | 233.3 | − | 5.37 | 5324 |
| 201 | 32815 | Metabolite - 11498 | 500.3 | − | 5.78 | 5674 |
| 201 | 32827 | Metabolite - 11510 | 385.2 | − | 3.92 | 3925 |
| 200 | 32830 | Metabolite - 11513 | 130.2 | + | 0.81 | 806 |
| 201 | 32839 | Metabolite - 11522 | 313.2 | − | 4.76 | 4754 |
| 201 | 32846 | Metabolite - 11529 | 624.3 | − | 4.85 | 4845 |
| 201 | 32847 | Metabolite - 11530 | 313.2 | − | 4.87 | 4866 |
| 201 | 32848 | Metabolite - 11531 has been identified as 6-beta-hydroxylithocholate Compound ID 36807 | 391.3 | − | 4.86 | 4850 |
| 201 | 32850 | Metabolite - 11533 | 243.2 | − | 4.91 | 4904 |
| 200 | 32854 | Metabolite - 11537 | 366.3 | + | 5.14 | 5200 |
| 201 | 32855 | Metabolite - 11538 | 311.3 | − | 4.93 | 4920 |
| 200 | 32857 | Metabolite - 11540 | 342.3 | + | 5.16 | 5239 |
| 201 | 32863 | Metabolite - 11546 | 448.4 | − | 5.02 | 5015 |
| 201 | 32867 | Metabolite - 11550 | 250.2 | − | 5.15 | 5130 |
| 200 | 32869 | Metabolite - 11552 | 200.3 | + | 5.42 | 5408 |
| 200 | 32875 | Metabolite - 11558 has been identified as 1-docosahexaenoylglycerol (1-monodocosahexaenoin) Compound ID 35153 | 420.2 | + | 5.64 | 5606 |
| 201 | 32877 | Metabolite - 11560 | 295.3 | − | 5.29 | 5245 |
| 201 | 32910 | Metabolite - 11593 | 189.2 | − | 0.79 | 790 |
| 200 | 32978 | Metabolite - 11656 | 227 | + | 0.6 | 612 |
| 200 | 33033 | Metabolite - 11689 | 432.2 | + | 3.11 | 3142 |
| 50 | 33089 | Metabolite - 11744 | 305.1 | + | 7.94 | 1531 |
| 50 | 33103 | Metabolite - 11758 | 397.2 | + | 11.3 | 1917 |
| 200 | 33131 | Metabolite - 11786 | 136 | + | 0.87 | 864 |
| 200 | 33132 | Metabolite - 11787 | 148.1 | + | 1.13 | 1126 |
| 200 | 33138 | Metabolite - 11793 | 601.1 | + | 3.57 | 3634 |
| 200 | 33140 | Metabolite - 11795 | 148.1 | + | 1.46 | 1457 |
| 200 | 33142 | Metabolite - 11797 | 441.1 | + | 1.54 | 1530 |
| 200 | 33150 | Metabolite - 11805 | 418.1 | + | 1.85 | 1845 |
| 200 | 33165 | Metabolite - 11820 | 948.3 | + | 4.68 | 4780 |
| 201 | 33173 | Metabolite - 11828 | 246.1 | − | 1.69 | 1703 |
| 201 | 33174 | Metabolite - 11829 has been identified as 4-acetaminophen sulfate Compound ID 36097 | 230 | − | 1.8 | 1813 |
| 201 | 33178 | Metabolite - 11833 | 260.1 | − | 1.97 | 1977 |
| 201 | 33183 | Metabolite - 11838 | 276 | − | 2.3 | 2314 |
| 201 | 33188 | Metabolite - 11843 | 230.1 | − | 2.69 | 2710 |
| 201 | 33190 | Metabolite - 11845 | 615 | − | 2.87 | 2891 |
| 201 | 33194 | Metabolite - 11849 | 266.2 | − | 3.2 | 3229 |
| 201 | 33195 | Metabolite - 11850 | 226.1 | − | 3.2 | 3228 |
| 201 | 33198 | Metabolite - 11853 | 187.1 | − | 3.59 | 3602 |

TABLE 8-continued

Analytical characteristics of unnamed metabolites.

| Lib ID | Comp ID | Name | MASS | Polarity | RT | RI |
|---|---|---|---|---|---|---|
| 201 | 33203 | Metabolite - 11858 | 437.1 | − | 4.42 | 4400 |
| 201 | 33204 | Metabolite - 11859 | 155.2 | − | 4.57 | 4553 |
| 201 | 33206 | Metabolite - 11861 | 229.2 | − | 4.63 | 4617 |
| 201 | 33209 | Metabolite - 11864 has been identified as taurolithocholate 3-sulfate Compound ID 36850 | 280.9 | − | 5.02 | 5012 |
| 201 | 33221 | Metabolite - 11876 | 635.3 | − | 5.3 | 5257 |
| 201 | 33225 | Metabolite - 11880 | 537.4 | − | 5.44 | 5378 |
| 200 | 33228 | Metabolite - 11883 | 544.3 | + | 5.54 | 5524 |
| 201 | 33237 | Metabolite - 11892 | 367.1 | − | 0.71 | 710 |
| 201 | 33252 | Metabolite - 11907 has been identified as octadecanedioate Compound ID #36850 | 313.3 | − | 5.06 | 5036 |
| 201 | 33253 | Metabolite - 11908 has been identified as 7-alpha-hydroxy-3-oxo-4-cholestenoate (7-Hoca) Compound ID # 36776 | 429.4 | − | 5.27 | 5244 |
| 201 | 33254 | Metabolite - 11909 | 297.3 | − | 5.3 | 5272 |
| 201 | 33353 | Metabolite - 12007 | 223 | − | 1.35 | 1376 |
| 50 | 33369 | Metabolite - 12023 | 204 | + | 11.96 | 1997 |
| 50 | 33386 | Metabolite - 12035 | 397.2 | + | 11.34 | 1921 |
| 201 | 33389 | Metabolite - 12038 | 245.3 | − | 5.82 | 5736 |
| 201 | 33390 | Metabolite - 12039 | 174 | − | 1.6 | 1617 |
| 201 | 33391 | Metabolite - 12040 | 259 | − | 0.95 | 942 |
| 201 | 33396 | Metabolite - 12045 | 203.1 | − | 2.81 | 2816 |
| 200 | 33403 | Metabolite - 12051 | 456.4 | + | 5.83 | 5739 |
| 200 | 33405 | Metabolite - 12053 | 476.3 | + | 3.24 | 3272 |
| 200 | 36738 | gamma-glutamylglutamate | 277.1 | + | 1.02 | 1032 |
| 200 | 33408 | Metabolite - 12056 | 156.2 | + | 1.12 | 1129 |
| 201 | 33412 | Metabolite - 12060 | 170.2 | − | 3.5 | 3497 |
| 201 | 33415 | Metabolite - 12063 | 427.2 | − | 4.82 | 4822 |
| 200 | 33472 | Metabolite - 12085 has been identified as oleoylcarnitine Compound ID 35160 | 426.4 | + | 5.21 | 5214 |
| 200 | 33507 | Metabolite - 12092 | 144.2 | + | 1.13 | 1142 |
| 200 | 33509 | Metabolite - 12094 | 153.1 | + | 1.65 | 1692 |
| 200 | 33510 | Metabolite - 12095 | 153.1 | + | 1.6 | 1638 |
| 200 | 33515 | Metabolite - 12100 | 221.1 | + | 1.76 | 1793 |
| 200 | 33519 | Metabolite - 12104 | 271.1 | + | 1.72 | 1755 |
| 200 | 33576 | Metabolite - 12159 | 196.3 | + | 2.75 | 2806 |
| 200 | 33626 | Metabolite - 12205 | 190.1 | + | 3.77 | 3859 |
| 201 | 33627 | Metabolite - 12206 | 255.1 | − | 0.64 | 654 |
| 201 | 33633 | Metabolite - 12212 | 229.1 | − | 3.57 | 3607 |
| 201 | 33638 | Metabolite - 12217 | 203.1 | − | 2.32 | 2343 |
| 201 | 33652 | Metabolite - 12230 | 217.1 | − | 3.32 | 3360 |
| 200 | 33654 | Metabolite - 12232 has been identified as N6-acetyllysine Compound ID 36752 | 189.2 | + | 1.16 | 1150 |
| 200 | 33666 | Metabolite - 12244 | 269.2 | + | 1.1 | 1147 |
| 201 | 33675 | Metabolite - 12253 | 188.1 | − | 1.68 | 1703 |
| 201 | 33682 | Metabolite - 12260 | 152.1 | − | 1.31 | 1324 |
| 200 | 33773 | Metabolite - 12348 | 211.2 | + | 4.36 | 4548 |
| 200 | 33821 | Metabolite - 12393 | 546.4 | + | 5.58 | 5600 |
| 200 | 33822 | Metabolite - 12394 | 568.4 | + | 5.5 | 5518 |
| 201 | 33883 | Metabolite - 12441 | 319.4 | − | 5.28 | 5291 |
| 201 | 33884 | Metabolite - 12442 | 223.4 | − | 5.28 | 5286 |
| 201 | 33901 | Metabolite - 12456 | 427.2 | − | 4.34 | 4338 |
| 200 | 34040 | Metabolite - 12510 | 160.2 | + | 3.29 | 3343 |
| 201 | 34062 | Metabolite - 12524 | 205.2 | − | 5.61 | 5567 |
| 200 | 34106 | Metabolite - 12542 | 585.3 | + | 4.96 | 4958 |
| 201 | 34201 | Metabolite - 12607 has been identified as 1-stearoylglycerophosphoinositol Compound ID # 19324 | 599.4 | − | 5.92 | 5806 |
| 201 | 34214 | Metabolite - 12620 | 619.4 | − | 5.59 | 5479 |
| 201 | 34217 | Metabolite - 12623 has been identified as 2-palmitoylglycerophosphoethanolamine Compound ID 35688 | 452.4 | − | 5.94 | 5833 |
| 200 | 34223 | Metabolite - 12629 | 520.3 | + | 3.33 | 3396 |
| 201 | 34244 | Metabolite - 12644 | 524.3 | − | 5.74 | 5650 |
| 200 | 34253 | Metabolite - 12650 | 446.2 | + | 3.11 | 3147 |
| 201 | 34314 | Metabolite - 12704 | 274 | − | 1.23 | 1252 |
| 201 | 34329 | Metabolite - 12719 | 300.1 | − | 1.73 | 1760 |
| 201 | 34344 | Metabolite - 12734 | 219.1 | − | 2.23 | 2214 |

TABLE 8-continued

Analytical characteristics of unnamed metabolites.

| Lib ID | Comp ID | Name | MASS | Polarity | RT | RI |
|---|---|---|---|---|---|---|
| 200 | 34359 | Metabolite - 12749 | 262.1 | + | 1.51 | 1562 |
| 200 | 34360 | Metabolite - 12750 has been identified as glutaroyl carnitine Compound ID 35439 | 276.2 | + | 1.53 | 1580 |
| 200 | 34362 | Metabolite - 12752 has been identified as hydroxyisovaleroyl carnitine Compound ID 35433 | 262.2 | + | 1.66 | 1696 |
| 200 | 34365 | Metabolite - 12755 | 271.2 | + | 1.93 | 1960 |
| 200 | 34366 | Metabolite - 12756 | 152.2 | + | 1.95 | 1975 |
| 200 | 34368 | Metabolite - 12758 | 249.1 | + | 1.98 | 2002 |
| 50 | 34441 | Metabolite - 12771 | 258.1 | + | 9.13 | 1669 |
| 50 | 34443 | Metabolite - 12773 | 204 | + | 13.51 | 2182 |
| 201 | 34453 | Metabolite - 12776 | 119.1 | − | 0.67 | 665 |
| 200 | 34460 | Metabolite - 12779 has been identified as leucylleucine Compound ID 36756 | 245.2 | + | 3.01 | 3057 |
| 200 | 34481 | Metabolite - 12798 | 240.1 | + | 1.84 | 1860 |
| 201 | 34516 | Metabolite - 12833 | 229.1 | − | 3.32 | 3337 |
| 201 | 34527 | Metabolite - 12844 | 539.3 | − | 4.12 | 4168 |
| 201 | 34530 | Metabolite - 12847 | 227.1 | − | 4.19 | 4240 |
| 201 | 34532 | Metabolite - 12849 | 331.2 | − | 4.69 | 4726 |
| 201 | 34674 | Metabolite - 12990 | 329.4 | − | 5.7 | 5611 |
| 50 | 12192 | Metabolite - 2358 has been identified as Metabolite - 13496 Compound ID 35270 | 372.1 | + | 12.64 | 2103.4 |
| 50 | 16074 | Metabolite - 02758 has been identified as Metabolite - 13497 Compound ID 35271 | 211 | + | 8.22 | 1597.1 |

While the invention has been described in detail and with reference to specific embodiments thereof, it will be apparent to one skilled in the art that various changes and modifications can be made without departing from the spirit and scope of the invention.

What is claimed is:

1. A method of distinguishing Crohn's disease from Ulcerative colitis in a subject, comprising
analyzing a biological sample from a subject to determine the level(s) of one or more biomarkers for inflammatory bowel disease in the sample, wherein the one or more biomarkers are selected from the group consisting of 6-beta-OH-lithocholate, 7-alpha-hydroxy-3-oxo-4-cholestenoate (7-HOCA), Deoxycholic acid, Glycodeoxycholic acid, and Hyodeoxycholic acid; and
comparing the level(s) of the one or more biomarkers in the sample to Crohn's disease-positive reference levels that distinguish over Ulcerative colitis and/or to Ulcerative Colitis-positive reference levels that distinguish over Crohn's disease in order to determine whether the subject has Crohn's disease or Ulcerative colitis.

2. The method of claim 1, further comprising analyzing a biological sample from a subject to determine the level(s) of one or more additional biomarkers for inflammatory bowel disease in the sample, wherein the one or more additional biomarkers are selected from the group consisting of lathosterol, hippurate, taurodeoxycholate, indoleacetate, cotinine, urea, 2-palmitoylglycerophosphoethanolamine, cholesterol, taurolithocholate 3-sulfate, p-cresol sulfate, 3-indolepropionate, chenodeoxycholate, 7-ketolithocholate, phosphate, dimethylarginine, ornithine, pyroglutamylglycine, 1,5-anhydroglucitol (1,5-AG), caproate (6:0), taurochenodeoxycholate, 3-phenylpropionate (hydrocinnamate), glycerophosphorylcholine (GPC), heptanoate (7:0), dehydroisoandrosterone sulfate (DHEA-S), sebacate, erythronate, benzoate, glycylvaline, mannitol, N-acetylornithine, taurocholate, bradykinin, 3-carboxy-4-methyl-5-propyl-2-furanpropanoate (CMPF), suberate, malate, 2-hydroxyhippurate (salicylurate), acetylphosphate, glycocholate, stachydrine, pentadecanoate (15:0), xanthine, beta-hydroxyisovalerate, and gamma-tocopherol.

3. The method of claim 1, wherein the sample is analyzed using one or more techniques selected from the group consisting of mass spectrometry, ELISA, and antibody linkage.

4. The method of claim 1, wherein the biological sample is a plasma sample.

* * * * *